(12) United States Patent
May et al.

(10) Patent No.: US 6,284,946 B1
(45) Date of Patent: Sep. 4, 2001

(54) BANANA DNA ASSOCIATED WITH FRUIT DEVELOPMENT

(75) Inventors: Gregory D. May, Ithaca, NY (US); Stephanie K. Clendennen, Lake Oswego, OR (US)

(73) Assignee: Boyce Thompson Institute for Plant Research Inc., Itacha, NY (US)

(*) Notice: Subject to any disclaimer, the term of this patent is extended or adjusted under 35 U.S.C. 154(b) by 0 days.

(21) Appl. No.: 09/160,351

(22) Filed: Sep. 25, 1998

Related U.S. Application Data

(60) Provisional application No. 60/060,062, filed on Sep. 25, 1997.
(51) Int. Cl.[7] .............................. C12N 5/04; C12N 15/29; C12N 15/82; C12N 15/90; A01H 5/00
(52) U.S. Cl. .................... 800/278; 435/69.1; 435/320.1; 435/410; 435/419; 435/468; 536/23.6; 800/298
(58) Field of Search .......................... 435/69.1, 320.1, 435/410, 419, 468; 536/23.6; 800/278, 295, 298

(56) References Cited

U.S. PATENT DOCUMENTS 5,886,164 * 3/1999 Bird et al. .......................... 536/23.2

FOREIGN PATENT DOCUMENTS

| WO95 15678 | 6/1995 | (WO) | ................. A01H/5/00 |
| WO96 37617 | 11/1996 | (WO) | ................. C12N/15/53 |
| WO97 38106 | 10/1997 | (WO) | ................. C12N/15/29 |
| WO98 11228 | 3/1998 | (WO) | ................. C12N/15/29 |
| WO98 53085 | 11/1998 | (WO) | ................. C12N/15/82 |

OTHER PUBLICATIONS

Sagl et al, Bio/technology, vol. 13, pp. 481–485, 1995.*
S. Clendennen et al., "Isolation and Identification of Genes Differentially Expressed During Banana Fruit Ripening" *Plant Physiology*, vol. 111, No. 2, p. 34 (Jun. 1996), XP002049413 Abstract.
R. Medina–Suarez et al., "Gene Expression in Banana Peel and Pulp During Ripening" *Plant Physiology*, vol. 111, No. 2, p. 122 (Jun. 1996) XP002049412, Abstract.
do Nascimento et al., "Banana Sucrose–Phosphate Synthase Gene Expression During Fruit Ripening", *Planta* vol. 203, pp. 283–288 (1997) XP002097147.
Dominguez–Puigjaner, "A cDNA Clone Highly Expressed in Ripe Banana Fruit Shows Homology to Pectate Lyases" *Plant Physiology*, vol. 114, No. 3, pp. 1071–1076 (Jul. 1997) XP002096841.
Huang, P–L et al., "Characterization and Expression Analysis of a Banana Gene Encoding 1–Aminocyclopropane–1–Carboxylate Oxidase", *Biochemistry and Molecular Biology International*, vol. 41, No. 5, pp. 941–950 (Apr. 1997) XP000675954.
Lopez–Gomez et al., "Ethylene Biosynthesis in Banana Fruit: Isolation of a Genomic Clone to ACC Oxidase and Expression Studies", *Plant Science*, vol. 123, No. 1/02, pp. 123–131 (1997) XP000676021.
Dominguez–Puigjaner et al., "Differential Protein Accumulation in Banana Fruit During Ripening", *Plant Physiology*, vol. 98, No. 1, pp. 157–162 (Jan. 1992) XP002049414.
Theisen, "Les Plantes Comme Bioreacteurs", *Biofuture*, vol. 168, pp. 47–51 (Jun. 1997), XP002096842.
Clendennen et al., "Differential Gene Expression in Ripening Banana Fruit", *Plant Physiology*, vol. 115, No. 2, pp. 463–469 (Oct. 1997) XP002049417.
Medina–Suarez et al., "Gene Expression in the Pulp of Ripening Bananas" *Plant Physiology*, vol. 115, No. 2, pp. 453–461 (Oct. 1997) XP002049416.

* cited by examiner

*Primary Examiner*—Gary Benzion
*Assistant Examiner*—Ashwin Mehta
(74) *Attorney, Agent, or Firm*—Burns, Doane, Swecker & Mathis, LLP

(57) ABSTRACT

The present invention provides isolated and purified genes which are differentially expressed during banana fruit development, and the protein products of these genes. The present invention further provides DNA regulatory elements which are differentially expressed during banana fruit development, chimeric genes comprising these DNA regulatory elements operably linked to heterologous DNA molecules, and plants transformed with said chimeric genes, providing for controlled expression of said heterologous DNA molecules during the development and ripening of the fruit of said plants, or in response to exogenous ethylene signals in said plants. The present invention also provides a method for expression of a heterologous protein in fruit comprising transforming fruiting plants with one or more chimeric genes according to the present invention, exposing said fruit to an endogenous or exogenous ethylene signal, and harvesting fruit containing said heterologous protein. The method of the present invention may further comprise isolated the proteins produced by said method from the harvested fruit. In a particularly preferred embodiment, the heterologous protein is a therapeutic protein, which may be isolated from the harvested fruit, or consumed directly in the transformed fruit by a patient in need of said therapeutic protein.

12 Claims, 91 Drawing Sheets

```
BANANA       M A I R S P A S L L L F A F L M L A L T G R L Q A R R S S C I G V Y W G Q N T D E G S L
CHICK PEA    . . . M E K C F N I . P S L . L I S L L I K S N A A G . A . . . . . . . . . G N . . . . .
GRAPE        . . . M A R T P Q S T P L L I S . S V L A L . T S Y A G G . A I . . . . . . . G N . . T .
ARABIDOPSIS  M T N M T L R K H V I Y . L . F I S C S L S K P S D A S R G G . A I . . . . . . . G N . . N .
TOBACCO      . . . . . M I K Y S . L L T A . V . F L . A L K L E A G D . V I . . . . . . . G N . . . . .
SUGAR BEET   . . . M A A K I V S V L F L I S . L I F A S F E S S H G . Q . V I . . . . . . . G . . . . .
```

FIG. 8A

```
BANANA       S D K Y A G I M L W T R Y H D R N S G Y S S Q V K S H V C P A R R F S N I L S M P V K S S K
CHICK PEA    . P . . . G . V . . . I . D . F N . A Q . . . . . N A I . G S . . . . . . . . . . . . . . . .
GRAPE        . P . . . G . V . . . . . S K . Y . D Q . . . . . . . S I . . . S . . . . . . . . . . . . . .
ARABIDOPSIS  . R . . . G . V . . . . . S K F W . D K N . . . . . . S I . L A S . . . . . . . . . . . . . .
TOBACCO      . P . . . G . V . . . . . S K F Y . . N . . . . . . . . A I . . A N . . . . . . . . . . . . .
SUGAR BEET   . A . . . G . V . . . . . S K A Y . . . . . . . . . . . A I . . . S . . . . . . . . . . . . .
```

FIG. 8B

```
MT F1    GGCACGAGTACATCCTCTGCTTCTTCGCCTTTCCTCTGAGCCTTTCGCCTTCCTCCTCGCTAACCATGT
MT F3                                                     GGCACAGGGCACGAGGTTGCCTCTGACATGT

MT F1    CGACCTGCGGCAACTGCGACTGCGTTGACAAGAGCCAGTGCGTGAAGAAGGGAAACAGCTA
MT F3    CGACCTGCGGCAACTGCGACTGCGCTGCAAGAGCCAGTGCGTGAAGAAGGGAAACAGCTA

MT F1    CGGTATCGATATTGTTGAGAGACCGAGAGAGAGCTACGTCGACNAGGTGATCGTTGCCGCAGAA
MT F3    CGCTACCGAGACTGTTGCGACCGAGAGAGAGCTTCTTGGATGGTGTAGTCGATGCCCCAGCA

MT F1    GCTGCCGAGCATGACGGCCAAGTGCAAGTGCGGCGCGCCTGCCGCCTGCACCGACTGCAAGT
MT F3    GCCGCCGAGACGGTTGCGACGGAGGGAGACTGCAAGTGCAAGTGCGGCCTGTGTTGACTGCCAAT

MT F1    GTGGCAACTGAGAAGCACTTGTCACTACCACTGTAATAAAGTTTGCAATGCATAAAAA
MT F3    GTGGCCAGTGACAGCTTCTCTTAGCTAGTAATGACAATATATAATATGTTCGAGTAAATAACT

MT F1    CAAAAGAACAAAAAAAAAAAAAGGAAGAAGAAGAAGGTGTGGCTATGTACTCTAATAATTCG
MT F3    TGGGGCTTGCATGCGTAATCGTTTATCGTTTATCAGTGTCATGATGTCAGATGGGATAGGGTTGTG

MT F1    GGCAGGCTGATAGGTTGTAANATGGGATAACGCAGTATCATCTGTTATCTCTGTCCTGT
MT F3    TGGGGCTTGCATGCGTAATCGTTTATCGTTGTCATGATGTCAGATGGGATAGGGTTGTG

MT F1    GGCAGGCTGATAGGTTGTAANATGGGATAACGCAGTATCATCTGTGTTATCTCTGTCCTGT
MT F3    TCTACCTTGTCTACATCTGTACTGTTATCATACATGCTAAATAACTGCTAAATAAGAATTATTAGTATTAA

MT F1    GTTTACAACTCTCCTATCTATCCTAGTCCATGAAATATTATTANTATTAAAAAAAAAAAA
MT F3    AAAAAAAAAAAAAAAA

MT F1    AAAAAAAA
```

FIG. 9

```
BANANA F-1   MS-TCGNCDCVDKSQCVKKGNSYGIDIVETEKSYVDEVI
BANANA F-3   ..-.....................ATET.A....FL.G.V
KIWIFRUIT    ...DK...A.........................IED.V
APPLE        ...GK.D.A.S....................NRSM.T.F
PAPAYA       ...D....A.ST..........-.....DLV........
                                  ...S......TA...I...IMT-.V
                 *            *

BANANA F-1   VAAEAAAEHDGKCKCGAACACTDCKCGN  (65)
BANANA F-3   D.PA....TE.D......PS..V..Q..Q (65)
KIWIFRUIT    MGVP....SG........TS.P.VN.T.D. (63)
APPLE        .D.P..............TG.S.VS.T..H (66)
PAPAYA       MD.P....N.........PS.S...N.T..H (65)
                 *        *    *       *
```

FIG. 10A taagcttccGTGCCAAAGCggtctgcctttctacgccgcatcgggaagggaaacacaaaaaagatcaggaagatgat
gctgacacgagaggtggaaggaagtttacgctctccataatagagattcctttgatgctctccggtgggtgtg
gagcacagacactaatgtgtccgtcgttccaatccctcacgtaatcgggccgtccggctataaataaccccccg
accgagcgaacgcttcaaccaggaacgcataccacacacaatttgttgagccgttgtgcttgtgcctctcgacATGT
CGACCTGCGCGCAACTGCGACTGCGCTGCGACAAGAGCCAGTGCGTGTtaagttctcttcctcccgccctcccacctcttgt
gatacacacaacaaatatgcatgagggttgagtttaatattgacacaagaaactgggtttgctcctgcaggAAGAAGGG
AAACAGCTACGCTACCGAGACTGTTGCGACCGAGAAGaggtattattgatctctcatgggtggggtgtgggagtatc
ttgtccgcatgatgaaattccacaacatgatgactcagcaaacaagatcctttattcttgagaaaacaactaaaagaag
aaaaaaaaacagagaatatatctgcgattatttctttttgagtgatgtggaattccatgccatagcttaaaactattt
cgaagtcgaagcatattacatacctcttgatgaattagtaaggatagtgattaaagtaagcaagcagagtaactac
ttacgttttttcatgtcatctctgtcttacAGCTTCTTGGATGTGTAGTCGATGCCCCACAGCCGCGAAACGGAGG
GAGACTGCAAGTGCTGGTCCTTCCTGCGCCTGTCGTTGACTGCCAATGTGGCCAGTGACAGCTTCTTAGCTAGTAATGACAA
TATATAATGTTCGAGTAAATAACTTGGGGCTTGCATGGCTAATCGTTTATCAGTGTCAGTGTCATGATGTCAGATGGGATAG
GGTTGTGTCTACCTTGTCTACATCTGTACTGTTATCATACATGATAAATAAAGAATTATTAGTATTaatttggtttcagg
tgataactactgctcctttcaaccgaatcactactgttacgtgaacaaacatgtaatagtagtgattcagtaggacgact
tttgtctatttaacttttggttgcaaaatatgttttcctgattcacgaaagagggtgtcatgagcattcgg
ctattgagcgatgttgatgaggcctcaaagggaagaatttatgcttaggactctgagttcgatgatggttgccaccgacctc
ctcaagtaccaagacacataccctttccttccgaggcctatccaacatgctcgtatcgtcgac

FIG. 13

```
                         |Not I       |Xba I         |BamH I           |Sma I
ATTGGACCCACGCGGTGGCGGCCGCTCTAGAATAGTGGATCCCCCGGGCT
++++++++++++++++++++++++++++++++++++++++++++++++++
TAACCTGGGTGCGCCACCGCCGGCGAGATCTTATCACCTAGGGGGCCCGA
   I  G  P  T  R  W  R  P  L  .  N  S  G  S  P  G  L
     L  D  P  R  G  G  G  R  S  R  I  V  D  P  P  G
  N  W  T  H  A  V  A  A  A  L  E  .  W  I  P  R  A

|Pst I
    | |EcoR I
GCAGGAATTCTAAAATCTATTCTTTTTATTTTATTAATTAAATTAAATT
++++++++++++++++++++++++++++++++++++++++++++++++++
CGTCCTTAAGATTTTAGATAAGAAAAATAAAATAATTAATTTAATTTAA
   Q  E  F  .  N  L  F  F  F  I  L  L  I  K  L  N
  C  R  N  S  K  I  Y  S  F  L  F  Y  .  L  N  .  I
     A  G  I  L  K  S  I  L  F  Y  F  I  N  .  I  K  L
AATTTTTTATTGTTTGGTATTTAGCCTAACATTCCCGGACTCCTCTATTT
++++++++++++++++++++++++++++++++++++++++++++++++++
TTAAAAAATAACAAACCATAAATCGGATTGTAAGGGCCTGAGGAGATAAA
   .  F  F  I  V  W  Y  L  .  H  S  R  T  P  L  F
  N  F  L  L  F  G  I  .  P  N  I  P  G  L  L  Y  F
     I  F  Y  C  L  V  F  S  L  T  F  P  D  S  S  I
TTGGAGATTGAATACAAAATTCTTCTCCCATCTAAAGTTATTTTAATTTT
++++++++++++++++++++++++++++++++++++++++++++++++++
AACCTCTAACTTATGTTTTAAGAAGAGGGTAGATTTCAATAAAATTAAAA
   L  E  I  E  Y  K  I  L  L  P  S  K  V  I  L  I  L
     W  R  L  N  T  K  F  F  S  H  L  K  L  F  .  F
  F  G  D  .  I  G  N  S  S  P  I  .  S  Y  F  N  F
GAAGATCATATGGCTGACATATAAAGCAAATATGTCAAAGGTAGTTTTCA
++++++++++++++++++++++++++++++++++++++++++++++++++
CTTCTAGTATACCGACTGTATATTTCGTTTATACAGTTTCCATCAAAAGT
      K  I  I  W  L  T  Y  K  A  N  M  S  K  V  V  F
     .  R  S  Y  G  .  H  I  K  Q  I  C  Q  R  .  F  S
   E  D  H  M  A  D  I  .  S  K  Y  V  K  G  S  F  H
CCGTCCACACGATAGAAACAACAAAGTAGGGTAATTAAATTTGTTCCGTC
++++++++++++++++++++++++++++++++++++++++++++++++++
GGCAGGTGTGCTATCTTTGTTGTTTCATCCCATTAATTTAAACAAGGCAG
      T  V  H  T  I  E  T  T  K  .  G  N  .  I  C  S  V
        P  S  T  R  .  K  Q  Q  S  R  V  I  K  F  V  P  S
         R  P  H  D  R  N  N  K  V  G  .  L  N  L  F  R
ATCACAAAGCACAACACCAAAATATTCACTTAATCAAATCCTCACTATAA
++++++++++++++++++++++++++++++++++++++++++++++++++
TAGTGTTTCGTGTTGTGGTTTTATAAGTGAATTAGTTTAGGAGTGATATT
      I  T  K  H  N  T  K  I  F  T  .  S  N  P  H  Y  K
     S  Q  S  T  T  P  K  Y  S  L  N  Q  I  L  T  I
  H  H  K  A  Q  H  Q  N  I  H  L  I  K  S  S  L  .
```

FIG. 15A-1

```
ATAATAATCC TTCAAA CTGCAACTCTAAACAATGAGGTTCTCTCTCCAG
++++++++++++++++++++++++++++++++++++++++++++++++++
TATTATTAGGAAGTTTGACGTTGAGATTTGTTACTCCAAGAGAGGGTC
   .  . S  F  K  L  Q  L  .  T  M  R  F  S  L  P
   N  N  N  P  S  N  C  N  S  K  Q  .  G  S  L  S  Q
      I  I  I  L  Q  T  A  T  L  N  N  E  V  L  S  P  S
CAACGTTCTTTTCTGAACACAAAGATTTGCCACAACCTTAGCTGACTTTT
++++++++++++++++++++++++++++++++++++++++++++++++++
XXXXXXXXXXXXXXXXXXXXXXXXXXXXXXXXXXXXXXXXXXXXXXXXXX
   A  T  F  F  S  E  H  K  D  L  P  Q  P  .  L  T  F
   Q  R  S  F  L  N  T  K  I  C  H  N  L  S  .  L  L
      N  V  L  F  .  T  Q  R  F  A  T  T  L  A  D  F
AATATCAGTGGTCTCTGGACAAGATTCTTGTTGCACGCTAAAATTCGAAC
++++++++++++++++++++++++++++++++++++++++++++++++++
TTATAGTCACCAGAGACCTGTTCTAAGAACAACGTGCGATTTTAAGCTTG
   N  I  S  G  L  W  T  R  F  L  L  H  A  K  I  R  T
      I  S  V  V  S  G  Q  D  S  C  C  T  L  K  F  E
   .  Y  Q  W  S  L  D  K  I  L  V  A  R  .  N  S  N
TAAAATCAGATCGAGTTATATCCGTAATTGAGATTGATGACCGAACCGAT
++++++++++++++++++++++++++++++++++++++++++++++++++
ATTTTAGTCTAGCTCAATATAGGCATTAACTCTAACTACTGGCTTGGCTA
      K  I  R  S  S  Y  I  R  N  .  D  .  .  P  N  R
   L  K  S  D  R  V  I  S  V  I  E  I  D  D  R  T  D
   .  N  Q  I  E  L  Y  P  .  L  R  L  M  T  E  P  I
TTTAAGAGTACTCTCCGTAACTTGGGATTAATAAAATTAATAAGGTAGGT
++++++++++++++++++++++++++++++++++++++++++++++++++
AAATTCTCATGAGAGGCATTGAACCCTAATTATTTTAATTATTCCATCCA
   F  .  E  Y  S  P  .  L  G  I  N  K  I  N  K  V  G
      F  K  S  T  L  R  N  L  G  L  I  K  L  I  R  .  V
         L  R  V  L  S  V  T  W  D  .  .  N  .  .  G  R
ATCAGTTATTTTAGATGATAAAAATCTTGATAGTTTGAATCTCATCTTAG
++++++++++++++++++++++++++++++++++++++++++++++++++
TAGTCAATAAAATCTACTATTTTTAGAACTATCAAACTTAGAGTAGAATC
      I  S  Y  F  R  .  .  K  S  .  .  F  E  S  H  L  S
      S  V  I  L  D  D  K  N  L  D  S  L  N  L  I  L
   Y  Q  L  F  .  M  I  K  I  L  I  V  .  I  S  S  .
AGTGAATAAAAATTAATTTTTATTATTATTATTAAACTAATTAGACTAAC
++++++++++++++++++++++++++++++++++++++++++++++++++
TCACTTATTTTTAATTAAAATAATAATAATAATTTGATTAATCTGATTG
      H  L  F  L  I  K  N  N  N  N  N  L  I  N  L  I
   V  T  Y  F  .  L  K  I  I  I  I  I  I  .  L  I  .  L
   S  L  I  F  N  .  K  .  .  .  .  F  D  .  S  D  W
```

FIG. 15A-2

```
GAAAAAAAAAAAGTTCTCTAGCCATTAAAGTCTGGTAGGACATAGAAATT
CTTTTTTTTTTCAAGAGATCGGTAATTTCAGACCATCCTGTATCTTTAA
G  K  K  K  S  S  L  A  I  K  V  W  .  D  I  E  I
 E  K  K  K  V  L  .  P  L  K  S  G  R  T  .  K  L
  K  K  K  K  F  S  S  H  .  S  L  V  G  H  R  N

AATGAATTAAACTGTAACCATAAGGTTGAATTTTTGAACACATGTACAGG
TTACTTAATTTGACATTGGTATTCCAACTTAAAAACTTGTGTACATGTCC
 N  E  L  N  C  N  H  K  V  E  F  L  N  T  C  T  G
  M  N  .  T  V  T  I  R  L  N  F  .  T  H  V  G
   .  .  I  K  L  .  P  .  G  .  I  F  E  H  M  Y  R
```

FIG. 15A-3

```
AAAATTGATTTGTTGAAGTCATGTCTAATCAATGCAGCAGTTTACAGCTT
TTTTAACTAAACAACTTCAGTACAGATTAGTTACGTCGTCAAATGTCGAA
   K  L  I  C  .  S  H  V  .  S  M  Q  Q  F  T  A
 E  N  .  F  V  E  V  M  S  N  Q  C  S  S  L  Q  L
   K  I  D  L  L  K  S  C  L  I  N  A  A  V  Y  S  L

GGTGTGACTTCCACAACTATAGGCTTATCCCCTGGGAGTCGAGGATCAAA
CCACACTGAAGGTGTTGATATCCGAATAGGGGACCCTCAGCTCCTAGTTT
   W  C  D  F  H  N  Y  R  L  I  P  W  E  S  R  I  K
 G  V  T  S  T  T  I  G  L  S  P  G  S  R  G  S  N
   V  .  L  P  Q  L  .  A  Y  P  L  G  V  E  D  Q

CGTGTGAGCAATATTCTCCCTTCCTGATGATAAACTATGATGGCTGTTAG
GCACACTCGTTATAAGAGGGAAGGACTACTATTTGATACTACCGACAATC
   R  V  S  N  I  L  P  S  .  .  T  M  M  A  V  R
   V  .  A  I  F  S  L  P  D  D  K  L  .  W  L  L
 T  C  E  Q  Y  S  P  F  L  M  I  N  Y  D  G  C  .

GTGTGTAAGCACTCCAAATTTTCCATCAATGTGGAATTGGAAGAGTTCAC
CACACATTCGTGAGGTTTAAAAGGTAGTTACACCTTAACCTTCTCAAGTG
   C  V  S  T  P  N  F  P  S  M  W  N  W  K  S  S
 G  V  .  A  L  Q  I  F  H  Q  C  G  I  G  R  V  H
   V  C  K  H  S  K  F  S  I  N  V  E  L  E  E  F  T

GCACTGACGGACCAACTCGGTTTGTTCAGTCTGGTGACTACTGCTGAGCA
CGTGACTGCCTGGTTGAGCCAAACAAGTCAGACCACTGATGACGACTCGT
   R  T  D  G  P  T  R  F  V  Q  S  G  D  Y  C  .  A
  A  L  T  D  Q  L  G  L  F  S  L  V  T  T  A  E  H
   H  .  R  T  N  S  V  C  S  V  W  .  L  L  L  S

TGAGAAAATGGTTGATGGTAGCAAGTTGCAAATGTACCTGACCTCATCTT
ACTCTTTTACCAACTACCATCGTTCAACGTTTACATGGACTGGAGTAGAA
   .  E  N  G  .  W  .  Q  V  A  N  V  P  D  L  I  L
   E  K  M  V  D  G  S  K  L  Q  M  Y  L  T  S  S
 M  R  K  W  L  M  V  A  S  C  K  C  T  .  P  H  L

AAAGACTGTTGATTAGATGCATGCATTGATTACGTCTCTTCCATCTTTAA
TTTCTGACAACTAATCTACGTACGTAACTAATGCAGAGAAGGTAGAAATT
   K  T  V  D  .  M  H  A  L  I  T  S  L  P  S  L
  .  R  L  L  I  R  C  M  H  .  L  R  L  F  H  L  .
   K  D  C  .  L  D  A  C  I  D  Y  V  S  S  I  F  N
```

FIG. 15B-1

```
CTCTTTTGATCGATGCATCGTCTTAATTAGGTCAAGGACATGTGATGACA
GAGAAAACTAGCTACGTAGCAGAATTAATCCAGTTCCTGTACACTACTGT
   T  L  L  I  D  A  S  S  .  L  G  Q  G  H  V  M  T
    L  F  .  S  M  H  R  L  N  .  V  K  D  M  .  .  Q
     S  F  D  R  C  I  V  L  I  R  S  R  T  C  D  D

AGAATCTATTCCACTATTTGTGACCCATATTCCAAATGGAACAAGACTTC
TCTTAGATAAGGTGATAAACACTGGGTATAAGGTTTACCTTGTTCTGAAG
   R  I  Y  S  T  I  C  D  P  Y  S  K  W  N  K  T  S
    E  S  I  P  L  F  V  T  H  I  P  N  G  T  R  L
     K  N  L  F  H  Y  L  .  P  I  F  Q  M  E  Q  D  F

CAAGTCCTCATCCAGAATTTTGGAAGGGATAAGGATGGTGGGGAGAAAGA
GTTCAGGAGTAGGTCTTAAAACCTTCCCTATTCCTACCACCCCTCTTTCT
    K  S  S  S  R  I  L  E  G  I  R  M  V  G  R  K
     P  S  P  H  P  E  F  W  K  G  .  G  W  W  G  E  R
      Q  V  L  I  Q  N  F  G  R  D  K  D  G  G  E  K  E

ACAAGCTGTTGCCTTTCGTTTTCTTCTATCAGGAAGCCAAGAG TTTCAAG
TGGTCGACAACGGAAAGCAAAAGAAGATAGTCCTTCGGTTTCTCAAAGTTC
   N  K  L  L  P  F  V  F  F  Y  Q  E  A  K  S  F  K
    T  S  C  C  L  S  F  S  S  I  R  K  P  R  V  S  R
     Q  A  V  A  F  R  F  L  L  S  G  S  Q  E  F  Q

AGGAGGGTAGACCTGAGGGGATGATGCCTGTGTCGAAACCT CTATATAAG
TCCTCCCATCTGGACTCCCCTACTACGGACACAGCTTTGGAGATATATTC
    R  R  V  D  L  R  G  .  C  L  C  R  N  L  Y  I  R
     G  G  .  T  .  G  D  D  A  C  V  E  T  S  I  .
      E  E  G  R  P  E  G  M  M  P  V  S  K  P  L  Y  K
                                 1425
GAGTAGGAACACAGCATGTTGATGA ACACAAACCATTTCAGCGGGGAAGA
CTCATCCTTGTGTCGTACAACTAC T TGTGTTTGGTAAAGTCGCCCCTTCT
    S  R  N  T  A  C  .  .  T  Q  T  I  S  A  G  K
     G  V  G  T  Q  H  V  D  E  H  K  P  F  Q  R  G  R
      E  .  E  H  S  M  L  M  N  T  N  H  F  S  G  E  E
                          1479            Hind III
AGAGAACCCTTTTGACAGAGTTGTTGTC ATG GCAACAAAAGCTTCTCTCT
TCTCTTGGGAAAACTGTCTCAACAACAGTACCGTTGTTTTCGAAGAGAGA
    K  R  T  L  L  T  E  L  L  S  W  Q  Q  K  L  L  S
     R  E  P  F  .  Q  S  C  C  H  G  N  K  S  F  S  L
      E  N  P  F  D  R  V  V  V  M  A  T  K  A  S  L
```

FIG. 15B-2

```
CCATAAAAGGCTTTGCCTTGCTGGTTTCAGTCCTTGTAGCAGTTCCAACA
GGTATTTTCCGAAACGGAACGACCAAAGTCAGGAACATCGTCAAGGTTGT
  P  .  K  A  L  P  C  W  F  Q  S  L  .  Q  F  Q  Q
   H  K  R  L  C  L  A  G  F  S  P  C  S  S  S  N
 S  I  K  G  F  A  L  L  V  S  V  L  V  A  V  P  T
                        24 X [TC]
AGTTCTCTCTCTCTCTCTCTCTCTCTCTCTCTCTCTCTCTCTCTCTCTCT
TCAAGAGAGAGAGAGAGAGAGAGAGAGAGAGAGAGAGAGAGAGAGAGAGA
   V  L  S  L  S  L  S  L  S  L  S  L  S  L  S  L
  K  F  S  L  S  L  S  L  S  L  S  L  S  L  S  L  S
 S  S  L  S  L  S  L  S  L  S  L  S  L  S  L  S  L
```

$$\frac{T}{ACA} \quad \frac{R}{AGA} \quad \frac{V}{GTG}$$

FIG. 15B-3

```
CTCATATTATACATTTGATTGTTAGCTCTTACAAATTTATTAGGGTTTTT
GAGTATAATATGTAAACTAACAATCGAGAATGTTTAAATAATCCCAAAAA
  S  H  I  I  H  L  I  V  S  S  Y  K  F  I  R  V  F
    L  I  L  Y  I  .  L  L  A  L  T  N  L  L  G  F  L
      S  Y  Y  T  F  D  C  .  L  L  Q  I  Y  .  G  F
                    Hind III
ATAAGAGTTCAAGCTTTTGGTAATTTAATCATGGTAGGTTATATTTTCAA
TATTCTCAAGTTCGAAAACCCTTAAATTAGTACCATCCAATATAAAAGTT
  I  R  V  Q  A  F  G  N  L  I  M  V  G  Y  I  F  K
    .  E  F  K  L  L  V  I  .  S  W  .  V  I  F  S
      Y  K  S  S  S  F  W  .  F  N  H  G  R  L  Y  F  Q
AACTTGTAACCTGCATTTTGTCTCTTTATTTCATGCAATATTCTTTTCCT
TTGAACCTTGGACGTAAAACCAGAGAAATAAAGTACGTTATCCGAAAAGGA
     T  C  N  L  H  F  V  S  L  F  H  A  I  F  F  S
  K  L  V  T  C  I  L  S  L  Y  F  M  Q  Y  S  F  P
    N  L  .  P  A  F  C  L  F  I  S  C  N  I  L  F  L
TGATTGGCTTACGTCATTTACTTGAGTTAGCTCATATGTAACTGTTTAAA
ACTAACCGAATGCAGTAAATGAACTCAATCGAGTATACATTGACAAATTT
  L  I  G  L  R  H  L  L  E  L  A  H  M  .  L  F  K
    .  L  A  Y  V  I  Y  L  S  .  L  I  C  N  C  L  N
      D  W  L  T  S  F  T  .  V  S  S  Y  V  T  V  .
TATTTGGGATTATTGGTTAACGGATAAAAAAAATTAAGATTTTAGATACA
CTAAACCCTAATAACCAATTGCCTATTTTTTTTAATTCTAAAATCTATGT
  Y  L  G  L  L  V  N  G  .  K  K  L  I  D  F  R  Y
    I  W  D  Y  W  L  T  D  K  K  N  .  L  I  L  D
      I  F  G  I  I  G  .  R  I  K  K  I  N  .  F  .  I
                       27 X [TA]
ATGCTATATATATATATATATATATATATATATATATATATATATATATA
TACGATATATATATATATATATATATATATATATATATATATATATATAT
    N  A  I  Y  I  Y  I  Y  I  Y  I  Y  I  Y  I  Y
  T  M  L  Y  I  Y  I  Y  I  Y  I  Y  I  Y  I  Y  I
    Q  C  Y  I  Y  I  Y  I  Y  I  Y  I  Y  I  Y  I  Y
TATATATATATTATAGGTAGAAACTTGGTATAATTCACACGTATGTTCGC
ATATATATATAATATCCATCTTTGAACCATATTAAGTGTCCATACAAGCG
  I  Y  I  Y  Y  R  .  K  L  G  I  I  H  T  Y  V  R
    Y  I  Y  I  I  G  R  N  L  V  .  F  T  R  M  F  A
      I  Y  I  L  .  V  E  T  W  Y  N  S  H  V  C  S
```

FIG. 15C-1

```
TTTATCTGAATAAAATGAGTAGTCCTTTCAATGCAGATTAGTCTTACTCC
++++++++++++++++++++++++++++++++++++++++++++++++++
AAATAGACTTATTTTACTCATCAGGAAAGTTACGTCTAATCAGAATGAGG
   F  I  .  I  K  .  V  V  L  S  M  Q  I  S  L  T  P
    L  S  E  .  N  E  .  S  F  Q  C  R  L  V  L  L
  L  Y  L  N  K  M  S  S  P  F  N  A  D  .  S  Y  S

ACTTGCAGATGCACGACCAATTTGCTTGATCATCTTCCATAGAGCACCAC
++++++++++++++++++++++++++++++++++++++++++++++++++
TGAACGTCTACGTGCTGGTTAAACGAACTAGTAGAAGGTATCTCGTGGTG
    L  A  D  A  R  P  I  C  L  I  I  F  H  R  A  P
   H  L  Q  M  H  D  Q  F  A  .  S  S  S  I  E  H  H
    T  C  R  C  T  T  N  L  L  D  H  L  P  .  S  T  T
```

```
                        ACA   NGA   GTG
                        ─── ─────── ───
                         T   Pst I   V
```

```
AGCTAAGTCTCCGATGTGTTCTACTGCAGGAGTGCAATCGATTGGTGTCT
                                ←───────
++++++++++++++++++++++++++++++++++++++++++++++++++
TCGATTCAGAGGCTACACAAGATGACGTCCTCACGTTAGCTAACCACAGA
 Q  L  S  L  R  C  V  L  L  Q  E  C  N  R  L  V  S
   S  .  V  S  D  V  F  Y  C  R  S  A  I  D  W  C  L
    A  K  S  P  M  C  S  T  A  G  V  Q  S  I  G  V

GCTACGGAATGCTCGGCAACAATCTTCCCCCGCCCAGCGAGGTGGTCAGT
++++++++++++++++++++++++++++++++++++++++++++++++++
CGATGCCTTACGAGCCGTTGTTAGAAGGGGGCGGGTCGCTCCACCAGTCA
  A  T  E  C  S  A  T  I  F  P  R  P  A  R  W  S  V
   L  R  N  A  R  Q  Q  S  S  P  A  Q  R  G  G  Q
  C  Y  G  M  L  G  N  N  L  P  P  P  S  E  V  V  S

CTCTACAAATCCAACAACATCGCGAGGATGAGACTCTACGATCCAAACCA
++++++++++++++++++++++++++++++++++++++++++++++++++
GAGATGTTTAGGTTGTTGTAGCGCTCCTACTCTGAGATGCTAGGTTTGGT
     S  T  N  P  T  T  S  R  G  .  D  S  T  I  Q  T
  S  L  Q  I  Q  Q  H  R  E  D  E  T  L  R  S  K  P
    L  Y  K  S  N  N  I  A  R  M  R  L  Y  D  P  N  Q
```

FIG. 15C-2

```
GGCCGCCCTGCAAGCCCTCAGGAACTCCAACATCCAAGTCCTGTTGGATG
CCGGCGGGACGTTCGGGAGTCCTTGAGGTTGTAGGTTCAGGACAACCTAC
 R  P  P  C  K  P  S  G  T  P  T  S  K  S  C  W  M
  G  R  P  A  S  P  Q  E  L  Q  H  P  S  P  V  G  C
   A  A  L  Q  A  L  R  N  S  N  I  Q  V  L  L  D

TCCCCCGATCCGACGTGCAGTCACTGGCCTCCAATCCTTCGGCCGCCGGC
AGGGGGCTAGGCTGCACGTCAGTGACCGGAGGTTAGGAAGCCGGCGGCCG
  S  P  D  P  T  C  S  H  W  P  P  I  L  R  P  P  A
   P  P  I  R  R  A  V  T  G  L  Q  S  F  G  R  R
 V  P  R  S  D  V  Q  S  L  A  S  N  P  S  A  A  G

BamH I
GACTGGATCCGGAGGAACGTCGTCGCCTACTGGCCCAGCGTCTCCTTTCG
CTGACCTAGGCCTCCTTGCAGCAGCGGATGACCGGGTCGCAGAGGAAAGC
    T  G  S  G  G  T  S  S  P  T  G  P  A  S  P  F
  R  L  D  P  E  E  R  R  R  L  L  A  Q  R  L  L  S
   D  W  I  R  R  N  V  V  A  Y  W  P  S  V  S  F  R

ATACATAGCTGTCGGAAACGAGCTGATCCCCGGATCGGATCTGGCGCAGT
TATGTATCGACAGCCTTTGCTCGACTAGGGGCCTAGCCTAGACCGCGTCA
 D  T  .  L  S  E  T  S  .  S  P  D  R  I  W  R  S
  I  H  S  C  R  K  R  A  D  P  R  I  G  S  G  A  V
   Y  I  A  V  G  N  E  L  I  P  G  S  D  L  A  Q
```

FIG. 15C-3

```
ACATCCTCCCCGCCATGCGCAACATCTACAATGCTTTGTCCTCGGCTGGC
TGTAGGAGGGGCGGTACGCGTTGTAGATGTTACGAAACAGGAGCCGACCG
 T  S  S  P  P  C  A  T  S  T  M  L  C  P  R  L  A
   H  P  P  R  H  A  Q  H  L  Q  C  F  V  L  G  W
 Y  I  L  P  A  M  R  N  I  Y  N  A  L  S  S  A  G
                                  ¦Sal I
CTGCAAAACCAGATCAAGGTCTCGACCGCGGTCGACACGGGCGTCCTCGG
GACGTTTTGGTCTAGTTCCAGAGCTGGCGCCAGCTGTGCCCGCAGGAGCC
   C  K  T  R  S  R  S  R  P  R  S  T  R  A  S  S
 P  A  K  P  D  Q  G  L  D  R  G  R  H  G  R  P  R
   L  Q  N  Q  I  K  V  S  T  A  V  D  T  G  V  L  G
CACGTCCTACCCTCCCTCCGCCGGCGCCTTCTCCTCCGCCGCCCAGGCGT
GTGCAGGATGGGAGGGAGGCGGCCGCGGAAGAGGAGGCGGCGGGTCCGCA
 A  R  P  T  L  P  P  P  A  P  S  P  P  P  P  R  R
   H  V  L  P  S  L  R  R  R  L  L  L  R  R  P  G  V
     T  S  Y  P  P  S  A  G  A  F  S  S  A  A  Q  A
ACCTGAGCCCCATCGTGCAGTTCTTGGCGAGTAACGGAGCGCCGCTCCTG
TGGACTCGGGGTAGCACGTCAAGAACCGCTCATTGCCTCGCGGCGAGGAC
 T  .  A  P  S  C  S  S  W  R  V  T  E  R  R  S  W
   P  E  P  H  R  A  V  L  G  E  .  R  S  A  A  P
 Y  L  S  P  I  V  Q  F  L  A  S  N  G  A  P  L  L
                               ¦Sma I    ¦Bgl II
GTCAATGTGTACCCTTATTTTAGCTACACCGGCAACCCGGGACAGATCTC
CAGTTACACATGGGAATAAAATCGATGTGGCCGTTGGGCCCTGTCTAGAG
     S  M  C  T  L  I  L  A  T  P  A  T  R  D  R  S
   G  Q  C  V  P  L  F  .  L  H  R  Q  P  G  T  D  L
 V  N  V  Y  P  Y  F  S  Y  T  G  N  P  G  Q  I  S
GCTGCCCTACGCCCTGTTCACGGCCTCCGGCGTCGTCGTGCAGGATGGGC
CGACGGGATGCGGGACAAGTGCCGGAGGCCGCAGCAGCACGTCCTACCCG
   R  C  P  T  P  C  S  R  P  P  A  S  S  C  R  M  G
 A  A  L  R  P  V  H  G  L  R  R  R  R  A  G  W  A
   L  P  Y  A  L  F  T  A  S  G  V  V  V  Q  D  G
                                  ¦Sal I
GATTCAGCTATCAGAACCTGTTCGACGCCATCGTCGACGCGGTCTTCGCG
CTAAGTCGATAGTCTTGGACAAGCTGCGGTAGCAGCTGCGCCAGAAGCGC
   D  S  A  I  R  T  C  S  T  P  S  S  T  R  S  S  R
     I  Q  L  S  E  P  V  R  R  H  R  R  R  G  L  R
 R  X  S  Y  Q  N  L  F  D  A  I  V  D  A  V  F  A
```

FIG. 15D-1

```
GCGCTGGAGAGAGTGGGAGGGGCGAACGTGGCGGTGGTGGTGTCGGAGAG
CGCGACCTCTCTCACCCTCCCCGCTTGCACCGCCACCACCACAGCCTCTC
   R  W  R  E  W  E  G  R  T  W  R  W  W  C  R  R
 G  A  G  E  S  G  R  G  E  R  G  G  G  G  V  G  E
  A  L  E  R  V  G  G  A  N  V  A  V  V  V  S  E  S
CGGGTGGCCGTCGGCGGGCGGAGGAGCCGAAGCGAGCACCAGCAACGCGC
GCCCACCGGCAGCCGCCCGCCTCCTCGGCTTCGCTCGTGGTCGTTGCGCG
 A  G  G  R  R  R  A  E  E  P  K  R  A  P  A  T  R
  R  V  A  V  G  G  R  R  S  R  S  E  H  Q  Q  R  A
   G  W  P  S  A  G  G  G  A  E  A  S  T  S  N  A
AGACGTACAACCAGAACTTGATCAGGCATGTTGGCGGAGGAACGCCGAGG
TCTGCATGTTGGTCTTGAACTAGTCCGTACAACCGCCTCCTTGCGGCTCC
   R  R  T  T  R  T  .  S  G  M  L  A  E  E  R  R  G
    D  V  Q  P  E  L  D  Q  A  C  W  R  R  N  A  E
 Q  T  Y  N  Q  N  L  I  R  H  V  G  G  G  T  P  R
AGACCAGGGAAGGAGATCGAGGCATACATATTCGAGATGTTCAACGAGAA
TCTGGTCCCTTCCTCTAGCTCCGTATGTATAAGCTCTACAAGTTGCTCTT
   D  Q  G  R  R  S  R  H  T  Y  S  R  C  S  T  R
 E  T  R  E  G  D  R  G  I  H  I  R  D  V  Q  R  E
  R  P  G  K  E  I  E  A  Y  I  F  E  M  F  N  E  N
CCAGAAGGCTGGAGGGATCGAGCAGAACTTTGGCCTGTTTTATCCCAACA
GGTCTTCCGACCTCCCTAGCTCGTCTTGAAACCGGACAAAATAGGGTTGT
   T  R  R  L  E  G  S  S  R  T  L  A  C  F  I  P  T
    P  E  G  W  R  D  R  A  E  L  W  P  V  L  S  Q  Q
     C  K  A  G  G  I  E  Q  N  F  G  L  F  Y  P  N
                                    |Hind III
AGCAGCCCGTATACCAAATAAGCTTT TAG AAACTAACTTGTAAGGTTGAT
TCGTCGGGCATATGGTTTATTCGAAAATCTTTGATTGAACATTCCAACTA
   S  S  P  Y  T  K  .  A  F  R  N  .  L  V  R  L  M
    A  A  R  I  P  N  K  L  L  E  T  N  L  .  G  .
 K  Q  P  V  Y  Q  I  S  F  .  K  L  T  C  K  V  D
                  5 X [CTAC]
GAATCATCTCCTACCTACCTACCTACGAATAAAACATGAAATAAAG
CTTAGTAGAGGATGGATGGATGGATGCTTATTTTGTACTTTATTTC
   N  H  L  L  P  T  Y  L  P  T  N  K  T  .  N  K
 .  I  I  S  Y  L  P  T  Y  L  R  I  K  H  E  I  K
  E  S  S  P  T  Y  L  P  T  Y  E  .  N  M  K  .  S
```

FIG. 15D-2

```
                  |EcoR I                        |CDNA EUCLS (POLY A)
CACCAAAATAAAGGGAGAATCTTGATCTTGGAGAAAGTTGAATCATGATG
+++++++++++++++++++++++++++++++++++++++++++++++++
GTGGTTTTATTTCCCTCTTAGAACTAGAACCTCTTTCAACTTAGTACTAC
 A  P  K  .  R  E  N  S  D  L  G  E  S  .  I  M  M
   H  Q  N  K  G  R  I  L  I  L  E  K  V  E  S  .  .
     T  N  I  K  G  E  F  .  S  W  R  K  L  N  H  D
ATATATAACAAACACCCCTCTTTACTCATTATCAGTATGTTACAAGTTTC
+++++++++++++++++++++++++++++++++++++++++++++++++
TATATATTGTTTGTGGGGAGAAATGAGTAATAGTCATCCAATGTTCAAAG
  I  Y  N  K  H  P  S  L  L  I  I  S  M  L  Q  V  S
    Y  I  T  N  T  P  L  Y  S  L  S  V  C  Y  K  F
  D  I  .  Q  T  P  L  F  T  H  Y  Q  Y  V  T  S  F
TTGAAACTTGAACGGATCACAATTTGGACCTACAAGTATTTTGGGTCATA
+++++++++++++++++++++++++++++++++++++++++++++++++
AACTTTGAACTTGCCTAGTGTTAAACCTGGATGTTCATAAAACCCAGTAT
   .  N  L  N  G  S  Q  F  G  P  T  S  I  L  G  H
   L  E  T  .  T  D  H  N  L  D  L  Q  V  F  W  V  I
    L  K  L  E  R  I  T  X  W  T  Y  K  Y  F  G  S  .
ATTATTTCATTGAACTATATATTCAAAAAAGATGTGTTTGGAGTGCTTA
+++++++++++++++++++++++++++++++++++++++++++++++++
TAATAAAGTAACTTGATATATAAGTTTTTTTCTACACAAACCTCACGAAT
 N  Y  F  I  E  L  Y  I  Q  K  K  M  C  L  E  C  L
   I  I  S  L  N  Y  I  F  K  K  R  C  V  W  S  A  .
     L  F  H  .  T  I  Y  S  K  K  D  V  F  G  V  L
ATACAGTATGACTTCAGTTTGCAAGATTACCTCTTCAGCGTCAGCTTCAG
+++++++++++++++++++++++++++++++++++++++++++++++++
TATGTCATACTGAAGTCAAACGTTCTAATGGAGAAGTCGCAGTCGAAGTC
   I  Q  Y  D  F  S  L  Q  D  Y  L  F  S  V  S  F  S
     Y  S  M  T  S  V  C  K  I  T  S  S  A  S  A  S
  N  T  V  .  L  Q  F  A  R  L  P  L  Q  R  Q  L  Q
CATGCCAAAAAACCATCATCTGCTATGGGGCATGTTTTACACCTTGATGG
+++++++++++++++++++++++++++++++++++++++++++++++++
GTACGGTTTTTTGGTAGTAGACGATACCCCGTACAAAATGTGGAACTACC
    M  P  K  N  H  H  L  L  W  G  M  F  Y  T  L  M
  A  C  Q  K  T  I  I  C  Y  G  A  C  F  T  P  .  W
   H  A  K  K  P  S  S  A  M  G  H  V  L  H  L  D  G
```

FIG. 15E-1

```
TGCTACATCATCATCATTCATGTTTCATTTTAGGTCTCGTGCTCTTTATA
ACGATGTAGTAGTAGTAAGTACAAAGTAAAATCCAGAGCACGAGAAATAT
 V  L  H  H  H  H  S  C  F  I  L  G  L  V  L  F  I
   C  Y  I  I  I  I  H  V  S  F  .  V  S  C  S  L  Y
    A  T  S  S  S  S  M  F  H  F  R  S  R  A  L  Y

TAGATCACATAAAAGTTTGGATCGCTTCAAGTTTCTAGGTTACATTGTAT
ATCTAGTGTATTTTCAAACCTAGCGAAGTTCAAAGATCCAATGTAACATA
 .  I  T  .  K  F  G  S  L  Q  V  S  R  L  H  C  M
   R  S  H  K  S  L  D  R  F  K  F  L  G  Y  I  V
    I  D  H  I  K  V  W  I  A  S  S  F  .  V  T  L  Y

GCAGCACTTTGAGCCTACTGAACATTGTGACTGCCTTTTAGAACATTGGA
CGTCGTGAAACTCGGATGACTTGTAACACTGACGGAAAATCTTGTAACCT
   Q  H  F  E  P  T  E  H  C  D  C  L  L  E  H  W
  C  S  T  L  S  L  L  N  I  V  T  A  F  .  N  I  G
    A  A  L  .  A  Y  .  T  L  .  L  P  F  R  T  L  D

Pst I
CTGCAGGAA
         ─── 3559
GACGTCCTT
 T  A  G
  L  Q  E
   C  R  K
```

FIG. 15E-2

```
                      ┆Sal I
         AGCGAGGTCGACTAATGAGCTACTAACATTAATGTCACAGATAGTAATAG
         TCGCTCCAGCTGATTACTCGATGATTGTAATTACAGTGTCTATCATTATC
           S   E   V   D   .   .   A   T   N   I   N   V   T   D   S   N   R
             A   R   S   T   N   E   L   L   T   L   M   S   Q   I   V   I
         Q   R   G   R   L   M   S   Y   .   H   .   C   H   R   .   .   .
         ATGAGAAGCCGTATCCAACACGCAATCTGTANACTTGGTCACAGGACTTC
         TACTCTTCGGCATAGGTTGTGCGTTAGACATNTGAACCAGTGTCCTGAAG
             .   E   A   V   S   N   T   Q   S   V   ?   L   V   T   G   L
         D   E   K   P   Y   P   T   R   N   L   ?   T   W   S   Q   D   F
           M   R   S   R   I   Q   H   A   I   C   ?   L   G   H   R   T   S
         TTATCCAAAGACTCGCCTCTGCGATTTCCCACATTCACCTCATTTGGTCC
         AATAGGTTTCTGAGCGGAGACGCTAAAGGGTGTAAGTGGAGTAAACCAGG
           L   I   Q   R   L   A   S   A   I   S   H   I   H   L   I   W   S
             L   S   K   D   S   P   L   R   F   P   T   F   T   S   F   G   P
         Y   P   K   T   R   L   C   D   F   P   H   S   P   H   L   V

┆Hind III
         ATAGGAAGCTTCACAGCGGGCAGGAATCCATTTCTCTATATAAGCACCAC
         TATCCTTCGAAGTGTCGCCCGTCCTTAGGTAAAGAGATATATTCGTGGTG
           I   G   S   F   T   A   G   R   N   P   F   L   Y   I   S   T   T
             .   E   A   S   Q   R   A   G   I   H   F   S   I   .   A   P
         H   R   K   L   H   S   G   Q   E   S   I   S   L   Y   K   H   H
         CTCCCACCCACACCACCACCACTACCACTGCTAAGGAGGATGAAGGCCTT
         GAGGGTGGGTGTGGTGGTGGTGATGGTGACGATTCCTCCTACTTCCGGAA
             S   H   P   H   H   H   H   Y   H   C   .   G   G   .   R   P
         P   P   T   H   T   T   T   T   T   T   A   K   E   D   E   G   L
           L   P   P   T   P   P   P   L   P   L   L   R   R   M   K   A   L
         GTTGTTGGTCATCTTTACCCTGGCCTCGTCGCTCGGCGCCTTCGCCGAGC
         CAACAACCAGTAGAAATGGGACCGGAGCAGCGAGCCGCGGAAGCGGCTCG
           C   C   W   S   S   L   P   W   P   R   R   S   A   P   S   P   S
             V   V   G   H   L   Y   P   G   L   V   A   R   R   L   R   R   A
                 L   L   V   I   F   T   L   A   S   S   L   G   A   F   A   E
```

FIG. 16A-1

```
AATGCGGAAGGCAAGCCGGGGGGGCTCTCTGCCCCGGCGGGCTGTGCTGT
TTACGCCTTCCGTTCGGCCCCCCCGAGAGACGGGGCCGCCCGACACGACA
  N  A  E  G  K  P  G  G  L  S  A  P  A  G  C  A  V
   M  R  K  A  S  R  G  G  S  L  P  R  R  A  V  L
  Q  C  G  R  Q  A  G  G  A  L  C  P  G  G  L  C  C

BamH I
AGCCAGTACGGCTGGTGCGGTAACACGGATCCATACTGCGGCCAAGGATG
TCGGTCATGCCGACCACGCCATTGTGCCTAGGTATGACGCCGGTTCCTAC
   A  S  T  A  G  A  V  T  R  I  H  T  A  A  K  D
  .  P  V  R  L  V  R  .  H  G  S  I  L  R  P  R  M
   S  Q  Y  G  W  C  G  N  T  D  P  Y  C  G  Q  G  C

CCAGAGCCAATGCGGCGGTAGCGGCGGTAGCGGCGGTGGCAGCGTGGCCT
GGTCTCGGTTACGCCGCCATCGCCGCCATCGCCGCCACCGTCGCACCGGA
  A  R  A  N  A  A  V  A  A  V  A  A  V  A  A  W  P
   P  E  P  M  R  R  .  R  R  .  R  R  W  Q  R  G  L
    Q  S  Q  C  G  G  S  G  G  S  G  G  G  S  V  A

CGATCATCAGCTCCTCCCTCTTCGAGCAGATGCTGAAGCATCGCAACGAC
GCTAGTAGTCGAGGAGGGAGAAGCTCGTCTACGACTTCGTAGCGTTGCTG
   R  S  S  A  P  P  S  S  S  R  C  .  S  I  A  T  T
    D  H  Q  L  L  P  L  R  A  D  A  E  A  S  Q  R
  S  I  I  S  S  S  L  F  E  Q  M  L  K  H  R  N  D

GCAGCCTGCCCCGGCAAGGGTTTCTACACGTACAACGCCTTCATCGCCGC
CGTCGGACGGGGCCGTTCCCAAAGATGTGCATGTTGCGGAAGTAGCGGCG
     Q  P  A  P  A  R  V  S  T  R  T  T  P  S  S  P
    R  S  L  P  R  Q  G  F  L  H  V  Q  R  L  H  R  R
   A  A  C  P  G  K  G  F  Y  T  Y  N  A  F  I  A  A

CGCCAACTCCTTCAGCGGGTTCGGGACGACCGGCGACGACCCAAGAAGAA
GCGGTTGAGGAAGTCGCCCAAGCCCTGCTGGCCGCTGCTGGGTTCTTCTT
   P  P  T  P  S  A  G  S  G  R  P  A  T  T  Q  E  E
    R  Q  L  L  Q  R  V  R  D  D  R  R  R  P  K  K  ?
  A  N  S  F  S  G  F  G  T  T  G  D  D  P  R  R
```

FIG. 16A-2

```
NAAGGAGATCGCGGCTTTCTTGGCGCANACGTCTCACGANACGACAGGTA
++++++++++++++++++++++++++++++++++++++++++++++++++
NTTCCTCTAGCGCCGAAAGAACCGCGTNTGCAGAGTGCTNTGCTGTCCAT
  ?  G  D  R  G  F  L  G  A  ?  V  S  R  ?  D  R  .
     K  E  I  A  A  F  L  A  ?  T  S  H  ?  T  T  G
  ?  R  R  S  R  L  S  W  R  ?  R  L  T  ?  R  Q  V
ATTCNCACATCTCCCGAAGCTCGTAAACTGTTTATGGGATANAAAACTGA
++++++++++++++++++++++++++++++++++++++++++++++++++
TAAGNGTGTAGAGGGCTTCGAGCATTTGACAAATACCCTATNTTTTGACT
     F  ?  H  L  P  K  L  V  N  C  L  W  D  ?  K  L
  N  S  H  I  S  R  S  S  .  T  V  Y  G  I  ?  N  .
  I  ?  T  S  P  E  A  R  K  L  F  M  G  ?  K  T  E
ATGTTTGGGGTTTGGCAGGTGGGTNGGCGACGCGCCCGATGGTCCGTACG
++++++++++++++++++++++++++++++++++++++++++++++++++
TACAAACCCCAAACCGTCCACCCANCCGCTGCGCGGGCTACCAGGCATGC
  N  V  W  G  L  A  G  G  ?  A  T  R  P  M  V  R  T
  M  F  G  V  W  Q  V  G  ?  R  R  A  R  W  S  V  R
     C  L  G  F  G  R  W  V  G  D  A  P  D  G  P  Y
CCTTGGGTTACTGCTTCGTCCAANAACAAAACCCTCATCGGANTACTGCG
++++++++++++++++++++++++++++++++++++++++++++++++++
GGAACCCAATGACGAAGCAGGTTNTTGTTTTGGGAGTAGCCTNATGACGC
     P  W  V  T  A  S  S  ?  N  K  T  L  I  G  ?  L  R
     L  G  L  L  L  R  P  ?  T  K  P  S  S  ?  Y  C
  A  L  G  Y  C  F  V  Q  ?  Q  N  P  H  R  ?  T  A
```

FIG. 16A-3

```
                                        ¦Pst I
TCCCANCTCCCANTGGCCGTGCGCTGCAGCAAAAAATACTACGGCCGAAG
AGGGTNGAGGGTNACCGGCACGCGACGTCGTTTTTATGATGCCGGCTTC
    P   ?   S   ?   W   P   C   A   A   A   K   N   T   T   A   E
      V   P   ?   P   ?   G   R   A   L   Q   Q   K   I   L   R   P   K
        P   ?   L   P   ?   A   V   R   C   S   K   K   Y   Y   G   R   S
CCCNTCCAAATTTCATNGTNAGCCANATTCTNACAGTTCNTCGCCGCGAT
GGGNAGGTTTAAAGTANCANTCGGTNTAAGANTGTCAAGNAGCGGCGCTA
    A   ?   P   N   F   ?   V   S   ?   I   L   T   V   ?   R   R   D
      P   ?   Q   I   S   ?   ?   A   ?   F   ?   Q   F   ?   A   A   I
        P   S   K   F   H   ?   ?   P   ?   S   ?   S   S   S   P   R
CGAGTTCACAACGATGCCNTTTCTAACGCAACAATCCGATGTGTTNTGCG
GCTCAAGTGTTGCTACGGNAAAGATTGCGTTGTTAGGCTACACAANACGC
    R   V   H   N   D   A   ?   S   N   A   T   I   R   C   V   ?   R
      E   F   T   T   M   P   F   L   T   Q   Q   S   D   V   ?   C
        S   S   S   Q   R   C   ?   F   .   R   N   N   P   M   C   ?   A
TGCAGCAANTACAANTACGGGCCGGCCGGGAGAGCCATCGGTTCNGACNT
ACGTCGTTNATGTTNATGCCCGGCCGGCCCTCTCGGTAGCCAAGNCTGNA
    A   A   ?   T   ?   T   G   R   P   G   E   P   S   V   ?   T
      V   Q   Q   ?   Q   ?   R   A   G   R   E   S   H   R   F   ?   ?
        C   S   ?   Y   ?   Y   G   P   A   G   R   A   I   G   S   D   ?
GNTCAACAACCCAGACCTGGTGGCCACNGACGCGACCATCTCNTTCAAGA
CNAGTTGTTGGGTCTGGACCACCGGTGNCTGCGCTGGTAGAGNAAGTTCT
    ?   S   T   T   Q   T   W   W   P   ?   T   R   P   S   ?   S   R
      ?   Q   Q   P   R   P   G   G   H   ?   R   D   H   L   ?   Q   D
        ?   N   N   P   D   L   V   A   T   D   A   T   I   S   F   K
CGGNTCTGTGGTTTTGGATGACTCNTCAGTCGCCCAAGCCGTNGTGCCAC
GCCNAGACACCAAAACCTACTGAGNAGTCAGCGGGTTCGGCANCACGGTG
    R   ?   C   G   F   G   .   L   ?   S   R   P   S   R   ?   A   T
      R   S   V   V   L   D   D   S   S   V   A   Q   A   V   V   P
        T   ?   L   W   F   W   M   T   ?   Q   S   P   K   P   ?   C   H
```

FIG. 16B-1

```
GACGTGATAACCGGGAGCTGGACGCCATCCAACGCCGACCAGGCGGCCGG
CTGCACTATTGGCCCTCGACCTGCGGTAGGTTGCGGCTGGTCCGCCGGCC
   T  .  P  G  A  G  R  H  P  T  P  T  R  R  P
 R  R  D  N  R  E  L  D  A  I  Q  R  R  P  G  G  R
   D  V  I  T  G  S  W  T  P  S  N  A  D  Q  A  A  G

AAGGCTTCCGGGCTACGGTGTCACCACCAACATCATCAATGGAGGGTTGG
TTCCGAAGGCCCGATGCCACAGTGGTGGTTGTAGTAGTTACCTCCCAACC
 E  G  F  R  A  T  V  S  P  P  T  S  S  M  E  G  W
   K  A  S  G  L  R  C  H  H  Q  H  H  Q  W  R  V  G
     R  L  P  G  Y  G  V  T  T  N  I  I  N  G  G  L

AGTGCGGGAAAGGGTACGATGCCAGGGTGGCGGATAGGATCGGCTTCTAC
TCACGCCCTTTCCCATGCTACGGTCCCACCGCCTATCCTAGCCGAAGATG
 S  A  G  K  G  T  M  P  G  W  R  I  G  S  A  S  T
   V  R  E  R  V  R  C  Q  G  G  G  .  D  R  L  L
 E  C  G  K  G  Y  D  A  R  V  A  D  R  I  G  F  Y

AAGAGGTACTGCGACTTGCTGGGGGTGAGCTACGGAGACAACTTGGACTG
TTCTCCATGACGCTGAACGACCCCCACTCGATGCCTCTGTTGAACCTGAC
     R  G  T  A  T  C  W  G  .  A  T  E  T  T  W  T
 Q  E  V  L  R  L  A  G  G  E  L  R  R  Q  L  G  L
   K  R  Y  C  D  L  L  G  V  S  Y  G  D  N  L  D  C

CTACAACCAGAGACCCTTTGCTTCTACAGCAGCTACAGCCACATTCTAGC
GATGTTGGTCTCTGGGAAACGAAGATGTCGTCGATGTCGGTGTAAGATCG
 A  T  T  R  D  P  L  L  L  Q  Q  L  Q  P  H  S  S
   L  Q  P  E  T  L  C  F  Y  S  S  Y  S  H  I  L  A
     Y  N  Q  R  P  F  A  S  T  A  A  T  A  T  F  .

GGTGAGCTATGGAGACAACTTGGAGTGCTACAACCAGAGACCCTTTACTT
CCACTCGATACCTCTGTTGAACCTCACGATGTTGGTCTCTGGGAAATGAA
   G  E  L  W  R  Q  L  G  V  L  Q  P  E  T  I  Y  L
     V  S  Y  G  D  N  L  E  C  Y  N  Q  R  P  F  T
 R  .  A  M  E  T  T  W  S  A  T  T  R  D  P  L  L
```

FIG. 16B-2

```
AGTCCGATACTACTGTGACGAATCCATGTAATAACGCAATAAACGCTATT
TCAGGCTATGATGACACTGCTTAGGTACATTATTGCGTTATTTGCGATAA
   V  R  Y  Y  C  D  E  S  M  .  .  R  N  K  R  Y
 .  S  D  T  T  V  T  N  P  C  N  N  A  I  N  A  I
   S  P  I  L  L  .  R  I  H  V  I  T  Q  .  T  L  L

ACTGAGATAGCGACTCCGTGAGTTGACTGTAGAAGTTGCGGAGGAAGTCT
TGACTCTATCGCTGAGGCACTCAACTGACATCTTCAACGCCTCCTTCAGA
   Y  .  D  S  D  S  V  S  .  L  .  K  L  R  R  K  S
   T  E  I  A  T  P  .  V  D  C  R  S  C  G  G  S  L
   L  R  .  R  L  R  E  L  T  V  E  V  A  E  E  V

Hind III
TCAATAAAAGCTTANCTACATACATGGCCCACAACTATCGTTGACCGTGA
AGTTATTTTCGAATNGATGTATGTACCGGGTGTTGATAGCAACTGGCACT
   S  I  K  A  ?  L  H  T  W  P  T  T  I  V  D  R  D
     Q  .  K  L  ?  Y  I  H  G  P  Q  L  S  L  T  V
   F  N  K  S  L  ?  T  Y  M  A  H  N  Y  R  .  P  .

TCATATGCATCCATCAAATGTCCTCAAATGTCTTGGAGTAAGTAAATGCG
AGTATACGTAGGTAGTTTACAGGAGTTTACAGAACCTCATTCATTTACGC
     H  M  H  P  S  N  V  L  K  C  L  G  V  S  K  C
   I  I  C  I  H  Q  M  S  S  N  V  L  E  .  V  N  A
   S  Y  A  S  I  K  C  P  Q  M  S  W  S  K  .  M  R
```

FIG. 16B-3

```
TATTCGATCGGTAAAATGAAGATGTTAGAATAAATAAAATTAATTATTTT
ATAAGCTAGCCATTTTACTTCTACAATCTTATTTATTTTAATTAATAAAA
 V  F  D  R  .  N  E  D  V  R  I  N  K  I  N  Y  F
  Y  S  I  G  K  M  K  M  L  E  .  I  K  L  I  I  F
   I  R  S  V  K  .  R  C  .  N  K  .  N  .  L  F

TTTATAATTATAAATATTTAATATATTTTTAATCTTAAAGATCCTAAA
AAATATTAATATTTATAAAATTATATAAAAATTAGAATTTCTAGGATTT
 F  I  I  N  I  L  I  Y  F  L  I  L  K  I  L  K
  L  L  .  I  F  .  Y  I  F  .  S  .  R  S  .
   F  Y  N  Y  K  Y  F  N  I  F  F  N  L  K  D  P  K

AACCCAATTATAAGGATTTTATATATGGATTGGGATACTAAGAATATTTA
TTGGGTTAATATTCCTAAAATATATACCTAACCCTATGATTCTTATAAAT
    I  .  L  .  G  F  Y  I  W  I  G  I  L  R  I  F
  K  S  N  Y  K  D  F  I  Y  G  L  G  Y  .  E  Y  L
   N  L  I  I  R  I  L  Y  M  D  W  D  T  K  N  I  .

Bgl II
ATTATAAAAATTAATATACTTTTTAATCTTAAAGATCTAATTATAAGTAT
TAATATTTTTAATTATATGAAAAATTAGAATTTCTAGATTAATATTCATA
 N  Y  K  N  .  Y  T  F  .  S  .  R  S  N  Y  K  Y
   I  I  K  I  N  I  L  F  N  L  K  D  L  I  I  S  I
    L  .  K  L  I  Y  F  L  I  L  K  I  .  L  .  V

TTTCTATATGGATTGGGATATTAACTCGATTTACTTATAAAAATTTTAAT
XXXXXTXTXXXTXXXXXTXTXXTTXXXXTXXXTXXXTXTTTTTXXXXTTX
 F  L  Y  G  L  G  Y  .  L  D  L  L  I  K  I  L  I
   F  Y  M  D  W  D  I  N  S  I  Y  L  .  K  F  .
    F  S  I  W  I  G  I  L  T  R  F  T  Y  K  N  F  N

ATAAAAATTTTAAATTTAAAAATTAAAATACTAAAAATATCTAAATATAA
TXTTTTTXXXXTTTXXXTTTTXXTTTTXTXXTTTTXTXXXTTTXTXTT
  .  K  F  .  I  .  K  L  K  Y  .  K  Y  L  N  I
   Y  K  N  F  K  F  K  N  .  N  T  K  N  I  .  I  .
     I  K  I  L  N  L  K  I  K  I  L  K  I  S  K  Y  N
```

FIG. 16C-1

```
CGGTAATCATGAGATCGAGAACGTGATGATTGAGATCATGAGATCGAGGT
GCCATTAGTACTCTAGCTCTTGCACTACTAACTCTAGTACTCTAGCTCCA
T  V  I  M  R  S  R  T  .  .  L  R  S  .  D  R  G
 R  .  S  .  D  R  E  R  D  D  .  D  H  E  I  E  V
  G  N  H  E  I  E  N  V  M  I  E  I  M  R  S  R

TGAGAGTAAAAAGGAAATTACGTTAATCATGGGAAATTTCGTTTTGTTTG
ACTCTCATTTTTCCTTTAATGCAATTAGTACCCTTTAAAGCAAAACAAAC
 .  E  .  K  G  N  Y  V  N  H  G  K  F  R  F  V  C
  E  S  K  K  E  I  T  L  I  M  G  N  F  V  L  F
L  R  V  K  R  K  L  R  .  S  W  E  I  S  F  C  L

CACGGTCGAGATGGTGACCGTGGACACCTAACATCCACAACCGGCATGCA
GTGCCAGCTCTACCACTGGCACCTGTGGATTGTAGGTGTTGGCCGTACGT
  T  V  E  M  V  T  V  D  T  .  H  P  Q  P  A  C
A  R  S  R  W  .  P  W  T  P  N  I  H  N  R  H  A
 H  G  R  D  G  D  R  G  H  L  T  S  T  T  G  M  Q

ATAACCATGTTGTCATATGTTAGCTTGTCTCATATCTTATGACCATGAAT
TATTGGTACAACAGTATACAATCGAACAGAGTATAGAATACTGGTACTTA
N  N  H  V  V  I  C  .  L  V  S  Y  L  M  T  M  N
 I  T  M  L  S  Y  V  S  L  S  H  I  L  .  P  .  I
  .  P  C  C  H  M  L  A  C  L  I  S  Y  D  H  .

CACATAGTCTTCACGAATATTAATTAAGCCAGCTTAGCATCACAGTTTTG
GTGTATCAGAAGTGCTTATAATTAATTCGGTCGAATCGTAGTGTCAAAAC
 H  I  V  F  T  N  I  N  .  A  S  L  A  S  Q  F  C
  T  .  S  S  R  I  L  I  K  P  A  .  H  H  S  F
S  H  S  L  H  E  Y  .  L  S  Q  L  S  I  T  V  L

CACCTTTGTACCATANCTGAAGTGTTCGTATGGCTTGACCCATCCCGAGT
GTGGAAACATGGTATNGACTTCACAAGCATACCGAACTGGGTAGGGCTCA
  T  F  V  P  ?  L  K  C  S  Y  G  L  T  H  P  E
A  P  L  Y  H  ?  .  S  V  R  M  A  .  P  I  P  S
 H  L  C  T  I  ?  E  V  F  V  W  L  D  P  S  R  V
```

FIG. 16C-2

```
GTATGGTCTCCCGGANCCTGGAGCGTGTTAACCCGAGGTCTAGTTGAGGG
CATACCAGAGGGCCTNGGACCTCGCACAATTGGGCTCCAGATCAACTCCC
 C  M  V  S  R  ?  L  E  R  V  N  P  R  S  S  .  G
   V  W  S  P  G  ?  W  S  V  L  T  R  G  L  V  E  G
      Y  G  L  P  ?  P  G  A  C  .  P  E  V  .  L  R

GCATAGACCTTGTTNTCTTAGGCAGAGGTTGAAGATCACTCCTTTAGCTA
CGTATCTGGAACAANAGAATCCGTCTCCAACTTCTAGTGAGGAAATCGAT
 A  .  T  L  ?  S  .  A  E  V  E  D  H  S  F  S  Y
   H  R  P  C  ?  L  R  Q  R  L  K  I  T  P  L  A
      G  I  D  L  V  ?  L  G  R  G  .  R  S  L  L  .  L

TCCGTTGGGTGCCTATATAAAGGTCGAAATCATGAGGGGGATTCNTAACT
AGGCAACCCACGGATATATTTCCAGCTTTAGTACTCCCCCTAAGNATTGA
    P  L  G  A  Y  I  K  V  E  I  M  R  G  I  ?  N
 I  R  W  V  P  I  .  R  S  K  S  .  G  G  F  ?  T
   S  V  G  C  L  Y  K  G  R  N  H  E  G  D  S  .  L

CGACCTATTCAATATTTGAGCTAGCAAGAGTTGGAGTTACGTGTATGAGG
GCTGGATAAGTTATAAACTCGATCGTTCTCAACCTCAATGCACATACTCC
    S  T  Y  S  I  F  E  L  A  R  V  G  V  T  C  M  R
      R  P  I  Q  Y  L  S  .  Q  E  L  E  L  R  V  .  G
         D  L  F  N  I  .  A  S  K  S  W  S  Y  V  Y  E

TTCGACCCCCAATGCTGTTCCTGGGGTCGTTTTATACCTATTCCTGCATC
AAGCTGGGGGTTACGACAAGGACCCCAGCAAAATATGGATAAGGACGTAG
    F  D  P  Q  C  C  S  W  G  R  F  Y  T  Y  S  C  M
      S  T  P  N  A  V  P  G  V  A  F  I  P  I  P  A
        V  R  P  P  M  L  F  L  G  S  L  L  Y  L  F  L  H

GTGATCATACATAGTAGCTTTAATCATCTTCAGTCATCATCGTACGTTGG
CACTAGTATGTATCATCGAAATTAGTAGAAGTCAGTAGTAGCATGCAACC
    .  S  Y  I  V  A  L  I  I  F  S  H  H  R  T  L
 C  D  H  T  .  .  L  .  S  S  S  V  I  I  V  R  W
    V  I  I  H  S  S  F  N  H  L  Q  S  S  S  Y  V  G
```

FIG. 16C-3

```
GTGCATGCATTGTCTAATTTACTCGATTCAATNTCGTTCGACACTGCTTC
CACGTACGTAACAGATTAAATGAGCTAAGTTANAGCAAGCTGTGACGAAG
 G  A  C  I  V  .  F  T  R  F  N  ?  V  R  H  C  F
  V  H  A  L  S  N  L  L  D  S  ?  S  F  D  T  A  S
   C  M  H  C  L  I  Y  S  I  Q  ?  R  S  T  L  L
                                               Xho I
CTACCTACTATGTGGCCCAATACATAGTTGTATTGTCTCATACGGCCTCG
GATGGATGATACACCGGGTTATGTATCAACATAACAGAGTATGCCGGAGC
 L  P  T  M  W  P  N  T  .  L  Y  C  L  I  R  P  R
  Y  L  L  C  G  P  I  H  S  C  I  V  S  Y  G  L
   P  T  Y  Y  V  A  Q  Y  I  V  V  L  S  H  T  A  S

AGCAAAGCGTGTGCAGAGGAACTGTGTCAAGTGGTTGGCTGGCCTCGGGC
TCGTTTCGCACACGTCTCCTTGACACAGTTCACCAACCGACCGGAGCCCG
  A  K  R  V  Q  R  N  C  V  K  W  L  A  G  L  G
 E  Q  S  V  C  R  G  T  V  S  S  G  W  L  A  S  G
   S  K  A  C  A  E  E  L  C  Q  V  V  G  W  P  R  A

TCATGGCATTGAGTTGGCTCGATACAACACATCGGCTTAGGGATACCATG
AGTACCGTAACTCAACCGAGCTATGTTGTGTAGCCGAATCCCTATGGTAC
 L  M  A  L  S  W  L  D  T  T  H  R  L  R  D  T  M
  S  W  H  .  V  G  S  I  Q  H  I  G  L  G  I  P  C
   H  G  I  E  L  A  R  Y  N  T  S  A  .  G  Y  H

CCGAGTCTATTGTGGTAGTTGACATGTCATGTGGGGTGGATGCCAAAATA
GGCTCAGATAACACCATCAACTGTACAGTACACCCCACCTACGGTTTTAT
 P  S  L  L  W  .  L  T  C  H  V  G  W  M  P  K  Y
  R  V  Y  C  G  S  .  H  V  M  W  G  G  C  Q  N
 A  E  S  I  V  V  V  D  M  S  C  G  V  D  A  K  I

TGCTATATCATTCTCTCCCTACAAAGGAGTTGTGCCATAGGAGAATCGTG
ACGATATAGTAAGAGAGGGATGTTTCCTCAACACGGTATCCTCTTAGCAC
  A  I  S  F  S  P  Y  K  G  V  V  P  .  E  N  R
 M  L  Y  H  S  L  P  T  K  E  L  C  H  R  R  I  V
   C  Y  I  I  L  S  L  Q  R  S  C  A  I  G  E  S  W
```

FIG. 16D-1

```
GACACGGCTTGGGTTCTGTGGTCGGTCCTTGTTCGCCTCAGTTGGGTGGA
CTGTGCCGAACCCAAGACACCAGCCAGGAACAAGCGGAGTCAACCCACCT
 G  H  G  L  G  S  V  V  G  P  C  S  P  Q  L  G  G
  D  T  A  W  V  L  W  S  V  L  V  R  L  S  W  V  D
   T  R  L  G  F  C  G  R  S  L  F  A  S  V  G  W

TTACTTCATCAAGTTGGCCNTCTGTTGGCTGGGCAAAGTACACTTGGTAG
AATGAAGTAGTTCAACCGGNAGACAACCGACCCGTTTCATGTGAACCATC
 L  L  H  Q  V  G  ?  L  L  A  G  Q  S  T  L  G  R
  Y  F  I  K  L  A  ?  C  W  L  G  K  V  H  L  V
   I  T  S  S  S  W  P  S  V  G  W  A  K  Y  T  W  .

GGATGGTCGAGACAAGNCCAAGGAAGGTTGGCTAAGACTTGGTTTTCGAC
CCTACCAGCTCTGTTCNGGTTCCTTCCAACCGATTCTGAACCAAAAGCTG
  D  G  R  D  K  ?  K  E  G  W  L  R  L  G  F  R
 G  M  V  E  T  ?  P  R  K  V  G  .  D  L  V  F  D
   G  W  S  R  Q  ?  Q  G  R  L  A  K  T  W  F  S  T

AATCAATTGTTTATGAGGCGAATGGTATCCCTCCGTTGGGGTGTCTGCTC
TTAGTTAACAAATACTCCGCTTACCATAGGGAGGCAACCCCACAGACGAG
 Q  S  I  V  Y  E  A  N  G  I  P  P  L  G  C  L  L
  N  Q  L  F  M  R  R  M  V  S  L  R  W  G  V  C  S
   I  N  C  L  .  G  E  W  Y  P  S  V  G  V  S  A

GTTTCGATTTGTTGCGATGGATTGTTTGTTGTAGGAGGCTTGGTTCGATT
CAAAGCTAAACAACGCTACCTAACAAACAACATCCTCCGAACCAAGCTAA
 V  S  I  C  C  D  G  L  F  V  V  G  G  L  V  R  L
  F  R  F  V  A  M  D  C  L  L  .  E  A  W  F  D
   R  F  D  L  L  R  W  I  V  C  C  R  R  L  G  S  I

GCTCTTAAGTCGGGAGAAGGTATTTGNTAAGGAGTTCAATTTGACCATGT
CGAGAATTCAXCCCTCTTCCATAAACNATTCCTCAAGTTAAACTGGTACA
  L  L  S  R  E  K  V  F  ?  K  E  F  N  L  T  M
 C  S  .  V  G  R  R  Y  L  ?  R  S  S  I  .  P  C
   A  L  K  S  G  E  G  I  ?  .  G  V  Q  F  D  H  V
```

FIG. 16D-2

```
TGAAGTGAATAAAAGGACTTGCCAAGAAGTTTGGCTCGACCGTGTTAAAG
ACTTCACTTATTTTCCTGAACGGTTCTTCAAACCGAGCTGGCACAATTTC
 L  K  .  I  K  G  L  A  K  K  F  G  S  T  V  L  K
    .  S  E  .  K  D  L  P  R  S  L  A  R  P  C  .  S
    E  V  N  K  R  T  C  Q  E  V  W  L  D  R  V  K

CCAGAGAATGTGTATGTCGAGGTCTATTCAACCATGTGGAAGCTAGAGAA
GGTCTCTTACACATACAGCTCCAGATAAGTTGGTACACCTTCGATCTCTT
 P  E  N  V  Y  V  E  V  Y  S  T  M  W  K  L  E  N
    Q  R  M  C  M  S  R  S  I  Q  P  C  G  S  .  R
    A  R  E  C  V  C  R  G  L  F  N  H  V  E  A  R  E

TGCACCAATTGTGAGGTTTGGCTTGCTCACGTTTAAAGCAGAAGGATATA
ACGTGGTTAACACTCCAAACCGAACGAGTGCAAATTTCGTCTTCCTATAT
 A  P  I  V  R  F  G  L  L  T  F  K  A  E  G  Y
 M  H  Q  L  .  G  L  A  C  S  R  L  K  Q  K  D  I
    C  T  N  C  E  V  W  L  A  H  V  .  S  R  R  I  Y

CTTGCTACGAGGTTTGCTCAACCATGTGGAAGCAATCAAATGCACTTGCT
GAACGATGCTCCAAACGAGTTGGTACACCTTCGTTAGTTTACGTGAACGA
 T  C  Y  E  V  C  S  T  M  W  K  Q  S  N  A  L  A
 L  A  T  R  F  A  Q  P  C  G  S  N  Q  M  H  L  L
    L  L  R  G  L  L  N  H  V  E  A  I  K  C  T  C
```

FIG. 16D-3

```
ATGAGGTTTGGCTTGACTTACTCGACAATGGACGCTNGTAAGTGAGAAGG
TACTCCAAACCGAACTGAATGAGCTGTTACCTGCGANCATTCACTCTTCC
 M  R  F  G  L  T  Y  S  T  M  D  A  ?  K  .  E  G
    .  G  L  A  .  L  T  R  Q  W  T  L  V  S  E  K
 Y  E  V  W  L  D  L  L  D  N  G  R  ?  .  V  R  R
                                   Spe I
GACTANCCAAGACTTAGTTGGCAAGGACTAGTCGATACTTGCTCGACAAT
CTGATNGGTTCTGAATCAACCGTTCCTGATCAGCTATGAACGAGCTGTTA
    T  ?  Q  D  L  V  G  K  D  .  S  I  L  A  R  Q
 G  L  ?  K  T  .  L  A  R  T  S  R  Y  L  L  D  N
    D  ?  P  R  L  S  W  Q  G  L  V  D  T  C  S  T  I
                                      Sal I
AGATGCCTATAGGTAATGGATTGACTGAGACTTAGTCGACAAAGACTAGC
TCTACGGATATCCATTACCTAACTGACTCTGAATCAGCTGTTTCTGATCG
    .  M  P  I  G  N  G  L  T  E  T  .  S  T  K  T  S
       R  C  L  .  V  M  D  .  L  R  L  S  R  Q  R  L  A
    D  A  Y  R  .  W  I  D  .  D  L  V  D  K  D  .
                                          Xho I
TGAGACTTAGTGGGCAATGGATGCCTATAAGTAAGAAAGGATGGCTCGAG
ACTCTGAATCACCCGTTACCTACGGATGTTCATTCTTTCCTACCGAGCTC
    .  D  L  V  G  N  G  C  L  .  V  R  K  D  G  S  R
       E  T  .  W  A  M  D  A  Y  K  .  E  R  M  A  R
 L  R  L  S  G  Q  W  M  P  I  S  K  K  G  W  L  E
ATTAATAAAGATCAAATAATTAATATAAATTTATCAAACACTTAATGGAC
TAATTATTTCTAGTTTATTAATTATATTTAAATAGTTTGTGAATTACCTG
    L  I  K  I  K  .  L  .  I  Y  Q  T  L  N  G
 D  .  .  R  S  N  N  .  Y  K  F  I  K  H  L  M  D
    I  N  K  D  Q  I  I  N  I  N  L  S  N  T  .  W  T
GCATATAAGTGAGAAAGGACGGATCGAGATTAATAAAGATCAAATAATTA
CGTATATTCACTCTTTCCTGCCTAGCTCTAATTATTTCTAGTTTATTAAT
 R  I  .  V  R  K  D  G  S  R  L  I  K  I  K  .  L
    A  Y  K  .  E  R  T  D  R  D  .  .  R  S  N  N  .
       H  I  S  E  K  G  R  I  E  I  N  K  D  Q  I  I
```

FIG. 16E-1

```
ATATAAGTTTATCAAACNCTTATTAANACATTGGACAAAAGAGGTACTAT
TATATTCAAATAGTTTGNGAATAATTNTGTAACCTGTTTTCTCCATGATA
  I . V Y Q T L I ? T L D K R G T M
   Y K F I K ? L L ? H W T K E V L
  N I S L S N ? Y . ? I G Q K R Y Y

GTAATATTAAAATTGGGAGGCACAAATATTATTTCCAAATACTTTTCTCC
CATTATAATTTTAACCCTCCGTGTTTATAATAAAGGTTTATGAAAAGAGG
  . Y . N W E A Q I L F P N T F L
  C N I K I G R H K Y Y F Q I L F S
   V I L K L G G T N I I S K Y F S P

TTAAGCCCTTCGCCACCATTGCCATTTTAATCTATTTTTCTATATAATT
AATTCGGGAAGCGGTGGTAACGGTAAAATTAGATAAAAAGATATATTAA
  L K P F A T I A I L I Y F F Y I I
   L S P S P P L P F . S I F S I . L
    . A L R H H C H F N L F F L Y N

ATCNCATAACATTCGTACATGAGATATGACATAAACCTTCGACCTGCTTT
TAGNGTATTGTAAGCATGTACTCTATACTGTATTTGGAAGCTGGACGAAA
  I ? . H S Y M R Y D I N L R P A L
   S H N I R T . D M T . T F D L L
   Y ? I T F V H E I . H K P S T C F

AGTAAACATNTTGATTATNGTGACACCAGAAGCCATAATATTGCTTACCT
TCATTTGTANAACTAATANCACTGTGGTCTTCGGTATTATAACGAATGGA
   V N ? L I ? V T P E A I I L L T
   . . T ? . L ? . H Q K P . Y C L P
    S K H ? D Y ? D T R S H N I A Y L

TAACATGATGGAGATGAACTTTAGTTGGTCCAANTATCTAATNAATGGAA
ATTGTACTACCTCTACTTGAAATCAACCAGGTTNATAGATTANTTACCTT
  L T . W R . T L V G P ? I . ? M E
   . H D G D E L . L V Q ? S N ? W K
   N M M E M N F S W S ? Y L ? N G
```

FIG. 16E-2

```
GTGGACAAGCACGATGACTAGGATGGCTACATGTTCATGTGTTGACTTTC
CACCTGTTCGTGCTACTGATCCTACCGATGTACAAGTACACAACTGAAAG
  V  D  K  H  D  D  .  D  G  Y  M  F  M  C  .  L  S
   W  T  S  T  M  T  R  M  A  T  C  S  C  V  D  F
 S  G  Q  A  R  .  L  G  W  L  H  V  H  V  L  T  F

CAAGTAATCAATCAAGCTGGAATCGAATAAGACGATTAAAGTAGGGCGAT
GTTCATTAGTTAGTTCGACCTTAGCTTATTCTGCTAATTTCATCCCGCTA
    K  .  S  I  K  L  E  S  N  K  T  I  K  V  G  R
  P  S  N  Q  S  S  W  N  R  I  R  R  L  K  .  G  D
 Q  V  I  N  Q  A  G  I  E  .  D  D  .  S  R  A  M

GACCATTAAGTTCAATGTCACGCTCATCAACATAATTCCAACACCGTGCA
CTGGTAATTCAAGTTACAGTGCGAGTAGTTGTATTAAGGTTGTGGCACGT
 .  P  L  S  S  M  S  R  S  S  T  .  F  Q  H  R  A
  D  H  .  V  Q  C  H  A  H  Q  H  N  S  N  T  V  Q
    T  I  K  F  N  V  T  L  I  N  I  I  P  T  P  C

Bgl II
GAAAGATCTTATCTTACATTGACTTGCCCATCCGGCCGCCGGCATCGATT
CTTTCTAGAATAGAATGTAACTGAACGGGTAGGCCGGCGGCCGTAGCTAA
  E  R  S  Y  L  T  L  T  C  P  S  G  R  R  H  R  L
   K  D  L  I  L  H  .  L  A  H  P  A  A  G  I  D
 R  K  I  L  S  Y  I  D  L  P  I  R  P  P  A  S  I
```

FIG. 16E-3

```
                                                            |EcoR I
GGCGGAAACGAAGGGTCAGTCTCCCAATTCACATTCAAAGGACGAATTCA
CCGCCTTTGCTTCCCAGTCAGAGGGTTAAGTGTAAGTTTCCTGCTTAAGT
   A  E  T  K  G  Q  S  P  N  S  H  S  K  D  E  F
 W  R  K  R  R  V  S  L  P  I  H  I  Q  R  T  N  S
   G  G  N  E  G  S  V  S  Q  F  T  F  K  G  R  I  H

TTTTCATCAGATGAGCACTTCAGTCCTGCTTGATTATATTTTATTATTAT
AAAAGTAGTCTACTCGTGAAGTCAGGACGAACTAATATAAAATAATAATA
  I  F  I  R  .  A  L  Q  S  C  L  I  I  F  Y  Y  Y
   F  S  S  D  E  H  F  S  P  A  .  L  Y  F  I  I  I
    F  H  Q  M  S  T  S  V  L  L  D  Y  I  L  L  L

TATTATTATTAATTGAATGGTAAGTTTACAGAATATATAGATATTTTAGT
ATAATAATAATTAACTTACCATTCAAATGTCTTATATATCTATAAAATCA
  Y  Y  Y  .  L  N  G  K  F  T  E  Y  I  D  I  L  V
   I  I  I  N  .  M  V  S  L  Q  N  I  .  I  F  .
  L  L  L  L  I  E  W  .  V  Y  R  I  Y  R  Y  F  S

TTCAATAAAATATTTTAAAAAATGATAAAGGGAGAAGGTGGATTTGATCT
AAGTTATTTTATAAAATTTTTTACTATTTCCCTCTTCCACCTAAACTAGA
   S  I  K  Y  F  K  K  .  .  R  E  K  V  D  L  I
  F  Q  .  N  I  L  K  N  D  K  G  R  R  W  I  .  S
   F  N  K  I  F  .  K  M  I  K  G  E  G  G  F  D  L

TAGGATTTTTATTGTGAGCAATAAAAGTCTTTAGTTAGAACTTCCAAAAT
ATCCTAAAAATAACACTCGTTATTTTCAGAAATCAATCTTGAAGGTTTTA
  L  G  F  L  L  .  A  I  K  V  F  S  .  N  F  Q  N
   .  D  F  Y  C  E  Q  .  K  S  L  V  R  T  S  K  M
    R  I  F  I  V  S  N  K  S  L  .  L  E  L  P  K

GTGTCAAATGAACCCTAATAAGTGGGTTTGGTCTATGGTTACGATGAGAT
CACAGTTTACTTGGGATTATTCACCCAAACCAGATACCAATGCTACTCTA
   V  S  N  E  P  .  .  V  G  L  V  Y  G  Y  D  E  I
    C  Q  M  N  P  N  K  W  V  W  S  M  V  T  M  R
  C  V  K  .  T  L  I  S  G  F  G  L  W  L  R  .  D
```

FIG. 16F-1

```
CAGTATTTGTATATAAAAAAATTATCAACTTGATTTTTATTTTTTAACCC
GTCATAAACATATATTTTTTAATAGTTGAACTAAAAATAAAAATTGGG
   S  I  C  I  .  K  N  Y  Q  L  D  F  Y  F  L  T
   S  V  F  V  Y  K  K  I  I  N  L  I  F  I  F  .  P
   Q  Y  L  Y  I  K  K  L  S  T  .  F  L  F  F  N  P

TTAATAAGTGGACATGATATATCATAATCAAATCATGTGATGTNTGATGA
AATTATTCACCTGTACTATATAGTATTAGTTTAGTACACTACANACTACT
   L  N  K  W  T  .  Y  I  I  I  K  S  C  D  V  .  .
      L  I  S  G  H  D  I  S  .  S  N  H  V  M  ?  D  E
         .  .  V  D  M  I  Y  H  N  Q  I  M  .  C  ?  M

GTNATAACATATTTTTAATAATNAAAATTATNAATAGAGAAAAAATAAG
CANTATTGTATAAAAAATTATTANTTTTAATANTTATCTCTTTTTTATTC
   V  I  T  Y  F  L  I  ?  K  I  ?  N  R  E  K  I  R
      ?  .  H  I  F  .  .  ?  K  L  ?  I  E  K  K  .
         S  ?  N  I  F  F  N  N  ?  K  Y  ?  .  R  K  N  K

ATTACTATCCCTTCTATNGATGTNTTATAATATTTTAATCCCTTTCNATA
TAATGATAGGGAAGATANCTACANAATATTATAAAATTAGGGAAAGNTAT
   L  L  S  L  L  ?  M  ?  Y  N  I  L  I  P  F  ?
   D  Y  Y  P  F  Y  ?  C  ?  I  I  F  .  S  L  S  I
      I  T  I  P  S  ?  D  V  L  .  Y  F  N  P  F  ?  Y

TAGATTCACGTAGAATAAGAAAGATTATAATCGCATCAAATCAAATACAG
ATCTAAGTGCATCTTATTCTTTCTAATATTAGCGTAGTTTAGTTTATGTC
   I  D  S  R  R  I  R  K  I  I  I  A  S  N  Q  I  Q
      .  I  H  V  E  .  E  R  L  .  S  H  Q  I  K  Y  R
         R  F  T  .  N  K  K  D  Y  N  R  I  K  S  N  T

AATNAAATCATGCTTTTGACTTAATTCGAAAAATAATCTTCCTCTCTTGA
TTANTTTAGTACGAAAACTGAATTAAGCTTTTTATTAGAAGGAGAGAACT
   N  ?  I  M  L  L  T  .  F  E  K  .  S  S  S  L  D
      ?  K  S  C  F  .  L  N  S  K  N  N  L  P  L  L
         E  ?  N  H  A  F  D  L  I  R  K  I  I  F  L  S  .
```

FIG. 16F-2

```
TAATATCCTTATTGATAAGCATTNTTATATATATATATATNTATATCAAC
++++++++++++++++++++++++++++++++++++++++++++++++++
ATTATAGGAATAACTATTCGTAANAATATATATATATATANATATAGTTG
   N  I  L  I  D  K  H  ?  Y  I  Y  I  Y  ?  Y  Q
 I  I  S  L  L  I  S  I  ?  I  Y  I  Y  ?  Y  I  N
  .  Y  P  Y  .  .  A  ?  L  Y  I  Y  I  ?  I  S  T

TTCTAAAANATATTTTTAAATTAATTAAATTTATCAAAATAAAAAGATAA
++++++++++++++++++++++++++++++++++++++++++++++++++
AAGATTTTNTATAAAAATTTAATTAATTTAAATAGTTTTATTTTTCTATT
  L  L  K  ?  I  F  K  L  I  K  F  I  K  I  K  R  .
   F  .  ?  I  F  L  N  .  L  N  L  S  K  .  K  D  K
    S  K  ?  Y  F  .  I  N  .  I  Y  Q  N  K  K  I

ACTAAATTAGTTCTGCATCATAATGTAGTAAGTGTAAGAACTTGTGAAAT
++++++++++++++++++++++++++++++++++++++++++++++++++
TGATTTAATCAAGACGTAGTATTACATCATTCACATTCTTGAACACTTTA
  T  K  L  V  L  H  H  N  V  V  S  V  R  T  C  E  I
   L  N  .  F  C  I  I  M  .  .  V  .  E  L  V  K
    N  .  I  S  S  A  S  .  C  S  K  C  K  N  L  .  N
                ¦ Xba I                      ¦ Spe I
ANGGATCTAGAACACTGATAGAAAATTCCAAACCATTACTAGTTCTACTT
++++++++++++++++++++++++++++++++++++++++++++++++++
TNCCTAGATCTTGTGACTATCTTTTAAGGTTTGGTAATGATCAAGATGAA
   ?  I  .  N  T  D  R  K  F  Q  T  I  T  S  S  T
    ?  G  S  R  T  L  I  E  N  S  K  P  L  L  V  L  L
     ?  D  L  E  H  .  .  K  I  P  N  H  Y  .  F  Y  L
```

FIG. 16F-3

```
GATGAAAACAAAACCATATAAAAGAATCCTCTTATATATATATATATA
CTACTTTTGTTTTGGTATATTTTCTTAGGAGAATATATATATATATAT
 . . K  Q  N  H  I  K  E  S  S  Y  I  Y  I  Y  I
   D  E  N  K  T  I  .  K  N  P  L  I  Y  I  Y  I  Y
     M  K  T  K  P  Y  K  R  I  L  L  Y  I  Y  I  Y

TATACTACTTTACTTATTCTTTGGACGTACAACACAAGTCAGGAAACCGA
ATATGATGAAATGAATAAGAAACCTGCATGTTGTGTTCAGTCCTTTGGCT
   Y  T  T  L  L  I  L  W  T  Y  N  T  S  Q  E  T  E
     I  L  L  Y  L  F  F  G  R  T  T  Q  V  R  K  P
   I  Y  Y  F  T  Y  S  L  D  V  Q  H  K  S  G  N  R

AACAAAGGTGGCGGAAAGTTGGCAGANGCTGAAGAGACTTTTCGTAGAAG
TTGTTTCCACCGCCTTTCAACCGTCTNCGACTTCTCTGAAAAGCATCTTC
     T  K  V  A  E  S  W  Q  ?  L  K  R  L  F  V  E
   K  Q  R  W  R  K  V  G  R  ?  .  R  D  F  S  .  K
     N  K  G  G  G  K  L  A  ?  A  E  E  T  F  R  R  S

TGAAGGAGACACACGTCTATAAGAATTGTCATGACTATACGCTGAAGAAA
ACTTCCTCTGTGTGCAGATATTCTTAACAGTACTGATATGCGACTTCTTT
   V  K  E  T  H  V  Y  K  N  C  H  D  Y  T  L  K  K
   .  R  R  H  T  S  I  R  I  V  M  T  I  R  .  R  K
     E  G  D  T  R  L  .  E  L  S  .  L  Y  A  E  E

AAGAGGGGAGAGAGAGAGAAGGAAGCGCCACTGTTGACCGGTCTTGTCCA
TTCTCCCCTCTCTCTCTCTTCCTTCGCGGTGACAACTGGCCAGAACAGGT
     K  R  G  E  R  E  K  E  A  P  L  L  T  G  L  V  H
     R  G  E  R  E  R  R  K  R  H  C  .  P  V  L  S
   K  E  G  R  E  R  E  G  S  A  T  V  D  R  S  C  P
                ¦Sal I                              ¦Sal I
TGAGGAATTGTTTGTCGACTAATGAGCAGTACAAACATTTGTGTCGACAG
ACTCCTTAACAAACAGCTXATTACTCGTCATGTTTGTAAACACAGCTGTC
     E  E  L  F  V  D  .  .  A  V  Q  T  F  V  S  T
   M  R  N  C  L  S  T  N  E  Q  Y  K  H  L  C  R  Q
     .  G  I  V  C  R  L  M  S  S  T  N  I  C  V  D  R
```

FIG. 16G-1

```
ATGGCAACAAATGAGAAGCGGTATCCCAACACGCAATCTGTAGCCTTTGG
TACCGTTGTTTACTCTTCGCCATAGGGTTGTGCGTTAGACATCGGAAACC
 D  G  N  K  .  E  A  V  S  Q  H  A  I  C  S  L  W
  M  A  T  N  E  K  R  Y  P  N  T  Q  S  V  A  F  G
   W  Q  Q  M  R  S  G  I  P  T  R  N  L  .  P  L

TCNCCAGACTTATCCAAAGACTTGCCTCTGCGATTTCCTCATGCGCCTCA
AGNGGTCTGAATAGGTTTCTGAACGGAGACGCTAAAGGAGTACGCGGAGT
 S  P  D  L  S  K  D  L  P  L  R  F  P  H  A  P  H
  ?  Q  T  Y  P  K  T  C  L  C  D  F  L  M  R  L
   V  ?  R  L  I  Q  R  L  A  S  A  I  S  S  C  A  S
```

Hind III

```
TCTGTTCCAAAGGAAGCTTCACAGCGGGCAGGAATCCATTTCTCTATATA
AGACAAGGTTTCCTTCGAAGTGTCGCCCGTCCTTAGGTAAAGAGATATAT
  L  F  Q  R  K  L  H  S  G  Q  E  S  I  S  L  Y
   I  C  S  K  G  S  F  T  A  G  R  N  P  F  L  Y  I
 S  V  P  K  E  A  S  Q  R  A  G  I  H  F  S  I  .

AGCACCACCTCCCACCCACACCACCACCACCACCACCACTGCTAAGGAGG
TCGTGGTGGAGGGTGGGTGTGGTGGTGGTGGTGGTGGTGACGATTCCTCC
 K  H  H  L  P  P  T  P  P  P  P  P  P  L  L  R  R
  S  T  T  S  H  P  H  H  H  H  H  H  H  C  .  G  G
   A  P  P  P  T  H  T  T  T  T  T  T  T  A  K  E

ATGAAGGCCTTGTTGCTGGTCATTTTTACCCTGGCCTCGTCGCTCGGCGC
TACTTCCGGAACAACGACCAGTAAAAATGGGACCGGAGCAGCGAGCCGCG
 M  K  A  L  L  L  V  I  F  T  L  A  S  S  L  G  A
  .  R  P  C  C  W  S  F  L  P  W  P  R  R  S  A
   D  E  G  L  V  A  G  H  F  Y  P  G  L  V  A  R  R

CTTCGCCGAGCAATGCGGAAGGCAAGCCGGGGGGGCTCTCTGCCCCGGCG
GAAGCGGCTCGTTACGCCTTCCGTTCGGCCCCCCCGAGAGACGGGGCCGC
   F  A  E  Q  C  G  R  Q  A  G  G  A  L  C  P  G
  P  S  P  S  N  A  E  G  K  P  G  G  L  S  A  P  A
 L  R  R  A  M  R  K  A  S  R  G  G  S  L  P  R  R
```

FIG. 16G-2

```
GGCTGTGCTGTAGCCAGTACGGCTGGTGCGGTAACACGGATCCATNCTGC
CCGACACGACATCGGTCATGCCGACCACGCCATTGTGCCTAGGTANGACG
 G  L  C  C  S  Q  Y  G  W  C  G  N  T  D  P  ?  C
  G  C  A  V  A  S  T  A  G  A  V  T  R  I  H  ?  A
   A  V  L  .  P  V  R  L  V  R  .  H  G  S  ?  L

GGTCAAGGATGCCANANCCAATGCNCANGCTCCACGCCCTCCCCTTCCAC
CCAGTTCCTACGGTNTNGGTTACGNGTNCGAGGTGCGGGAGGGGAAGGTG
 G  Q  G  C  ?  ?  Q  C  ?  ?  S  T  P  S  P  S  T
  V  K  D  A  ?  ?  N  A  ?  A  P  R  P  P  L  P
   R  S  R  M  P  ?  P  M  ?  ?  L  H  A  L  P  F  H

TCCGAGCGGCGGTGGCANNGTTGGCTCGATCATCATCTCCTCCCTCTTCN
AGGCTCGCCGCCACCGTNNCAACCGAGCTAGTAGTAGAGGAGGGAGAAGN
   P  S  G  G  G  ?  V  G  S  I  I  S  S  L  F
 L  R  A  A  V  A  ?  L  A  R  S  S  S  P  P  S  S
  S  E  R  R  W  ?  ?  W  L  D  H  H  L  L  P  L  ?

AGCAGATGCTGAAGCATCNCANCGACNCAGCCNGCCCCGGCAANGGCTTC
TCGTCTACGACTTCGTAGNTTGCTGNGTCGGNCGGGGCCGTTNCCGAAG
 ?  Q  M  L  K  H  ?  ?  D  ?  A  ?  P  G  ?  G  F
  S  R  C  .  S  I  ?  ?  T  Q  P  A  P  A  ?  A  S
   A  D  A  E  A  S  ?  R  ?  S  ?  P  R  Q  ?  L
```

FIG. 16G-3

```
TACNCGTNCACCGCCTTCATCTCCGCCGCCANCTCCTTCANCGGGTTCGG
ATGNGCANGTGGCGGAAGTAGAGGCGGCGGTNGAGGAAGTNGCCCAAGCC
  Y  ?  ?  T  A  F  I  S  A  A  ?  S  F  ?  G  F  G
    T  R  ?  P  P  S  S  P  P  P  ?  P  S  ?  G  S
  L  ?  V  H  R  L  H  L  R  R  ?  L  L  ?  R  V  R

GACNACCNGCGACCACTCCACNAATAANANGGANATCNCGGCTTTCTTGG
CTGNTGGNCGCTGGTGAGGTGNTTATTNTNCCTNTAGNGCCGAAAGAACC
  T  T  ?  D  H  S  T  N  ?  ?  ?  I  ?  A  F  L
  G  ?  P  A  T  T  P  ?  I  ?  ?  ?  S  R  L  S  W
    D  ?  ?  R  P  L  H  ?  .  ?  G  ?  ?  G  F  L  G

TNCNGACNTCTCNCGAGACNACANGTAATCCNTNCNTCTCCCGAGGCTCG
ANGNCTGNAGAGNGCTCTGNTGTNCATTAGGNANGNAGAGGGCTCCGAGC
  V  ?  T  S  ?  E  T  T  ?  N  P  ?  ?  S  R  G  S
    ?  ?  ?  L  ?  R  ?  ?  V  I  ?  ?  S  P  E  A  R
  ?  D  ?  S  R  D  ?  ?  .  S  ?  ?  L  P  R  L

TCTNCAGNTTATNGATAGACANCTNAATGCATTGGGTTNGGCACGTGGGT
AGANGTCNAATANCTATCTGTNGANTTACGTAACCCAANCCGTGCACCCA
  S  ?  ?  Y  ?  .  T  ?  ?  C  I  G  ?  G  T  W  V
    L  Q  ?  ?  D  R  ?  L  N  A  L  G  ?  A  R  G
  V  ?  ?  L  ?  I  D  ?  ?  M  H  W  V  ?  H  V  G

GGTCCACCGTGCCCNATGGCCNTTCGCGTGGGGTTACTGCTTCGTCCAGN
CCAGGTGGCACGGGNTACCGGNAAGCGCACCCCAATGACGAAGCAGGTCN
    V  H  R  A  ?  W  P  F  A  W  G  Y  C  F  V  Q
  W  S  T  V  P  ?  G  ?  S  R  G  V  T  A  S  S  ?
  G  P  P  C  P  M  A  ?  R  V  G  L  L  L  R  P  ?

AACAGAACCCTCATCGGACTACTGCGTCGCCAGCTCGCANTGGCCGTGCG
TTGTCTTGGGAGTAGCCTGATGACGCAGCGGTCGAGCGTNACCGGCACGC
  ?  Q  N  P  H  R  T  T  A  S  P  A  R  ?  G  R  A
    N  R  T  L  I  G  L  L  R  R  Q  L  A  ?  A  V  R
    T  E  P  S  S  D  Y  C  V  A  S  S  ?  W  P  C
```

FIG. 16H-1

```
CTGCANGCAANAAATACTACGGCCGAAGCCCCATCCAAATCTCATTCAAC
GACGTNCGTTNTTTATGATGCCGGCTTCGGGGTAGGTTTAGAGTAAGTTG
  L  ?  A  ?  N  T  T  A  E  A  P  S  K  S  H  S  T
   C  ?  Q  ?  I  L  R  P  K  P  H  P  N  L  I  Q
  A  A  ?  ?  K  Y  Y  G  R  S  P  I  Q  I  S  F  N

TACAACTACGGGCCGGCCGGGAAAACCATCGGCTCCGACCTGCTCAACAA
ATGTTGATGCCCGGCCGGCCCTTTTGGTAGCCGAGGCTGGACGAGTTGTT
   T  T  T  G  R  P  G  K  P  S  A  P  T  C  S  T
  L  Q  L  R  A  G  R  E  N  H  R  L  R  P  A  Q  Q
   Y  N  Y  G  P  A  G  K  T  I  G  S  D  L  L  N  N

CCCAGACCTGGTGGCCACCGACCCGACCATCTCCTTCAAGACGGCTCTGT
GGGTCTGGACCACCGGTGGCTGGGCTGGTAGAGGAAGTTCTGCCGAGACA
   T  Q  T  W  W  P  P  T  R  P  S  P  S  R  R  L  C
  P  R  P  G  G  H  R  P  D  H  L  L  Q  D  G  S  V
   P  D  L  V  A  T  D  P  T  I  S  F  K  T  A  L

GGTTCTGGATGACTCCTCAGTCGCCCAAGCCGTCGTGCCACGACGTGATA
CCAAGACCTACTGAGGAGTCAGCGGGTTCGGCAGCACGGTGCTGCACTAT
   G  S  G  .  L  L  S  R  P  S  R  R  A  T  T  .  .
  V  L  D  D  S  S  V  A  Q  A  V  V  P  R  R  D
   W  F  W  M  T  P  Q  S  P  K  P  S  C  H  D  V  I

ACCGGGAGCTGGACGCCATCCAACGCCGACCGGGCGGCCGGAAGGCTTCC
TGGCCCTCGACCTGCGGTAGGTTGCGGCTGGCCCGCCGGCCTTCCGAAGG
     P  G  A  G  R  H  P  T  P  T  G  R  P  E  G  F
  N  R  E  L  D  A  I  Q  R  R  P  G  G  R  K  A  S
   T  G  S  W  T  P  S  N  A  D  R  A  A  G  R  L  P

GGGCTACGGTGTCACCACCAACATCATCAATGGAGGGTTGGAGTGCGGGA
CCCGATGCCACAGTGGTGGTTGTAGTAGTTACCTCCCAACCTCACGCCCT
  R  A  T  V  S  P  P  T  S  S  M  E  G  W  S  A  G
   G  L  R  C  H  H  Q  H  H  Q  W  R  V  G  V  R  E
    G  Y  G  V  T  T  N  I  I  N  G  G  L  E  C  G
```

FIG. 16H-2

```
AAGGGTCCGATGCCAGGGTGGCGGATAGGATCGGCTTCTACAANAGGTAC
TTCCCAGGCTACGGTCCCACCGCCTATCCTAGGCGAAGATGTTNTCCATG
  K  G  P  M  P  G  W  R  I  G  S  A  S  T  ?  G  T
   R  V  R  C  Q  G  G  G  .  D  R  L  L  Q  ?  V
  K  G  S  D  A  R  V  A  D  R  I  G  F  Y  ?  R  Y

TGCGACTTGCTGGGGGTGAGCTACGGAGACAACTTGGACTGCTACAACCA
ACGCTGAACGACCCCCACTCGATGCCTCTGTTGAACCTGACGATGTTGGT
   A  T  C  W  G  .  A  T  E  T  T  W  T  A  T  T
  L  R  L  A  G  G  E  L  R  R  Q  L  G  L  L  Q  P
   C  D  L  L  G  V  S  Y  G  D  N  L  D  C  Y  N  ?

NAGTCCCTTTACTTANTCCGATACTATGTGCGAATCCATGTAATAACGCA
NTCAGGGAAATGAATNAGGCTATGATACACGCTTAGGTACATTATTGCGT
  ?  V  P  L  L  ?  R  I  L  C  A  N  P  C  N  N  A
   ?  S  L  Y  L  ?  R  Y  Y  V  R  I  H  V  I  T  Q
    S  P  F  T  *  S  D  T  M  C  E  S  M  .  .  R

ATAAACGCTACTGCTGAAATAGCGACTCCGTGAGTTGATTGTAGAAGTTG
TATTTGCGATGACGACTTTATCGCTGAGGCACTCAACTAACATCTTCAAC
  I  N  A  T  A  E  I  A  T  P  .  V  D  C  R  S  C
   .  T  L  L  L  K  .  R  L  R  E  L  I  V  E  V
    N  K  R  Y  C  .  N  S  D  S  V  S  .  L  .  K  L
                                             |POLY A
                                             |
CGGAGGAAATCTTCAATAAAAGCTAAGCTGAACAAGTTCATGGCCCTCAA
GCCTCCTTTAGAAGTTATTTTCGATTCGACTTGTTCAAGTACCGGGAGTT
     G  G  N  L  Q  .  K  L  S  .  T  S  S  W  P  S
  A  E  E  I  F  N  K  S  .  A  E  Q  V  H  G  P  Q
   R  R  K  S  S  I  K  A  K  L  N  K  F  M  A  L  N

TCATCGTTGATCGTCGTCAGATGCATCCATCAAATGTCTTGGAGTNAGTN
AGTAGCAACTAGCAGCAGTCTACGTAGGTAGTTTACAGAACCTCANTCAN
   I  I  V  D  R  R  Q  M  H  P  S  N  V  L  E  ?  V
    S  S  L  I  V  V  R  C  I  H  Q  M  S  W  S  ?  ?
  H  R  .  S  S  S  D  A  S  I  K  C  L  G  V  S
```

FIG. 16H-3

```
AATGCGTTTTCNATCGGTAAATTGAAGATGTTAGAATAAATAAAATTATT
TTACGCAAAAGNTAGCCATTTAACTTCTACAATCTTATTTATTTTAATAA
  N  A  ?  S  I  G  K  L  K  M  L  E  .  I  K  L  F
    M  R  ?  ?  S  V  N  .  R  C  .  N  K  .  N  Y
  ?  C  V  F  ?  R  .  I  E  D  V  R  I  N  K  I  I

TATTTTTTATAATTATAAATATTTAATATATTTTTAATCTTAAAGATC
ATAAAAAATATTAATATTTATAAAATTATATAAAAATTAGAATTTCTAG
    I  F  Y  N  Y  K  Y  F  N  I  F  F  N  L  K  D
  L  F  F  I  I  I  N  I  L  I  Y  F  L  I  L  K  I
   Y  F  L  .  L  .  I  F  .  Y  I  F  .  S  .  R  S

CTAAAAAATCTNATTATAAGGATTTTATATATGGATTGGGATACTAANAA
GATTTTTTAGANTAATATTCCTAAAATATATACCTAACCCTATGATTNTT
  P  K  K  S  ?  Y  K  D  F  I  Y  G  L  G  Y  .  ?
    L  K  N  L  I  I  R  I  L  Y  M  D  W  D  T  ?  K
     .  K  I  ?  L  .  G  F  Y  I  W  I  G  I  L  ?

¦BamH I
AANTTNATTATNAAAATTAATATACTTTTAATCTTAAGGATCCTAAAAAA
TTNAANTAATANTTTTAATTATATGAAAATTAGAATTCCTAGGATTTTTT
  ?  ?  I  ?  K  I  N  I  L  L  I  L  R  I  L  K  K
    ?  ?  L  ?  K  L  I  Y  F  .  S  .  G  S  .  K
  K  ?  ?  Y  ?  N  .  Y  T  F  N  L  K  D  P  K  K

ACATAATTATAAGGATTTTCTATATGGATNGGGATACTAACAANATNTAA
TGTATTAATATTCCTAAAAGATATACCTANCCCTATGATTGTTNTANATT
    H  N  Y  K  D  F  L  Y  G  ?  G  Y  .  Q  ?  ?
  N  I  I  I  R  I  F  Y  M  D  ?  D  T  N  ?  ?
   T  .  L  .  G  F  S  I  W  ?  G  I  L  T  ?  ?  N

TTGTAAAAATTTNAATATAAAATTGTTAAATCTAAAAATTAAAATACTAA
AACATTTTTAAANTTATATTTTAACAATTTAGATTTTTAATTTTATGATT
  I  V  K  I  ?  I  .  N  C  .  I  .  K  L  K  Y  .
    L  .  K  F  ?  Y  K  I  V  K  S  K  N  .  N  T  K
     C  K  N  ?  N  I  K  L  L  N  L  K  I  K  I  L
```

FIG. 16J-1

```
                                                             ┊Xho I
                          ┊EcoR V                   ┊Bgl II ┊
   AAATATATANTAATCATGATATCGAGAATGTGGCGCTTAGATCTCGAGAT
   TTTATATATNATTAGTACTATAGCTCTTACACCGCGAATCTAGAGCTCTA
     K  Y  I  ?  I  M  I  S  R  M  W  R  L  D  L  E  I
       N  I  ?  .  S  .  Y  R  E  C  G  A  .  I  S  R
     K  I  Y  ?  N  H  D  I  E  N  V  A  L  R  S  R  D

CGAGGTTGAGACTANAGNGGAAATTATGTTAATCATGGGAAATTTTCTTT
   GCTCCAACTCTGATNTCNCCTTTAATACAATTAGTACCCTTTAAAAGAAA
     E  V  E  T  ?  ?  E  I  M  L  I  M  G  N  F  L
     S  R  L  R  L  ?  ?  K  L  C  .  S  W  E  I  F  F
       R  G  .  D  ?  ?  G  N  Y  V  N  H  G  K  F  S  F

TGTTTCCAAGACGATGACCGTGGAAACCTAACATCCGCAATCGGTCATGC
   ACAAAGGTTCTGCTACTGGCACCTTTGGATTGTAGGCGTTAGCCAGTACG
     L  F  P  R  R  .  P  W  K  P  N  I  R  N  R  S  C
       C  F  Q  D  D  D  R  G  N  L  T  S  A  I  G  H  A
         V  S  K  T  M  T  V  E  T  .  H  P  Q  S  V  M

AATAACCATGTTATCATCANTGAACTTGTCGTCGTCATCTTACGGCCACA
   TTATTGGTACAATAGTAGTNACTTGAACAGCAGCAGTAGAATGCCGGTGT
     N  N  H  V  I  I  ?  E  L  V  V  V  I  L  R  P  Q
       I  T  M  L  S  S  ?  N  L  S  S  S  S  Y  G  H
     Q  .  P  C  Y  H  ?  .  T  C  R  R  H  L  T  A  T

AATCACAGTCTTCTANCAAGGCACGAATATTAATGAGTCCAAGCTAGTAT
   TTAGTGTCAGAAGATNGTTCCGTGCTTATAATTACTCAGGTTCGATCATA
     I  T  V  F  ?  Q  G  T  N  I  N  E  S  N  V  V
     K  S  Q  S  S  ?  K  A  R  I  L  M  S  P  T  .  Y
       N  H  S  L  L  ?  R  H  E  Y  .  .  V  Q  R  S  I

CTATATTGTTTTACATTTTATACCGTANTCGAGGTGTTCGCACGATTTTG
   GATATAACAAAATGTAAAATATGGCATNAGCTCCACAAGCGTGCTAAAAC
     S  I  L  F  Y  T  F  I  P  ?  S  R  C  S  H  D  L
       L  Y  C  F  T  L  L  Y  R  ?  R  G  V  R  T  I  W
         Y  I  V  L  H  F  Y  T  V  ?  E  V  F  A  R  F
```

FIG. 16J-2

```
GCCCATCCCAAGTGCATAAGATCATTGATATGACCTCTACGTTGGAGCGT
++++++++++++++++++++++++++++++++++++++++++++++++++
CGGGTAGGGTTCACGTATTCTAGTAACTATACTGGAGATGCAAGCTCGCA
  A  H  P  K  C  I  R  S  L  I  .  P  L  R  W  S  V
    P  I  P  S  A  .  D  H  .  Y  D  L  Y  V  G  A
  G  P  S  Q  V  H  K  I  I  D  M  T  S  T  L  E  R

¦ Bgl II
              ¦
GTTAACCCGAGATCTAGTTGAGGGGGCATAGGTCTCATTTNTCTACGTGG
++++++++++++++++++++++++++++++++++++++++++++++++++
CAATTGGGCTCTAGATCAACTCCCCCGTATCCAGAGTAAANGGATGCACC
  L  T  R  D  L  V  E  G  A  .  V  S  F  ?  Y  V
  C  .  P  E  I  .  L  R  G  H  R  S  H  ?  S  T  W
    V  N  P  R  S  S  .  G  G  I  G  L  I  ?  L  R  G

AGGTTAAAGATCACCTTTATTNCANCCCTTGTAGATTCTAAACTNGAGGT
++++++++++++++++++++++++++++++++++++++++++++++++++
TCCAATTTCTAGTGGAAATAANGTNGGGAACATCTAAGATTTGANCTCCA
  E  V  K  D  H  L  Y  ?  ?  P  C  R  F  .  T  ?  G
    R  L  K  I  T  F  I  ?  ?  L  V  D  S  K  L  E  V
  G  .  R  S  P  L  ?  ?  P  L  .  I  L  N  ?  R

NGATCTCTNTAGGAGATCGGTCTCCCTTGGAACTCTNTAGGGGTNCC
+++++++++++++++++++++++++++++++++++++++++++++++ ► 739
NCTAGAGANATCCTCTAGCCAGAGGGAACCTTGAGANATCCCCANGG
  ?  S  L  .  E  I  G  L  P  W  N  S  ?  G  V  P
    D  L  ?  R  R  S  V  S  L  G  T  L  .  G  ?
  ?  I  S  ?  G  D  R  S  P  L  E  L  ?  R  G  ?
```

FIG. 16J-3

```
 BamH I
GGATCCCAACTTTTAGGAATGGATCTTAAAATTTTAGTTATAAGTTCAAA
CCTAGGGTTGAAAATCCTTACCTAGAATTTTAAAATCAATATTCAAGTTT
  G  S  Q  L  L  G  M  D  L  K  I  L  V  I  S  S  K
   D  P  N  F  .  E  W  I  L  K  F  .  L  .  V  Q
  R  I  P  T  F  R  N  G  S  K  N  F  S  Y  K  F  K

GTTAGAAAAATCTTTACCAAGAGCTTTGAGTCCATTGATGACATCCGTGA
CAATCTTTTTAGAAATGGTTCTCGAAACTCAGGTAACTACTGTAGGCACT
   L  E  K  S  L  P  R  A  L  S  P  L  M  T  S  V
  S  .  K  N  L  Y  Q  E  L  .  V  H  .  .  H  P  .
    V  R  K  I  F  T  K  S  F  E  S  I  D  D  I  R  E

AACGGTGTACATGTCTCCGATGGACTCACTTGGTTTCATTCGGAAAAGTT
TTGCCACATGTACAGAGGCTACCTGAGTGAACCAAAGTAAGCCTTTTCAA
  K  R  C  T  C  L  R  W  T  H  L  V  S  F  G  K  V
   N  G  V  H  V  S  D  G  L  T  W  F  H  S  E  K  F
    T  V  Y  M  S  P  M  D  S  L  G  F  I  R  K  S

CGAAAGAGTGCATAAGAATATTGATTTTGGATTCTTTCACTCGGTTGGTG
GCTTTCTCACGTATTCTTATAACTAAAACCTAAGAAAGTGAGCCAACCAC
  R  K  S  A  .  E  Y  .  F  W  I  L  S  L  G  W  C
   E  R  V  H  K  N  I  D  F  G  F  F  H  S  V  G
    S  K  E  C  I  R  I  L  I  L  D  S  F  T  R  L  V

CCTTCATGAGTGACCTCAAGAGTCCTCCAAATATCAAAAGCCGAATCACA
GGAAGTACTCACTGGAGTTCTCAGGAGGTTTATAGTTTTCGGCTTAGTGT
   L  H  E  .  P  Q  E  S  S  K  Y  Q  K  P  N  H
  A  F  M  S  D  L  K  S  P  P  N  I  K  S  R  I  T
   P  S  .  V  T  S  R  V  L  Q  I  S  K  A  E  S  Q

EcoR I
AATTGAAATGTGATTGAATTCATTTTTGTCTAATGCACAAAACAGGGCAT
TTAACTTTACACTAACTTAAGTAAAAACAGATTACGTGTTTTGTCCCGTA
  K  L  K  C  D  .  I  H  F  C  L  M  H  K  T  G  H
   N  .  N  V  I  E  F  I  F  V  .  C  T  K  Q  G  I
    I  E  M  .  L  N  S  F  L  S  N  A  Q  N  R  A
```

FIG. 17A-1

```
TCATAGCCTTTGTGTTTAAAGCAAAAACATTCTTCTCCGATTCATCCCAT
AGTATCGGAAACACAAATTTCGTTTTTGTAAGAAGAGGCTAAGTAGGGTA
  S . P L C L K Q K H S S P I H P I
    H S L C V . S K N I L L R F I P
      . I A F V F K A K T F F S D S S H

TCGCTCATCGGAAGAGAAAATTTTTGAAATCCATTTTCGACAATAGACCA
AGCGAGTAGCCTTCTCTTTTAAAAACTTTAGGTAAAAGCTGTTATCTGGT
   R S S E E K I F E I H F R Q . T
  F A H R K R K F L K S I F D N R P
    S L I G R E N F . N P F S T I D Q

¦Nco I
              ¦
AAGCTCGAAATCCATGGAAATGAGGAAGATCCTCATATGAGTTTTCCAAT
TTCGAGCTTTAGGTACCTTTACTCCTTCTAGGAGTATACTCAAAAGGTTA
   K A R N P W K . G R S S Y E F S N
    K L E I H G N E E D P H M S F P I
      S S K S M XE M R K I L I . V F Q

ACATGTAATTCGACTCATTAAACATAGGTGGATGTGTAATGAAATGACCC
TGTACATTAAGCTGATGAATTTGTATCCACCTACACATTACTTTACTGGG
   T C N S T H . T . V D V . . N D P
    H V I R L I K H R W M C N E M T
  Y M . F D S L N I G G C V M K . P

TCATGCSCTATCTCTCTTGGGTATTAAACCAAATATGAGAGTGAGCCTTG
AGTACGSGATAGAGAGAACCCATAATTTGGTTTATACTCTCACTCGGAAC
      H A L S L L G I K P N M R V S L
  L M ? Y L S W V L N Q I . E . A L
    S C ? I S L G Y . T K Y E S E P C

CTCTGATACCAATTGTTAGGATCAGAGTGGCACTAAGAGAGGGGGGGAGA
GAGACTATGGTTAACAATCCTAGTCTCACCGTGATTCTCTCCCCCCCTCT
   A L I P I V R I R V A L R E G G S
    L . Y Q L L G S E W H . E R G G V
      S D T N C . D Q S G T K R G G E
```

FIG. 17A-2

```
                                                              ┆EcoR I
GAATTAGTGCAGTGGATTAAAACTTATAAGTTTAAAAATGAATTCGTAAA
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
CTTAATCACGTCACCTAATTTTGAATATTCAAATTTTTACTTAAGCATTT
   E  L  V  Q  W  I  K  T  Y  K  F  K  N  E  F  V  N
      N  .  C  S  G  L  K  L  I  S  L  K  M  N  S  .
   .  I  S  A  V  D  .  N  L  .  V  .  K  .  I  R  K

TACGAGAAGATTTCGTTTTAATAGTAACTTGAGTAGATGAAAACCAAAAG
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
ATGCTCTTCTAAAGCAAAATTATCATTGAACTCATCTACTTTTGGTTTTC
   T  R  R  F  R  F  N  S  N  L  S  R  .  K  P  K
   I  R  E  D  F  V  L  I  V  T  .  V  D  E  N  Q  K
   Y  E  K  I  S  F  .  .  .  L  E  .  M  K  T  S  S

TTAACAGTAGTGTAAATAACAATTTCGGGAAAGTAAGAACTCACACATTC
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
AATTGTAATCACATTTATTGTTAAAGCCCTTTCATTCTTGAGTGTGTAAG
   V  N  S  S  V  N  N  N  F  G  K  V  R  T  H  T  F
      L  T  V  V  .  I  T  I  S  G  K  .  E  L  T  H  S
   .  Q  .  C  K  .  Q  F  R  E  S  K  N  S  H  I

AAGGAACATACCAATTTAAAGTGGTTCGGTCAAAATGACCTACATCCACT
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
TTCCTTGTATGGTTAAATTTCACCAAGCCAGTTTTACTGGATGTAGGTGA
   K  E  H  T  N  L  K  W  F  G  Q  N  D  L  H  P  L
      R  N  I  P  I  .  S  G  S  V  K  M  T  Y  I  H
   Q  G  T  Y  Q  F  K  V  V  R  S  K  .  P  T  S  T
```

FIG. 17A-3

```
TGTGAAGCCTTCTTCGAAGAGGCTCCCAACTTCCACTAGCAAATCACTTT
ACACTTCGGAAGAAGCTTCTCCGAGGGTTGAAGGTGATCGTTTAGTGAAA
  V  K  P  S  S  K  R  L  P  T  S  T  S  K  S  L
L  .  S  L  L  R  R  G  S  Q  L  P  L  A  N  H  F
  C  E  A  F  F  E  E  A  P  N  F  H  .  Q  I  T  L
GAAGGGGAAGGACAAATACCTCTCTTACNACCTTTTACAATGGTTCATAC
CTTCCCCTTCCTGTTTATGGAGAGAATGNTGGAAAATGTTACCAAGTATG
  .  R  G  R  T  N  T  S  L  T  T  F  Y  N  G  S  Y
   E  G  E  G  Q  I  P  L  L  ?  P  F  T  M  V  H  T
    K  G  K  D  K  Y  L  S  Y  ?  L  L  Q  W  F  I
TCTTACAAATTTTCAACGAGAAAGAAGGAGGTGAACATGCAAGCAATTGA
AGAATGTTTAAAAGTTGCTCTTTCTTCCTCCACTTGTACGTTCGTTAACT
  S  Y  K  F  S  T  R  K  K  E  V  N  M  Q  A  I  E
   L  T  N  F  Q  R  E  R  R  R  .  T  C  K  Q  L
L  L  Q  I  F  N  E  K  E  G  G  E  H  A  S  N  .
AAACAAGACTTGCTAAAGACTTTGCTAAGGCTTTTTTTCTCAATCTATTG
TTTGTTCTGAACGATTTCTGAAACGXTTCCGAAAAAAGAGTTAGATAAC
  N  K  T  C  .  R  L  C  .  G  F  F  S  Q  S  I
   K  T  R  L  A  K  D  F  A  K  A  F  F  L  N  L  L
    K  Q  D  L  L  R  T  L  L  R  L  F  F  S  I  Y  C
CTTCTCAAAAGTTGTATTCTCTGCTGAGAATTGAGGGGTATTTATAGACC
GAAGAGTTTTCAACATAAGAGACGACTCTTAACTCCCCATAAATATCTGG
  A  S  Q  K  L  Y  S  L  L  R  I  E  G  Y  L  .  T
   L  L  K  S  C  I  L  C  .  E  L  R  G  I  Y  R  P
    F  S  K  V  V  F  S  A  E  N  .  G  V  F  I  D
CCAAGAGGATTTAAATTTGGGCTCCAAATTTCGAATGCTCTTGGGTTCCC
GGTTCTCCTAAATTTAAACCCGAGGTTTAAAGCTTACGAGAACCCAAGGG
  P  R  G  F  K  F  G  L  Q  I  S  N  A  L  G  F  P
   Q  E  D  L  N  L  G  S  K  F  R  M  L  L  G  S
    P  K  R  I  .  I  W  A  P  N  F  E  C  S  W  V  P
```

FIG. 17B-1

```
GAGGTTGCCGGTGCCACCGCCTGTCAGTGTTTGACACTGGACAGTGTACT
CTCCAACGGCCACGGTGGCGGACAGTCACAAACTGTGACCTGTCACATGA
  R  L  P  V  P  P  P  V  S  V  .  H  W  T  V  Y
R  G  C  R  C  H  R  L  S  V  F  D  T  G  Q  C  T
  E  V  A  G  A  T  A  C  Q  C  L  T  L  D  S  V  L

AGCGGTGCCGCCGCCGGACCTCTCGGGTGTTGGGCGGTGCCACCGCCTAG
TCCCCACGGCGGCGGCCTGGAGAGCCCACAACCCGCCACGGTGGCGGATC
  .  R  C  H  R  R  T  S  R  V  L  G  G  A  T  A  .
S  G  A  T  A  G  P  L  G  C  W  A  V  P  P  P  R
  A  V  P  P  P  D  L  S  G  V  G  R  C  H  R  L

ACTTTTTCAGCTCACTGGTTGGATTCCAAACTTGACCCAAACCAGTCCGA
TGAAAAAGTCGAGTGACCAACCTAAGGTTTGAACTGGGTTTGGTCAGGCT
  T  F  S  A  H  W  L  D  S  K  L  D  P  N  Q  S  E
  L  F  Q  L  T  G  W  I  P  N  L  T  Q  T  S  P
D  F  F  S  S  L  V  G  F  Q  T  .  P  K  P  V  R

ACTCGGGTCCAATTGACCCGTAACCGGATTATAGGATTAACCCTTAATCC
TGAGCCCAGGTTAACTGGGCATTGGCCTAATATCCTAATTGGGAATTAGG
  L  G  S  N  .  P  V  T  G  L  .  D  .  P  L  I
N  S  G  S  I  D  P  .  P  D  Y  R  I  N  P  .  S
  T  R  V  Q  L  T  R  N  R  I  I  G  L  T  L  N  P

TAACCCTAATTATATGCAAACTACGCAACTGAAAATATAGTCCTAAGCAA
ATTGGGATTAATATACGTTTGATGCGTTGACTTTTATATCAGGATTCGTT
  L  T  L  I  I  C  K  L  R  N  .  K  Y  S  P  K  Q
  .  P  .  L  Y  A  N  Y  A  T  E  N  I  V  L  S  K
N  P  N  Y  M  Q  T  T  Q  L  K  I  .  S  .  A

GTTTTTAACCGGCAAACGTCGAGTCTTCTTCCGGCGATCTTTCGGCAGAC
CAAAAATTGGCCGTTTGCAGCTCAGAAGAAGGCCGCTGGAAAGCCGTCTG
  V  F  N  R  Q  T  S  S  L  L  P  A  I  F  R  Q  T
    F  L  T  G  K  R  R  V  F  F  R  R  S  F  G  R
S  F  .  P  A  N  V  E  S  S  S  G  D  L  S  A  D
```

FIG. 17B-2

```
TTCTGATATACCTTTGGATTTCTTCTAGCGGACTCCTAGTAGGGTCCCGA
AAGACTATAAGGAAACCTAAAGAAGATCGCCTGAGGATCATCCCAGGGCT
  S  D  I  P  L  D  F  F  .  R  T  P  S  R  V  P
 L  L  I  Y  L  W  I  S  S  S  G  L  L  V  G  S  R
  F  .  Y  T  F  G  F  L  L  A  D  S  .  .  G  P  D
TCTTGTGGCGAGTTTAGCGAGTAGCCGAACCTTCTCGGTGATCTCCGCAA
AGAACACCGCTCAAATCGCTCATCGGCTTGGAAGAGCCACTAGAGACGTT
  I  L  W  R  V  .  R  V  A  E  P  S  R  .  S  P  Q
   S  C  G  E  F  S  E  .  P  N  L  L  G  D  L  R  K
 L  V  A  S  L  A  S  S  R  T  F  S  V  I  S  A
ACCGCCGATGATCTCTTCGGCAGACTTTCGAAAACTTCGACAAGTCCCCG
TGGCGGCTACTAGAGAAGCCGTCTGAAAGCTTTTGAAGCTGTTCAGGGGC
  T  A  D  D  L  F  G  R  L  S  K  T  S  T  S  P  R
   P  P  M  I  S  S  A  D  F  R  K  L  R  Q  V  P
 N  R  R  .  S  L  R  Q  T  F  E  N  F  D  K  S  P
ATTTCTTCTCGGTTGGTTCCGACAGCATCTCTAACGAAACTTCGGACACC
TAAAGAAGAGCCAACCAAGGCTGTCGTAGAGATTGCTTTGAAGCCTGTGG
  F  L  L  G  W  F  R  Q  H  L  .  R  N  F  G  L
   D  F  F  S  V  G  S  D  S  I  S  N  E  T  S  D  S
 I  S  S  R  X  V  P  T  A  S  L  T  K  L  R  T  P
TTGAATGTCCATCGAACTTGACTCCGGTAGGCTTGCTTTATATTTTCAGG
AACTTACAGGTAGCTTGAACTGAGGCCATCCGAACGAAATATAAAAGTCC
  L  E  C  P  S  N  L  T  P  V  G  L  L  Y  I  F  R
   L  N  V  H  R  T  .  L  R  .  A  C  F  I  F  S  G
 .  M  S  I  E  L  D  S  G  R  L  A  L  Y  F  Q
CTATCATAGTTAATCCTACATACTTAACTCAATAATATGGATTAGATTAA
GATAGTATCAATTAGGATGTATGAATTGAGTTATTATACCTAATCTAATT
  L  S  .  L  I  L  H  T  .  L  N  N  M  D  .  I  N
   Y  H  S  .  S  Y  I  L  N  S  I  I  W  I  R  L
 A  I  I  V  N  P  T  Y  L  T  Q  .  Y  G  L  D  .
```

FIG. 17B-3

```
TTAACCCATCAATTGATTTCATCATCAAAATTCGACATTCAACAAACATC
AATTGGGTAGTTAACTAAAGTAGTAGTTTTAAGCTGTAAGTTGTTTGTAG
  . P  I  N  .  F  H  H  Q  N  S  T  F  N  K  H
  I  N  P  S  I  D  F  I  I  K  I  R  H  S  T  N  I
  L  T  H  Q  L  I  S  S  S  K  F  D  I  Q  Q  T  S

CGTACTCAATAACCCATCAGGC TATA GTTACGTGACTATCTACTGTGATC
GCATGAGTTATTGGGTAGTCCGATATCAATGCACTGATAGATGACACTAG
  P  Y  S  I  T  H  Q  A  I  V  T  .  L  S  T  V  I
  R  T  Q  .  P  I  R  L  .  L  R  D  Y  L  L  .  S
    V  L  N  N  P  S  G  Y  S  Y  V  T  I  Y  C  D

CGTACGTGAAGTTAGCGAGTCATGATCCAGGTCGTGTCACTTATTGGCCG
GCATGCACTTCAATCGCTCAGTACTAGGTCCAGCACAGTGAATAACCGGC
  R  T  .  S  .  R  V  M  I  Q  V  V  S  L  I  G  R
    V  R  E  V  S  E  S  .  S  R  S  C  H  L  L  A
  P  Y  V  K  L  A  S  H  D  P  G  R  V  T  Y  W  P

AACACGTATCCCTTATCCAAATCCAGTCTTCTCAACTCTTCTAGCCTACC
TTGTACATAGGGAATAGGTTTAGGTCAGAAGAGTTGAGAAGATCGGATGG
    T  R  I  P  Y  P  N  P  V  F  S  T  L  L  A  Y
  E  H  V  S  L  I  Q  I  Q  S  S  Q  L  F  .  P  T
  N  T  Y  P  L  S  K  S  S  L  L  N  S  S  S  L  P

EcoR I
CGTCTCTTTTTTTATTACTTTTGAAAGAATTCAAATCAAAACAGATACAA
GCAGAGAAAAAATAATGAAAACTTTCTTAAGTTTAGTTTTGTCTATGTT
  P  S  L  F  L  L  L  L  K  E  F  K  S  K  Q  I  Q
    R  L  F  F  Y  Y  F  .  K  N  S  N  Q  N  R  Y  K
      V  S  F  F  I  T  F  E  R  I  Q  I  K  T  D  T

AATAACACGGTGAGACACTGTGACATGCTAGTCTCTGGAAAGCATTAATT
TTATTGTGCCACTCTGTGACACTGTACGATCAGAGACCTTTCGTAATTAA
  N  N  T  V  R  H  C  D  M  L  V  S  G  K  H  .  F
    I  T  R  .  D  T  V  T  C  .  S  L  E  S  I  N
      K  .  H  G  E  T  L  .  H  A  S  L  W  K  A  L  I
```

FIG. 17C-1

```
CGCGCATCCACAGACGTCGTCAGCTTCATCACCCACTTTTTCCTACATAA
GCGCGTAGGTGTCTGCAGCAGTCGAAGTAGTGGGTGAAAAAGGATGTATT
  A  H  P  Q  T  S  S  A  S  S  P  T  F  S  Y  I
 S  R  I  H  R  R  R  Q  L  H  H  P  L  F  P  T  .
R  A  S  T  D  V  V  S  F  I  T  H  F  F  L  H  N
```

Hind III
```
CCATGTCGCATGGCTTTGTTG ATG ACAGACCACCACAAGCTTGCCTTTGG
GGTACAGCGTACCGAAACAACTACTGTCTGGTGGTGTTCGAACGGAAACC
  T  M  S  H  G  F  V  D  D  R  P  P  Q  A  C  L  W
 P  C  R  M  A  L  L  M  T  D  H  H  K  L  A  F  G
H  V  A  W  L  C  .  .  Q  T  T  T  S  L  P  L TTGTGCCTAACAGAGAGAGAGAGACAGACCGATAGCCTCCTCATTCACT A
AACACGGATTGTCTCTCTCTCTGTCTGGCTATCGGAGGAGTAAGTGAT
  L  C  L  T  E  R  E  R  Q  T  D  S  L  L  I  H  Y
 C  A  .  Q  R  E  R  D  R  P  I  A  S  S  F  T
V  V  P  N  R  E  R  E  T  D  R  .  P  P  H  S  L TG GCGATCCGATCGCCAGCTTCGCTGCTGTTATTTGCGTTCCTG ATG CTT
ACCGCTAGGCTAGCGGTCGAAGCGACGACAATAAACGCAAGGACTACGAA
    G  D  P  I  A  S  F  A  A  V  I  C  V  P  D  A
   M  A  I  R  S  P  A  S  L  L  L  F  A  F  L  M  L
  W  R  S  D  R  Q  L  R  C  C  Y  L  R  S  .  C  L
```

Pst I
```
GCGCTCACGGGAAGACTGCAGGCCCGGCGCAGCTCATGCATTGGCGTCTA
CGCGAGTGCCCTTCTGACGTCCGGGCCGCGTCGAGTACGTAACCGCAGAT
  C  A  H  G  K  T  A  G  P  A  Q  L  M  H  W  R  L
 A  L  T  G  R  L  Q  A  R  R  S  S  C  I  G  V  Y
R  S  R  E  D  C  R  P  G  A  A  H  A  L  A  S
```

Hind III
```
CTGGGGACAAAACACCGACGAGGGAAGCTTAGCAGATGCTTGTGCCACAG
GACCCCTGTTTTGTGGCTGCTCCCTTCGAATCGTCTACGAACACGGTGTC
  L  G  T  K  H  R  R  G  K  L  S  R  C  L  C  H  R
 W  G  Q  N  T  D  E  G  S  L  A  D  A  C  A  T
T  G  D  K  T  P  T  R  E  A  .  Q  M  L  V  P  Q
```

FIG. 17C-2

```
GCAACTACGAATACGTGAACATCGCCACCCTTTTCAAGTTTGGCATGGGC
CGTTGATGCTTATGCACTTGTAGCGGTGGGAAAAGTTCAAACCGTACCCG
   Q  L  R  I  R  E  H  R  H  P  F  Q  V  W  H  G
 G  N  Y  E  Y  V  N  I  A  T  L  F  K  F  G  M  G
  A  T  T  N  T  .  T  S  P  P  F  S  S  L  A  W  A

CAAACTCCAGAGATCAACCTCGCCGGCCACTGTGACCCTCGGAACAACGG
GTTTGAGGTCTCTAGTTGGAGCGGCCGGTGACACTGGGAGCCTTGTTGCC
   P  N  S  R  D  Q  P  R  R  P  L  .  P  S  E  Q  R
 Q  T  P  E  I  N  L  A  G  H  C  D  P  R  N  N  G
  D  L  Q  R  S  T  S  P  A  T  V  T  L  G  T  T

CTGCGCGCGCTTGAGCAGCGAAATCCAGTCCTGCCAGGAGCGTGGCGTCA
GACGCGCGCGAACTCGTCGCTTTAGGTCAGGACGGTCCTCGCACCGCAGT
   L  R  A  L  E  Q  R  N  P  V  L  P  G  A  W  R  Q
  C  A  R  L  S  S  E  I  Q  S  C  Q  E  R  G  V
 A  A  R  A  .  A  A  K  S  S  P  A  R  S  V  A  S

AGGTGATGCTCTCCATCGGAGGTGGCGGGTCTTATGGCCTGAGTTCCACC
TCCACTACGAGAGGTAGCCTCCACCGCCCAGAATACCGGACTCAAGGTGG
   G  D  A  L  H  R  R  W  R  V  L  W  P  E  F  H
 K  V  M  L  S  I  G  G  G  G  S  Y  G  L  S  S  T
  R  .  C  S  P  S  E  V  A  G  L  M  A  .  V  P  P
```

FIG. 17C-3

```
GAAGACGCCAAGGACGTAGCGTCATACCTCTGGCACAGTTTCTTGGGTGG
CTTCTGCGGTTCCTGCATCGCAGTATGGAGACCGTGTCAAAGAACCCACC
 R  R  R  Q  G  R  S  V  I  P  L  A  Q  F  L  G  W
  E  D  A  K  D  V  A  S  Y  L  W  H  S  F  L  G  G
   K  T  P  R  T  .  R  H  T  S  G  T  V  S  W  V
                    ┆Xho I
TTCTGCTGCTCGCTACTCGAGACCCCTCGGGGATGCGGTTCTGGATGGCA
AAGACGACGAGCGATGAGCTCTGGGGAGCCCCTACGCCAAGACCTACCGT
 F  C  C  S  L  L  E  T  P  R  G  C  G  S  G  W  H
  S  A  A  R  Y  S  R  P  L  G  D  A  V  L  D  G
   V  L  L  L  A  T  R  D  P  S  G  M  R  F  W  M  A

TAGACTTCAACATCGCCGGAGGGAGCACAGAACACTATGATGAACTTGCC
ATCTGAAGTTGTAGCGGCCTCCCTCGTGTCTTGTGATACTACTTGAACGG
   R  L  Q  H  R  R  E  H  R  T  L  .  T  C  R
  I  D  F  N  I  A  G  S  T  E  H  Y  D  E  L  A  A
 .  T  S  T  S  P  E  A  Q  N  T  M  M  N  L  P  L

GCTTTCCTCAAGGCCTACAACGAGCAGGAGGCCGGAACGAAGAAAGTTCA
CGAAAGGAGTTCCGGATGTTGCTCGTCCTCCGGCCTTGCTTCTTTCAAGT
 F  P  Q  G  L  Q  R  A  G  G  R  N  E  E  E  S  S
   F  L  K  A  Y  N  E  Q  E  A  G  T  K  K  K  V  H
     S  S  R  P  T  T  S  R  R  P  E  R  R  R  K  F

CTTGAGTGCTCGTCCGCAGTGTCCTTTCCCGGATTACTGGCTTGGCAACG
GAACTCACGAGCAGGCGTCACAGGAAAGGGCCTAATGACCGAACCGTTGC
 L  E  C  S  S  A  V  S  F  P  G  L  L  A  W  Q  R
   L  S  A  R  P  Q  C  P  F  P  D  Y  W  L  G  N
 T  .  V  L  V  R  S  V  L  S  R  I  T  G  L  A  T
                      ┆Bgl II
CACTCAGAACAGATCTCTTCGACTTCGTGTGGGTGCAGTTCTTCAACAAC
GTGAGTCTTGTCTAGAGAAGCTGAAGCACACCCACGTCAAGAAGTTGTTG
   T  Q  N  R  S  L  R  L  R  V  G  A  V  L  Q  Q
  A  L  R  T  D  L  F  D  F  V  W  V  Q  F  F  N  N
 H  S  E  Q  I  S  S  T  S  C  G  C  S  S  S  T  T
```

FIG. 17D-1

```
CCTTCGTGCCATTTCTCCCAGAACGCTATCAATCTTGCAAATGCGTTCAA
GGAAGCACGGTAAAGAGGGTCTTGCGATAGTTAGAACGTTTACGCAAGTT
 P  F  V  P  F  L  P  E  R  Y  Q  S  C  K  C  V  Q
   P  S  C  H  F  S  Q  N  A  I  N  L  A  N  A  F  N
     L  R  A  I  S  P  R  T  L  S  I  L  Q  M  R  S

CAATTGGGTCATGTCCATCCCTGCGCAAAAGCTGTTCCTTGGGCTTCCTG
GTTAACCCAGTACAGGTAGGGACGCGTTTTCGACAAGGAACCCGAAGGAC
 Q  L  G  H  V  H  P  C  A  K  A  V  P  W  A  S  C
   N  W  V  M  S  I  P  A  Q  K  L  F  L  G  L  P
     T  I  G  S  C  P  S  L  R  K  S  C  S  L  G  F  L

CTGCTCCTGAGGCTGCTCCAACTGGTGGCTACATTCCACCCCATGATCTC
GACGAGGACTCCGACGAGGTTGACCACCGATGTAAGGTGGGGTACTAGAG
 C  S  .  G  C  S  N  W  W  L  H  S  T  P  .  S
  A  A  P  E  A  A  P  T  G  G  Y  I  P  P  H  D  L
    L  L  L  R  L  L  Q  L  V  A  T  F  H  P  M  I  S

ATATCTAAAGTTCTTCCGATCCTAAAGGATTCCGACAAGTACGCAGGAAT
TATAGATTTCAAGAAGGCTAGGATTTCCTAAGGCTGTTCATGCGTCCTTA
 H  I  .  S  S  S  D  P  K  G  F  R  Q  V  R  R  N
   I  S  K  V  L  P  I  L  K  D  S  D  K  Y  A  G  I
     Y  L  K  F  F  R  S  .  R  I  P  T  S  T  Q  E

CATGCTGTGGACTAGATACCACGACAGAAACTCCGGCTACAGTTCTCAAG
GTACGACACCTGATCTATGGTGCTGTCTTTGAGGCCGATGTCAAGAGTTC
 H  A  V  D  .  I  P  R  Q  K  L  R  L  Q  F  S  S
   M  L  W  T  R  Y  H  D  R  N  S  G  Y  S  S  Q
     S  C  C  G  L  D  T  T  T  E  T  P  A  T  V  L  K

TCAAGTCCCACGTGTGTCCAGCGCGTCGGTTCTCCAACATCTTATCTATG
AGTTCAGGGTGCACACAGGTCGCGCAGCCAAGAGGTTGTAGAATAGATAC
 Q  V  P  R  V  S  S  A  S  V  L  Q  H  L  I  Y
  V  K  S  H  V  C  P  A  R  R  F  S  N  I  L  S  M
    S  S  P  T  C  V  Q  R  V  G  S  P  T  S  Y  L  C
```

FIG. 17D-2

```
CCGGTGAAGTCTTCCAAGTAAACCTGAACGGCGTAGATGATCGGTGGTCG
GGCCACTTCAGAAGGTTCATTTGGACTTGCCGCATCTACTAGCCACCAGC
 A  G  E  V  F  Q  V  N  L  N  G  V  D  D  R  W  S
  P  V  K  S  S  K  .  T  .  T  A  .  M  I  G  G  R
   R  .  S  L  P  S  K  P  E  R  R  R  .  S  V  V

AAAACTCCGATCATCATGGGTCCCCATCCGTATCCGTGCGTTGCTACGTT
TTTTGAGGCTAGTAGTACCCAGGGGTAGGCATAGGCACGCAACGATGCAA
 K  T  P  I  I  M  G  P  H  P  Y  P  C  V  A  T  L
  K  L  R  S  S  W  V  P  I  R  I  R  A  L  L  R
   E  N  S  D  H  H  G  S  P  S  V  S  V  R  C  Y  V

ATGGTGTTTCCCTTGTATGTTGGTCTTTTCAATAATATAATAAGGGGTTA
TACCACAAAGGGAACATACAACCAGAAAAGTTATTATATTATTCCCCAAT
    W  C  F  P  C  M  L  V  F  S  I  I  .  .  G  V
 Y  G  V  S  L  V  C  W  S  F  Q  .  Y  N  K  G  L
  M  V  F  P  L  Y  V  G  L  F  N  N  I  I  R  G  .

GTTTTACGTTTCCATATTTTCCATGTTCGAAAACAGTATATTTGCTGCCC
CAAAATGCAAAGGTATAAAAGGTACAAGCTTTTGTCATATAAACGACGGG
  S  F  T  F  P  Y  F  P  C  S  K  T  V  Y  L  L  P
   V  L  R  F  H  I  F  H  V  R  K  Q  Y  I  C  C  P
    F  Y  V  S  I  F  S  M  F  E  N  S  I  F  A  A
```

FIG. 17D-3

```
CTTCCAAATTTGAAAAAGATAAAATAAATATATAACTAAAAATATCCTCT
GAAGGTTTAAACTTTTTCTATTTTATTTATATATTGATTTTTATAGGAGA
 L  P  N  L  K  K  I  K  .  I  Y  N  .  K  Y  P  L
   F  Q  I  .  K  R  .  N  K  Y  I  T  K  N  I  L
 P  S  K  F  E  K  D  K  I  N  I  .  L  K  I  S  S

TTTTTTTTCTTTCGACAAATATATAACTCTTAACTTTCCCAATTGTTTA
AAAAAAAAGAAAGCTGTTTATATATTGAGAATTGAAGGGGTTAACAAAT
   F  F  F  F  R  Q  I  Y  N  S  .  L  S  Q  L  F
 F  F  F  S  F  D  K  Y  I  T  L  N  F  P  N  C  L
   F  F  F  L  S  T  N  I  .  L  L  T  F  P  I  V  .

AGCAAAAGATATAAATCCTCTTCCACACAAAAGACGAATCCATGATTGCT
TCGTTTTCTATATTTAGGAGAAGGTGTGTTTTCTGCTTAGGTACTAACGA
   K  Q  K  I  .  I  L  F  H  T  K  D  E  S  M  I  A
 S  K  R  Y  K  S  S  S  T  Q  K  T  N  P  .  L  L
   A  K  D  I  N  P  L  P  H  K  R  R  I  H  D  C

GGATTGCTGTCTACTGGTGCCGAAATGGCGACGAGAGAAGCTTGTGCTAC
CCTAACGACAGATGACCACGGCTTTACCGCTGCTCTCTTCGAACACGATG
   G  L  L  S  T  G  A  E  M  A  T  R  E  A  C  A  T
   D  C  C  L  L  V  P  K  W  R  R  E  K  L  V  L
 W  I  A  V  Y  W  C  R  N  G  D  E  R  S  L  C  Y

CTGCAATTACAAGTTCGTCAACATTGTCTTCCTTGCCATGTTTGGTGACG
GACGTTAATGTTCAAGCAGTTGTAACAGAAGGAACGGTACAAACCACTGC
   C  N  Y  K  F  V  N  I  V  F  L  A  M  F  G  D
 P  A  I  T  S  S  S  T  L  S  S  L  P  C  L  V  T
   L  Q  L  Q  V  R  Q  H  C  L  P  C  H  V  W  .  R

CCATACTCCCGTGATCAGGACACACCTCTGGAACAGTTTCTTGGGAAGTT
GGTATGAGGGCACTAGTCCTGTGTGGAGACCTTGTCAAAGAACCCTTCAA
   A  I  L  P  .  S  G  H  T  S  G  T  V  S  W  E  V
 P  Y  S  R  D  Q  D  T  P  L  E  Q  F  L  G  K  L
   H  T  P  V  I  R  T  H  L  W  N  S  F  L  G  S
```

FIG. 17E-1

```
AATCTTCTTCTCGGCTCCTCGGCGACCAATCTTGTGAGGTTCTTCTCCTG
TTAGAAGAAGAGCCGAGGAGCCGCTGGTTAGAACACTCCAAGAAGAGGAC
  N  L  L  L  G  S  S  A  T  N  L  V  R  F  F  S  .
    I  F  F  S  A  P  R  R  P  I  L  .  G  S  S  P
  .  S  S  S  R  L  L  G  D  Q  S  C  E  V  L  L  L

AATGGTGTCCACTTCGACATCGAAGGTCTACCTGAGCGCANATCCACAGT
TTACCACAGGTGAAGCTGTAGCTTCCAGATGGACTCGCGTNTAGGTGTCA
    M  V  S  T  S  T  S  K  V  Y  L  S  A  ?  P  Q
  E  W  C  P  L  R  H  R  R  S  T  .  A  ?  I  H  S
   N  G  V  H  F  D  I  E  G  L  P  E  R  ?  S  T  V

TCCGACTACGTGTGGGTGCAGTTCTACTACACAGGCAACTCGCAGATGCC
AGGCTGATGCACACCCACGTCAAGATGATGTGTCCGTTGAGCGTCTACGG
  F  R  L  R  V  G  A  V  L  L  H  R  Q  L  A  D  A
    S  D  Y  V  W  V  Q  F  Y  Y  T  G  N  S  Q  M  P
      P  T  T  C  G  C  S  S  T  T  Q  A  T  R  R  C

CGGTAACAATGGGTTCTCCATCCTGCATGGAAGGTGTTCCCTGGACTTCC
GCCATTGTTACCCAAGAGGTAGGACGTACCTTCCACAAGGGACCTGAAGG
  R  .  Q  W  V  L  H  P  A  W  K  V  F  P  G  L  P
    G  N  N  G  F  S  I  L  H  G  R  C  S  L  D  F
     P  V  T  M  G  S  P  S  C  M  E  G  V  P  W  T  S
                                   ¦Sac I      ¦Spe I
TGCTGCTCCTCAGGCTGCTGGAAGGAGCTCCATTCCACTAGTGATCTTAC
ACGACGAGGAGTCCGACGACCTTCCTCGAGGTAAGGTGATCACTAGAATG
    A  A  P  Q  A  A  G  R  S  S  I  P  L  V  I  L
  L  L  L  L  R  L  L  E  G  A  P  F  H  .  .  S  Y
    C  C  S  S  G  C  W  K  E  L  H  S  T  S  D  L  T

ACGTGTCTTATCATCAAGAATTATAGCAAGTACCGAGGGATTATTAAAAT
TGCACAGAATAGTAGTTCTTAATATCGTTCATGGCTCCCTAATAATTTTA
  H  V  S  Y  H  Q  E  L  .  Q  V  P  R  D  Y  .  N
    T  C  L  I  I  K  N  Y  S  K  Y  R  G  I  I  K  I
      R  V  L  S  S  R  I  I  A  S  T  E  G  L  L  K
```

FIG. 17E-2

```
AAAAAAAAAGGGAAGAATGGGAATTAGAATTAAAACTGAAACCGGCCATG
TTTTTTTTTCCCTTCTTACCCTTAATCTTAATTTTGACTTTGGCCGGTAC
  K  K  K  G  K  N  G  N  .  N  .  N  .  N  R  P  .
    K  K  K  G  R  M  G  I  R  I  K  T  E  T  G  H
  K  K  K  R  E  E  W  E  L  E  L  K  L  K  P  A  M

AAGAACGTTTTCGAGTGAAGACAACGACAGTATGAGACGGTAGTTTGCTA
TTCTTGCAAAAGCTCACTTCTGTTGCTGTCATACTCTGCCATCAAACGAT
    R  T  F  R  V  K  T  N  D  S  M  R  R  .  F  A
  E  E  R  F  E  .  R  Q  T  T  V  .  D  G  S  L  L
    K  N  V  S  S  E  D  K  R  Q  Y  E  T  V  V  C  Y

TGGACATGGATCGTTCCCAAAGCAGTCCAAGTCTTTATGAACCGGTCTAT
ACCTGTACCTAGCAAGGGTTTCGTCAGGTTCAGAAATACTTGGCCAGATA
  M  D  M  D  R  S  Q  S  S  P  S  L  Y  E  P  V  Y
    W  T  W  I  V  P  K  A  V  Q  V  F  M  N  R  S  I
      G  H  G  S  F  P  K  Q  S  K  S  L  .  T  G  L

CGGTTCAGCCTTCAAGAACCGCGAGGATAACCGGCCCAAGAGAAACAACA
GCCAAGTCGGAAGTTCTTGGCGCTCCTATTGGCCGGGTTCTCTTTGTTGT
  R  F  S  L  Q  E  P  R  G  .  P  A  Q  E  K  Q  Q
    G  S  A  F  K  N  R  E  D  N  R  P  K  R  N  N
  S  V  Q  P  S  R  T  A  R  I  T  G  P  R  E  T  T
```

FIG. 17E-3

```
AATTGTGGTGAGCTTTTANTATAAACCGAACGGTGCCGTCCGTCAGATGT
TTAACACCACTCGAAAATNATATTTGGCTTGCCACGGCAGGCAGTCTACA
    I  V  V  S  F  ?  Y  K  P  N  G  A  V  R  Q  M
 K  L  W  .  A  F  ?  I  N  R  T  V  P  S  V  R  C
  N  C  G  E  L  L  ?  .  T  E  R  C  R  P  S  D  V

¦Bgl II
TAAATGGACGGCGGATAGATCTCCAGAGTAAATCTGAGGAAAATCGTTCC
ATTTACCTGCCGCCTATCTAGAGGTCTCATTTAGACTCCTTTTAGCAAGG
  L  N  G  R  R  I  D  L  Q  S  K  S  E  E  N  R  S
   .  M  D  G  G  .  I  S  R  V  N  L  R  K  I  V  P
    K  W  T  A  D  R  S  P  E  .  I  .  G  K  S  F

GGCCCCCCTACCACGACCCACGCGATCCGTCCTCTCCCCCACCCCCTACA
CCGGGGGGATGGTGCTGGGTGCGCTAGGCAGGAGAGGGGGTGGGGGATGT
  G  P  P  T  T  T  H  A  I  R  P  L  P  H  P  L  H
   A  P  L  P  R  P  T  R  S  V  L  S  P  T  P  Y
  R  P  P  Y  H  D  P  R  D  P  S  S  P  P  P  P  T

EcoR I¦
CCTTTTTCTTCTTCCGCTCCTGCGATCGGTTATTTGATTTTGTGTATGAT
GGAAAAAGAAGAAGGCGAGGACGCTAGCCAATAAACTAAAACACATACTA
    L  F  L  L  P  L  L  R  S  V  I  .  F  C  V  .
   T  F  F  F  F  R  S  C  D  R  L  F  D  F  V  Y  D
    P  F  S  S  S  A  P  A  I  G  Y  L  I  L  C  M  I

ATCCAATTTCTTTTCTGGAGTGGTATCCTATTCTAATTTCTTAGATTGTT
TAGGTTAAAGAAAAGACCTCACCATAGGATAAGATTAAAGAATCTAACAA
  Y  P  I  S  F  L  E  W  Y  P  I  L  I  S  .  I  V
   I  Q  F  L  F  W  S  G  I  L  F  .  F  L  R  L  L
    S  N  F  F  S  G  V  V  S  Y  S  N  F  L  D  C

GTATTGAACCATCAGTTTTGGTTTAAGCGCATGATGGCGGAGAGTTTCGG
CATAACTTGGTAGTCAAAACCAAATTCGCGTACTACCGCCTCTCAAAGCC
   V  L  N  H  Q  F  W  F  K  R  M  M  A  E  S  F  G
    Y  .  T  I  S  F  G  L  S  A  .  W  R  R  V  S
   C  I  E  P  S  V  L  V  .  A  H  D  G  G  E  F  R
```

FIG. 17F-1

```
GAGATGGGAGTCAGATCCCTTGTTTTCTGCTGCCGAAGTGGTGCAAGATT
CTCTACCCTCAGTCTAGGGAACAAAAGACGACGGCTTCACCACGTTCAAA
   R  W  E  S  D  P  L  F  S  A  A  E  V  V  Q  D
 G  D  G  S  Q  I  P  C  F  L  L  P  K  W  C  K  I
  E  M  G  V  R  S  L  V  F  C  C  R  S  G  A  R  F

CGGCCGATAGGTTTTTTCTCTCATTTAAGCTCAATTATGCGGTCATTCT
GCCGGCTATCCAAAAAGAGAGTAAAATTCGAGTTAATACGCCAGTAAGA
 S  A  D  R  F  F  L  S  F  .  A  Q  L  C  G  H  S
   R  P  I  G  F  F  S  H  F  K  L  N  Y  A  V  I  L
    G  R  .  V  F  S  L  I  L  S  S  I  M  R  S  F

TGTTAGGCTTTGGAGAATTTGCTCTATTTCGAAAGAAATTGCTGCTTTCT
ACAATCCGAAACCTCTTAAACGAGATAAAGCTTTCTTTAACGACGAAAGA
  C  .  A  L  E  N  L  L  Y  F  E  R  N  C  C  F  L
   V  R  L  W  R  I  C  S  I  S  K  E  I  A  A  F
    L  L  G  F  G  E  F  A  L  F  R  K  K  L  L  S

AGTTTTGATTAGTCCCTATAAAATTTGCTTTCGGTTCTGAATATCCGAGA
TCAAAACTAATCAGGGATATTTTAAACGAAAGCCAAGACTTATAGGCTCT
   V  L  I  S  P  Y  K  I  C  F  R  F  .  I  S  E
  .  F  .  L  V  P  I  K  F  A  F  G  S  E  Y  P  R
    S  F  D  .  S  L  .  N  L  L  S  V  L  N  I  R  E

| EcoR I
ATGTCGTATCGTCAATGACGATTCTTTTTTAGAATTCTAATACTTTGTCC
TACAGCATAGCAGTTACTGCTAAGAAAAAATCTTAAGATTATGAAACAGG
  N  V  V  S  S  M  T  I  L  F  .  N  S  N  T  L  S
   M  S  Y  R  Q  .  R  F  F  F  R  I  L  I  L  C  P
    C  R  I  V  N  D  D  S  F  L  E  F  .  Y  F  V

TGTTTTCTGTGATTTAATGGAGAAAATATTGTTCCTTTTAGTGATCTATG
ACAAAAGACACTAAATTACCTCTTTTATAACAAGGAAAATCACTAGATAC
  C  F  L  .  F  N  G  E  N  I  V  P  F  S  D  L  C
   V  F  C  D  L  M  E  K  I  L  F  L  L  V  I  Y
    L  F  S  V  I  .  W  R  K  Y  C  S  F  .  .  S  M
```

FIG. 17F-2

```
CTCTCCCGACCATTAGGATGAGGGTTGAAGGTGAAAATACTTTCTGGTAA
GAGAGGGCTGGTAATCCTACTCCCAACTTCCACTTTTATGAAAGACCATT
  S  P  D  H  .  D  E  G  .  R  .  K  Y  F  L  V
A  L  P  T  I  R  M  R  V  E  G  E  N  T  F  W  .
 L  S  R  P  L  G  .  G  L  K  V  K  I  L  S  G  N

TTTTCCTCTCTAAATTCTTCCAAACACGACACAAGTATAATTATAGACCA
AAAAGGAGAGATTTAAGAAGGTTTGTGCTGTGTTCATATTAATATCTGGT
 I  F  L  S  K  F  F  Q  T  R  H  K  Y  N  Y  R  P
 F  S  S  L  N  S  S  K  H  D  T  S  I  I  I  D  Q
   F  P  L  .  I  L  P  N  T  T  Q  V  .  L  .  T

AGATTGATTCTTCTTATGCACCGATTCTCACTTCCCTTCCCTCTGTGTTA
TCTAACTAAGAAGAATACGTGGCTAAGAGTGAAGGGAAGGGAGACACAAT
  R  L  I  L  L  M  H  R  F  S  L  P  F  P  L  C  Y
   D  .  F  F  L  C  T  D  S  H  F  P  S  L  C  V
 K  I  D  S  S  Y  A  P  I  L  T  S  L  P  S  V  L

TGGTTATCGTTGTTACTGATGGTTGCTTAACTCATGGGGTAGCGCCTGGG
ACCAATAGCAACAATGACTACCAACGAATTGAGTACCCCATCGCGGACCC
  G  Y  R  C  Y  .  W  L  L  N  S  W  G  S  A  W
 M  V  I  V  V  T  D  G  C  L  T  H  G  V  A  P  G
  W  L  S  L  L  L  M  V  A  .  L  M  G  .  R  L  G
```

FIG. 17F-3

```
                    Pst I
                     │ Sal I
                     │  │
TGATCCGTTGACCTGCAGGTCGAC
ACTAGGCAACTGGACGTCCAGCTG ───▶ 4924
 V  I  R  .  P  A  G  R
  .  S  V  D  L  Q  V  D
   D  P  L  T  C  R  S  T
```

FIG. 17G-1

```
                                                           Hind III
                    Xho I        Sal I                     ┌── START HERE
        TCACTGGTACGGGGCCCCCCTCGAGGTCGACGGTATCGATAAGCTTTGAT
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
        AGTGACCATGCCCCGGGGGGAGCTCCAGCTGCCATAGCTATTCGAAACTA
          S   L   V   R   G   P   P   R   G   R   R   Y   R   .   A   L   I
            H   W   Y   G   A   P   L   E   V   D   G   I   D   K   L   .
          L   T   G   T   G   P   P   S   R   S   T   V   S   I   S   F   D TTGATCTCTCTTCTTCAATCTCTCTCTCTCTCTCTCTCTCTCTCTGTATG
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
        AACTAGAGAGAAGAAGTTAGAGAGAGAGAGAGAGAGAGAGAGAGACATAC
          S   S   L   N   L   S   L   S   L   S   L   S   L   Y
        S   L   L   S   I   S   L   S   L   S   L   S   L   S   L   C   M
          L   F   S   Q   S   L   S   L   S   L   S   L   S   L   S   V   C TCTTTAAATATGGTTGTAATGCTGAATTGCTATGTTTATCTTGGCCAAAC
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
        AGAAATTTATACCAACATTACGACTTAACGATACAAATAGAACCGGTTTG
          V   F   K   Y   G   C   N   A   E   L   L   C   L   S   W   P   N
            S   L   N   M   V   V   M   L   N   C   Y   V   Y   L   G   Q   T
          L   .   I   W   L   .   C   .   I   A   M   F   I   L   A   K TGTGTCCATCTTTGAGCAGATAAATCTGGCGATAATGTTCTTTTTACTGA
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
        ACCCAGGTAGAAACTCGTCTATTTAGACCGCTATTACAAGAAAAATGACT
          C   V   H   L   .   A   D   K   S   G   D   N   V   L   F   T   E
            V   S   I   F   E   Q   I   N   L   A   I   M   F   F   L   L
          L   C   P   S   L   S   R   .   I   W   R   .   C   S   F   Y   .

Pst I
        AAGCACTGCAGGATGAGGGCCTGAAATCACATCGGACGCCCACTGGGTCA
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
        TTCGTGACGTCCTACTCCCGGACTTTAGTGTAGCCTGCGGGTGACCCAGT
          S   T   A   G   .   G   P   E   I   T   S   D   A   H   W   V
            K   A   L   Q   D   E   G   L   K   S   H   R   T   P   T   G   S
          K   H   C   R   M   R   A   .   N   H   I   G   R   P   L   G   H

Nco I
        TGATGATATGGACTCCTCCACAGCGAGCAGCCATGGGATGTGAGATCCAC
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
        ACTACTATACCTGAGGAGGTGTCGCTCGTCGGTACCCTACACTCTAGGTG
          M   M   I   W   T   P   P   Q   R   A   A   M   G   C   E   I   H
            .   Y   G   L   L   H   S   E   Q   P   W   D   V   R   S   T
          D   D   M   D   S   S   T   A   S   S   H   G   M   .   D   P
```

FIG. 18A-1

```
ATAGCAGCGTAGATAAGGGAAGCCCGCAACACTAGGCTGTTGTTGTTCCA
TATCGTCGCATCTATTCCCTTCGGGCGTTGTGATCCGACAACAACAAGGT
  I  A  A  .  I  R  E  A  R  N  T  R  L  L  F  Q
     .  Q  R  R  .  G  K  P  A  T  L  G  C  C  C  S
   H  S  S  V  D  K  G  S  P  Q  H  .  A  V  V  V  P

GTAAAGATCGAAAGGTCAGGCGACAGTGACGATCGACTTTTCGAGCATG
CATTTCTAGCTTTCCAGTCCGCTGTCACTGCTAGCTGAAAAGCTCGTAC
     .  R  S  K  G  Q  A  T  V  T  I  D  F  F  E  H
   S  K  D  R  K  V  R  R  Q  .  R  S  T  F  S  S  M
   V  K  I  E  R  S  G  D  S  D  D  R  L  F  R  A  .

ATGACAACGACGACCTGCTCCTGCAATATCCGTCCCCTACCGTAGAGTGG
TACTGTTGCTGCTGGACGAGGACGTTATAGGCAGGGGATGGCATCTCACC
   D  D  N  D  D  L  L  L  Q  Y  P  S  P  T  V  E  W
 M  T  T  T  T  C  S  C  N  I  R  P  L  P  .  S  G
    .  Q  R  R  P  A  P  A  I  S  V  P  Y  R  R  V

GAATAAATGGGTTTGTAGTTGCACTATTTCTCGCAGGAATTAATTGAAAG
CTTATTTACCCAAACATCAACGTGATAAAGAGCGTCCTTAATTAACTTTC
   E  .  M  G  L  .  L  H  Y  F  S  Q  E  L  I  E  S
     N  K  W  V  C  S  C  T  I  S  R  R  N  .  L  K
   G  I  N  G  F  V  V  A  L  F  L  A  G  I  N  .  K

CCCTGCAAATTGCTGTTTCTCTTTCCTTATATTAAACCTTCCTCCTGTTA
GGGACGTTTAACGACAAAGAGAAAGGAATATAATTTGGAAGGAGGACAAT
   P  A  N  C  C  F  S  F  L  I  L  N  L  P  P  V
 A  L  Q  I  A  V  S  L  S  L  Y  .  T  F  L  L  L
   P  C  K  L  L  F  L  F  P  Y  I  K  P  S  S  C  Y

¦ BamH I          ¦ Bgl II
CATTAAAATTGCATGTTAAGACATTTCTGTATGGATCCGAACATGAGATC
GTAATTTTAACGTACAATTCTGTAAAGACATACCTAGGCTTGTACTCTAG
   T  L  K  L  H  V  K  T  F  L  Y  G  S  E  H  E  I
 H  .  N  C  M  L  R  H  F  C  M  D  P  N  M  R  S
    I  K  I  A  C  .  D  I  S  V  W  I  R  T  .  D
```

FIG. 18A-2

```
TATCATTGAAGTAATGGGTAGGATTTACATTATCATCATCATCATCT
ATAGTAACTTCATTACCCATCCTAAATGTAATAGTAGTAGTAGTAGA
  Y  H  .  S  N  G  .  D  L  H  Y  H  H  H  H  L
     I  I  E  V  M  G  R  I  Y  I  I  I  I  I  I
  L  S  L  K  .  W  V  G  F  T  L  S  S  S  S  S
```

Nco I
```
CCATGGGTTTGGATCTAATTAGACCGAAAACCTCATTTAAAATCCAACCC
GGTACCCAAACCTAGATTAATCTGGCTTTTGGAGTAAATTTTAGGTTGGG
  H  G  F  G  S  N  .  T  E  N  L  I  .  N  P  T
  S  M  G  L  D  L  I  R  P  K  T  S  F  K  I  Q  P
    P  W  V  W  I  .  L  D  R  K  P  H  L  K  S  N  P

CAATATTGGCTTGACTTGCTCCATCTCCAAGAAAAATACAACAAGAACAA
GTTATAACCGAACTGAACGAGGTAGAGGTTCTTTTTATGTTGTTCTTGTT
  P  I  L  A  .  L  A  P  S  P  R  K  I  Q  Q  E  Q
   Q  Y  W  L  D  L  L  H  L  Q  E  K  Y  N  K  N  N
    N  I  G  L  T  C  S  I  S  K  K  N  T  T  R  T

CAAAAATTTAGGATGCACATTGAATTGATTTGGTCACTATGAGAGAATCA
GTTTTTAAATCCTACGTGTAACTTAACTAAACCAGTGATACTCTCTTAGT
  Q  K  F  R  M  H  I  E  L  I  W  S  L  .  E  N  H
   K  N  L  G  C  T  L  N  .  F  G  H  Y  E  R  I
    T  K  I  .  D  A  H  .  I  D  L  V  T  M  R  E  S
```

FIG. 18A-3

```
TGGATTAAAAATATTAAAATAAAAAATAAATCATAATCATCTACTCACTC
ACCTAATTTTTATAATTTTATTTTTTATTTAGTATTAGTAGATGAGTGAG
   G   L   K   I   L   K   .   K   I   N   H   N   H   L   L   T
 M   D   .   K   Y   .   N   K   K   .   I   I   I   I   Y   S   L
W   I   K   N   I   K   I   K   N   K   S   .   S   S   T   H   S
TAACGATTCACATTCTATCCACCAAATTTGACATCGGCTTCTAATTAATT
ATTGCTAAGTGTAAGATAGGTGGTTTAAACTGTAGCCGAAGATTAATTAA
   L   T   I   H   I   L   S   T   K   F   D   I   G   F   .   L   I
   .   R   F   T   F   Y   P   P   N   L   T   S   A   S   N   .   F
     N   D   S   H   S   I   H   Q   I   .   H   R   L   L   I   N
TCATATATTAGGTTCTAAAAAATCTCTCCCTTTGACAGATGAATAAATAT
TGTTTTTTTTCCTTGTTTTTTTGTGTGGGTTTCTGTCTTCTTTTTTTTT
   S   Y   I   R   F   .   K   I   S   P   F   D   R   .   I   N   I
     H   I   L   G   S   K   K   S   L   P   L   T   D   E   .   I
 F   I   Y   .   V   L   K   N   L   S   L   .   Q   M   N   K   Y
TTCTTTTAATTCGTTAGGGAAGGATCTAATATAATATATATATATATATA
AAGAAAATTAAGCAATCCCTTCCTAGATTATATTATATATATATATATAT
   S   F   N   S   L   G   K   D   L   I   .   Y   I   Y   I   Y
 F   L   L   I   R   .   G   R   I   .   Y   N   I   Y   I   Y   I
   F   F   .   F   V   R   E   G   S   N   I   I   Y   I   Y   I   Y
TATTTATTTATTAGATTCTAACCATTTCTCTCACAAGAATATGAATCGAC
ATAAATAAATAATCTAAGATTGGTAAAGAGAGTGTTCTTATACTTAGCTG
   I   F   I   Y   .   I   L   T   I   S   L   T   R   I   .   I   D
   Y   L   F   I   R   F   .   P   F   L   S   Q   E   Y   E   S   T
     I   Y   L   L   D   S   N   H   F   S   H   P   N   M   N   R
                                         SEQ A ———▶
GGCCATATCTGCAAAAACCCACCAATT[G]TTCACAGTAAACGCTCATT[G]AA
CCGGTATAGACGTTTTTGGGTGGTTAACAAGTGTCATTTGCGAGTAACTT
     G   H   I   C   K   N   P   P   I   V   H   S   K   R   S   L   N
     A   I   S   A   K   T   H   Q   L   F   T   V   N   A   H   .
 R   P   Y   L   Q   K   P   T   N   C   S   Q   .   T   L   I   E
```

FIG. 18B-1

```
TTAAGGTCGAAATTACTTTTAAATTTCTAGAGATTTCCAATAAAATATAC
AATTCCAGCTTTAATGAAAATTTAAAGATCTCTAAAGGTTATTTTATATG
 .  G  R  N  Y  F  .  I  S  R  D  F  Q  .  N  I
   I  K  V  E  I  T  F  K  F  L  E  I  S  N  K  I  Y
     L  R  S  K  L  L  N  F  .  R  F  P  I  K  Y  T

TCGTATCTTTTACAGTGATGATGCTCCGGATGATAAGATGGAAGGATGCG
AGCATAGAAAATGTCACTACTACGAGGCCTACTATTCTACCTTCCTACGC
 L  V  S  F  T  V  M  M  L  R  M  I  R  W  K  D  A
   S  Y  L  L  Q  .  .  C  S  G  .  .  D  G  R  M  R
     R  I  F  Y  S  D  D  A  P  D  D  K  M  E  G  C

TGTGTCAGCCGCCTGCGATCTCTGTGGCGGGGACGAGACGAAGACAAGGA
ACACAGTCGGCGGACGCTAGAGACACCGCCCCTGCTCTGCTTCTGTTCCT
 C  V  S  R  L  R  S  L  W  R  G  R  D  E  D  K  D
   V  S  A  A  C  D  L  C  G  G  D  E  T  K  T  R
     C  C  Q  P  P  A  I  S  V  A  G  T  R  R  R  Q  G

CGTGAGCGGACGATACCAAGTCTTCTCCTCCCCCACCACGCACGTCTCAG
GAACTCGCCTGCTATGGTTCAGAAGAGGAGGGGGTGGTGCGTGCAGAGTC
 V  S  G  R  Y  Q  V  F  S  S  P  T  T  H  V  S
   T  .  A  D  D  T  K  S  S  P  P  P  P  R  T  S  Q
     R  E  R  T  I  P  S  L  L  L  P  H  H  A  R  L  R

ATTCCCGATACGGCCTATCCCGGTGGCGTGTGGACTGCACAGACGAACGA
TAAGGGCTATGCCGGATAGGGCCACCGCACACCTGACGTGTCTGCTTGCT
 D  S  R  Y  G  L  S  R  W  R  V  D  C  T  D  E  R
   I  P  D  T  A  Y  P  G  G  V  W  T  A  Q  T  N  E
     F  P  I  R  P  I  P  V  A  C  G  L  H  R  R  T

GTAAATGCCCATCCCCCCTCTTTCATTCTTTCTCTTTGCGTGTGTGAGAG
CATTTACGGGTAGGGGGGAGAAAGTAAGAAAGAGAAACGCACACACTCTC
 V  N  A  H  P  P  S  F  I  L  S  L  C  V  C  E  R
   .  M  P  I  P  P  L  S  F  F  L  F  A  C  V  R
     S  K  C  P  S  P  L  F  H  S  F  S  L  R  V  .  E
```

FIG. 18B-2

```
GAGCGCCTATAAATAAGCACGAAACAAGCCCCTTTTCTCTCCAAGAACAC
CTCGCGGATATTTATTCGTGCTTTGTTCGGGGAAAAGAGAGGTTCTTGTG
   S  A  Y  K  .  A  R  N  K  P  L  F  S  P  R  T
 G  A  P  I  N  K  H  E  T  S  P  F  S  L  Q  E  H
  E  R  L  .  I  S  T  K  Q  A  P  F  L  S  K  N  T

ACCACACCATTCACACACTACATCCTCTGCTTCTTCGAGCCTTTTCGCCT
TGGTGTGGTAAGTGTGTGATGTAGGAGACGAAGAAGCTCGGAAAAGCGGA
   H  H  T  I  H  T  L  H  P  L  L  L  R  A  F  S  P
 T  T  P  F  T  H  Y  I  L  C  F  F  E  P  F  R  L
  P  H  H  S  H  T  T  S  S  A  S  S  S  L  F  A

Sal I
TCCTTCCTCGTCTAACCATGTCGACCTGCGGCAACTGCGACTGCGTTGAC
AGGAAGGAGCAGATTGGTACAGCTGGACGCCGTTGACGCTGACGCAACTG
   S  F  L  V  .  P  C  R  P  A  A  T  A  T  A  L  T
 P  S  S  S  N  H  V  D  L  R  Q  L  R  L  R  .
  F  L  P  R  L  T  M  S  T  C  G  N  C  D  C  V  D

AAGAGCCAGTGCGTGTAAGTCATCCTCCATCCCTCCACCTCTTCTTCTTC
TTCTCGGTCACGCACATTCAGTAGGAGGTAGGGAGGTGGAGAAGAAGAAG
   R  A  S  A  C  K  S  S  S  I  P  P  P  L  L  L
 Q  E  P  V  R  V  S  H  P  P  S  L  H  L  F  F  F
  K  S  Q  C  V  .  V  I  L  H  P  S  T  S  S  S  S
```

FIG. 18B-3

```
                                                                    Sal I
TTCTTCTTCTTCTTCTTCTAACCTCGCCCCGTTTGTGTTTGATGAGTCGA
AAGAAGAAGAAGAAGAAGATTGGAGCGGGGCAAACACAAACTACTCAGCT
  L L L L L L L T S P R L C L M S R
    F F F F F F F . P R P V C V . . V D
      S S S S S S N L A P F V F D E S

SEQ B →
ACTCTTCCCACATCGCTCGTCAAAACTCA G AGCTTTATTAGGGAACTCAG
TGAGAAGGGTGTAGCGAGCAGTTTTGAGTCTCGAAATAATCCCTTGAGTC
   L F P H R S S K L R A L L G N I S
     S S H I A R Q N S E L Y . G T S
   T L P T S L V K T Q S F I R E H Q

C AATACTATATGTATATGTANAAGGTCAACGTTGGCTGAAGAACTTGGTT
GTTATGATATACATATACATNTTCCAGTTGCAACCGACTTCTTGAACCAA
     N T I C I C ? R S T L A E E L G
   A I L Y V V Y V ? G Q R W L K N L V
     Q Y Y M Y M ? K V N V G . R T W F

TTGCCTTTGCAGGAAGAAAGGAAACAGCTACGGTATCGATATTGTTGAGA
AACGGAAACGTCCTTCTTTCCTTTGTCGATGCCATAGCTATAACAACTCT
   F A F A G R K E T A T V S I L L R
     L P L Q E E R K Q L R Y R Y C . D
       C L C R K K G N S Y G I D I V E

CCGAGAAGAGGTACTGATTAGCTTCTTCTCCCTCCTCCTCGTCGAGGATG
GGCTCTTCTCCATGACTAATCGAAGAAGAGGGAGGAGGAGCAGCTCCTAC
   P R R G T D . L L L P P P R R G .
     R E E V L I S F F S L L L V E D
   T E K R Y . L A S S P S S S S R M

ATCAAACTAATTAGGATTACACCTTATTACCTTACCTAATGCTTTTTCCG
TAGTTTGATTAATCCTAATGTGGAATAATGGAATGGATTACGAAAAAGGC
   S N . L G L H L I T L P N A F S
   D Q T N . D Y T L L P Y L M L F P
     I K L I R I T P Y Y L T . C F F R
```

FIG. 18C-1

```
                                  Sal I
TATTCGTTTCGTCTCTTCAGCTACGTCGACGAGGTGATCGTTGCCGCAGA
++++++++++++++++++++++++++++++++++++++++++++++++++
ATAAGCAAAGCAGAGAAGTCGATGCAGCTGCTCCACTAGCAACGGCGTCT
 V  F  V  S  S  L  Q  L  R  R  R  G  D  R  C  R  R
   Y  S  F  R  L  F  S  Y  V  D  E  V  I  V  A  A  E
     I  R  F  V  S  S  A  T  S  T  R  .  S  L  P  Q

AGCTGCCGAGCATGACGGCAAGTGCAAGTGCGGCGCCGCCTGCGCCTGCA
++++++++++++++++++++++++++++++++++++++++++++++++++
TCGACGGCTCGTACTGCCGTTCACGTTCACGCCGCGGCGGACGCGGACGT
 S  C  R  A  .  R  Q  V  Q  V  R  R  R  L  R  L  H
   A  A  E  H  D  G  K  C  K  C  G  A  A  C  A  C
     K  L  P  S  M  T  A  S  A  S  A  A  P  P  A  P  A

CCGACTGCAAGTGTGGCAAC[TGA]GAAGCACTTGTGTCACTACCACTAAAA
++++++++++++++++++++++++++++++++++++++++++++++++++
GGCTGACGTTCACACCGTTGACTCTTCGTGAACACAGTGATGGTGATTTT
 R  L  Q  V  W  Q  L  R  S  T  C  V  T  T  T  K
   T  D  C  K  C  G  N  .  E  A  L  V  S  L  P  L  N
     P  T  A  S  V  A  T  E  K  H  L  C  H  Y  H  .  I

AAAAGTTTGCAATGCATAAAAAACAAAAGAACAAAAAAAAAAAAGGAAGA
++++++++++++++++++++++++++++++++++++++++++++++++++
TTTTCAAACGTTACGTATTTTTTGTTTTCTTGTTTTTTTTTTTTCCTTCT
 .  K  F  A  M  H  K  K  Q  K  N  K  K  K  K  G  R
   K  S  L  Q  C  I  K  N  K  R  T  K  K  K  K  E  E
     K  V  C  N  A  .  K  T  K  E  Q  K  K  K  R  K

AGAAGAAGGTGTGGCTATGTACTCTAATAATTCGGGCAGGCTGATAAGTT
++++++++++++++++++++++++++++++++++++++++++++++++++
TCTTCTTCCACACCGATACATGAGATTATTAAGCCCGTCCGACTATTCAA
 R  R  R  C  G  Y  V  L  .  .  F  G  Q  A  D  R  L
   E  E  G  V  A  M  Y  S  N  N  S  G  R  L  I  G
     K  K  K  V  W  L  C  T  L  I  I  R  A  G  .  .  V

GTAAGATGGGATAACGCAGTATCATCTGTGTTATCTCTGTCCTGTGTTAC
++++++++++++++++++++++++++++++++++++++++++++++++++
CATTCTACCCTATTGCGTCATAGTAGACACAATAGAGACAGGACACAATG
 .  D  G  I  T  Q  Y  H  L  C  Y  L  C  P  V  L
   C  K  M  G  .  R  S  I  I  C  V  I  S  V  L  C  Y
     V  R  W  D  N  A  V  S  S  V  L  S  L  S  C  V  T
```

FIG. 18C-2

```
AACTCTCCTATCTATCCTAGTCAATGAAATATTATTAGTATTAATCTGGT
TTGAGAGGATAGATAGGATCAGTTACTTTATAATAATCATAATTAGACCA
 Q  L  S  Y  L  S  .  S  M  K  Y  Y  .  Y  .  S  G
  N  S  P  I  Y  P  S  Q  .  N  I  I  S  I  N  L  V
   T  L  L  S  I  L  V  N  E  I  L  L  V  L  L  W

TGTGTCATTCATATATGCTGCTGCTGCTGCTGCTTCCTCTTTCACCAATC
ACACAGTAAGTATATACGACGACGACGACGACGAAGGAGAAAGTGGTTAG
 C  V  I  H  I  C  C  C  C  C  C  F  L  F  H  Q  S
  V  S  F  I  Y  A  A  A  A  A  A  S  S  F  T  N
   L  C  H  S  Y  M  L  L  L  L  L  L  P  L  S  P  I

AACCCAAAGGATCGATTGCACTGTAAGGCCCAACTTCCTCACCGATATGC
TTGGGTTTCCTAGCTAACGTGACATTCCGGGTTGAAGGAGTGGCTATACG
 T  Q  R  I  D  C  T  V  R  P  N  F  L  T  D  M
  Q  P  K  G  S  I  A  L  .  G  P  T  S  S  P  I  C
   N  P  K  D  R  L  H  C  K  A  Q  L  P  H  R  Y  A

← SEQ D
TCGCTCAGTTACGATGAATGAACAGCAACCAAACGAGTCTGC
AGCGAGTCAATGCTACTTACTT[G]TCGTTGGTTTGCTCAGAC[G]  → 2392
 L  A  Q  L  R  .  M  N  S  N  Q  T  S  L
  S  L  S  Y  D  E  .  T  A  T  K  R  V  C
   R  S  V  T  M  N  E  Q  Q  P  N  E  S  A
```

FIG. 18C-3

```
                              Sal I
              Apa I           Acc I           Cla I
                 Xho I          Hinc II         Hind III
TCACTGGTACGGGGCCCCCCTCGAGGTCGACGGTATCGATAAGCTTTGAT
AGTGACCATGCCCCGGGGGGAGCCCCAGCTGCCATAGCTATTCGAAACTA
  S  L  V  R  G  P  P  R  G  R  R  Y  R  .  A  L  I
    H  W  Y  G  A  P  L  E  V  D  G  I  D  K  L  .
 X  T  G  T  G  P  P  S  R  S  T  V  S  I  S  F  D CTCTTCTCTCAATCTCTCTCTCTCTCTCTCTCTCTCTCTCTCTCTGTATG
GAGAAGAGAGTTAGAGAGAGAGAGAGAGAGAGAGAGAGAGAGAGACATAC
  S  S  L  N  L  S  L  S  L  S  L  S  L  S  L  Y
 S  L  L  S  I  S  L  S  L  S  L  S  L  S  L  C  M
   L  F  S  Q  S  L  S  L  S  L  S  L  S  L  S  V  C CTTTAAATATGGTTGTAATGCTGAATTGCTATGTTTATCTTGGCCCAAAC
GAAATTTATACCAACATTACGACTTAACGATACAAATAGAACCGGGTTTG
  X  F  K  Y  G  C  N  A  E  L  L  C  L  S  W  P  N
   S  L  N  M  V  V  M  L  N  C  Y  V  V  Y  L  G  Q  T
    L  .  I  W  L  .  C  .  I  A  M  F  I  L  A  K TGTGTCCATCTTTGAGCAGATAAATCTGGCGATAATGTTCTTTTTACTGA
ACACAGGTAGAAACTCGTCTATTTAGACCGCTATTACAAGAAAAATGACT
  C  V  H  L  .  A  D  K  S  G  D  N  V  L  F  T  E
    V  S  I  F  E  Q  I  N  L  A  I  M  F  F  L  L
   L  C  P  S  L  S  R  .  I  W  R  .  C  S  F  Y  .

Pst I
AAGCACTGCAGGATGAGGGCCTGAAATCACATCGGACGCCCACTGGGTCA
TTCGTGACGTCCTACTCCCGGACTTTAGTGTAGCCTGCGGGTGACCCAGT
   S  T  A  G  .  G  P  E  I  T  S  D  A  H  W  V
  K  A  L  Q  D  E  G  L  K  S  H  R  T  P  T  G  S
    K  H  C  R  M  R  A  .  N  H  I  G  R  P  L  G  H

TGATGATATGGACTCCTCCACAGCGAGCAGCCATGGGATGTGAGATCCAC
ACTACTATACCTGAGGAGGTGTCGCTCGTCGGTACCCTACACTCTAGGTG
  M  M  I  W  T  P  P  Q  R  A  A  M  G  C  E  I  H
    .  Y  G  L  L  H  S  E  Q  P  W  D  V  R  S  T
   D  D  M  D  S  S  T  A  S  S  H  G  M  .  D  P
```

FIG. 19A-1

```
ATAGCAGCGTAGATAAGGGAAGCCCGCAACACTAGGCTGTTGTTGTTCCA
TATCGTCGCATCTATTCCCTTCGGGCGTTGTGATCCGACAACAACAAGGT
 X  A  A  .  I  R  E  A  R  N  T  R  L  L  L  F  Q
    .  Q  R  R  .  G  K  P  A  T  L  G  C  C  C  S
 H  S  S  V  D  K  G  S  P  Q  H  .  A  V  V  V  P

GTAAAGATCGAAAGGTCAGGCGACAGTGACGATCGACTTTTTCGAGCATG
CATTTCTAGCTTTCCAGTCCGCTGTCACTGCTAGCTGAAAAAGCTCGTAC
    .  R  S  K  G  Q  A  T  V  T  I  D  F  F  E  H
 S  K  D  R  K  V  R  R  Q  .  R  S  T  F  S  S  M
 V  K  I  E  R  S  G  D  S  D  D  R  L  F  R  A  .

ATGACAACGACGACCTGCTCCTGCAATATCCGTCCCCTACCGTAGAGTGG
TACTGTTGCTGCTGGACGAGGACGTTATAGGCAGGGGATGGCATCTCACC
 D  D  N  D  D  L  L  L  Q  Y  P  S  P  T  V  E  W
 M  T  T  T  T  C  S  C  N  I  R  P  L  P  .  S  G
    .  Q  R  R  P  A  P  A  I  S  V  P  Y  R  R  V

GAATAAATGGGTTTGTAGTTGCACTATTTCTCGCAGGAATTAATTGAAAG
CTAATTTACCCAAACATCAACGTGATAAAGAGCGTCCTTAATTAACTTTC
 E  .  M  G  L  .  L  H  Y  F  S  Q  E  L  I  E  S
    N  K  W  V  C  S  C  T  I  S  R  R  N  .  L  K
 G  I  N  G  F  V  V  A  L  F  L  A  G  I  N  .  K
```

FIG. 19A-2

```
CCCTGCAAATTGCTGTTTCTCTTTCCTTATATTAAACCTTCCTCCTGTTA
GGGACGTTTAACGACAAAGAGAAAGGAATATAATTTGGAAGGAGGACAAT
   P  A  N  C  C  F  S  F  L  I  L  N  L  P  P  V
 A  L  Q  I  A  V  S  L  S  L  Y  .  T  F  L  L  L
   P  C  K  L  L  F  L  F  P  Y  I  K  P  S  S  C  Y
                                       ┊BamH I
CATTAAAATTGCATGTTAAGACATTTCTGTATGGATCCGAACATGAGATC
GTAATTTTAACGTACAATTCTGTAAAGACATACCTAGGCTTGTACTCTAG
 T  L  K  L  H  V  K  T  F  L  Y  G  S  E  H  E  I
   H  .  N  C  M  L  R  H  F  C  M  D  P  N  M  R  S
     I  K  I  A  C  .  D  I  S  V  W  I  R  T  .  D

TATCATTGAAGTAATGGGTAGGATTTACATTATCATCATCATCATCATCT
ATAGTAACTTCATTACCCATCCTAAATGTAATAGTAGTAGTAGTAGTAGA
 Y  H  .  S  N  G  .  D  L  H  Y  H  H  H  H  H  L
   I  I  E  V  M  G  R  I  Y  I  I  I  I  I  I  I
     L  S  L  K  .  W  V  G  F  T  L  S  S  S  S  S

┊BstX I
CCATGGGTTTGGATCTAATTAGACCGAAAACCTCATTTAAAATCCAACCC
GGTACCCAAACCTAGATTAATCTGGCTTTTGGAGTAAATTTTAGGTTGGG
     H  G  F  G  S  N  .  T  E  N  L  I  .  N  P  T
   S  M  G  L  D  L  I  R  P  K  T  S  F  K  I  Q  P
 P  W  V  W  I  .  L  D  R  K  P  H  L  K  S  N  P
```

FIG. 19A-3

```
XXATATTGGCTTGACTTGCTCCATCTCCAAGAAAAATACAACAAGAACAA
XXTATAACCGAACTGAACGAGGTAGAGGTTCTTTTTATGTTGTTCTTGTT
 X  I  L  A  .  L  A  P  S  P  R  K  I  Q  Q  E  Q
   X  Y  W  L  D  L  L  H  L  Q  E  K  Y  N  K  N  N
     N  I  G  L  T  C  S  I  S  K  K  N  T  T  R  T

CAAAAATTTAGGATGCACATTGAATTGATTTGGTCACTATGAGAGAATCA
GTTTTTAAATCCTACGTGTAACTTAACTAAACCAGTGATACTCTCTTAGT
 Q  K  F  R  M  H  I  E  L  I  W  S  L  .  E  N  H
   K  N  L  G  C  T  L  N  .  F  G  H  Y  E  R  I
     T  K  I  .  D  A  H  .  I  D  L  V  T  M  R  E  S

TGGATTAAAAATATTAAAATAAAAAATAAATCATAATCATCTACTCACTC
ACCTAATTTTTATAATTTTATTTTTATTTAGTATTAGTAGATGAGTGAG
 G  L  K  I  L  K  .  K  I  N  H  N  H  L  L  T
   .  D  .  K  Y  .  N  K  K  .  I  I  I  I  Y  S  L
     W  I  K  N  I  K  N  K  S  .  S  S  T  H  S

TAACGATTCACATTCTATCCACCAAATTTGACATCGGCTTCTAATTAATT
ATTGCTAAGTGTAAGATAGGTGGTTTAAACTGTAGCCGAAGATTAATTAA
 L  T  I  H  I  L  S  T  K  F  D  I  G  F  .  L  I
   .  R  F  T  F  Y  P  P  N  L  T  S  A  S  N  .  F
     N  D  S  H  S  I  H  Q  I  .  H  R  L  L  I  N

TCATATATTAGGTTCTAAAAAATCTCTCCCTTTGACAGATGAATAAATAT
AGTATATAATCCAAGATTTTTTAGAGAGGGAAACTGTCTACTTATTTATA
 S  Y  I  R  F  .  K  I  S  P  F  D  R  .  I  N  I
   H  I  L  G  S  K  K  S  L  P  L  T  D  E  .  I
     F  I  Y  .  V  L  K  N  L  S  L  .  Q  M  N  K  Y

TTCTTTTAATTCGTTAGGGAAGGATCTAATATAATATATATATATATATA
AAGAAAATTAAGCAATCCCTTCCTAGATTATATTATATATATATATATAT
 S  F  N  S  L  G  K  D  L  I  .  Y  I  Y  I  Y
   F  L  L  I  R  .  G  R  I  .  Y  N  I  Y  I  Y  I
     F  F  .  F  V  R  E  G  S  N  I  I  Y  I  Y  I  Y
```

FIG. 19B-1

```
TATTTATTTATTAGATTCTAACCATTTCTCTCACCAGAATATGAATCGAC
ATAAATAAATAATCTAAGATTGGTAAAGAGAGTGGTCTTATACTTAGCTG
 I  F  I  Y  .  I  L  T  I  S  L  T  R  I  .  I  D
   Y  L  F  I  R  F  .  P  F  L  S  P  E  Y  E  S  T
     I  Y  L  L  D  S  N  H  F  S  H  Q  N  M  N  R
                                      MTZ SEQ A ──▶
GGCCATATCTGCAAAAACCCACCAATTGTTCACAGTAAACGCTCATTGAA
CCGGTATAGACGTTTTTGGGTGGTTAACAAGTGTCATTTGCGAGTAACTT
 G  H  I  C  K  N  P  P  I  V  H  S  K  R  S  L  N
   A  I  S  A  K  T  H  Q  L  F  T  V  N  A  H  .
     R  P  Y  L  Q  K  P  T  N  C  S  Q  .  T  L  I  E

Xba I
TTAAGGTCGAAATTACTTTTAAATTTCTAGAGATTTCCAATAAAATATAC
AATTCCAGCTTTAATGAAAATTTAAAGATCTCTAAAGGTTATTTTATATG
 .  G  R  N  Y  F  .  I  S  R  D  F  Q  .  N  I
   I  K  V  E  I  T  F  K  F  L  E  I  S  N  K  I  Y
     L  R  S  K  L  L  L  N  F  .  R  F  P  I  K  Y  T
TCGTATCTTTTACAGTGATGATGCTCCGGATGATAAGATGGAAGGATGCG
AGCATAGAAAATGTCACTACTACGAGGCCTACTATTCTACCTTCCTACGC
 L  V  S  F  T  V  M  M  L  R  M  I  R  W  K  D  A
   S  Y  L  L  Q  .  .  C  S  G  .  .  D  G  R  M  R
     R  I  F  Y  S  D  D  A  P  D  D  K  M  E  G  C
TGTGTCAGCCGCCTGCGATCTCTGTGGCGGGGACGAGACGAAGACAAGGA
ACACAGTCGGCGGACGCTAGAGACACCGCCCCTGCTCTGCTTCTGTTCCT
 C  V  S  R  L  R  S  L  W  R  G  R  D  E  D  K  D
   V  S  A  A  C  D  L  C  G  G  D  E  T  K  T  R
     V  C  Q  P  P  A  I  S  V  A  G  T  R  R  R  Q  G
CGTGAGCGGACGATACCAAGTCTTCTCCTCCCCCACCACGCACGTCTCAG
GCACTCGCCTGCTATGGTTCAGAAGGAGGGGGTGGTGCGTGCAGAGTC
   V  S  G  R  Y  Q  V  F  S  S  P  T  T  H  V  S
 T  .  A  D  D  T  K  S  S  P  P  P  P  P  R  T  S  Q
   R  E  R  T  I  P  S  L  L  L  P  H  H  A  R  L  R
```

FIG. 19B-2

```
ATTCCCGATACGGCCTATCCCGGTGGCGTGTGGACTGCACAGACGAACGA
TAAGGGCTATGCCGGATAGGGCCACCGCACACCTGACGTGTCTGCTTGCT
 D  S  R  Y  G  L  S  R  W  R  V  D  C  T  D  E  R
  I  P  D  T  A  Y  P  G  G  V  W  T  A  Q  T  N  E
   F  P  I  R  P  I  P  V  A  C  G  L  H  R  R  T

GTAAATGCCCATCCCCCCTCTTTCATTCTTTCTCTTTGCGTGTGTGAGAG
CATTTACGGGTAGGGGGGAGAAAGTAAGAAAGAGAAACGAACACACTCTC
 V  N  A  H  P  P  S  F  I  L  S  L  C  V  C  E  R
  .  M  P  I  P  P  L  S  F  F  L  F  A  C  V  R
   S  K  C  P  S  P  L  F  H  S  F  S  L  R  V  .  E

GAGCGCCTATAAATAAGCACGAAACAAGCCCCTTTTCTCTCCAAGAACAC
CTCGCGGATATTTATTCGTGCTTTGTTCGGGGAAAAGAGAGGTTCTTGTG
  S  A  Y  K  .  A  R  N  K  P  L  F  S  P  R  T
 G  A  P  I  N  K  H  E  T  S  P  F  S  L  Q  E  H
   E  R  L  .  I  S  T  K  Q  A  P  F  L  S  K  N  T

ACCACACCATTCACACACTACATCCTCTGCTTCTTCGAGCCTTTTCGCCT
TGGTGTGGTAAGTGTGTGATGTAGGAGACGAAGAAGCTCGGAAAAGCGGA
 H  H  T  I  H  T  L  H  P  L  L  L  R  A  F  S  P
  T  T  P  F  T  H  Y  I  L  C  F  F  E  P  F  R  L
   P  H  H  S  H  T  T  S  S  A  S  S  S  L  F  A
```

FIG. 19B-3

```
                          Sal I
                          ┊ Acc I
                          ┊ ┊ Hind II                      Hind II
  X C C T T C C T C G T C T A A C C A T G T C G A C C T G C G G C A A C T G C G A C T G C G T T G A C
  X G G A A G G A G C A G A T T G G T A C A G C T G G A C G C C G T T G A C G C T G A C G C A A C T G
     S  F  L  V  .  P  C  R  P  A  A  T  A  T  A  L  T
       P  S  S  S  N  H  V  D  L  R  Q  L  R  L  R  .
     X  L  P  R  L  T  M  S  T  C  G  N  C  D  C  V  D ┊ INTRON
  A A G A G C C A G T G C G T G T A A G T C A T C C T C C A T C C C T C C A C C T C T T C C C C T T C
  T T C T C G G T C A C G C A C A T T C A G T A G G A G G T A G G G A G G T G G A G A A G G G G A A G
     R  A  S  A  C  K  S  S  S  I  P  P  P  L  L  L
    Q  E  P  V  R  V  S  H  P  P  S  L  H  L  F  F  F
     K  S  Q  C  V  .  V  I  L  H  P  S  S  S  S  S Hind II
                                                              Acc I
                                                              Sal I
  T T C T T C T T C T T C T T C T A A C C T C G C C C C G T T T G T G T T T G A T G A G T C G A
  A A G A A G A A G A A G A A G A T T G G A G C G G G G C A A A C A C A A A C T A C T C A G C T
     L  L  L  L  L  L  L  T  S  P  R  L  C  L  M  S  R
       F  F  F  F  F  F  F  .  P  R  P  V  C  V  .  . V  D
     S  S  S  S  S  S  N  L  A  P  F  V  F  D  E  S MTZ SEQ B ──────▶
  C T C T T C C C A C A T C G C T C G T C A A A A C T C A G A G C T T T A T T A G G G A A C A T C A G
  G A G A A G G G T G T A G C G A G C A G T T T T G A G T C T C G A A A T A A T C C C T T G T A G T C
     L  F  P  H  R  S  S  K  L  R  A  L  L  G  N  I  S
       S  S  H  I  A  R  Q  N  S  E  L  Y  .  G  T  S
     T  L  P  T  S  L  V  K  T  Q  S  F  I  R  E  H  Q
```

FIG. 19C-1

```
                                              Hinc II
CAATACTATATGTATATGTANAAGGTCAACGTTGGCTGAAGAACTTGGTT
++++++++++++++++++++++++++++++++++++++++++++++++++
GTTATGATATACATATACATNTTCCAGTTGCAACCGACTTCTTGAACCAA
   N  T  I  C  I  C  ?  R  S  T  L  A  E  E  L  G
 A  I  L  Y  V  Y  V  ?  G  Q  R  W  L  K  N  L  V
   G  Y  Y  M  Y  M  ?  K  V  N  V  G  .  R  T  W  F INTION                        MT2 Bam/ MT2 SEQ B
TTGCCTTTGCAGGAAGAANGGAAACAGCTACNGTATCNATATTGGTTGNA
++++++++++++++++++++++++++++++++++++++++++++++++++
AACGGAAACGTCCTTCTTNCCTTTGTCGATGNCATAGNTATAACCAACNT
  F  A  F  A  G  R  ?  E  T  A  T  V  S  I  L  L  ?
   L  P  L  Q  E  E  ?  K  Q  L  ?  Y  ?  Y  C  . ?
    C  L  C  R  K  ?  G  N  S  Y  ?  I  ?  I  V  ?

CCGAAAANAGGTACTGATTANCTTCTTCTCCCTCCTCCTCGTCGANGATG
++++++++++++++++++++++++++++++++++++++++++++++++++
GGCTTTTNTCCATGACTAATNGAAGAAGAGGGAGGAGGAGCAGCTNCTAC
  P  K  ?  G  T  D  ?  L  L  L  P  P  P  R  R  ?  .
   R  K  ?  V  L  I  ?  F  F  S  L  L  L  V  ?  D
 T  E  ?  R  Y  .  L  ?  S  S  P  S  S  S  S  ?  M

ATCAAACTAATTAGGATTACNCCTTATTAC
++++++++++++++++++++++++++++++ — 1880
TAGTTTGATTAATCCTAATGNGGAATAATG
   S  N  .  L  G  L  ?  L  I  T
 D  Q  T  N  .  D  Y  ?  L  L
    I  K  L  I  R  I  T  P  Y  Y
```

FIG. 19C-2

BANANA DNA ASSOCIATED WITH FRUIT DEVELOPMENT this application claims benefit to U.S. provisional application No. 60/060,062 filed Sep. 25, 1997.

BACKGROUND OF THE INVENTION

1. Field of the Invention

The present invention relates to genes which are differentially expressed during banana fruit development, the protein products of these genes, and DNA regulatory elements which are differentially expressed during banana fruit development.

2. Description of the Related Art

Bananas represent a crop of great importance to both the world economy and as a means of supplying subsistence to a large portion of the world's population. The global banana export market is about 10% of the world's production with a $4 billion dollar value. Banana fruit are the fourth most important food in the developing world (May, G D et al. (1995) *Biotechnology* 13:486–492) with approximately 100 million people acquiring their main energy source from bananas. Bananas, like kiwifruit, papayas, and apples, are climacteric fruit, meaning they ripen in association with an ethylene signal. In the ripening process, starch degradation is associated with a respiratory climacteric in the fruit. Banana fruit ripening is characterized by a number of biochemical and physiological changes including fruit softening, changes in peel color and an increase in respiratory activity (Seymour, G B (1993) in: Seymour G B, et al. (eds) *Biochemistry of Fruit Ripening*, pp 83–106. Chapman & Hall, London). Although ethylene is produced by the fruit, ripening can also be stimulated by the application of exogenous ethylene. Alternatively, endogenous ethylene production may be stimulated, e.g., by exposing fruit to acetylene.

More specifically, the post-harvest physiology of the banana (*Musa acuminata* cv. Grand Nain) is characterized by initial harvest, a green storage phase, followed by a burst in ethylene production that signals the beginning of the climacteric period. Associated with this respiratory climacteric is a massive conversion of starch to sugars in the pulp, during which the activities of enzymes involved in starch biosynthesis decrease while those involved in starch breakdown and mobilization increase rapidly (Wu et al. (1989) *Acta Phytophysiol. Sin.* 15:145–152; Agravante et al. (1990) *J. Jpn. Soc. Food Sci. Technol.* 37:911–915; Iyare et al. (1992) *J. Sci. Food Agric.* 58: 173–176; Cordenunsi et al. (1995), *J. Agric. Food Chem.* 43:347–351; Hill et al. (1995) *Planta* 196:335–343 and 197:313–323). In addition, the rate of respiration rises sharply (Beaudry et al. (1987) *Plant Physiol.* 8:277–282; Beaudry et al. (1989) *Plant Physiol.* 91:1436–1444).

Other changes that occur during ripening include: fruit softening as a result of enzymatic degradation of structural carbohydrates (Agravante et al. (1991) *J. Jpn. Soc. Food Sci. Technol.* 38:527–532; Kojima et al. (1994) *Physiol. Plant.* 90:772–778); a decline in those polyphenol compounds responsible for the astringency of the green unripe fruit which are catalyzed by polyphenol oxidase and peroxidases (Mendoza et al. (1994) in I Uritani et al., eds., Postharvest Biochemistry of Plant Food-Materials in the Tropics. Japan Scientific Societies Press, Tokyo, pp 177–191); an increase in the activity of alcohol acetyltransferase, the enzyme that catalyzes the synthesis of isoamyl acetate—the major aroma compound of banana fruit (Harada et al. (1985) *Plant Cell Physiol.* 26:1067–1074); and a de-greening of the peel as a result of chlorophyll breakdown by chlorophyllase (Thomas et al. (1992) *Int. J. Food Sci. Technol.* 27:57–63). Stages of banana fruit ripening are scored by peel color index (PCI) numbers, on a scale from 1—very green, to 7—yellow-flecked with brown flecks (Color Preferences Chart, Customer Services Department, Chiquita Brands, Inc.,). PCI can be correlated with other biochemical and physiological parameters associated with fruit development and ripening such as ethylene biosynthesis and respiratory rate. The respiratory rate usually peaks at PCI 2 and PCI 4, respectively, in ethylene-treated bananas (Agravante et al. (1991) supra).

Associated with the respiratory climacteric is a large increase in the rate of protein synthesis (Mugugaiyan (1993) *Geobios,* 20:18–21), as well as differential protein accumulation (Dominguez-Puigjaner et al. (1992) *Plant Physiol.* 98:157–162). Poly-galacturonase (PG) has been identified as a protein that increases in banana pulp during ripening, as determined by 2-D gel electrophoresis and immuno-hybridization (id.). Many of the changes that occur during ripening require de novo protein synthesis (Areas et al. (1988) *J. Food Biochem.* 12:51–60); therefore, a secondary approach to investigate changes that occur during a ripening is to isolate transcripts encoding proteins associated with the ripening process. Analogous studies of differential gene expression have been successfully employed in other plant species.

Other enzymes associated with developing and ripening of fruit include proteinase inhibitors and chitinases (Dopico et al. (1993) *Plant Molec. Bio.* 21:437), stress-related enzymes (Ledger et al. (1994) *Plant Molec. Biol.* 25:877), β-oxidation pathway enzymes (Bojorquez et al. (1995), *Plant Molec. Biol.* 28:811), and metabolite-detoxifying enzymes (Picton et al. (1993) *Plant Molec. Biol.* 23:193). Chitinases are abundant proteins found in a wide variety of plants. Although chitinases are produced by a diversity of plant species, the presence of chitin has not been reported in higher plants. Since chitin is the major structural component of fungal cell walls, it has been proposed that chitinases serve as defense proteins with antifungal activity. Chitinases are reported to be induced in higher plants by a number of different types of stress (Linthorst (1991) *Crit. Rev. Plant Sci.* 10:123; Punja et al. (1993) *J. Nematol.* 25:526; Collinge et al. (1993) *Plant J.* 3:31). Many plant chitinases are expressed constitutively, although at a low level.

As noted above, in ripening climacteric fruit, starch degradation is associated with a respiratory climacteric in the fruit. Reactive oxygen species (ROS) are byproducts of cellular respiration, especially under conditions which result in high levels of NADH. ROS generation during respiration may be at the site of ubiquinones in the electron transport chain. Both yeast and mammalian metallothioniens may play a direct role in the cellular defense against oxidative stress by functioning as antioxidants (Dalton et al. (1994) *Nucl. Acids Res.* 22:5016–5203; Tamai et al. (1993) *Proc Nat Acad Sci (USA)* 90:8013–8017; Bauman et al. (1991) *Toxicol. Appl. Pharmacol.* 110:347–354). MT may play an additional role in supplying metal ions to Cu- and Zn-superoxide dismutase (SOD), an enzyme that catalyzes the disproportionation of superoxide anion to hydrogen peroxide and dioxygen and is thought to play an important role in protecting cells from oxygen toxicity.

Transcripts encoding MT or MT-like proteins have been isolated from many different plants (recently reviewed in Robinson et al. (1993) *Biochem J.* 295:1–10). There is accumulating evidence that the plant MT mRNAs are translated, and the protein may have a function in the plant tissues from which transcripts have been isolated. A seed-associated polypeptide ($E_c$ protein) has been purified from wheat and sequenced (Kawashima et al. 1992), and more recently, MT was reported to have been isolated from Arabidopsis (meeting abstract). Based on deduced amino acid sequences, plant MT proteins are approximately 70 aa and have characteristic cysteine-rich regions at the N and C termini, separated by a variable spacer region. Based on the number and distribution of the cysteine residues, plant MTs have been classified into two distinct types (Robinson et al. (1993), supra). Type 1 MTs have 6 N-terminal and 6 C-terminal cysteine residues, whereas type 2 have 8 cysteine residues in the N-terminal domain and 6 at the C-terminus. Although there are no strict patterns of MT expression, in general type 1 transcript abundance is high in roots, and is often metal-inducible, whereas type 2 is expressed primarily in leaves. Other transcripts have been isolated that encode proteins with homology to plant MTs but cannot be classified as either type 1 or type 2, and these include seed-specific proteins or transcripts from barley and wheat (see, Robinson et al. (1993), supra). In *Arabidopsis thaliana*, MT proteins are encoded by a gene family containing five members, two copies encoding a type 2 MT and 3 encoding a MT with homology to type 1 (Zhou et al. (1995) *Mol. Gen. Genet.* 248:318–328).

In plants transcripts encoding metallothionein-like proteins have often been isolated by differential screening. Type 2 MT have recently been isolated from plants expressed in association with senescence, leaf abcission (Coupe et al. (1995) *Planta* 197:442447), and fruit ripening (Ledger et al. (1994) *Plant Molec. Biol.* 25:877–886). Using differential screening, Ledger and Gardner (id.) found transcripts encoding MT-like proteins in developing kiwifruit. One, pKIWI503, was specifically upregulated late in fruit development, during ripening of the mature fruit.

A major component of the export market is the level of ripening control which is exerted by modern banana shipping systems. Bananas for export must be shipped under refrigeration at 12–14° C., often under controlled atmosphere (CA) conditions (i.e., low oxygen combined with $CO_2$) which reduces the effects of ethylene produced by the fruit. Exposure to ethylene for 24 hours at concentrations of 100–1000 μl per liter is used to trigger the ripening climacteric. This "gassing" step is typically done near the final point in the distribution system. Although this system is entirely functional, resulting in marketability of high quality fruit with minimal losses, there remains a role for engineered ethylene control in the banana export market. Bananas for export are harvested green at approximately 75% of full size. This is done to ensure, even with the use of low temperature and CA, that few if any of the bananas start ripening during shipment. Allowing the bananas to remain on the plant longer would result in more carbohydrate accumulation to the fruit and a direct, zero cost increase in yield. If engineered ethylene control were implemented in banana, this increased yield would come at no increased risk of premature ripening during shipment.

Moreover, linking exogenous genes to isolated gene promoters that are differentially expressed during banana ripening, and in response to ethylene, would allow for the production of exogenous protein in banana tied to the ripening process, and in other plants, controlled by ripening or exposure to ethylene.

SUMMARY OF THE INVENTION

Accordingly, a major object of the present invention is to provide isolated and purified genes which are differentially expressed during banana fruit development, and to provide the protein products of these genes.

A further object of the present invention is to provide DNA regulatory elements which are differentially expressed during banana fruit development, and chimeric genes comprising these DNA regulatory elements operably linked to heterologous DNA molecules, and plants transformed with said chimeric genes, providing for controlled expression of said heterologous DNA molecules during the development of the fruit of said plants, or in response to exogenous development signals, such as ethylene signals in said plants.

A still further object of the present invention is to provide a method for expression of a heterologous protein in fruit comprising transforming fruiting plants with one or more chimeric genes according to the present invention, exposing said fruit to the appropriate natural or exogenous development signal, such as an ethylene signal, and harvesting fruit containing said heterologous protein. The method of the present invention may further comprise isolated the proteins produced by said method from the harvested fruit. In a particularly preferred embodiment, the heterologous protein is a therapeutic protein, which may be isolated from the harvested fruit, or consumed directly in the transformed fruit by a patient in need of said therapeutic protein.

With the foregoing and other objects, advantages and features of the invention that will become hereinafter apparent, the nature of the invention may be more clearly understood by reference to the following detailed description of the preferred embodiments of the invention and to the appended claims.

30 expressed as fusion proteins with β-galactosidase in pBluescript and hybridized with P31 antiserum. The polyclonal antiserum recognizes a 35 kDa polypeptide in bacterial cultures containing in-frame cDNA inserts (pBAN3-36 and pBAN3-45) that is not present in bacterial cells containing either the pBluescript cloning vector without an insert (no insert) or chitinase cDNA inserts that are not in-frame with the β-galactosidase gene (pBAN3-30 and pBAN3-31).

Figure 7A:
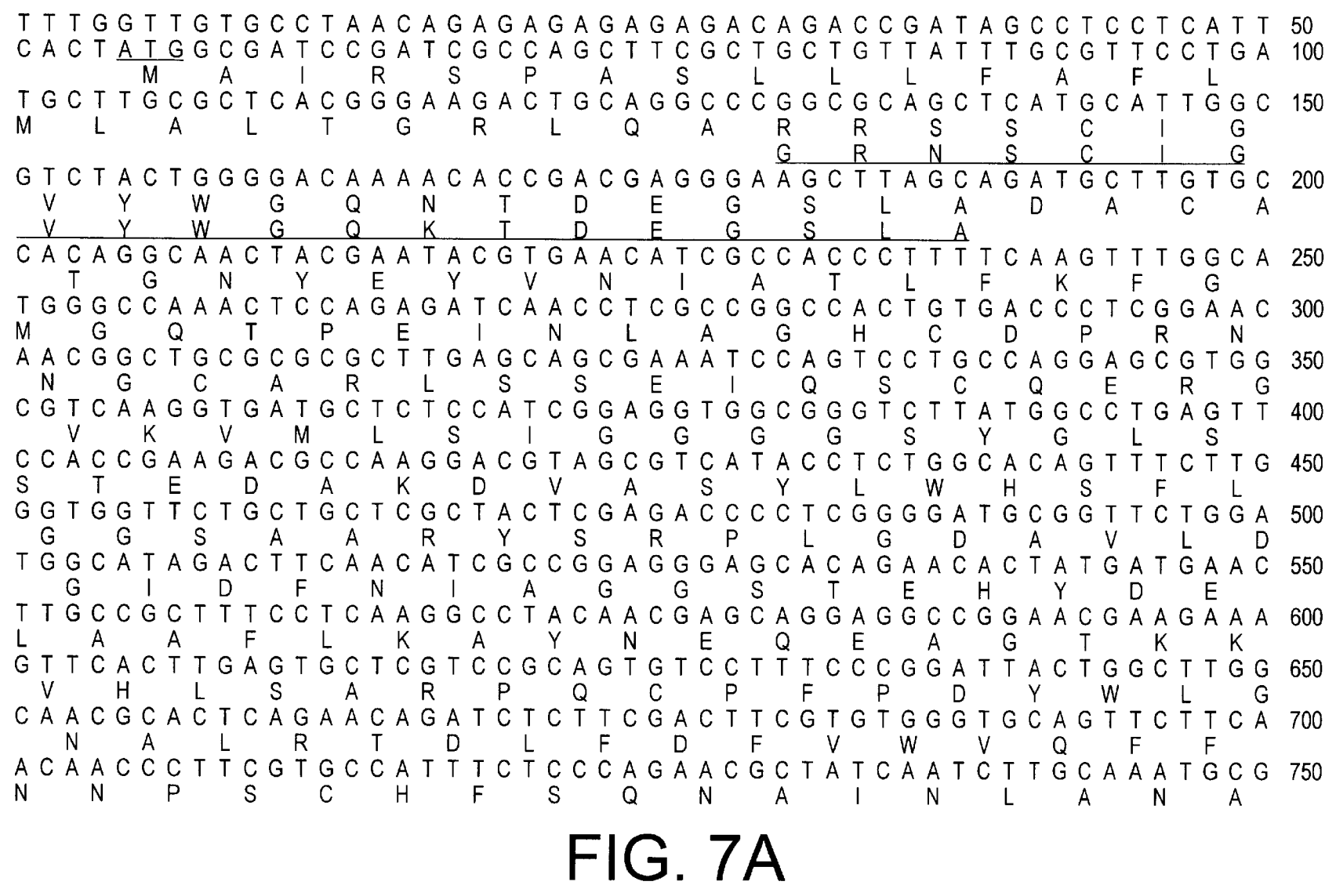
Figure 7B:
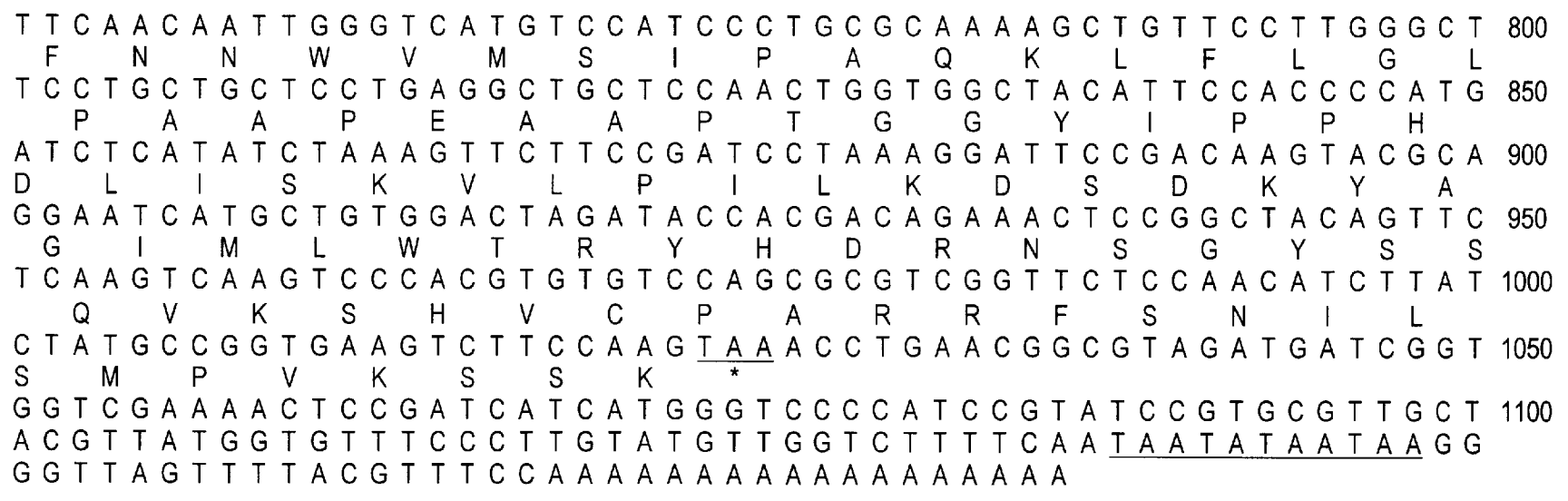

FIG. 7. [SEQ ID NOS.: 1 and 2] Complete nucleotide sequence of the cDNA clone pBAN3-30 and deduced amino acid sequence of the pBAN3-30 translation product. The N-terminal amino acid sequence obtained from purified P31 is aligned with the translation product and underlined, and is identical to the deduced amino acid sequence of pBAN3-30 at 17 of 20 residues. The translation initiation codon ATG starting at position 55 of pBAN3-30 is underlined as well as the in-frame stop codon at position 1024. Other features of the cDNA sequence include several putative polyadenylation signals between positions 1136 and 1148 (underlined).

FIG. 8(A–B). [SEQ ID NOS.: 3–8] Amino acid alignments of A) amino- and B)-carboxy-terminal regions of banana P31 with class III acidic chitinase sequences from chickpea (Cicer arietinum, 16), grape (Vitis vinifera, Busam et al. unpublished), Arabidopsis thaliana (17), tobacco (Nicotiana tabacum, 18), sugar beet (Beta vulgaris, 19). Dots indicate the amino acid residues identical to the banana P31 amino acid sequence on the top line. Dashes indicate gaps introduced to aid the alignment. A) Amino-terminal alignment illustrates the lack of sequence homology of the signal-peptide sequence of plant chitinases. B) The carboxy-terminal region indicates the 18 residue C-terminal extension unique to the banana P31 sequence.

FIG. 9. [SEQ ID NOS.: 9–10] cDNA sequences of MT F-1 and F-3.

Figure 10B:
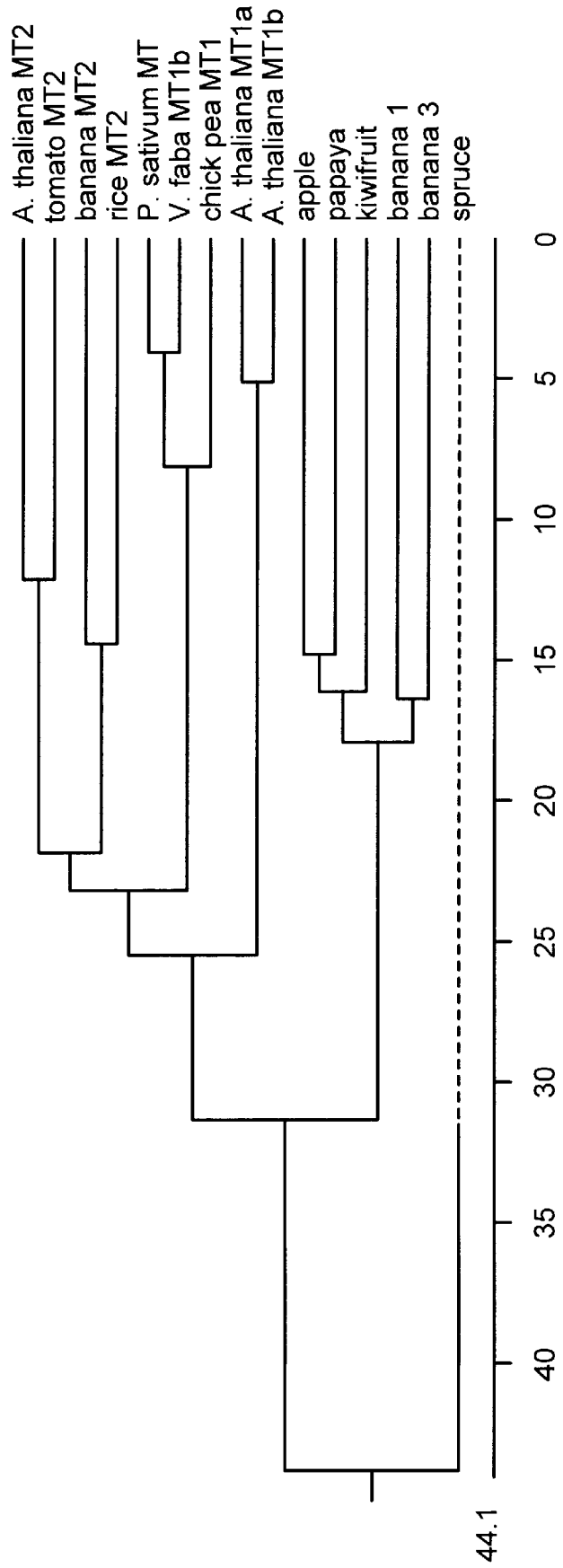

FIG. 10(A–B). A) [SEQ ID NOS.: 11–15] Alignment of deduced amino acid sequences of banana and kiwifruit, apple and papaya fruit-associated metallothionein-like proteins. Alignment was performed using Clustal (default settings). Amino acid alignment of fruit-associated MTs. Asterisks above the sequence indicate the pattern of conserved cysteine residues. A dash denotes a gap inserted in the sequence to aid in alignment. A dot indicates that the amino acid in that position is identical to the banana F1 sequence on the top line. (The total number of amino acids is indicated in parentheses at the end of the sequence.) B) Phylogenetic tree of plant MT sequences indicating that the fruit-associated MT are distinct from MT1 and MT2. GenBank Accession numbers for sequences: banana F1; banana F3; kiwifruit (1-2781 1); papaya (EMBL Y08322); apple (U61974); white spruce (L47746); Vicia faba MT1b (X91078); chickpea MT1 (Cicer arietinum) (X95708); P. sativum MT (Z23097); Oryza sativa MT-2 (D89931); banana MT2; L. esculentum MT-2 (Z68138); Arabidopsis thaliana MT2b (U1 1256); Arabidopsis thaliana MT1b (U1 1254); Arabidopsis thaliana MT1a (U1 1253).

Figure 11:

FIG. 11. Northern blot analysis of MT transcript distribution in banana. Total RNA (5 μg/lane) from different banana tissues was separated in a formaldehyde-containing 2% agarose gel, transferred to nylon membrane, and hybridized with an F1 or F3 cDNA probe. The large transcript hybridizes more strongly to the F1 probe, and is approximately 540 bases. The smaller transcript hybridizes more strongly to the F3 cDNA probe, and is approximately 370 bases. Lane labels: Pu=pulp; Pe=perl; R=root; C=corm; L=leaf.

Figure 12:
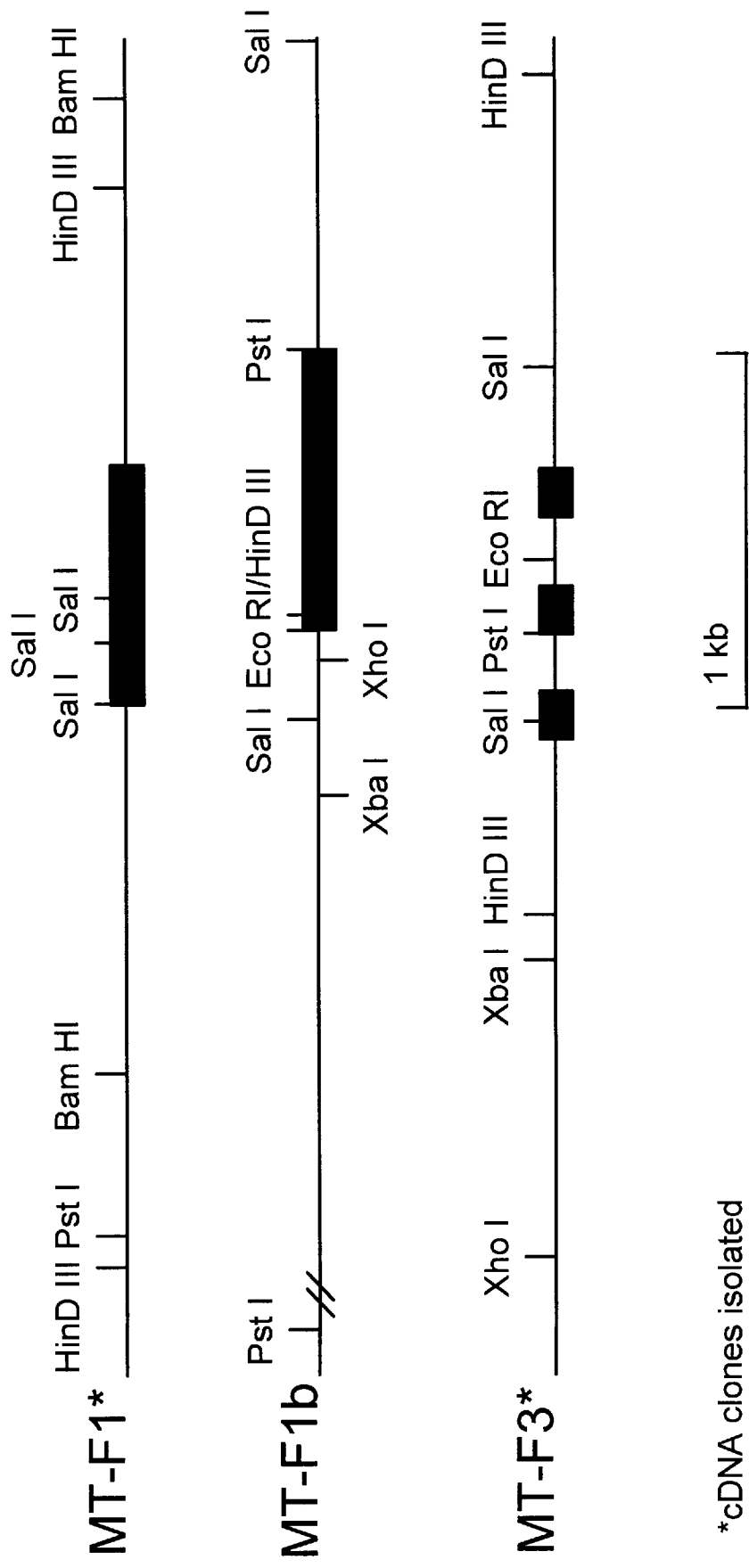

FIG. 12. Restriction maps of MT genomic clones. The maps represent the coding region and at least 1 kb of flanking DNA. The approximate scale is indicated by a dark bar.

FIG. 13. [SEQ ID NOS.: 16] Nucleotide sequence of MT P3 genomic clone, from the 5' Hind11 site to the 3' Sal1 site. A 10-base 5' sequence motif beginning at −313 from the translation start site (in capital letters) shares homology with an antioxidant response element. The putative TATA box (starting at position −96 from the translation start site) is underlined, and the three exons (beginning from the translation start site) are depicted in capital letters. At the 3' end of the sequence, the stop codon is underlined, as well as a potential polyadenylation signal (TAAATAAA).

Figure 14:
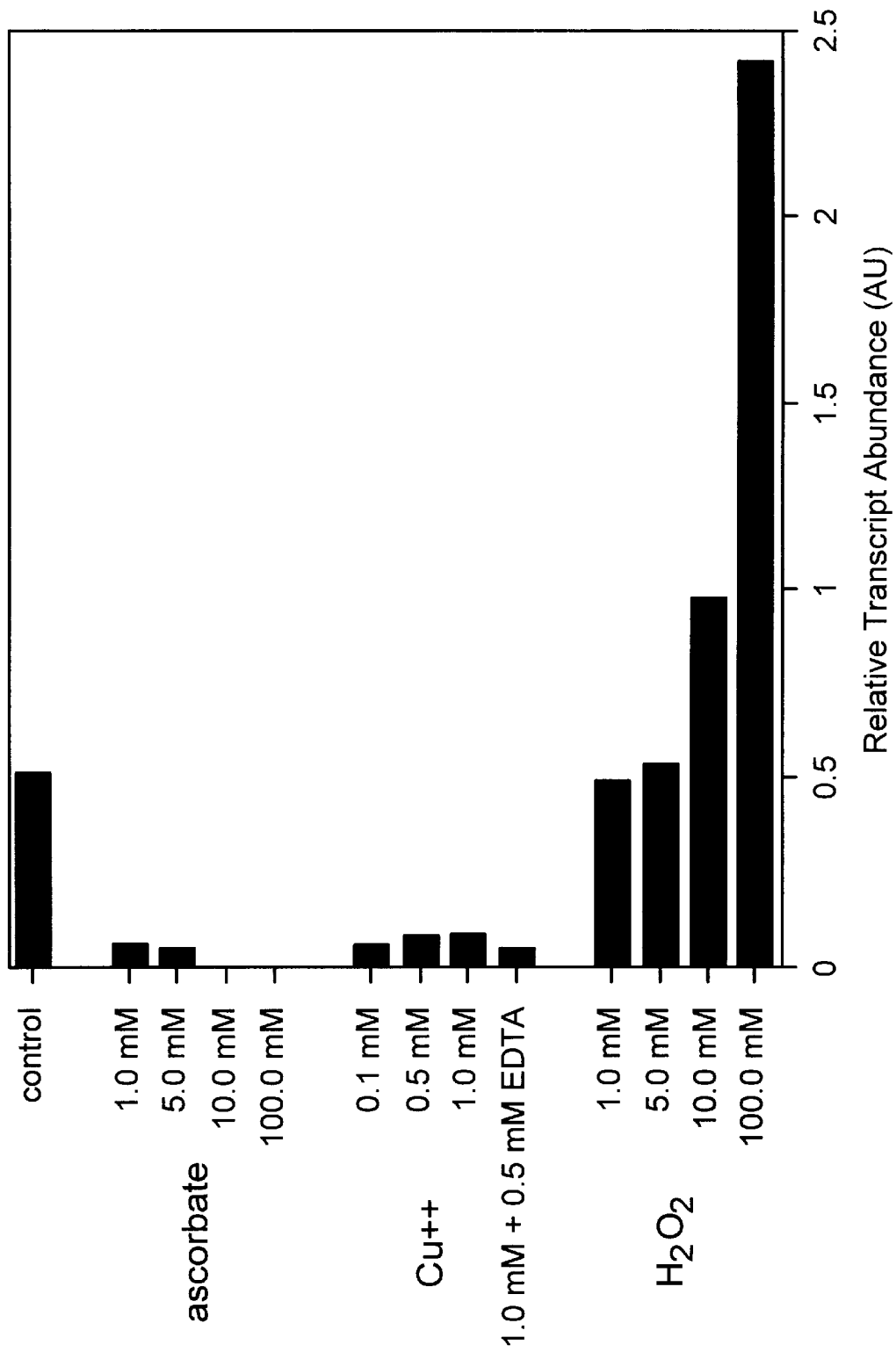

FIG. 14. Relative MT transcript abundance in banana pulp-derived protoplasts increases in the presence of hydrogen peroxide but not metal ions, as compared to the untreated control. RNA dot-blots were hybridized to the F3 cDNA probe and hybridization signal intensity, expressed in arbitrary units (AU), was normalized to 18S rRNA as a measure of total RNA loaded.

FIG. 15A–E. [SEQ ID NOS.: 17–21] Gluc. DNA and amino acid sequence

FIG. 16A–I. [SEQ ID NOS.: 22–26] Endo. DNA and amino acid sequence.

FIG. 17A–G. [SEQ ID NOS.: 27–31] Chitinase DNA and amino acid sequence.

FIG. 18A–C. [SEQ ID NOS.: 32–36] MT/F1 DNA and amino acid sequence.

FIG. 19A–C. [SEQ ID NOS.: 37–41] F1/MT#2 DNA and amino acid sequence.

DETAILED DESCRIPTION OF THE PREFERRED EMBODIMENTS OF THE INVENTION

The present invention provides isolated and purified banana proteins which are differentially produced in banana fruit during ripening. In a preferred embodiment, said proteins are selected from the group consisting of starch synthases, granule-bound starch synthases, chitinases, endochitinases, β-1,3 glucanases, thaumatin-like proteins, ascorbate peroxidases, metallothioneins, lectins, and other senescence-related genes.

The proteins of the present invention may be isolated from ripening fruit using protein purification methods well known in the art. In particular, fruit containing the protein of the present invention may be subjected to chromatographic techniques which separate proteins present in the extract according to size, affinity and charge. Fractions obtained from each chromatographic step are analyzed for the desired enzymatic activity and subjected to further purification steps. A particularly preferable method for obtaining purified proteins according to the present invention is high performance liquid chromatography (HPLC).

After a protein according to the present invention has been purified, its amino acid sequence can be determined using amino acid sequencing methods well known in the art. A particularly preferable method is Edman degradation. Having obtained sequence information on the protein of the present invention, one can design oligonucleotide probes for isolating the DNA encoding the protein of the present invention, using conventional screening methods, or amplification methods such as polymerase chain reaction (PCR). It is particularly preferable to design such oligonucleotides in a completely degenerate manner, such that oligonucleotides containing each codon encoding a particular amino acid are present in the oligonucleotide mix. Alternatively, inosine can be used at positions in the codon where degeneracies are known to be present. In a particularly preferred embodiment, the proteins of the present invention are encoded by a DNA molecule selected from the group consisting of clones pBAN 3–33, pBAN 3-18, pBAN 3-30, pBAN 3-24, pBAN 1-3, pBAN 3-28, pBAN 3-25, pBAN 3-6, pBAN 3-23, pBAN 3-32, and pBAN 3-46.

The present invention thus further provides an isolated and purified banana DNA molecule which is differentially expressed in banana fruit during ripening. More specifically, the present invention provides a DNA molecule which is differentially expressed in banana fruit during ripening, wherein said DNA molecule encodes a protein selected from the group consisting of a starch synthase, a granule-bound starch synthase, a chitinase, an endochitinase, a β-1,3 glucanase, a thaumatin-like protein, an ascorbate peroxidase, a metallothionein, a lectin, or another senescence-related gene. In a particularly preferred embodiment, these DNA molecules are the clones pBAN 3-33, pBAN 3-18, pBAN 3-30, pBAN 3-24, pBAN 1-3, pBAN 3-28, pBAN 3-25, pBAN 3-6, pBAN 3-23, pBAN 3-32, and pBAN 3-46. In another preferred embodiment, the DNA molecule of the present invention has a nucleotide sequence selected from the group consisting of SEQ ID NO: 1; SEQ ID NO: 2; and SEQ ID NO: 3.

In general, the procedures for isolating the DNA encoding a protein according to the present invention, subjecting it to partial digestion, isolating DNA fragments, ligating the fragments into a cloning vector, and transforming a host are well known in recombinant DNA technology. Accordingly, one of ordinary skill in the art can use or adapt the detailed protocols for such procedures as found in Sambrook et al. (1989), *Molecular Cloning: A Laboratory Manual,* 2nd. Ed., Cold Spring Harbor Laboratory, Cold Spring Harbor, N.Y., 3 volumes, or in any other manual on recombinant DNA technology.

Once the gene encoding a protein of the present invention has been obtained from one species, it can serve as a hybridization probe to isolate corresponding genes from the other species by cross-hybridization under low to moderate stringency conditions. Such conditions are usually found empirically by determining the conditions wherein the probe specifically cross-hybridizes to its counterpart gene with a minimum of background hybridization. Nucleic acid hybridization is a well known technique and thoroughly detailed in Sambrook et al.

As noted above, the DNA encoding the proteins of the present invention can be originally isolated using PCR. Corresponding DNAs from other species can also be isolated using PCR, and oligonucleotides for performing these subsequent PCR reactions can be optimized using the sequence information obtained from DNA cloned from the first species.

Moreover, peptides and fragments as well as chemically modified derivatives of the proteins of the present invention are also contemplated by the present invention. Briefly, any peptide fragment, derivative or analog which retains substantially the same biological activity of the protein of the present invention, and is differentially produced during fruit ripening, is contemplated. An analog may be defined herein as a peptide or fragment which exhibits the biological activity of the protein of the present invention, and which is differentially expressed during fruit ripening, but which has an amino acid substitution, insertion or deletion in comparison to the wild-type protein. Such an analog can be prepared by the "conservative" substitution of an amino acid having similar chemical properties. One of ordinary skill in the art can readily identify suitable substitutions.

Thus, it should also be appreciated that also within the scope of the present invention are DNA sequences encoding a protein according to the present invention having the same amino acid sequence as the wild-type protein, but also those DNA sequences which are degenerate to the wild-type sequence. By "degenerate to" is meant that a different three-letter codon is used to specify a particular amino acid. It is well known in the art that the following codons can be used interchangeably to code for each specific amino acid:

| Amino Acid | Abbrev. | Codons |
| --- | --- | --- |
| Phenylalanine | (Phe or F) | UUU, UUC |
| Leucine | (Leu or L) | UUA, UUG, CUU, CUC, CUA, CUG |
| Isoleucine | (Ile or I) | AUU, AUC, AUA |
| Methionine | (Met or M) | AUG |
| Valine | (Val or V) | GUU, GUC, GUA, GUG |
| Serine | (Ser or S) | UCU, UCC, UCA, UCG, AGU, AGC |
| Proline | (Pro or P) | CCU, CCC, CCA, CCG |
| Threonine | (Thr or T) | ACU, ACC, ACA, ACG |
| Alanine | (Ala or A) | GCU, GCG, GCA, GCG |
| Tyrosine | (Tyr or Y) | UAU, UAC |
| Histidine | (His or H) | CAU, CAC |
| Glutamine | (Gln or Q) | CAA, CAG |
| Asparagine | (Asn or N) | AAU, AAC |
| Lysine | (Lys or K) | AAA, AAG |
| Aspartic Acid | (Asp or D) | GAU or GAC |
| Glutamic Acid | (Glu or E) | GAA or GAG |
| Cysteine | (Cys or C) | UGU or UGC |
| Arginine | (Arg or R) | CGU, CGC, CGA, CGG, AGA, AGG |
| Glycine | (Gly or G) | GGU, GGC, GGA, GGG |
| Stop codon | | UAA (ochre), UAG (amber), UGA (opal) |

It should be understood that the codons specified above are for RNA sequences. The corresponding codons for DNA have T substituted for U.

Mutations can be made in the wild-type sequence such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The following is one example of various groupings of amino acids:

| Amino acids with nonpolar R groups | |
| --- | --- |
| Alanine | Proline |
| Valine | Phenylalanine |
| Leucine | Tryptophan |
| Isoleucine | Methionine |
| Amino acids with uncharged polar R groups | |
| Glycine | Tyrosine |

-continued

| | |
|---|---|
| Serine | Asparagine |
| Threonine | Glutamine |
| Cysteine | |

Amino acids with charged polar R groups (negatively charged at Ph 6.0)

| | |
|---|---|
| Aspartic acid | Glutamic acid |

Basic amino acids (positively charged at pH 6.0)

| | |
|---|---|
| Lysine | Arginine |
| Histidine (at pH 6.0) | |

Another grouping may be according to molecular weight (i.e., size of R groups):

| | | | |
|---|---|---|---|
| Glycine | 75 | Aspartic acid | 133 |
| Alanine | 89 | Glutamine | 146 |
| Serine | 105 | Lysine | 146 |
| Proline | 115 | Glutamic acid | 147 |
| Valine | 117 | Methionine | 149 |
| Threonine | 119 | Histidine (at pH 6.0) | 155 |
| Cysteine | 121 | Phenylalanine | 165 |
| Leucine | 131 | Arginine | 174 |
| Isoleucine | 131 | Tyrosine | 181 |
| Asparagine | 132 | Tryptophan | 204 |

Another grouping may be those amino acids with phenyl groups:

| | |
|---|---|
| Phenylalanine | Tryptophan |
| Tyrosine | |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridging with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Purification of the proteins of the present invention from natural or recombinant sources can be accomplished by conventional purification means such as ammonium sulfate precipitation, gel filtration chromatography, ion exchange chromatography, adsorption chromatography, affinity chromatography, chromatofocusing, HPLC, FPLC, and the like. Where appropriate, purification steps can be done in batch or in columns.

Peptide fragments of the proteins of the present invention can be prepared by proteolysis or by chemical degradation. Typical proteolytic enzymes are trypsin, chymotrypsin, V8 protease, subtilisin and the like; the enzymes are commercially available, and protocols for performing proteolytic digests are well known. Peptide fragments are purified by conventional means, as described above. Peptide fragments can often be identified by amino acid composition or sequence. Peptide fragments are useful as immunogens to obtain antibodies against the proteins of the present invention.

In accordance with the present invention, all or a part of a DNA molecule according to the present invention can be stably inserted in a conventional manner into the nuclear genome of a plant cell, and the so-transformed plant cell can be used to produce a transgenic plant showing improved expression of the DNA molecule according to the present invention. In this regard, a disarmed Ti-plasmid, containing a DNA molecule according to the present invention, in Agrobacterium (e.g., *A. tumefaciens*) can be used to transform a plant cell using the procedures described, for example, in EP 116.718 and EP 270,822, PCT publication 84.02913, EPA 87400544.0 and Gould et al. ((1991) *Plant Physiol.* 95: 426) which are incorporated herein by reference). Preferred Ti-plasmid vectors contain the foregoing DNA sequence between the border sequence, or at least located to the left of the right border sequence, of the T-DNA of the Ti-plasmid.

A DNA molecule according to the present invention may also be operatively linked to a promoter capable of regulating the expression of said DNA molecule, to form a chimeric gene. Said chimeric gene may then be incorporated into a replicable expression vector, as described below, for use in transforming plants. The replicable expression vectors may also be used to obtain the polypeptides of the present invention by well known methods in recombinant DNA technology.

Replicable expression vectors according to the present invention comprise a nucleic acid encoding the subject gene, i.e., the coding sequence is operably linked in proper reading frame to a nucleotide sequence element which directs expression of a protein of the present invention. In particular, the nucleotide sequence elements may include a promoter, a transcription enhancer element, a termination signal, a translation signal, or a combination of two or more of these elements, generally including at least a promoter element.

Replicable expression vectors are generally DNA molecules engineered for controlled expression of a desired gene, especially where it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated. The replicable expression vectors of this invention can express the protein of the present invention at high levels. Many of these vectors are based on pBR322, M13 and lambda and are well known in the art and employ such promoters as trp, lac, $P_L$, T7 polymerase and the like. Hence, one skilled in the art has available many choices of replicable expression vectors, compatible hosts, and well-known methods for making and using the vectors.

Other types of vectors can be used to transform plant cells, using procedures such as direct gene transfer (as described, for example, in EP 233,247), pollen mediated transformation (as described, for example, in EP 270,356, PCT publication WO 95/01856, and U.S. Pat. No. 4,407,956), liposome-mediated transformation (as described, for example, in U.S. Pat. No. 4,5376,475) and other methods such as the methods for transforming monocots described in Fromm et al. ((1990) *Bio/Technology* 8:833) and Gordon-Kamm et al.((1990) *Plant Cell* 2:603).

Preferably, the gene according to the present invention is inserted in a plant genome downstream of, and under the control of, a promoter which can direct the expression of the gene in the plant cells. Preferred promoters include, but are not limited to, the strong constitutive 35S promoter (Odell et al. (1985) *Nature* 313:810) of cauliflower mosaic virus; 35S promoter have been obtained from different isolates (Hull et al. (1987) *Virology* 86:482). Other preferred promoters include the TR1' promoter and the TR2' promoter (Velten et al.(1984) *EMBO J.* 3:2723) Alternatively, a promoter can be utilized which is not constitutive but rather is specific for one or more tissues or organs. For example, a gene according to the present invention can be selectively expressed in the green tissues of a plant by placing the gene under control of a light-inducible promoter such as the promoter of the ribulose-1,5-phosphate-carboxylase small subunit gene as described in EPA 8300921.1. Another alternative is to use a promoter whose expression is inducible by temperature or chemical factors.

It as also preferred that a gene according to the present invention be inserted upstream of suitable 3' transcription regulation signals (i.e., transcript 3' end formation and polyadenylation signals) such as the 3' untranslated end of the octopine synthase gene (Gielen et al.(1984) *EMBO J.*, 3:835–845) or T-DNA gene 7 (Velten and Schell (1985) *Nucl. Acids Res.* 13:6981–6998).

The resulting transformed plant of this invention expresses the inserted gene and is characterized by the production of high levels of the gene product. Such a plant can be used in a conventional breeding scheme to produce more transformed plants with the same improved phenotypic characteristics, or to introduce the gene into other varieties of the same or related plant species. Seeds, which are obtained from transformed plants, contain the gene as a stable genomic insert.

The present invention further encompasses compositions comprising one or more proteins according to the present invention, and a carrier therefor.

The present invention also provides isolated and purified banana DNA regulatory elements which are 5' or 3' to a gene which is differentially expressed during banana fruit development. In a preferred embodiment, said DNA regulatory elements are promoters. Said regulatory elements control the expression of genes to which they are operatively linked, and are senstitive to a plant development signal. In a preferred embodiment, the plant development signal is an ethyelene signal. The ethylene signal may be ethyelene gas released by ripening fruit, either naturally or stimulated artificially; alternatively, the ethylene signal is produced by exposure of the plant or fruit to exogenous ethylene gas.

The DNA regulatory elements of the present invention may be linked to native plant genes via homologous recombination, e.g., via the method of U.S. Pat. No. 5,272,071, the contents of which are incorporated herein by reference. Alternatively, the DNA regulatory elements of the present invention may be operatively linked to a DNA molecule which is desired to be expressed in a plant in response to a development signal, thus forming a chimeric gene. Transformation of plants with such a chimeric gene, as described above, provides for controlled expression in fruit encoded by said DNA molecule. In a particularly preferred embodiment, said DNA molecule encodes a therapeutic protein.

The DNA molecules of the present invention may be used to transform any plant in which expression of the particular protein encoded by said DNA molecules is desired. In addition, the regulatory elements of the present invention may be used to trigger gene expression in any plant in which gene expression is desired. Suitable plants for transformation with the DNA molecules and regulatory elements of the present invention include Banana (e.g., *Musa acuminata*); kiwifruit (e.g., *Actinidia deliciosa*); grape (e.g., *Vitis vinifera, V. labrusca, V. rotundifolia*); peach, nectarine, plum, apricot, cherry, almond (e.g., *Prunus persica, P. domestica, P. salicina, P. avium, P. cerasus, P. amygdalus*); pear (e.g., *Pyrus communis, P. pynifolia.*); apple (e.g., *Malus x domestica*); eggplant (e.g., *Solanum melongena*); tomato (e.g., *Lycopersicon lycopersicum, L. esculentum*); peppers (e.g., *Capciscum sp.*); peas and beans (e.g., *Phaseolus vulgaris, P. lunatus, P. Limensis, Cicer arietimum, Vigna angularis, Pisum sativum, Glycine max*); cucumbers, melons, squash and pumpkins (e.g., *Cucumis melo, C. sativus, Citrullus lanatus, Cucurbita maxima, C. pepo*); maize (e.g., *Zea mays*); rice (e.g., *Oryza sativa*); wheat; barley (e.g., *Hordeum vulgare*); tobacco (e.g., *Nicotiana tabacum*); potato (e.g., *Solanum tuberosum*); beet (e.g., *Beta vulgafis*); carrot (e.g., *Daucus carota*); parsnip (e.g., *Pastinaca sativa*); turnip, rutabaga (e.g., *Brassica rapa, B. napus*); and radish (e.g., *Raphanus sativus*). It will be understood that this is not an exclusive list, but merely suggestive of the wide range of utility of the DNA molecules and regulatory elements of the present invention.

The present invention thus also provides a method for expression of heterologous protein in fruit comprising transforming fruiting plants with a chimeric gene, replicable expression vector, or plasmid comprising a ripening-associated promoter, as described above, exposing said fruit to an ethylene signal, and harvesting fruit containing said heterologous protein. The protein may be isolated from the harvested fruit using conventional methods, including those described above. Alternatively, where the protein is a therapeutic protein, in a preferred embodiment the fruit may be directly consumed by a patient in need of the therapeutic protein, thus providing for convenient oral administration of the protein.

The following examples are presented in order to more fully illustrate the preferred embodiments of the invention. They should in no way be construed, however, as limiting the broad scope of the invention.

EXAMPLE 1

Differential Gene Expression in Ripening Banana (*Musa acuminata* cv. Grand Nain) Fruit The experiments described in this example were designed to isolate those banana genes that are differentially expressed in ripening banana fruit.

MATERIALS AND METHODS

Plant Materials

Ethylene treated and untreated banana fruit (*Musa acuminata* cv. Grand Nain) were obtained from the Northside Banana Company (Houston, Tex.). The pulp and peel of fruit representing each of the seven different stages of ripening (PCI 1 through 7) were separated and quick-frozen in liquid nitrogen. Tissues from ten individual fruit were pooled to obtain a uniform representative sample for each ripening stage and ground to a fine powder under liquid nitrogen in a stainless steel Waring blender. Ground samples were stored at −80° C. until utilized. Leaf, corm and root tissue were obtained from greenhouse-grown plants (cv Grand Nain), ground in liquid nitrogen using a mortar and pestle, and stored at −-80° C.

RNA Isolation

Pre-warmed (65° C.) RNA extraction buffer (1.4% (w/v) SDS, 2% (w/v) polyvinylpyrrolidone, 0.5 M NaCl, 0.1M sodium acetate, 0.05 M EDTA, pH 8.0, 0.1% (v/v) β-mercaptoethanol) was added to previously ground samples of pulp from PCI 1 and PCI 3 at a 5:1 tissue to buffer ratio. Samples were homogenized with two or three 30 second pulses of a Polytron tissue homogenizer (Brinkman) and incubated at 65° C. for 15 min. Starch and other cell debris were pelleted by centrifugation at 2,400 g for 10 min at room temperature and the supernatant transferred to a disposable 50 ml polypropylene screw-cap tube. After the addition of 0.2 vol. of 5 M potassium acetate, pH 4.8, samples were mixed by inversion and incubated on ice for 30 min. The resulting precipitate was pelleted by centrifugation at 20.2k rpm for 10 min at 4° C. in a Sorvall SW28 rotor. The supernatant was transferred to a disposable polypropylene centrifuge tube, and the high-molecular weight RNA was precipitated by the addition of lithium chloride to a final concentration of 2.5 M and incubation overnight at 4° C. RNA was isolated from leaf and root tissues using a CTAB isolation buffer modified from Doyle and Doyle (1987). Root and leaf tissues were ground to a powder in liquid nitrogen using a mortar and pestle. Five grams of frozen powder were added to 10 ml of prewarmed (65° C.) CTAB RNA extraction buffer (100 mM Tris-Borate, pH 8.2, 1.4 M NaCl, 20 mM EDTA, 2% (w/v) CTAB (hexadecyltrimethylammonium bromide), 0.1% (v/v) β-mercaptoethanol). Samples were homogenized with two or three 30 second pulses of a Polytron tissue homogenizer (Brinkman), and the homogenate was incubated at 65° C. for one hour. Samples were cooled to room temperature, extracted twice with an equal volume of chloroform, and the phases were separated by centrifugation. Following centrifugation, lithium chloride was added to a final concentration of 2M, and RNA was allowed to precipitate overnight at 4° C. RNA was pelleted at 4° C. for 20 min at 20 kg, washed with 70% ethanol and re-suspended in DEPC-treated $H_2O$. The RNA was phenol:chloroform (1:1) extracted and ethanol precipitated.

cDNA Library Construction

Pulp PCI 1 and 3 cDNA libraries were generated using poly(A)+mRNA prepared from total RNA using a magnetic bead separation protocol (Dynal) according to the manufacturer's instructions. Lambda Zap cDNA libraries were generated according to the supplier's protocol (Stratagene).

Differential Screening

Approximately $5 \times 10^4$ plaque-forming units (pfu) from each cDNA library were plated onto LB plates using the appropriate E. coli host strain. Duplicate plaque-lifts were generated by placing Nytran nylon filters (Schleicher and Schuell) onto plaque-containing plates for one and four minutes for the first and second filters, respectively. Filter-bound DNA was denatured for two min in 1.5 M NaCl, 0.5 M NaOH, and neutralized for four minutes in 1.5 M NaCl, 0.5 M Tris (pH 8.0). Filters were rinsed in 0.5 M Tris (pH 8.0), blotted dry, and UV crosslinked (Stratalinker, Stratagene).

Labeled first-strand cDNA probes used in the differential screening were synthesized from 15 mg total RNA in the presence of 1.5 μm [α-$^{32}$P] dCTP (3000 mCi/mmol) using an oligo(dT)$_{15}$, primer (Promega) and 15U MMLV reverse transcriptase according to the manufacturer's instructions (Promega). The mRNA template was removed by hydrolysis in 100 mm NaOH at 65° C. for 30 min. The reaction was neutralized in 100 mm Tris-HCl (pH 8.0), and the labeled first-strand cDNA was ethanol precipitated in the presence of 20 μg of carrier yeast tRNA.

Filters were pre-hybridized for 30 min in 1 mM EDTA, 0.25 M phosphate buffer (pH 7.2), 7% (w/v) SDS, and hybridized overnight at 65° C. in the same solution containing the denatured probe ($1 \times 10^7$ cpm/ml). Hybridized filters were washed twice for 30 min each at 65° C. in Wash Solution One (1 mM EDTA, 40 mM phosphate buffer, pH 7.2, 5% (w/v) SDS) and three times for 30 min each at 65° C. in Wash Solution Two (1 mM EDTA, 40 mM phosphate buffer pH 7.2, 1% (w/v) SDS). The air-dried filters were subjected to autoradiography (X-Omat X-ray film, Kodak) for 72 h at −80° C. with an intensifying screen.

Banana pulp cDNA libraries from PCI 1 and PCI 3 were each probed separately and differentially with labeled cDNA from pulp at PCI 1 and PCI 3. Plaques which demonstrated strong differential signal intensities between both probes were selected as positives. Positive plaques were then subjected to secondary screening to purify single isolates by utilizing the same probes as in the primary screening. pBluescript phagemids were excised from the isolated plaques according to the manufacturer's recommendations (Stratagene).

Sequence Analysis

Small-scale alkaline lysis plasmid preparations followed by phenol:chloroform extraction and ethanol precipitation (Sambrook et al., 1989) yielded template plasmid DNA suitable for automated sequencing. Plasmid DNA templates were sequenced, using the T3 primer, on an ABI 373A DNA sequencer (Applied Biosystems, Foster City, Calif.). Vector and 3' poly(A) residue sequences were removed from the output sequence. Edited sequences were loaded into the NCBI form for BLAST (9.1) searching on a network server (www.ncbi.nlm.nih.gov), and searches were performed using the default settings of BLASTN (Altschul et al., 1990). For some cDNA clones, no significant homology (defined as a high score above 100) with sequences in the databases was identified using BLASTN. In that event, the default settings of the BLASTX search, an algorithm that translates the nucleic acid sequence in all six frames and searches a non-redundant amino acid database for matches, were used (Gish and States, 1993).

Dot-blot Hybridization

Comparisons of the relative transcript abundance of the individual cDNA clones between PCI 1, 3 and 5 pulp were made through dot-blot hybridization experiments. Plasmids containing the cDNA inserts were affixed to nylon membrane and hybridized with first-strand cDNA from generated from PCI 1, 3 or 5 pulp RNA. The equivalent of $1 \times 10^{11}$ copies of each plasmid (approximately 0.5 μg of plasmid DNA containing a 1 kb cDNA insert) was heat denatured (95° C. for 10 min), and quenched on ice. Using a vacuum dot-blot apparatus (BioRad), target DNA was applied to HyBond N+ nylon membrane (Amersham). Membranes were air-dried, UV crosslinked (Stratalinker), and hybridized as described above using $2 \times 10^6$ cpm/ml of PCI 1, 3, and 5 radiolabeled first strand cDNA as probe. Following hybridization, membranes were exposed to a phosphorescent screen (PhosphorImager, Molecular Dynamics) and the scanned image was analyzed with the ImageQuant quantitation software.

Northern Analyses

Total RNA was isolated from banana pulp and peel at PCI 3, and from root, corm, and leaf tissues of greenhouse-grown Grand Nain banana plants. Ten micrograms of each of the RNA samples were separated by electrophoresis through formaldehyde-containing agarose gels and transferred to Nytran Plus nylon membrane (Schleicher and Schuell) using a vacuum transfer apparatus (BioRad) according to the manufacturer's recommendations. Equal RNA loading was confirmed by staining the RNA-containing nylon membranes with methylene blue (Sambrook et al.,1989). The RNA blots were hybridized with a cDNA probe representing the largest isolate from each of the eleven nonredundant groups of clones. DNA probes were synthesized using the Rad-Prime DNA Labeling System (Gibco BRL), and hybridized as described above.

RESULTS

Differential screening of approximately $10^5$ plaques with labeled pulp cDNAs resulted in the identification of approximately 100 plaques with a signal intensity sufficient to be detected by autoradiography after a 72 hour exposure to X-ray film. It was apparent from the signal intensities observed between differentially hybridized plaque lifts that the relative abundance of a number of transcripts changed between PCI 1 and 3. A total of 38 cDNA clones were isolated from banana pulp libraries by differential screening.

Sequence alignment and homology searches indicate that eleven non-redundant groups of cDNAs were identified (Table 1). Using sequence homology, BLAST searches were able to assign, with high scores between 167 and 1294, a putative identity for all clones. Amino acid sequence homology searches using the BLASTX algorithm were necessary to assign an identity to the clones encoding the putative lectin and senescence-related protein. According to the results of the sequence homology searches, all of the banana sequences are more similar to other plant genes than to genes from other organisms. There were many redundant isolates, especially of the smaller cDNAs such as those encoding the different metallothioneins. Ten clones encoding a putative chitinase, an especially abundant protein in banana pulp (R. López-Gómez, unpublished data), were isolated.

Figure 1:
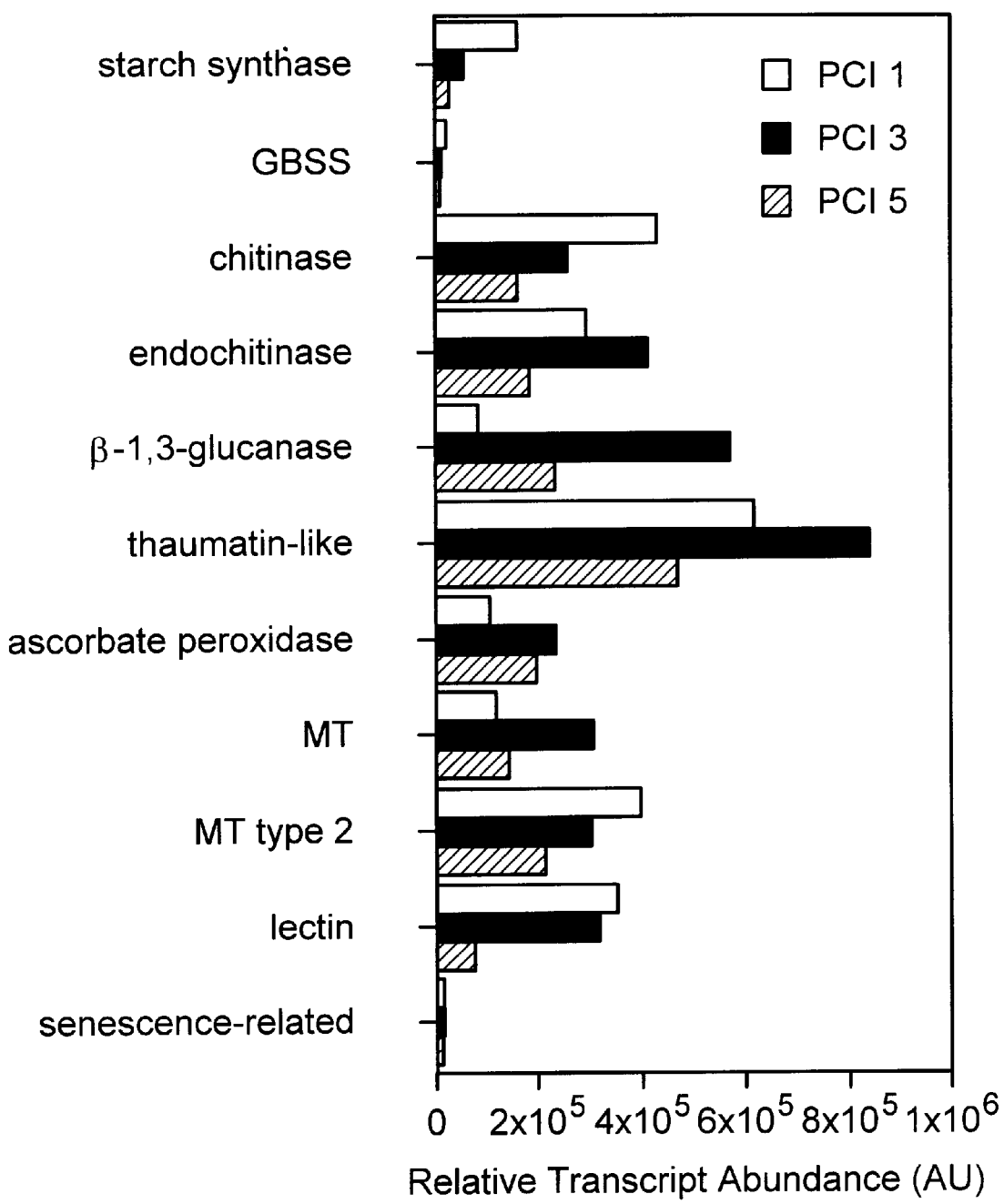
FIG. 1. Relative abundance of ripening-associated transcripts in banana pulp at PCI 1, 3 and 5. Plasmids containing the indicated cDNA were affixed to nylon membrane and hybridized with pulp radio-labeled first-strand cDNAs. Relative transcript abundance is expressed in arbitrary units (AU).
Figure 2:
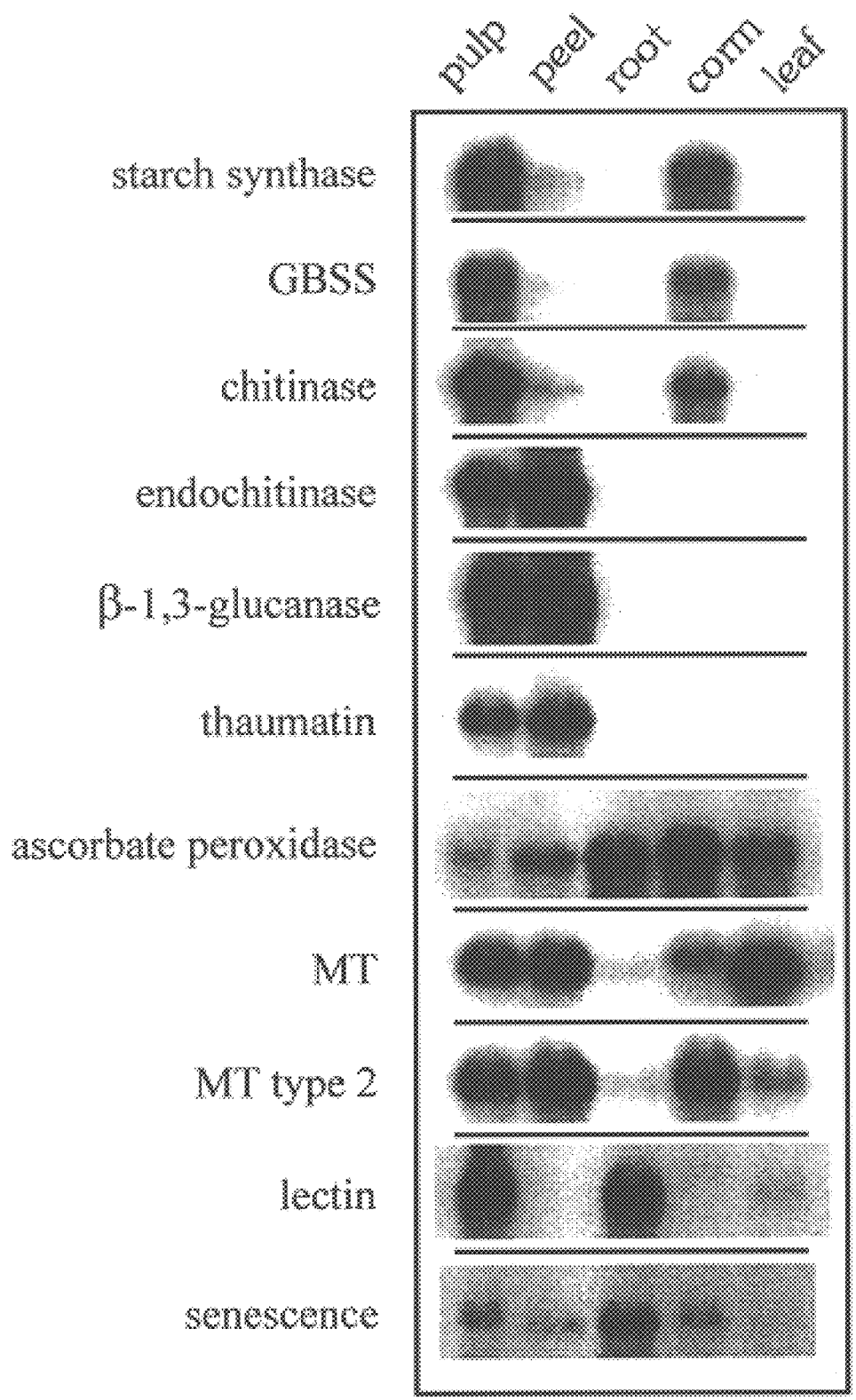
FIG. 2. Northern analyses of total RNA from pulp and peel (at PCI 3), root, corm, and leaf tissues hybridized with cDNA probes representing each of the eleven classes of differentially expressed transcripts. Putative identities of each transcript are indicated to the left of the panel.

Relative abundance among the different transcripts was estimated by hybridizing isotopically labeled first-strand cDNA to an excess of cloned cDNA which was previously dot-blotted onto nylon membrane. This technique also allowed for the confirmation of differential expression of these transcripts in pulp between PCI 1 and 3, and at a later stage of ripening, PCI 5 (FIG. 1). Relative transcript abundance of starch synthase, GBSS, chitinase, and a type 2 methallothionein decreased in pulp between PCI 1 and 3, and continued to decrease through PCI 5. There was a peak in the abundance of several of the transcripts in PCI 3 pulp, including endochitinase, glucanase, thaumatin, ascorbate peroxidase, and metallothionein. The differential expression of these banana transcripts before and after the peak in ethylene biosynthesis indicates that the transcripts that increase in abundance between PCI 1 and PCI 3 respond to ethylene. The differential expression of the eleven different groups of cDNAs in banana pulp between ripening stages PCI 1 and 3 was confirmed by Northern analyses (data not shown). Results from the dotblot hybridization were also used to estimate relative abundance of each class of cDNA in the pulp of ripening banana fruit, with thaumatin and P-1,3-glucanase being the first and second most abundant transcripts, respectively (FIG. 1).

TABLE I

Genes that are differentially expressed during banana fruit ripening. Putative cDNA identities are based on sequence homology. Number of homologous clones isolated indicated in parentheses. High scores obtained using BLASTN or BLASTX. Changes in pulp relative transcript abundance from PCI 1–3 indicated as "up" or "down" based on dot-blot hybridizations. Transcript sizes estimated from Northern analyses of pulp total RNA.

| Homology to: | Clone | High Score [P(N)[a]] | PCI 1 to 3 | Transcript size (kb) |
|---|---|---|---|---|
| sweet potato starch synthase (2) | pBAN 3-33 | 198 [6.8e-6] | down | 2.2 |
| cassava GBSS (4) | pBAN 3-18 | 1,121 [6.5e-95] | down | 2.2 |
| winged bean chitinase (10) | pBAN 3-30 | 300 [7.9e-31] | down | 1.2 |
| rice endochitinase (2) | pBAN 3-24 | 773 [3.4e-93] | up | 1.2 |
| soybean β-1,3-glucanase (2) | pBAN 1-3 | 524 [3.4e-33] | up | 1.3 |
| katemfe fruit thaumatin (2) | pBAN 3-28 | 635 [3.0e-125] | up | 1.0 |
| rice ascorbate peroxidase | pBAN 3-25 | 1,294 [4.0e-110] | up | 1.1 |
| kiwifruit metallothionein (5) | pBAN 3-6 | 218 [1.7e-11] | up | 0.5 |
| castor bean MT type 2[b] (6) | pBAN 3-23 | 518 [2.4e-33] | down | 0.6 |
| jack fruit lection (α subunit)[c] (3) | pBAN 3-32 | 177 [2.0e-19] | down | 0.8 |
| asparagus senescence-related gene[c] | pBAN 3-46 | 167 [3.1e-16] | up | 1.0 |

[a]Probability of homology occurring by chance (see Altschul et al., 1990)

Although these cDNAs are relatively abundant in the pulp of banana fruit, their patterns of expression are not limited to these tissues. Northern analyses indicate that starch synthase, GBSS, and chitinase transcripts were abundant in pulp and corm tissues, and present in peel. Expression of the endochitinase, thaumatin-like protein, and β-1,3 glucanase transcripts was limited to the pulp and peel of the fruit. Both classes of metallothionein transcripts were expressed in all tissues analyzed, but were most abundant in the pulp and peel. In comparison, MT was more abundant in leaves than Type-2 MT, while the converse was observed in the corm. Lectin transcripts were most abundant in pulp and root tissues, whereas the ascorbate peroxidase and senescence-related protein transcripts were ubiquitously expressed.

Many of the physiological changes that occur during banana fruit ripening are in response to ethylene produced in the pulp (Don-Tinguez and Vendrell, 1993; Burdon et al., 1994). In addition, ethylene also serves as a signal for other physiological changes including senescence. The cDNA clones identified in this study were isolated by differential screening at stages of fruit ripening corresponding to periods before and after the peak in ethylene biosynthesis (Agravante et al., 1991). Therefore, it is likely that some of the transcripts that increase in abundance between those stages of ripening may be regulated by ethylene, even if they do not have a direct role in the ripening process. The role of ethylene in the regulation of PR proteins (glucanase, chitinase, endochitinase, thaumatin) has been well documented. Ethylene is also believed to influence expression of ascorbate peroxidase (Mehlhorn, 1990) and metallothionein (Coupe et al., 1995)

EXAMPLE 2

The Abundant 31-Kilodalton Banana Pulp Protein is Homologous to Class-III Acidic Chitinases The experiments described in this example were designed to identify and characterize the abundant 31 kD protein from the pulp of banana fruit (*Musa acuminata* cv. Grand Nain), and to isolate a cDNA encoding this protein.

MATERIALS AND METHODS

Plant Materials

Ethylene treated and untreated banana fruit (*Musa acuminata* cv. Grand Nain) were obtained from the Northside Banana Company (Houston, Tex.). The pulp and peel of fruit representing each of the seven different stages of ripening (PCI 1 through 7) were separated and quick-frozen in liquid nitrogen. Tissues from ten individual fruit were pooled to obtain a uniform representative sample for each ripening stage and ground to a fine powder under liquid nitrogen in a stainless steel Waring blender. Ground samples were stored at −80° C. until utilized. Other banana tissues were obtained from greenhouse-grown plants (cv Grand Nain).

Protein Isolation for Antiserum Production, N-terminal Sequencing, and Western Blotting Soluble banana pulp proteins were differentially precipitated from pulp extracts with ammonium sulfate. P31 was most abundant in the 40 to 60% ammonium sulfate fraction, as determined by SDS-PAGE separation (Laemmli, U.K. (1970) *Nature* 227:680), followed by Coommassie blue staining (Sambrook et al. (1989) *Molecular Cloning, a Laboratory Manual*, Ed. 2 Cold Spring Harbor Press, Plainview, N.Y.). The 31 kDa protein band was excised from the gel, homogenized and used to immunize a rabbit for antiserum production, according to standard protocols. In addition, proteins from the 40 to 60% ammonium sulfate fraction were separated by SDS-PAGE and transferred PVDF protein sequencing membrane and stained with Coommassie blue. The stained 31 kDa protein band was excised from the membrane and the N-terminal sequence was determined.

Total protein isolated from banana root, corm, leaf, meristem, peel, and pulp at different stages of ripening were separated by SDS-PAGE and electrophoretically transferred to PVDF membrane. The membranes were incubated with the primary antiserum at 1:500 dilution, and the bound antibodies were visualized using chemiluminescence.

Northern Blot Analyses

Total RNA was isolated from banana leaf, corm, root, peel, and floral structures and from banana pulp at PCI 1 through 7 (López-Gómez, R., et al. (1992) 5:440). Agarose gel electrophoresis, and northern blotting and hybridization were performed according to standard protocols (Sambrook et al., supra). The cDNA clone pBAN3-30 was radiolabeled with $^{32}$P-dCTP by random priming and used as a probe.

pBAN3-30 Isolation and Sequence Analysis pBAN3-30 was isolated from a banana pulp cDNA library by differential screening (Clendennen, S. K. et al. (1997) *Plant Physiology*). The complete sequence of the cDNA insert was determined on both strands, and the open reading frame was translated. Sequence homology of pBAN3-30 and the translation product (P31) were determined using the BLAST search algorithm for searching GenBank (Altschul, S. F., et al. (1990) *J. Molec. Biol.* 215:403). For the amino acid alignments, plant chitinase sequences showing significant homology to P31 were downloaded from GenBank and aligned manually.

Expression of Recombinant P31

A total of ten homologous chitinase clones were isolated from the banana pulp cDNA library by differential screening, including pBAN3-30, pBAN3-31, pBAN3-36, and pBAN3-45 (Clendennen et al., supra). These four clones were used for the expression of P31 for western blot analysis of the translation products. It was determined that pBAN3-36 and pBAN3-45 contained chitinase coding sequences that were in-frame with respect to β-galactosidase in the pBluescript cloning vector. All four of the cDNA clones, in *E. coli* XL1-blue host cells, were grown to log phase in selective media and then induced by IPTG. Total bacterial proteins were separated by SDS-PAGE and transferred to PVDF membrane. The western blot was hybridized with P31 antiserum and visualized using chemiluminescence.

RESULTS

P31 Isolation and Tissue Distribution

Figure 3:
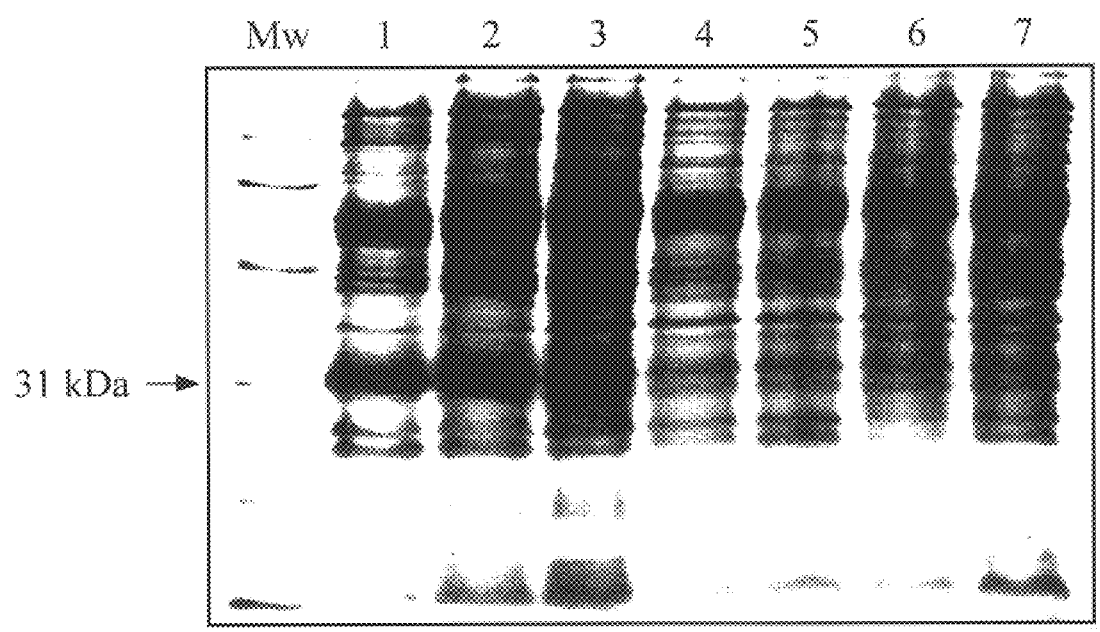
FIG. 3. Total banana pulp protein extract at different stages of ripening, separated by SDS-PAGE and stained with Coomassie blue. Protein profiles during ripening show the presence of an abundant protein of 31 kDa that decreases in relative abundance during ripening.
Figure 4:
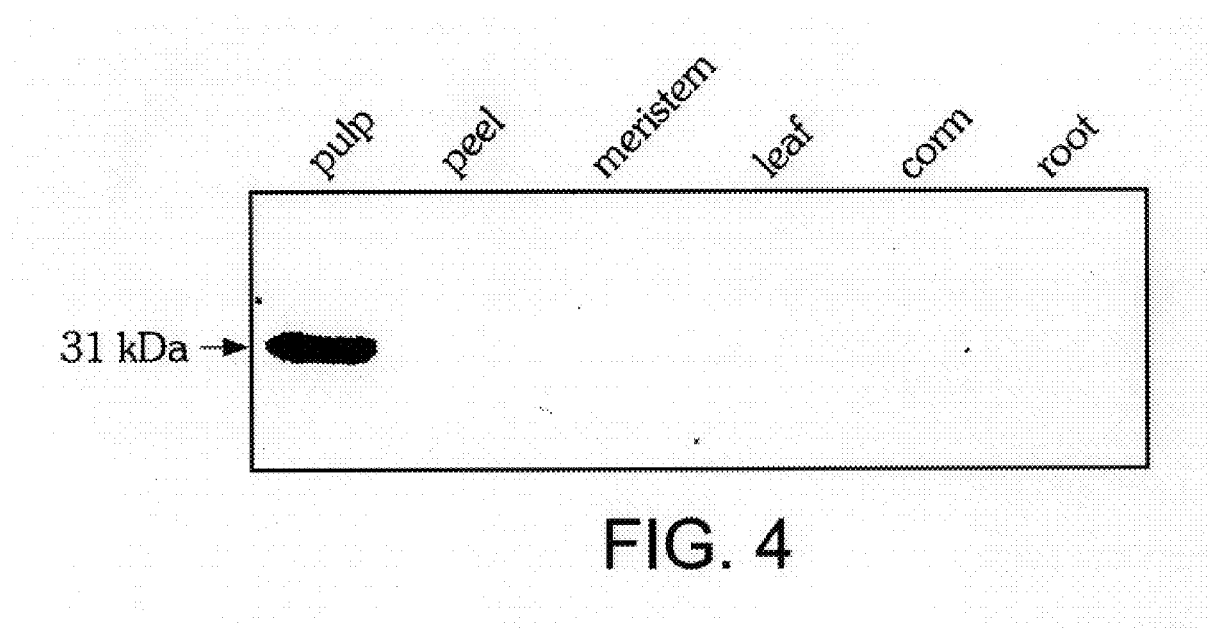
FIG. 4. Western blot analysis of total soluble protein extracted from different banana tissues and hybridized with polyclonal antiserum against purified P31. The antiserum detects a 31 kDa protein in pulp which is not present in peel, meristem, leaf, corm, or root tissue.

SDS-PAGE analysis of total proteins isolated from pulp of banana fruit at seven ripening stages indicated changes in abundance of several proteins (FIG. 1). The most abundant protein during the pre-climacteric stage (Peel Color Index or PCI 1 and 2) is a 31 kDa protein (P31) which seemed to decrease slightly in abundance as ripening proceeded (FIG. 3). This protein (P31) was partially purified by a combination of ammonium sulfate precipitation and separation by SDS-PAGE. Polyclonal antiserum was raised against the purified protein. The P31 antiserum recognizes a single 31 kDa polypeptide in banana pulp that is not present in banana peel, meristem, corm, or root tissue (FIG. 4). These results indicate that P31 is fruit-specific.

The N-terminus of the partially purified protein was sequenced and the resultant 20-amino acid sequence is: GRNSCIGVYWGQKTDEGSLA (data also appear in FIG. 7). A search of the amino acid sequence databhase (GenBank) revealed that the N-terminus of P31 shares significant homology to amino-terminal peptide sequences from purified acidic chitinases of Mongolian snake-gourd (*Trichosanthes kirilowii*; see Savary et al. (1994) *Plant Physiol.* 106:1195) and chick pea (*Cicer arietinum*; see, Vogelsgang, R., et al. (1993) *Planta* 189:60).

P31 Expression in Ripening Pulp

P31 expression in banana pulp during ripening was investigated at the protein and transcript levels. Western blot analysis of banana pulp proteins isolated at each of seven chronological stages of ripening (FIG. 5, top panel) indicates that P31 decreases in relative abundance during ripening, consistent with the observations of P31 abundance after separation by SDS-PAGE and staining with Coomassie blue. Using differential screening, several ripening-associated genes were isolated from a banana pulp cDNA library, including clones with significant homology to chitinases (Clendennen et al., supra). For determination of relative chitinase transcript abundance during ripening, total RNA was isolated from banana pulp during ripening, at PCI 1 through 7, and probed with labeled pBAN3-30. Northern blot analysis (FIG. 5, bottom panel) shows that the P31 message is strongly expressed ruing the first few ripening stages (PCI 1 through 3) after which the chitinase transcript declines in banana pulp through the later stages of ripening. This observation is consistent with the result obtained through western analysis. Northern and western blot analysis together suggest that expression of P31 is both fruit-specific and developmentally regulated in banana. While both the P31 protein and the chitinase transcript are abundant during the pre-climacteric stages of fruit ripening (PCI 1 through 3), their relative levels decrease as ripening progresses.

pBAN3-30 Encodes P31

Figure 5:
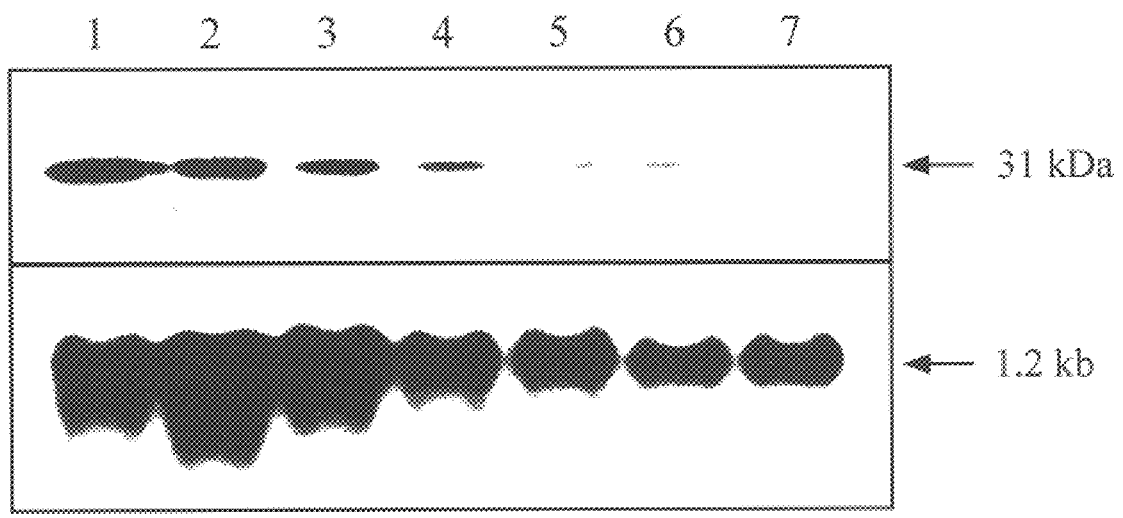
FIG. 5. Expression of P31 (top panel) and pBAN3-30 (bottom panel) in banana pulp during ripening. Total protein and RNA were isolated from banana pulp at each of seven stages of banana fruit ripening (PCI 1 through 7, numbered at top of figure). Pulp proteins were separated by SDS-PAGE and hybridized with the P31 antiserum. Total RNA (10 μg per lane) was separated by agarose gel electrophoresis and transferred to nylon membrane, and hybridized with a $^{32}P$-labeled banana chitinase cDNA probe (pBAN3-30). Both the P31 protein and the corresponding chitinase transcript at 1.2 kilobases are abundant in pulp during the early stages of ripening by decrease as ripening progresses.
Figure 6:
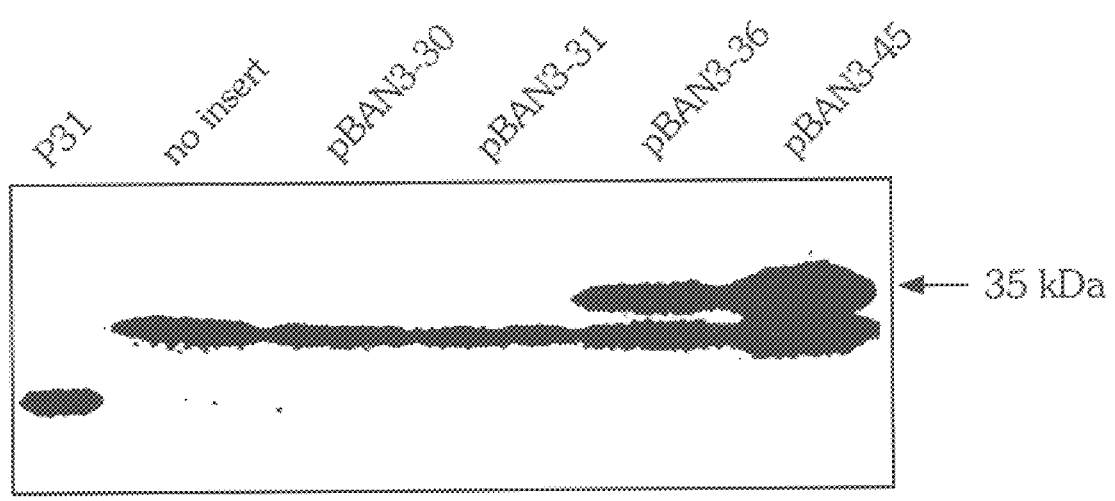
FIG. 6. Western blot analysis of the translation products of four banana chitinase cDNA clones homologous to pBAN3-

Three lines of evidence lead us to conclude that pBAN3-30 encodes the abundant 31 kDa pulp protein. First, the expression pattern of the pBAN3-30 transcript during ripening matches very closely with the profile of P31 abundance during ripening as determined by western blot analysis using the P31 antiserum, as seen in FIG. 5. Second, the P31 antiserum recognizes the translation product of the chitinase cDNA insert. The translation products of the cDNA clones pBAN3-36 and pBAN3-45, which are homologous to pBAN3-30 but have been determined to be in-frame with respect to the β-galactosidase gene in the pBluescript cloning vector (Stratagene), were expressed as fusion proteins with β-galactosidase. These fusion proteins were analyzed by western blotting and incubation with the P31 antiserum. The P31 antiserum recognizes a 35 kDa polypeptide produced in the IPTG-induced bacterial cells containing an in-frame chitinase cDNA (pBAN3-36 and pBAN3-45) that is not present in cell extracts from bacteria containing only the pBluescript plasmid (no insert) or out-of-frame chitinase cDNA inserts (pBAN3-30 and pBAN3-31) (FIG. 6). Finally, the N-terminal amino acid sequence obtained from the purified protein, which is underlined in FIG. 7, is identical to the deduced amino acid sequence of pBAN3-30 at 17 of 20 residues. This match is improved when the first amino acid residue, which is usually considered to be uncertain, is discounted. Despite the high sequence homology, the amino acid sequence from the partially purified protein is not completely identical to the amino acid sequence deduced from the cDNA clone pBAN3-30. It is possible that a contaminating polypeptide co-migrated with P31 and influenced the amino acid sequence results. Alternatively, it is possible that P31 is encoded by a gene family in banana, members of which are highly homologous, though not identical, and cannot be distinguished from one another by northern or western analyses.

Sequence Analysis of pBAN3-30

The complete nucleotide sequence of pBAN3-30 and the deduced amino acid sequence of the translation product is shown in FIG. 7. The cDNA insert is 1186 bp long and includes the entire chitinase coding region. The ATG beginning at position 55 is likely to be the translation initiation codon because the nucleotide sequence flanking the first ATG codon matches 8 of the 12 bases in the consensus for translation start sites in plants (Joshi, C. P. (1987) *Nucl. Acids Res.* 15:6543), whereas the sequences flanking another potential in-frame downstream start site (at position 100) is identical at only 5 of the 12 bases. There is an in-frame termination codon at position 1024 and several putative polyadenlyation signals between positions 1136 and 1148.

The open reading frame spans 323 amino acids from which a translation product of 35,232 Da is predicted. A GenBank search using the full cDNA sequence reveals significant homology between pBAN3-30 and chitinase genes characterized from winged bean (*Psophocarpus tetragonolobus*, M Esaka and T. Teramoto, unpublished), cow pea (*Vigna unguiculata*, L.T.T. Vo et al., unpublished), azuki bean (*Vigna angularis*; see, Ishige, F., et al. (1993) *Plant Cell Physiol.* 34:103), maize (*Zea mays*; see, Didierjean, L., et al. (1996) *Planta* 199: 1), and chick pea (*Cicer arietinum*; see, Vogelsgang, R., et al. (1993) *Plant Physiol.* 103:297). The deduced amino acid sequence of pBAN3-30 encoding P31 in banana shares sequence homology with other plant chitinases, especially with class III acidic chitinases that have been characterized from various dicots. At the amino acid level, the banana acidic chitinase amino acid sequence shows significant homology, 47–53% identity, to acidic chitinases from *Arabidopsis thaliana* (Samac, D. A., et al. (1990) *Plant Physiol.* 93:907), wine grape (*Vitis vinifera*, Busam et al, unpublished), tobacco (*Nicotiana tabacum*; see, Lawton, K. et al. (1992) *Plant Molec. Biol.* 19:735), chickpea, sugar beet (*Beta vulgaris*; see, Nielsen, K. K., et al. (1993) *Molec. Plant-Microbe Interact.* 6:495), winged bean, and cucumber (*Cucumis sativus*; see, Lawton, K. A. et al. (1994) *Molec. Plant-Microbe Interact.* 7:48).

An amino acid sequence alignment of the amino-terminal and carboxy-terminal regions of several plant acid chitinases with P31 from banana appears in FIG. 8. Hydrophilicity analysis of the deduced protein sequence of P31 reveals a hydrophobic region from amino acid 1 to 25 (underlined in FIG. 8A). This region may represent a signal sequence that would direct targeting to the ER. If this putative signal peptide is removed, the remaining sequence closely matches the N-terminal sequence obtained from the purified protein, which suggests that P31 is post-translationally processed. This signal peptide does not share significant homology with the signal peptide sequences of other plant class III acidic chitinases (see FIG. 8A), which are typically localized to the extracellular space (Punja, Z. K. et al. (1993) *J. Nematol.* 25:526; Collinge, D. V., et al. (1993) *Plant J.* 3:31; Lawton, K. et al. (1992) *Plant Molec. Biol.* 19:735; Graham, L. S., et al. (1994) *Canad. J. Botany* 72:1057; Bol, J. F. (1990) *Ann. Rev. Phytopathol.* 28:113–138).

In addition to the N-terminal signal peptide, the banana P31 sequence is distinguished from other chitinase sequences by the presence of an 19 amino acid C-terminal extension (underlined in FIG. 8B). C-terminal propeptides (CTPPs) have been identified in a number of monocot and dicot polypeptides that direct proteins to the plant vacuole. Among others, CTPPs have been characterized in vacuolar lectins from barley and rice, and from vacuolar β-1,3-glucanase and chitinase from tobacco (see, Bednarel, S. Y. (1992) *Plant Molec. Biol.* 20:133, for review). In general there is little sequence homology among plant vacuolar targeting sequences. However, weak homology can be detected between the C-terminal extension of P31 (SNILSMP) and vacuolar targeting sequences that have been characterized in the sweet potato storage protein sporamin (NPIRLP) (Linthorst, H.J.M. (1991) *Crit. Rev. Plant Sci* 10:123) and in a 2S albumin from Brazil nut (NLSPMRCP) (Saalbach, G. et al. (1996) *Plant Physiol.* 112:975).

Based on amino acid sequences, chitinases can be grouped into four classes. Class I includes a majority of chitinases described, possessing an N-terminal cysteine-rich lectin or "hevein" (chitin-binding) domain and a highly conserved catalytic domain. Class II chitinases lack the N-terminal cysteine-rich domain but have a high amino acid sequence identity to the main structure of class I chitinases. Class III chitinases show little sequence similarity to plant enzymes in class I or II, but may in fact be more similar to bacterial chitinases. The majority of class III chitinases are classified as such on the basis of homology to previously described lysozymes with chitinase activity. Class IV chitinases contain a cysteine-rich domain and conserved main structure which resemble those of class I chitinases by are significantly smaller due to four deletions (Punja, Z. K., et al. (1993) *J. Nenatol.* 25:526; Collinge, D. V., et al. (1993) *Plant J.* 3:31; Graham, L. S., et al. (1994) *Canad. J. Botany* 72:1057). Although the banana pulp chitinase shares significant sequence homology with other plant class III acidic chitinases, the predicted isoelectric point of P31 is 7.63 (neutral). In addition, studies to determine the chitinase active sites in bacterial chitinases appear to be conserved in plant, bacterial, and fungal sequences (Perlick, A. M., et al. (1996) *Plant Physiol.* 110:147). At least five highly conserved amino acids have been shown to be necessary for chitinase activity, and the deduced amino acid sequence of P31 indicates that only three of the five amino acids necessary for chitinase activity are conserved in banana P31 (not shown) (Watanabe, T., et al. (1993) *J. Biol. Chem.* 268:18567; Tsujibo, H., et al. (1993) *Biosci. Biotech. Biochem.* 57:1396).

Role of Chitinase in Banana Pulp

In plants, class III chitinases have been reported to be induced in responseto various stresses such as pathogenesis and wounding (Ishige, F., et al. (1993) *Plant Cell Physiol.* 34:103; Lawton, K., et al. (1992) *Plant Molec. Biol.* 19:735; Nielsen, K. K., et al. (1993) *Molec. Plant-Microbe Interact.* 6:495; Lawton, K. A., et al. (1994) *Molec. Plant-Microbe Interact.* 7:48; Mehta, R.A., et al. (1991) Plant Cell Physiol. 32:1057). Recently, it has been reported that the expression of several pathogenesis and stress-related proteins, including chitinases, is associated with fruit ripening. Several genes encoding pathogenesis-related proteins such as endochitinase are associated with ripening in banana pulp (Clendennen, S. K., et al. (1997) *Plant Physiol.*). Considering the antifungal activity that they exhibit in other plants, it is possible that chitinases fulfill a protective role during fruit development and ripening. However, in contrast to the ripening-associated PR-proteins studied in cherry, avocado, and tomato, banana P31 decreases in abundance during ripening. Although it is possible that the banana chitinase serves a protective role during fruit development, an alternate hypothesis is that the chitinase in banana pulp has been recruited to serve as a storage protein in this tissue.

Storage proteins are a heterogeneous group of proteins for which no defined assay is available. According to a recent review (Staswick, P. E. (1994) *Ann. Rev. Plant Physiol. Plant Molec. Biol.* 45:303), storage proteins generally share the features listed below; we relate traits of P31 to general features of storage proteins.

1) Storage proteins are very abundant. We have found P31 to be very abundant in unripe banana pulp, accounting for approximately 20 to 30% of total soluble pulp protein. 2) Storage proteins are preferentially degraded during a subsequent developmental stage. For example, a vegetative storage protein characterized from the bark of poplar trees accumulates during fall and winter and is degraded during shoot growth in the spring. P31 is preferentially degraded during banana fruit ripening. Both the transcript and protein abundance decrease during ripening. If P31 is indeed a storage protein in banana pulp, this preferential degradation implies the existence of a protease specific to the storage protein, and inhibition of the protease would inhibit degradation of the storage protein. 3) Storage proteins are generally localized in storage vacuoles within the cell. The sub-cellular localization of P31 has not yet been determined. According to the deduced amino acid sequence of P31, there is a putative signal peptide sequence for P31 that is 25 amino acids long and hydrophobic. In addition, the amino acid sequence of P31 from banana pulp is distinguished from other plat class III acid chitinases by the presence of an 18 amino acid C-terminal extension that shows some homology to previously characterized C-terminal vacuolar targeting signals, suggesting vacuolar localization of P31. 4) Many storage proteins contain a large proportion of amino acid residues with nitrogen-containing R-groups. Amino acid composition analysis of P31 indicates that 22% of residues have N-containing R-groups (Trp, Gln, Asn, Lys, Arg, His). This is approximately the same proportion of N-containing amino acids in vegetative storage proteins from soybean and poplar (21–25%). Interestingly, the amino acid composition of P31 is not significantly higher than the N— of other plant chitinases (17–23%). 5) Storage proteins typically lack any other metabolic or structural role. However, this is not necessarily true for soybean vegetative storage protein, which has retained a minimal acid phosphatase activity, and patatin, a potato tuber storage protein that exhibits residual lipid acyl hydrolase activity. Preliminary evidence suggests that protein extracts from banana pulp have very low chitinase activity, as measured by soluble chitobiose released from radiolabeled chitin. In addition, only three of the five amino acids which have been determined to be essential for chitinase activity are conserved in P31. Taken together, this evidence lends support to the hypothesis that P31, while sharing sequence homology with plant chitinases, may actually be serving as a storage protein in banana pulp.

EXAMPLE 3

A Novel Fruit-Associated Class of Metallothionein-Like Proteins from Banana (*Musa acuminata* cv Grand nain) Characterization of the Gene Family and Induction by $H_2O_2$ In the experiments described in this Example, the gene family encoding the fruit-associated MTs is characterized, and sequence and functional evidence is provided that at least one member functions as an antioxidant during fruit ripening.

MATERIALS AND METHODS

Plant Materials

Ethylene treated and untreated banana fruit (*Musa acuminata* cv. Grand Nain) were obtained from the Northside Banana Company (Houston, Tex.). The pulp and peel of fruit representing different stages of ripening (PCI 1 and 3) were separated and quick-frozen in liquid nitrogen. Tissues from ten individual fruit were pooled to obtain a uniform representative sample for each ripening stage and ground to a fine powder under liquid nitrogen in a stainless steel Waring blender. Ground samples were stored at −80° C. until utilized. Leaf, corm and root tissue were obtained from greenhouse-grown plants (cv Grand Nain), ground in liquid nitrogen using a mortar and pestle, and stored at −80° C.

RNA Isolation and Northern Blotting

Pre-warmed (65° C.) RNA extraction buffer (1.4% (w/v) SDS, 2% (w/v) polyvinylpyrrolidone, 0.5 M NaCl, 0.1M sodium acetate, 0.05 M EDTA (pH 8.0) 0.1% (v/v) β-mercaptoethanol) was added to previously ground samples of pulp at a ratio of 5 ml buffer per gram of tissue. Samples were homogenized with several short bursts of a tissue homogenizer (Polytron, Brinkman) and incubated at 65° C. for 15 min. Starch and other cell debris were pelleted by centrifugation at 2,400 g for 10 min at room temperature and the supernatant transferred to a disposable polypropylene tube. After the addition of 0.2 vol. of 5 M potassium acetate (pH 4.8), the samples were mixed and incubated on ice for 30 min. The resulting precipitate was pelleted by centrifugation at 20,200 rpm for 10 min at 4° C. in a Sorvall SW28 rotor. The supernatant was transferred to a disposable polypropylene centrifuge tube, and the high-molecular weight RNAs were precipitated by the addition of lithium chloride to a final concentration of 2.5 M and incubation overnight at 4° C.

RNA was extracted from previously frozen ground peel, root, leaf, and corm tissue using CTAB extraction.

Five micrograms of total RNA from root, corm, and leaf tissue of greenhouse-grown plants, and from peel and pulp (PCI 3) were separated by electrophoresis in formaldehyde-containing 2% agarose gels and transferred to nylon membrane (Nytran Plust, Schleicher and Schuell) using 20×SSPE as a transfer buffer and a vacuum transfer apparatus (Bio-Rad). Equal RNA loading was confirmed by staining the RNA on the nylon membranes with methylene blue (Sambrook et al., 1989). RNA blots were prehybridized in 1 mM EDTA, 0.25 M phosphate buffer (pH 7.2), 7% (w/v) SDS, and hybridized overnight at 65° C. in the same solution containing the denatured probe ($1 \times 10^7$ cpm/ml). Hybridized filters were washed twice for 30 min each at 65° C. in Wash Solution One [1 mM EDTA, 40 mM phosphate buffer (pH 7.2) 5% (w/v) SDS] and three times for 30 min each at 65° C. in Wash Solution Two [1 mM EDTA, 40 mM phosphate buffer (pH 7.2), 1% (w/v) SDS]. The air-dried filters were subjected to autoradiography (X-Omat X-ray film, Kodak) at −80° C. with an intensifying screen. The RNA blots were hybridized with a cDNA probe representing either the MT cDNA clone isolated from library 1 or 3, using the Rad-Prime DNA Labeling System (Gibco BRL) to label the DNA probes.

Genomic DNA Isolation and Southern Blotting

Leaf tissue was ground with a mortar and pestle under liquid nitrogen and added to a tube containing pre-warmed (65° C.) DNA isolation buffer. The mixture was incubated at 65° C. for 30 minutes, then extracted twice with an equal volume of chloroform. After the second extraction, DNA was precipitated from the aqueous phase by the addition of an equal volume of isopropanol, and mixed by gently inverting the tube. DNA was pelleted by centrifugation, washed with 70% ethanol, dried briefly, and resuspended in TE (pH 8.0). DNA samples were treated with RNase, then phenol extract with TE buffered phenol by rocking gently, chloroform extracted, and precipitated with 2.5 vol ethanol.

For the genomic Southern blots, 15 μg of genomic DNA was digested with restriction endonucleases BamHI, HinDIII, EcoRI, PstI, and SalI (Promega), and restriction fragments were separated by electrophoresis on a 0.7% agarose gel. DNA in the gel was denatured (1.5 M NaCl, 0.5 M NaOH) and neutralized (1.5 M NaCl, 0.5 M Tris, pH 8.0) before being transferred to nylon membrane (S&S Nytran Plus) using a BioRad vacuum transfer apparatus. DNA was covalently crosslinked to membrane by UV irradiation (Stratalinker, Stratagene), and the membrane was hybridized separately with probes corresponding to the MT cDNA clones isolated from the banana pulp cDNA libraries from PCI 1 and 3 (MT-F1 and MT-F3).

Genomic Library Screening and Mapping

Approximately $6 \times 10^5$ primary plaques from a *Musa acuminata* cv Grand Nain λ FIX genomic library (Stratagene) were screened with the MT cDNA probe isolated from the PCI pulp cDNA library (MT-F1). Plaque-lifts containing filter-bound λphage DNA was denatured for two min in 1.5 M NaCl, 0.5 M NaOH, and neutralized for four minutes in 1.5 M NaCl, 0.5 M Tris (pH 8.0). Filters were rinsed in 0.5 M Tris (pH 8.0), blotted dry, and the DNA was covalently crosslinked to the filters by UV irradiation (Stratalinker, Stratagene). Plaque-lifts were hybridized as described previously. Twenty-four positives were plaque purified, and λphage DNA was isolated for generating maps of the region containing the MT gene. Southern blot analysis was used to determine the identity of the MT clone according to diagnostic restriction sites. Fragments of the genomic clones containing the coding region and 5' and 3' flanking region were subcloned into pBluescript KS, and subclones were mapped and sequenced.

Sequencing and Data Analysis

Small-scale alkaline lysis plasmid preparations followed by phenol:chloroform extraction and ethanol precipitation (Sambrook et al., 1989) yielded template plasmid DNA suitable for automated sequencing. Plasmid DNA templates were sequenced, using the T3 primer, on an ABI 373A DNA sequencer (Applied Biosystems, Foster City, Calif.).

Using the BLASTX search algorithm, it was determined that the banana cDNA clones shared significant sequence homology with MT cDNA clones isolated from other fruit. The deduced amino acid sequences of plant MT cDNA clones were aligned using Clustal. A dendrogram showing the relationship among several different classes of plat MTs was generated from the deduced amino acid sequences using Clustal.

Protoplast Isolation and Dot Blot Analysis of MT Transcript Abundance

Protoplasts from banana pulp at PCI 4 were isolated as described in Khalid et al. (in preparation). $1 \times 10^5$ protoplasts were incubated under experimental conditions for 4 h at room temperature in protoplast isolation buffer (Khalid et al. 1997), with gentle rocking to keep the cells suspended. The treatments included incubation with different concentrations of ascorbate (buffered to pH 7.0), $CuCl_2$, and hydrogen peroxide from 1 to 100 mM. After the incubation, a crude RNA preparation from the protoplasts was spotted onto nylon membrane in duplicate. One membrane was hybridized to the F3 cDNA probe to determine relative transcript abundance of fruit-associated MT. The second membrane was hybridized with an 18S ribosomal RNA probe to assess RNA loading. The membranes were then exposed to a phosphorescent screen (PhosphorImager, Molecular Dynamics) and the scanned images were quantified with the ImageQuant software. The relative abundance was normalized to the measure of total RNA loaded, and is expressed in arbitrary units.

RESULTS

The cDNA sequence of the banana fruit-associated MT clones is shown in FIG. 9. The clones were isolated by differential screening of pulp cDNA libraries (Clendennen and May, 1997). F1 was isolated from the PCI1 library, whereas F3 was isolated from the PCI3 library. The cDNA clones are slightly variable in size, and most of the differences in size and primary sequence occurs in the 3' untranslated region (UTR), with F1 having approximately 70 more bases than F3. The two banana cDNA sequences are 60% identical at the nucleotide level, and 81% identical within the coding region.

While both of the banana fruit-associated MT polypeptides are 65 amino acids, the two cDNA clones encode distinct polypeptides. The N-terminal and C-terminal domains are well conserved, and separated by a variable spacer. In FIG. 10A, an alignment of deduced amino acid sequences shows the degree of similarity among the different fruit-associated MTs from banana, kiwifruit, papaya, and apple. In panel B, the relationships among a variety of plant MTs is depicted in a dendrogram generated from a cluster together, as do the type 1 MT sequences. The fruit-associated MT sequences (banana, kiwifruit, papaya, and apple) cluster together and are distinct from both type I and type 2 plant MTs.

Despite the sequence similarity, the size difference between the transcripts of the two banana MT cDNA clones allows them to be separated on a high percentage (2%) agarose gel and detected by northern blotting and hybridization separately with each probe (FIG. 11). Transcript sizes of F1 and F3 as determined from northern analysis are approximately 540 and 430 bases, respectively. The larger transcript (F1) is abundant in pulp, peel, and corm. It is also present in low abundance in banana leaves, but is not detected in roots. The smaller transcript (F3) is most abundant in leaves, present in pulp and peel, and barely detectable in root and corm tissue.

Southern analysis using both cDNAs as probes indicates the presence of up to five copies of the fruit type MT—two copies with homology to F1 and three copies with homology to F3 (data not shown). Twenty-four genomic clones of fruit MT were isolated from the genomic library, and restriction maps of the region containing the MT gene indicated that three distinct genes had been isolated. Clones representing both the F1 and F3 cDNA clones were isolated from the genomic library, as well as a gene with homology to the fruit-associated MT F!, but for which no cDNA clone has been isolated (named MT-F1b). Subclones of these different MT genes were generated and the region containing the coding region as well as 5' and 3' flanking regions were mapped. Maps of the different MT genes, including the coding region and at least 1 kb of 5' and 3' flanking regions appear in FIG. 12. Based on mapping and sequence data it can be determined that the MT F3 gene is comprised of three exons separated by two introns. The mapping resolution was not fine enough to determine the existence or position of introns in the other MT genes. The nucleotide sequence of the F3 genomic clone from the HindIII site to the SalI site, which includes the complete coding region, is depicted in FIG. 13. Several features of the sequence are highlighted in the figure, including a 10-base 5' sequence motif beginning at −313 from the translation start site (in capital letters) that shares homology with an antioxidant response element. The putative TATA-box (starting at position −96 from the translation start site) is underlined, and the three exons (beginning from the translation start site) are depicted in capital letters. At the 3' end of the sequence, the stop codon is underlined, as well as a potential polyadenylation signal (TAAATAAA).

Because of the putative ARE identified in the 5' flanking sequence, the effect of antioxidants (ascorbate), oxidizing agents ($H_2O_2$), and metal ions ($Cu^{++}$) on MT transcript abundance was determined in banana pulp protoplasts. $H_2O_2$, but not copper ions, resulted in dramatic and dose-dependent increase in the relative abundance of the fruit-associated MT transcript (FIG. 14). The presence of ascorbate resulted in a reduction in the relative MT transcript abundance as compared to an untreated control.

DISCUSSION

Eleven non-redundant groups of ripening-associated cDNA clones were isolated from banana pulp cDNA libraries by differential screening and identified by sequence homology (Clendennen and May, 1997). One of the groups of cDNA clones includes a previously uncharacterized type of metallothionein (MT), the transcript of which is found abundantly in ripening banana pulp. There are two classes of this ripening-associated MT transcript in banana pulp that vary in primary sequence and in size. Both the larger (F1) and the smaller (F3) transcripts increase in abundance in banana pulp during ripening, but F1 increases more dramatically than F3. In addition, the tissue distribution of these transcripts differs: MT-F1 is expressed abundantly in the pulp and peel, and slightly in corm tissue, whereas MT-F3 is expressed abundantly in pulp, peel, and leaves, and very slightly in roots. Based on the isolation of two distinct cDNA clones, it was suspected that the fruit-associated MTs were encoded by a small gene family. Southern analysis confirmed this, and suggested the presence of up to five members of the fruit-associated MT gene family in banana. Three different MT genes were identified after screening twenty-four genomic clones that hybridized to F1 and F3 cDNA probes, as determined by restriction mapping of the segment containing the coding region. Genomic clones representing both cDNA clones were isolated.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A DNA molecule selected from the group consisting of clones pBAN 3-6, and pBAN 3-23.

2. A chimeric gene comprising a DNA molecule according to claim 1 operably linked to a heterologous promoter.

3. A replicable expression vector comprising the chimeric gene of claim 2.

4. A plant genome, comprising the chimeric gene of claim 2.

5. A plant cell, comprising the chimeric gene of claim 2.

6. A plant comprising the chimeric gene of claim 2, wherein said chimeric gene is stably inserted into the plant genome.

7. An isolated DNA molecule belonging to the group consisting of the DNA sequences shown in FIG. 18 (SEQ ID NO: 32 and SEQ ID NO: 33), the DNA sequences shown in FIG. 19 (SEQ ID NO: 37 and SEQ ID NO: 38), the DNA sequence encoding the amino acid sequence of SEQ ID NO:

34, the DNA sequence encoding the amino acid sequence of SEQ ID NO: 35, the DNA sequence encoding the amino acid sequence of SEQ ID NO: 36, the DNA sequence encoding the amino acid sequence of SEQ ID NO: 39, the DNA sequence encoding the amino acid sequence of SEQ ID NO: 40, and the DNA sequence encoding the amino acid sequence of SEQ ID NO: 41.

8. A chimeric gene comprising a DNA molecule according to claim 7 operably linked to a heterologous promoter.

9. A replicable expression vector comprising the chimeric gene of claim 8.

10. A plant genome, comprising the chimeric gene of claim 8.

11. A plant cell, comprising the chimeric gene of claim 8.

12. A plant comprising the chimeric gene of claim 8, wherein said chimeric gene is stably integrated into the plant genome.

* * * * *

SEQUENCE LISTING

<160> NUMBER OF SEQ ID NOS: 41

<210> SEQ ID NO 1
<211> LENGTH: 1186
<212> TYPE: DNA
<213> ORGANISM: Musa acuminata
<220> FEATURE:
<221> NAME/KEY: CDS
<222> LOCATION: (55)..(1026)

<400> SEQUENCE: 1

```
tttggttgtg cctaacagag agagagagac agaccgatag cctcctcatt cact atg        57
                                                               Met
                                                                1 gcg atc cga tcg cca gct tcg ctg ctg tta ttt gcg ttc ctg atg ctt       105
Ala Ile Arg Ser Pro Ala Ser Leu Leu Leu Phe Ala Phe Leu Met Leu
         5                  10                  15 gcg ctc acg gga aga ctg cag gcc cgg cgc agc tca tgc att ggc gtc       153
Ala Leu Thr Gly Arg Leu Gln Ala Arg Arg Ser Ser Cys Ile Gly Val
     20                  25                  30
```

-continued

| | |
|---|---|
| tac tgg gga caa aac acc gac gag gga agc tta gca gat gct tgt gcc<br>Tyr Trp Gly Gln Asn Thr Asp Glu Gly Ser Leu Ala Asp Ala Cys Ala<br>    35                             40                            45 | 201 |
| aca ggc aac tac gaa tac gtg aac atc gcc acc ctt ttc aag ttt ggc<br>Thr Gly Asn Tyr Glu Tyr Val Asn Ile Ala Thr Leu Phe Lys Phe Gly<br>50                          55                            60                          65 | 249 |
| atg ggc caa act cca gag atc aac ctc gcc ggc cac tgt gac cct cgg<br>Met Gly Gln Thr Pro Glu Ile Asn Leu Ala Gly His Cys Asp Pro Arg<br>              70                              75                            80 | 297 |
| aac aac ggc tgc gcg cgc ttg agc agc gaa atc cag tcc tgc cag gag<br>Asn Asn Gly Cys Ala Arg Leu Ser Ser Glu Ile Gln Ser Cys Gln Glu<br>                  85                            90                          95 | 345 |
| cgt ggc gtc aag gtg atg ctc tcc atc gga ggt ggc ggg tct tat ggc<br>Arg Gly Val Lys Val Met Leu Ser Ile Gly Gly Gly Gly Ser Tyr Gly<br>                  100                      105                          110 | 393 |
| ctg agt tcc acc gaa gac gcc aag gac gta gcg tca tac ctc tgg cac<br>Leu Ser Ser Thr Glu Asp Ala Lys Asp Val Ala Ser Tyr Leu Trp His<br>115                         120                          125 | 441 |
| agt ttc ttg ggt ggt tct gct gct cgc tac tcg aga ccc ctc ggg gat<br>Ser Phe Leu Gly Gly Ser Ala Ala Arg Tyr Ser Arg Pro Leu Gly Asp<br>130                       135                        140                      145 | 489 |
| gcg gtt ctg gat ggc ata gac ttc aac atc gcc gga ggg agc aca gaa<br>Ala Val Leu Asp Gly Ile Asp Phe Asn Ile Ala Gly Gly Ser Thr Glu<br>                  150                      155                          160 | 537 |
| cac tat gat gaa ctt gcc gct ttc ctc aag gcc tac aac gag cag gag<br>His Tyr Asp Glu Leu Ala Ala Phe Leu Lys Ala Tyr Asn Glu Gln Glu<br>                165                      170                          175 | 585 |
| gcc gga acg aag aaa gtt cac ttg agt gct cgt ccg cag tgt cct ttc<br>Ala Gly Thr Lys Lys Val His Leu Ser Ala Arg Pro Gln Cys Pro Phe<br>              180                      185                          190 | 633 |
| ccg gat tac tgg ctt ggc aac gca ctc aga aca gat ctc ttc gac ttc<br>Pro Asp Tyr Trp Leu Gly Asn Ala Leu Arg Thr Asp Leu Phe Asp Phe<br>195                       200                          205 | 681 |
| gtg tgg gtg cag ttc ttc aac aac cct tcg tgc cat ttc tcc cag aac<br>Val Trp Val Gln Phe Phe Asn Asn Pro Ser Cys His Phe Ser Gln Asn<br>210                       215                        220                      225 | 729 |
| gct atc aat ctt gca aat gcg ttc aac aat tgg gtc atg tcc atc cct<br>Ala Ile Asn Leu Ala Asn Ala Phe Asn Asn Trp Val Met Ser Ile Pro<br>                230                      235                          240 | 777 |
| gcg caa aag ctg ttc ctt ggg ctt cct gct gct cct gag gct gct cca<br>Ala Gln Lys Leu Phe Leu Gly Leu Pro Ala Ala Pro Glu Ala Ala Pro<br>                245                      250                          255 | 825 |
| act ggt ggc tac att cca ccc cat gat ctc ata tct aaa gtt ctt ccg<br>Thr Gly Gly Tyr Ile Pro Pro His Asp Leu Ile Ser Lys Val Leu Pro<br>                  260                      265                          270 | 873 |
| atc cta aag gat tcc gac aag tac gca gga atc atg ctg tgg act aga<br>Ile Leu Lys Asp Ser Asp Lys Tyr Ala Gly Ile Met Leu Trp Thr Arg<br>275                       280                        285 | 921 |
| tac cac gac aga aac tcc ggc tac agt tct caa gtc aag tcc cac gtg<br>Tyr His Asp Arg Asn Ser Gly Tyr Ser Ser Gln Val Lys Ser His Val<br>290                       295                        300                      305 | 969 |
| tgt cca gcg cgt cgg ttc tcc aac atc tta tct atg ccg gtg aag tct<br>Cys Pro Ala Arg Arg Phe Ser Asn Ile Leu Ser Met Pro Val Lys Ser<br>                310                      315                          320 | 1017 |
| tcc aag taa acctgaacgg cgtagatgat cggtggtcga aaactccgat<br>Ser Lys | 1066 |
| catcatgggt cccatccgt atccgtgcgt tgctacgtta tggtgtttcc cttgtatgtt | 1126 |
| ggtcttttca ataatataat aagggggttag ttttacgttt ccaaaaaaaa aaaaaaaaa | 1186 |

```
<210> SEQ ID NO 2
<211> LENGTH: 323
<212> TYPE: PRT
<213> ORGANISM: Musa acuminata

<400> SEQUENCE: 2

Met Ala Ile Arg Ser Pro Ala Ser Leu Leu Leu Phe Ala Phe Leu Met
  1               5                  10                  15

Leu Ala Leu Thr Gly Arg Leu Gln Ala Arg Arg Ser Ser Cys Ile Gly
             20                  25                  30

Val Tyr Trp Gly Gln Asn Thr Asp Glu Gly Ser Leu Ala Asp Ala Cys
             35                  40                  45

Ala Thr Gly Asn Tyr Glu Tyr Val Asn Ile Ala Thr Leu Phe Lys Phe
 50                  55                  60

Gly Met Gly Gln Thr Pro Glu Ile Asn Leu Ala Gly His Cys Asp Pro
 65                  70                  75                  80

Arg Asn Asn Gly Cys Ala Arg Leu Ser Ser Glu Ile Gln Ser Cys Gln
                 85                  90                  95

Glu Arg Gly Val Lys Val Met Leu Ser Ile Gly Gly Gly Ser Tyr
            100                 105                 110

Gly Leu Ser Ser Thr Glu Asp Ala Lys Asp Val Ala Ser Tyr Leu Trp
            115                 120                 125

His Ser Phe Leu Gly Gly Ser Ala Ala Arg Tyr Ser Arg Pro Leu Gly
130                 135                 140

Asp Ala Val Leu Asp Gly Ile Asp Phe Asn Ile Ala Gly Gly Ser Thr
145                 150                 155                 160

Glu His Tyr Asp Glu Leu Ala Ala Phe Leu Lys Ala Tyr Asn Glu Gln
                165                 170                 175

Glu Ala Gly Thr Lys Lys Val His Leu Ser Ala Arg Pro Gln Cys Pro
            180                 185                 190

Phe Pro Asp Tyr Trp Leu Gly Asn Ala Leu Arg Thr Asp Leu Phe Asp
            195                 200                 205

Phe Val Trp Val Gln Phe Asn Asn Pro Ser Cys His Phe Ser Gln
            210                 215                 220

Asn Ala Ile Asn Leu Ala Asn Ala Phe Asn Asn Trp Val Met Ser Ile
225                 230                 235                 240

Pro Ala Gln Lys Leu Phe Leu Gly Leu Pro Ala Ala Pro Glu Ala Ala
                245                 250                 255

Pro Thr Gly Gly Tyr Ile Pro Pro His Asp Leu Ile Ser Lys Val Leu
            260                 265                 270

Pro Ile Leu Lys Asp Ser Asp Lys Tyr Ala Gly Ile Met Leu Trp Thr
            275                 280                 285

Arg Tyr His Asp Arg Asn Ser Gly Tyr Ser Ser Gln Val Lys Ser His
    290                 295                 300

Val Cys Pro Ala Arg Arg Phe Ser Asn Ile Leu Ser Met Pro Val Lys
305                 310                 315                 320

Ser Ser Lys

<210> SEQ ID NO 3
<211> LENGTH: 90
<212> TYPE: PRT
<213> ORGANISM: Musa acuminata

<400> SEQUENCE: 3

Met Ala Ile Arg Ser Pro Ala Ser Leu Leu Leu Phe Ala Phe Leu Met
```

```
                     1               5                   10                  15
             Leu Ala Leu Thr Gly Arg Leu Gln Ala Arg Arg Ser Ser Cys Ile Gly
                              20                  25                  30

Val Tyr Trp Gly Gln Asn Thr Asp Glu Gly Ser Leu Ser Asp Lys Tyr
                              35                  40                  45

Ala Gly Ile Met Leu Trp Thr Arg Tyr His Asp Arg Asn Ser Gly Tyr
                              50                  55                  60

Ser Ser Gln Val Lys Ser His Val Cys Pro Ala Arg Arg Phe Ser Asn
              65                  70                  75                  80

Ile Leu Ser Met Pro Val Lys Ser Lys
                              85                  90

<210> SEQ ID NO 4
<211> LENGTH: 67
<212> TYPE: PRT
<213> ORGANISM: Musa acuminata

<400> SEQUENCE: 4

Met Glu Lys Cys Phe Asn Ile Ile Pro Ser Leu Leu Ile Ser Leu
              1               5                   10                  15

Leu Ile Lys Ser Ser Asn Ala Ala Gly Ile Ala Val Tyr Trp Gly Gln
                              20                  25                  30

Asn Gly Asn Glu Gly Ser Leu Ser Pro Lys Tyr Gly Val Met Ile
                              35                  40                  45

Trp Asp Arg Phe Asn Asp Ala Gln Ser Gly Tyr Ser Asn Ala Ile Lys
                      50                  55                  60

Gly Ser Val
              65

<210> SEQ ID NO 5
<211> LENGTH: 69
<212> TYPE: PRT
<213> ORGANISM: Musa acuminata

<400> SEQUENCE: 5

Met Ala Arg Thr Pro Gln Ser Thr Pro Leu Leu Ile Ser Leu Ser Val
              1               5                   10                  15

Leu Ala Leu Ile Lys Thr Ser Tyr Ala Gly Gly Ile Ala Ile Tyr Trp
                              20                  25                  30

Gly Gln Asn Gly Asn Glu Gly Thr Leu Ser Pro Lys Tyr Gly Gly Val
                              35                  40                  45

Met Ile Trp Ser Lys Phe Tyr Asp Asp Gln Ser Gly Tyr Ser Asn Ser
                      50                  55                  60

Ile Lys Gly Ser Val
              65

<210> SEQ ID NO 6
<211> LENGTH: 73
<212> TYPE: PRT
<213> ORGANISM: Musa acuminata

<400> SEQUENCE: 6

Met Thr Asn Met Thr Leu Arg Lys His Val Ile Tyr Pro Leu Leu Phe
              1               5                   10                  15

Ile Ser Cys Ser Leu Ser Lys Pro Ser Asp Ala Ser Arg Gly Gly Ile
                              20                  25                  30

Ala Ile Tyr Trp Gly Gln Asn Gly Asn Glu Gly Asn Leu Ser Arg Lys
                              35                  40                  45
```

-continued

Tyr Gly Gly Val Met Ile Trp Ser Lys Phe Trp Asp Asp Lys Asn Gly
                50                  55                  60

Tyr Ser Asn Ser Ile Leu Ala Ser Val
 65                  70

<210> SEQ ID NO 7
<211> LENGTH: 64
<212> TYPE: PRT
<213> ORGANISM: Musa acuminata

<400> SEQUENCE: 7

Met Ile Lys Tyr Ser Pro Leu Leu Thr Ala Ser Val Ser Phe Leu Lys
  1               5                  10                  15

Ala Leu Lys Leu Glu Ala Gly Asp Ile Val Ile Tyr Trp Gly Gln Asn
                 20                  25                  30

Gly Asn Glu Gly Asn Leu Ser Pro Lys Tyr Gly Gly Val Met Ile Trp
             35                  40                  45

Ser Lys Phe Tyr Asp Asn Gly Tyr Ser Asn Ala Ile Leu Ala Asn Val
 50                  55                  60

<210> SEQ ID NO 8
<211> LENGTH: 67
<212> TYPE: PRT
<213> ORGANISM: Musa acuminata

<400> SEQUENCE: 8

Met Ala Ala Lys Ile Val Ser Val Leu Phe Leu Ile Ser Ser Leu Ile
  1               5                  10                  15

Phe Ala Ser Phe Glu Ser Ser His Gly Gly Gln Ile Val Ile Tyr Trp
                 20                  25                  30

Gly Gln Asn Gly Asn Glu Gly Asn Leu Ser Ala Lys Tyr Gly Gly Val
             35                  40                  45

Met Ile Trp Ser Lys Ala Tyr Asp Asn Gly Tyr Ser Asn Ala Ile Leu
 50                  55                  60

Ala Ser Val
 65

<210> SEQ ID NO 9
<211> LENGTH: 496
<212> TYPE: DNA
<213> ORGANISM: Musa acuminata
<220> FEATURE:
<221> NAME/KEY: misc_feature
<222> LOCATION: (163)..(471)
<223> OTHER INFORMATION: Nucleotides 163, 387 & 471 are n wherein n = a
      or g or c or t/u.

<400> SEQUENCE: 9
ggcacgagta catcctctgc ttcttcgagc cttttcgcct tccttcctcg tctaaccatg      60
tcgacctgcg gcaactgcga ctgcgttgac aagagccagt gcgtgaagaa gggaaacagc     120
tacggtatcg atattgttga gaccgagaag agctacgtcg acnaggtgat cgttgccgca     180
gaagctgccg agcatgacgg caagtgcaag tgcggcgccg cctgcgcctg caccgactgc     240
aagtgtggca actgagaagc acttgtgtca ctaccactaa ataaagttt gcaatgcata      300 aaaaacaaaa gaacaaaaaa aaaaaggaa gaagaagaag gtgtggctat gtactctaat     360
aattcgggca ggctgatagg ttgtaanatg ggataacgca gtatcatctg tgttatctct     420
gtcctgtgtt tacaactctc ctatctatcc tagtccatga aatattatta ntattaaaaa     480
aaaaaaaaaa aaaaaa                                                      496

<210> SEQ ID NO 10
<211> LENGTH: 416
<212> TYPE: DNA
<213> ORGANISM: Musa acuminata

<400> SEQUENCE: 10

```
ggcacgaggg cacgaggttg cctctcgaca tgtcgacctg cggcaactgc gactgcgctg    60
acaagagcca gtgcgtgaag aagggaaaca gctacgctac cgagactgtt gcgaccgaga   120
agagcttctt ggatggtgta gtcgatgccc cagcagccgc cgagacggag ggagactgca   180
agtgtggtcc ttcctgcgcc tgtgttgact gccaatgtgg ccagtgacag cttcttagct   240
agtaatgaca atatataata tgttcgagta ataacttgg ggcttgcatg gctaatcgtt    300
tatcagtgtg tcatgatgtc agatgggata gggttgtgtc taccttgtct acatctgtac   360
tgttatcata catgataaat aaagaattat tagtattaaa aaaaaaaaa aaaaaa        416
```

<210> SEQ ID NO 11
<211> LENGTH: 65
<212> TYPE: PRT
<213> ORGANISM: Musa acuminata

<400> SEQUENCE: 11

```
Met Ser Thr Cys Gly Asn Cys Asp Cys Val Asp Lys Ser Gln Cys Val
  1               5                  10                  15

Lys Lys Gly Asn Ser Tyr Gly Ile Asp Ile Val Glu Thr Glu Lys Ser
             20                  25                  30

Tyr Val Asp Glu Val Ile Val Ala Ala Glu Ala Ala Glu His Asp Gly
         35                  40                  45

Lys Cys Lys Cys Gly Ala Ala Cys Ala Cys Thr Asp Cys Lys Cys Gly
     50                  55                  60

Asn
 65
```

<210> SEQ ID NO 12
<211> LENGTH: 67
<212> TYPE: PRT
<213> ORGANISM: Musa acuminata

<400> SEQUENCE: 12

```
Met Ser Thr Cys Gly Asn Cys Asp Cys Ala Asp Lys Ser Gln Cys Val
  1               5                  10                  15

Lys Lys Gly Asn Ser Tyr Ala Thr Glu Thr Val Ala Thr Glu Lys Ser
             20                  25                  30

Phe Leu Asp Gly Val Val Asp Ala Pro Ala Ala Ala Glu Thr Glu Gly
         35                  40                  45

Asp Cys Lys Cys Gly Pro Ser Cys Ala Cys Val Asp Cys Lys Gln Cys
     50                  55                  60

Gly Asn Gln
 65
```

<210> SEQ ID NO 13
<211> LENGTH: 63
<212> TYPE: PRT
<213> ORGANISM: Musa acuminata

<400> SEQUENCE: 13

Met Ser Asp Lys Cys Gly Asn Cys Asp Cys Ala Asp Ser Ser Gln Cys

```
                 1               5                  10                 15
Val Lys Lys Gly Asn Ser Thr Glu Thr Val Ala Thr Asp Lys Ser Phe
                20                  25                 30

Ile Glu Asp Val Val Met Gly Val Pro Ala Ala Glu Ser Gly Gly Asp
         35                  40                 45

Cys Lys Cys Gly Thr Ser Cys Pro Cys Val Asn Cys Thr Cys Asp
         50                  55                 60
```

<210> SEQ ID NO 14
<211> LENGTH: 66
<212> TYPE: PRT
<213> ORGANISM: Musa acuminata

<400> SEQUENCE: 14

```
Met Ser Gly Lys Cys Asp Asn Cys Asp Cys Ala Asp Ser Thr Gln Cys
 1               5                  10                 15

Val Lys Lys Gly Asn Ser Tyr Asp Leu Val Thr Val Ala Thr Asp Asn
                20                  25                 30

Arg Ser Met Glu Thr Val Phe Met Asp Val Pro Ala Ala Glu Ser Gly
         35                  40                 45

Gly Asp Cys Lys Cys Gly Thr Gly Cys Ser Cys Val Ser Cys Thr Cys
         50                  55                 60

Asp His
65
```

<210> SEQ ID NO 15
<211> LENGTH: 65
<212> TYPE: PRT
<213> ORGANISM: Musa acuminata

<400> SEQUENCE: 15

```
Met Ser Asp Lys Cys Asp Asn Cys Asp Cys Ala Asp Ser Thr Gln Cys
 1               5                  10                 15

Val Lys Lys Gly Ser Ser Tyr Thr Ala Val Thr Ile Ala Thr Asp Asn
                20                  25                 30

Arg Ile Met Thr Val Val Met Asp Val Pro Ala Ala Glu Asn Gly Gly
         35                  40                 45

Asp Cys Lys Cys Gly Pro Ser Cys Ser Cys Val Asn Cys Thr Cys Asp
         50                  55                 60

His
65
```

<210> SEQ ID NO 16
<211> LENGTH: 1423
<212> TYPE: DNA
<213> ORGANISM: Musa acuminata

<400> SEQUENCE: 16

```
taagcttccg tgccaaagcg gtctgccttt ctacgccgca tcgggaaggg gaaacacaaa    60
aaaaagatca ggaagatgat gctgacacga gaggtggaag gaagtttacc gctctcccat   120
aatagagatt cctttggatg cttctcccgg tgggtgtgtg gagcacagac actgaatgtg   180
gtccgtcgtt ccaatccctc acgtaatcgg gccgtctccg gctataaata accccccccg   240
accgagcgaa cgcttctaac caggaacgca taccacacca caatttgttg agccgttgtg   300
cttgttgcct ctcgacatgt cgacctgcgg caactgcgac tgcgctgaca agagccagtg   360
cgtgtaagtt ctcttcctcc ccgccctccc acctctttgt gatacacaca acaaatatgc   420
```

-continued

| | |
|---|---|
| atgagggttg agtttaatat tgaccacaag aacttgggtt tgctcctgca ggaagaaggg | 480 |
| aaacagctac gctaccgaga ctgttgcgac cgagaagagg tattattgat ctctctcatg | 540 |
| ggtgagggtg tgggagtatc ttgtccgcat gatgaaattc cacaacatga tgactcagca | 600 |
| aacaagatcc ttttattctt gagaaaacaa ctaaagaag aaaaaaaaaa cagagaatat | 660 |
| atctgcgatt atttcttttt gagtgatgtg gaattccatg ccatagctta aaactatttt | 720 |
| cgaagtcgaa gcatattaca tacctcttga tgaattagta aggatgatta aaagtaagcc | 780 |
| atctaaagca gagtaactac ttacgtttct ttcatgtcat ctctgtctta cagcttcttg | 840 |
| gatggtgtag tcgatgcccc agcagccgcc gaaacggagg gagactgcaa gtgtggtcct | 900 |
| tcctgcgcct gtgttgactg ccaatgtggc cagtgacagc ttcttagcta gtaatgacaa | 960 |
| tatataatat gttcgagtaa ataacttggg gcttgcatgg ctaatcgttt atcagtgtgt | 1020 |
| catgatgtca gatgggatag ggttgtgtct accttgtcta catctgtact gttatcatac | 1080 |
| atgataaata aagaattatt agtattaatt tggtttcagg tgataactac tgctcctttc | 1140 |
| aaccgaatca ctactgttac gtgaacaaac atgtaatagt agtgattcag taggacgact | 1200 |
| tttgtctatt taacttttgc tttgggttgc aaaaatatgt tcttcctgat tcacgaaaga | 1260 |
| gggtgtccat gagcattcgg ctattgagcg atgttggatg aggcctcaaa gggaagaatt | 1320 |
| tatgcttagg actctgagtt cgatggttgc caccgacctc ctcaagtacc aagacacata | 1380 |
| cccttccttc cgaggcctat ccaacatcgc tcgtatcgtc gac | 1423 |

<210> SEQ ID NO 17
<211> LENGTH: 3559
<212> TYPE: DNA
<213> ORGANISM: Musa acuminata
<220> FEATURE:
<221> NAME/KEY: misc_feature
<222> LOCATION: Complement((1)..(3559))

<400> SEQUENCE: 17

| | |
|---|---|
| attggaccca cgcggtggcg gccgctctag aatagtggat cccccgggct gcaggaattc | 60 |
| taaaatctat tctttttat tttattaatt aaattaaatt aatttttat tgtttggtat | 120 |
| ttagcctaac attcccggac tcctctattt ttggagattg aatacaaaat tcttctccca | 180 |
| tctaaagtta ttttaatttt gaagatcata tggctgacat ataaagcaaa tatgtcaaag | 240 |
| gtagttttca ccgtccacac gatagaaaca acaaagtagg gtaattaaat ttgttccgtc | 300 |
| atcacaaagc acaacaccaa atattcact taatcaaatc ctcactataa ataataatcc | 360 |
| ttcaaactgc aactctaaac aatgaggttc tctctcccag caacgttctt ttctgaacac | 420 |
| aaagatttgc cacaaccta gctgactttt aatatcagtg gtctctggac aagattcttg | 480 |
| ttgcacgcta aaattcgaac taaaatcaga tcgagttata ccgtaattg agattgatga | 540 |
| ccgaaccgat tttaagagta ctctccgtaa cttgggatta ataaaattaa taggtaggt | 600 |
| atcagttatt ttagatgata aaaatcttga tagtttgaat ctcatcttag tcacttattt | 660 |
| ttaattaaaa ataataataa taatttgatt aatctgattg gaaaaaaaaa aagttctcta | 720 |
| gccattaaag tctggtagga catagaaatt aatgaattaa actgtaaacca taaggttgaa | 780 |
| tttttgaaca catgtacagg aaaattgatt tgttgaagtc atgtctaatc aatgcagcag | 840 |
| tttacagctt ggtgtgactt ccacaactat aggcttatcc cctgggagtc gaggatcaaa | 900 |
| cgtgtgagca atattctccc ttcctgatga taaactatga tggctgttag gtgtgtaagc | 960 |
| actccaaatt ttccatcaat gtggaattgg aagagttcac gcactgacgg accaactcgg | 1020 |

-continued

```
tttgttcagt ctggtgacta ctgctgagca tgagaaaatg gttgatggta gcaagttgca    1080
aatgtacctg acctcatctt aaagactgtt gattagatgc atgcattgat tacgtctctt    1140
ccatctttaa ctcttttgat cgatgcatcg tcttaattag gtcaaggaca tgtgatgaca    1200
agaatctatt ccactatttg tgacccatat tccaaatgga acaagacttc caagtcctca    1260
tccagaattt tggaagggat aaggatggtg gggagaaaga acaagctgtt gcctttcgtt    1320
ttcttctatc aggaagccaa gagtttcaag aggagggtag acctgagggg atgatgcctg    1380
tgtcgaaacc tctatataag gagtaggaac acagcatgtt gatgaacaca aaccatttca    1440
gcggggaaga agagaaccct tttgacagag ttgttgtcat ggcaacaaaa gcttctctct    1500
ccataaaagg ctttgccttg ctggtttcag tccttgtagc agttccaaca agttctctct    1560
ctctctctct ctctctctct ctctctctct ctctctctct ctcatattat acatttgatt    1620
gttagctctt acaaatttat tagggttttt ataagagttc aagcttttgg taatttaatc    1680
atggtaggtt atattttcaa aacttgtaac ctgcattttg tctctttatt tcatgcaata    1740
ttcttttcct tgattggctt acgtcattta cttgagttag ctcatatgta actgtttaaa    1800
tatttgggat tattggttaa cggataaaaa aaattaattg attttagata caatgctata    1860
tatatatata tatatatata tatatatata tatatatata tatatatata ttataggtag    1920
aaacttggta taattcacac gtatgttcgc tttatctgaa taaaatgagt agtcctttca    1980
atgcagatta gtcttactcc acttgcagat gcacgaccaa tttgcttgat catcttccat    2040
agagcaccac agctaagtct ccgatgtgtt ctactgcagg agtgcaatcg attggtgtct    2100
gctacggaat gctcggcaac aatcttcccc cgcccagcga ggtggtcagt ctctacaaat    2160
ccaacaacat cgcgaggatg agactctacg atccaaacca ggccgccctg caagccctca    2220
ggaactccaa catccaagtc ctgttggatg tcccccgatc cgacgtgcag tcactggcct    2280
ccaatccttc ggccgccggc gactggatcc ggaggaacgt cgtcgcctac tggcccagcg    2340
tctcctttcg atacatagct gtcggaaacg agctgatccc cggatcggat ctggcgcagt    2400
acatcctccc cgccatgcgc aacatctaca atgctttgtc ctcggctggc ctgcaaaacc    2460
agatcaaggt ctcgaccgcg gtcgacacgg gcgtcctcgg cacgtcctac cctccctccg    2520
ccggcgcctt ctcctccgcc gcccaggcgt acctgagccc catcgtgcag ttcttggcga    2580
gtaacggagc gccgctcctg gtcaatgtgt accttatttt tagctacacc ggcaacccgg    2640
gacagatctc gctgccctac gccctgttca cggcctccgg cgtcgtcgtg caggatgggc    2700
gattcagcta tcagaacctg ttcgacgcca tcgtcgacgc ggtcttcgcg gcgctggaga    2760
gagtgggagg ggcgaacgtg gcggtggtgg tgtcggagag cgggtggccg tcggcgggcg    2820
gaggagccga agcgagcacc agcaacgcgc agacgtacaa ccagaacttg atcaggcatg    2880
ttggcggagg aacgccgagg agaccaggga aggagatcga ggcatacata ttcgagatgt    2940
tcaacgagaa ccagaaggct ggagggatcg agcagaactt tggcctgttt tatcccaaca    3000
agcagcccgt ataccaaata agcttttaga aactaacttg taaggttgat gaatcatctc    3060
ctacctacct acctacctac gaataaaaca tgaaataaag caccaaaata aagggagaat    3120
tctgatcttg gagaaagttg aatcatgatg atatataaca acacccctc tttactcatt    3180 atcagtatgt tacaagtttc ttgaaacttg aacggatcac aatttggacc tacaagtatt    3240
ttgggtcata attatttcat tgaactatat attcaaaaaa agatgtgttt ggagtgctta    3300
atacagtatg acttcagttt gcaagattac ctcttcagcg tcagcttcag catgccaaaa    3360
aaccatcatc tgctatgggg catgttttac accttgatgg tgctacatca tcatcattca    3420
```

```
tgtttcattt taggtctcgt gctctttata tagatcacat aaaagtttgg atcgcttcaa    3480
gtttctaggt tacattgtat gcagcacttt gagcctactg aacattgtga ctgcctttta    3540
gaacattgga ctgcaggaa                                                 3559
```

<210> SEQ ID NO 18
<211> LENGTH: 3559
<212> TYPE: DNA
<213> ORGANISM: Musa acuminata

<400> SEQUENCE: 18

```
taacctgggt gcgccaccgc cggcgagatc ttatcaccta gggggcccga cgtccttaag     60
attttagata agaaaaaata aaataattaa tttaatttaa ttaaaaaata acaaaccata    120
aatcggattg taagggcctg aggagataaa aacctctaac ttatgtttta agaagagggt    180
agatttcaat aaaattaaaa cttctagtat accgactgta tatttcgttt atacagtttc    240
catcaaaagt ggcaggtgtg ctatctttgt tgtttcatcc cattaattta acaaggcag     300
tagtgtttcg tgttgtggtt ttataagtga attagtttag gagtgatatt tattattagg    360
aagtttgacg ttgagatttg ttactccaag agagagggtc gttgcaagaa aagacttgtg    420
tttctaaacg gtgttggaat cgactgaaaa ttatagtcac cagagacctg ttctaagaac    480
aacgtgcgat tttaagcttg attttagtct agctcaatat aggcattaac tctaactact    540
ggcttggcta aaattctcat gagaggcatt gaaccctaat tattttaatt attccatcca    600
tagtcaataa aatctactat ttttagaact atcaaactta gagtagaatc agtgaataaa    660
aattaatttt tattattatt attaaactaa ttagactaac cttttttttt ttcaagagat    720
cggtaatttc agaccatcct gtatctttaa ttacttaatt tgacattggt attccaactt    780
aaaaacttgt gtacatgtcc ttttaactaa acaacttcag tacagattag ttacgtcgtc    840
aaatgtcgaa ccacactgaa ggtgttgata tccgaatagg ggaccctcag ctcctagttt    900
gcacactcgt tataagaggg aaggactact atttgatact accgacaatc cacacattcg    960
tgaggtttaa aaggtagtta caccttaacc ttctcaagtg cgtgactgcc tggttgagcc   1020
aaacaagtca gaccactgat gacgactcgt actcttttac caactaccat cgttcaacgt   1080
ttacatggac tggagtagaa tttctgacaa ctaatctacg tacgtaacta atgcagagaa   1140
ggtagaaatt gagaaaacta gctacgtagc agaattaatc cagttcctgt acactactgt   1200
tcttagataa ggtgataaac actgggtata aggtttacct tgttctgaag gttcaggagt   1260
aggtcttaaa accttcccta ttcctaccac ccctctttct tgttcgacaa cggaaagcaa   1320
aagaagatag tccttcggtt ctcaaagttc tcctcccatc tggactcccc tactacggac   1380
acagctttgg agatatattc ctcatccttg tgtcgtacaa ctacttgtgt ttggtaaagt   1440
cgccccttct tctcttggga aaactgtctc aacaacagta ccgttgtttt cgaagagaga   1500
ggtattttcc gaaacggaac gaccaaagtc aggaacatcg tcaaggttgt tcaagagaga   1560
gagagagaga gagagagaga gagagagaga gagagagaga gagtataata tgtaaactaa   1620
caatcgagaa tgtttaaata atcccaaaaa tattctcaag ttcgaaaacc attaaattag   1680
taccatccaa tataaaagtt ttgaacattg gacgtaaaac agagaaataa agtacgttat   1740
aagaaaagga actaaccgaa tgcagtaaat gaactcaatc gagtatacat tgacaaattt   1800
ataaacccta ataccaatt gcctattttt tttaattaac taaaatctat gttacgatat   1860
atatatatat atatatatat atatatatat atatatatat atatatatat aatatccatc   1920
```

-continued

```
tttgaaccat attaagtgtg catacaagcg aaatagactt attttactca tcaggaaagt    1980
tacgtctaat cagaatgagg tgaacgtcta cgtgctggtt aaacgaacta gtagaaggta    2040
tctcgtggtg tcgattcaga ggctacacaa gatgacgtcc tcacgttagc taaccacaga    2100
cgatgcctta cgagccgttg ttagaagggg gcgggtcgct ccaccagtca gagatgttta    2160
ggttgttgta gcgctcctac tctgagatgc taggtttggt ccggcgggac gttcgggagt    2220
ccttgaggtt gtaggttcag gacaacctac aggggctag gctgcacgtc agtgaccgga    2280
ggttaggaag ccggcggccg ctgacctagg cctccttgca gcagcggatg accgggtcgc    2340
agaggaaagc tatgtatcga cagcctttgc tcgactaggg gcctagccta gaccgcgtca    2400
tgtaggaggg gcggtacgcg ttgtagatgt tacgaaacag gagccgaccg gacgttttgg    2460
tctagttcca gagctggcgc cagctgtgcc cgcaggagcc gtgcaggatg ggagggaggc    2520
ggccgcggaa gaggaggcgg cgggtccgca tggactcggg gtagcacgtc aagaaccgct    2580
cattgcctcg cggcgaggac cagttacaca tgggaataaa atcgatgtgg ccgttgggcc    2640
ctgtctagag cgacgggatg cgggacaagt gccggaggcc gcagcagcac gtcctacccg    2700
ctaagtcgat agtcttggac aagctgcggt agcagctgcg ccagaagcgc cgcgacctct    2760
ctcaccctcc ccgcttgcac cgccaccacc acagcctctc gcccaccggc agccgcccgc    2820
ctcctcggct cgctcgtgg tcgttgcgcg tctgcatgtt ggtcttgaac tagtccgtac    2880
aaccgcctcc ttgcggctcc tctggtccct cctctagct ccgtatgtat aagctctaca    2940
agttgctctt ggtcttccga cctccctagc tcgtcttgaa accggacaaa ataggggttgt    3000 tcgtcgggca tatggtttat tcgaaaatct ttgattgaac attccaacta cttagtagag    3060
gatggatgga tggatggatg cttatttgt actttatttc gtggttttat ttccctctta    3120
agactagaac ctctttcaac ttagtactac tatatattgt ttgtggggag aaatgagtaa    3180
tagtcataca atgttcaaag aactttgaac ttgcctagtg ttaaacctgg atgttcataa    3240
aacccagtat taataaagta acttgatata taagtttttt tctacacaaa cctcacgaat    3300
tatgtcatac tgaagtcaaa cgttctaatg gagaagtcgc agtcgaagtc gtacggtttt    3360
ttggtagtag acgataccc gtacaaaatg tggaactacc acgatgtagt agtagtaagt    3420
acaaagtaaa atccagagca cgagaaatat atcagtgta ttttcaaacc tagcgaagtt    3480
caaagatcca atgtaacata cgtcgtgaaa ctcggatgac ttgtaacact gacggaaaat    3540
cttgtaacct gacgtccttt                                                3559
```

<210> SEQ ID NO 19
<211> LENGTH: 1131
<212> TYPE: PRT
<213> ORGANISM: Musa acuminata

<400> SEQUENCE: 19

```
Ile Gly Pro Thr Arg Trp Arg Pro Leu Asn Ser Gly Ser Pro Gly Leu
  1               5                  10                  15

Gln Glu Phe Asn Leu Phe Phe Phe Ile Leu Leu Ile Lys Leu Asn Phe
                 20                  25                  30

Phe Ile Val Trp Tyr Leu Ala His Ser Arg Thr Pro Leu Phe Leu Glu
             35                  40                  45

Ile Glu Tyr Lys Ile Leu Leu Pro Ser Lys Val Ile Leu Ile Leu Lys
         50                  55                  60

Ile Ile Trp Leu Thr Tyr Lys Ala Asn Met Ser Lys Val Val Phe Thr
 65                  70                  75                  80
```

-continued

```
Val His Thr Ile Glu Thr Thr Lys Gly Asn Ile Cys Ser Val Ile Thr
                85                  90                  95
Lys His Asn Thr Lys Ile Phe Thr Ser Asn Pro His Tyr Lys Ser Phe
            100                 105                 110
Lys Leu Gln Leu Thr Met Arg Phe Ser Leu Pro Ala Thr Phe Phe Ser
        115                 120                 125
Glu His Lys Asp Leu Pro Gln Pro Leu Thr Phe Asn Ile Ser Gly Leu
    130                 135                 140
Trp Thr Arg Phe Leu Leu His Ala Lys Ile Arg Thr Lys Ile Arg Ser
145                 150                 155                 160
Ser Tyr Ile Arg Asn Asp Pro Asn Arg Phe Glu Tyr Ser Pro Leu Gly
                165                 170                 175
Ile Asn Lys Ile Asn Lys Val Gly Ile Ser Tyr Phe Arg Lys Ser Phe
            180                 185                 190
Glu Ser His Leu Ser His Leu Phe Leu Ile Lys Asn Asn Asn Asn Asn
        195                 200                 205
Leu Ile Asn Leu Ile Gly Lys Lys Ser Ser Leu Ala Ile Lys Val
    210                 215                 220
Trp Asp Ile Glu Ile Asn Glu Leu Asn Cys Asn His Lys Val Glu Phe
225                 230                 235                 240
Leu Asn Thr Cys Thr Gly Lys Leu Ile Cys Ser His Val Ser Met Gln
                245                 250                 255
Gln Phe Thr Ala Trp Cys Asp Phe His Asn Tyr Arg Leu Ile Pro Trp
            260                 265                 270
Glu Ser Arg Ile Lys Arg Val Ser Asn Ile Leu Pro Ser Thr Met Met
        275                 280                 285
Ala Val Arg Cys Val Ser Thr Pro Asn Phe Pro Ser Met Trp Asn Trp
    290                 295                 300
Lys Ser Ser Arg Thr Asp Gly Pro Thr Arg Phe Val Gln Ser Gly Asp
305                 310                 315                 320
Tyr Cys Ala Glu Asn Gly Trp Gln Val Ala Asn Val Pro Asp Leu Ile
                325                 330                 335
Leu Lys Thr Val Asp Met His Ala Leu Ile Thr Ser Leu Pro Ser Leu
            340                 345                 350
Thr Leu Leu Ile Asp Ala Ser Ser Leu Gly Gln Gly His Val Met Thr
        355                 360                 365
Arg Ile Tyr Ser Thr Ile Cys Asp Pro Tyr Ser Lys Trp Asn Lys Thr
    370                 375                 380
Ser Lys Ser Ser Arg Ile Leu Glu Gly Ile Arg Met Val Gly Arg
385                 390                 395                 400
Lys Asn Lys Leu Leu Pro Phe Val Phe Phe Tyr Gln Glu Ala Lys Ser
                405                 410                 415
Phe Lys Arg Arg Val Asp Leu Arg Gly Cys Leu Cys Arg Asn Leu Tyr
            420                 425                 430
Ile Arg Ser Arg Asn Thr Ala Cys Thr Gln Thr Ile Ser Ala Gly Lys
        435                 440                 445
Lys Arg Thr Leu Leu Thr Glu Leu Leu Ser Trp Gln Gln Lys Leu Leu
    450                 455                 460
Ser Pro Lys Ala Leu Pro Cys Trp Phe Gln Ser Leu Gln Phe Gln Gln
465                 470                 475                 480
Val Leu Ser Leu Ser Leu Ser Leu Ser Leu Ser Leu Ser Leu Ser Leu
                485                 490                 495
Ser His Ile Ile His Leu Ile Val Ser Ser Tyr Lys Phe Ile Arg Val
```

```
                500                 505                 510
Phe Ile Arg Val Gln Ala Phe Gly Asn Leu Ile Met Val Gly Tyr Ile
                515                 520                 525

Phe Lys Thr Cys Asn Leu His Phe Val Ser Leu Phe His Ala Ile Phe
    530                 535                 540

Phe Ser Leu Ile Gly Leu Arg His Leu Leu Glu Leu Ala His Met Leu
545                 550                 555                 560

Phe Lys Tyr Leu Gly Leu Leu Val Asn Gly Lys Lys Leu Ile Asp Phe
                565                 570                 575

Arg Tyr Asn Ala Ile Tyr Ile Tyr Ile Tyr Ile Tyr Ile Tyr Ile Tyr
                580                 585                 590

Ile Tyr Ile Tyr Ile Tyr Tyr Arg Lys Leu Gly Ile Ile His Thr Tyr
                595                 600                 605

Val Arg Phe Ile Ile Lys Val Val Leu Ser Met Gln Ile Ser Leu Thr
                610                 615                 620

Pro Leu Ala Asp Ala Arg Pro Ile Cys Leu Ile Ile Phe His Arg Ala
625                 630                 635                 640

Pro Gln Leu Ser Leu Arg Cys Val Leu Leu Gln Glu Cys Asn Arg Leu
                645                 650                 655

Val Ser Ala Thr Glu Cys Ser Ala Thr Ile Phe Pro Arg Pro Ala Arg
                660                 665                 670

Trp Ser Val Ser Thr Asn Pro Thr Thr Ser Arg Gly Asp Ser Thr Ile
                675                 680                 685

Gln Thr Arg Pro Pro Cys Lys Pro Ser Gly Thr Pro Thr Ser Lys Ser
                690                 695                 700

Cys Trp Met Ser Pro Asp Pro Thr Cys Ser His Trp Pro Pro Ile Leu
705                 710                 715                 720

Arg Pro Pro Ala Thr Gly Ser Gly Thr Ser Ser Pro Thr Gly Pro
                725                 730                 735

Ala Ser Pro Phe Asp Thr Leu Ser Glu Thr Ser Ser Pro Asp Arg Ile
                740                 745                 750

Trp Arg Ser Thr Ser Ser Pro Pro Cys Ala Thr Ser Thr Met Leu Cys
                755                 760                 765

Pro Arg Leu Ala Cys Lys Thr Arg Ser Arg Ser Arg Pro Arg Ser Thr
                770                 775                 780

Arg Ala Ser Ser Ala Arg Pro Thr Leu Pro Pro Ala Pro Ser Pro
785                 790                 795                 800

Pro Pro Pro Arg Arg Thr Ala Pro Ser Cys Ser Ser Trp Arg Val Thr
                805                 810                 815

Glu Arg Arg Ser Trp Ser Met Cys Thr Leu Ile Leu Ala Thr Pro Ala
                820                 825                 830

Thr Arg Asp Arg Ser Arg Cys Pro Thr Pro Cys Ser Arg Pro Pro Ala
                835                 840                 845

Ser Ser Cys Arg Met Gly Asp Ser Ala Ile Arg Thr Cys Ser Thr Pro
                850                 855                 860

Ser Ser Thr Arg Ser Ser Arg Arg Trp Arg Glu Trp Glu Gly Arg Thr
865                 870                 875                 880

Trp Arg Trp Trp Cys Arg Arg Ala Gly Gly Arg Arg Arg Ala Glu Glu
                885                 890                 895

Pro Lys Arg Ala Pro Ala Thr Arg Arg Thr Thr Thr Thr Ser Gly
                900                 905                 910

Met Leu Ala Glu Glu Arg Arg Gly Asp Gln Gly Arg Arg Ser Arg His
                915                 920                 925
```

```
Thr Tyr Ser Arg Cys Ser Thr Arg Thr Arg Leu Glu Gly Ser Ser
    930                 935                 940
Arg Thr Leu Ala Cys Phe Ile Pro Thr Ser Ser Pro Tyr Thr Lys Ala
945                 950                 955                 960
Phe Arg Asn Leu Val Arg Leu Met Asn His Leu Leu Pro Thr Tyr Leu
                965                 970                 975
Pro Thr Asn Lys Thr Asn Lys Ala Pro Lys Arg Glu Asn Ser Asp Leu
            980                 985                 990
Gly Glu Ser Ile Met Met Ile Tyr Asn Lys His Pro Ser Leu Leu Ile
        995                 1000                1005
Ile Ser Met Leu Gln Val Ser Asn Leu Asn Gly Ser Gln Phe Gly Pro
    1010                1015                1020
Thr Ser Ile Leu Gly His Asn Tyr Phe Ile Glu Leu Tyr Ile Gln Lys
1025                1030                1035                1040
Lys Met Cys Leu Glu Cys Leu Ile Gln Tyr Asp Phe Ser Leu Gln Asp
                1045                1050                1055
Tyr Leu Phe Ser Val Ser Phe Ser Met Pro Lys Asn His His Leu Leu
            1060                1065                1070
Trp Gly Met Phe Tyr Thr Leu Met Val Leu His His His Ser Cys
        1075                1080                1085
Phe Ile Leu Gly Leu Val Leu Phe Ile Ile Thr Lys Phe Gly Ser Leu
    1090                1095                1100
Gln Val Ser Arg Leu His Cys Met Gln His Phe Glu Pro Thr Glu His
1105                1110                1115                1120
Cys Asp Cys Leu Leu Glu His Trp Thr Ala Gly
                1125                1130
```

<210> SEQ ID NO 20
<211> LENGTH: 1126
<212> TYPE: PRT
<213> ORGANISM: Musa acuminata

<400> SEQUENCE: 20

```
Leu Asp Pro Arg Gly Gly Gly Arg Ser Arg Ile Val Asp Pro Pro Gly
  1               5                  10                  15
Cys Arg Asn Ser Lys Ile Tyr Ser Phe Leu Phe Tyr Leu Asn Asn Phe
                20                  25                  30
Leu Leu Phe Gly Ile Pro Asn Ile Pro Gly Leu Leu Tyr Phe Trp Arg
            35                  40                  45
Leu Asn Thr Lys Phe Phe Ser His Leu Lys Leu Phe Phe Arg Ser Tyr
        50                  55                  60
Gly His Ile Lys Gln Ile Cys Gln Arg Phe Ser Pro Ser Thr Arg Lys
 65                  70                  75                  80
Gln Gln Ser Arg Val Ile Lys Phe Val Pro Ser Ser Gln Ser Thr Thr
                85                  90                  95
Pro Lys Tyr Ser Leu Asn Gln Ile Leu Thr Ile Asn Asn Asn Pro Ser
                100                 105                 110
Asn Cys Asn Ser Lys Gln Gly Ser Leu Ser Gln Gln Arg Ser Phe Leu
            115                 120                 125
Asn Thr Lys Ile Cys His Asn Leu Ser Leu Leu Ile Ser Val Val Ser
        130                 135                 140
Gly Gln Asp Ser Cys Cys Thr Leu Lys Phe Glu Leu Lys Ser Asp Arg
145                 150                 155                 160
Val Ile Ser Val Ile Glu Ile Asp Asp Arg Thr Asp Phe Lys Ser Thr
```

-continued

```
                165                 170                 175
Leu Arg Asn Leu Gly Leu Ile Lys Leu Ile Arg Val Ser Val Ile Leu
                180                 185                 190
Asp Asp Lys Asn Leu Asp Ser Leu Asn Leu Ile Leu Val Thr Tyr Phe
            195                 200                 205
Leu Lys Ile Ile Ile Ile Ile Leu Ile Leu Glu Lys Lys Val Leu
    210                 215                 220
Pro Leu Lys Ser Gly Arg Thr Lys Leu Met Asn Thr Val Thr Ile Arg
225                 230                 235                 240
Leu Asn Phe Thr His Val Gln Glu Asn Phe Val Glu Val Met Ser Asn
                245                 250                 255
Gln Cys Ser Ser Leu Gln Leu Gly Val Thr Ser Thr Thr Ile Gly Leu
                260                 265                 270
Ser Pro Gly Ser Arg Gly Ser Asn Val Ala Ile Phe Ser Leu Pro Asp
            275                 280                 285
Asp Lys Leu Trp Leu Leu Gly Val Ala Leu Gln Ile Phe His Gln Cys
        290                 295                 300
Gly Ile Gly Arg Val His Ala Leu Thr Asp Gln Leu Gly Leu Phe Ser
305                 310                 315                 320
Leu Val Thr Thr Ala Glu His Glu Lys Met Val Asp Gly Ser Lys Leu
                325                 330                 335
Gln Met Tyr Leu Thr Ser Ser Arg Leu Leu Ile Arg Cys Met His Leu
                340                 345                 350
Arg Leu Phe His Leu Leu Phe Ser Met His Arg Leu Asn Val Lys Asp
            355                 360                 365
Met Gln Glu Ser Ile Pro Leu Phe Val Thr His Ile Pro Asn Gly Thr
    370                 375                 380
Arg Leu Pro Ser Pro His Pro Glu Phe Trp Lys Gly Gly Trp Trp Gly
385                 390                 395                 400
Glu Arg Thr Ser Cys Cys Leu Ser Phe Ser Ser Ile Arg Lys Pro Arg
                405                 410                 415
Val Ser Arg Gly Gly Thr Gly Asp Asp Ala Cys Val Glu Thr Ser Ile
            420                 425                 430
Gly Val Gly Thr Gln His Val Asp Glu His Lys Pro Phe Gln Arg Gly
        435                 440                 445
Arg Arg Glu Pro Phe Gln Ser Cys Cys His Gly Asn Lys Ser Phe Ser
450                 455                 460
Leu His Lys Arg Leu Cys Leu Ala Gly Phe Ser Pro Cys Ser Ser Ser
465                 470                 475                 480
Asn Lys Phe Ser Leu Ser Leu Ser Leu Ser Leu Ser Leu Ser Leu Ser
                485                 490                 495
Leu Ser Leu Ile Leu Tyr Ile Leu Leu Ala Leu Thr Asn Leu Leu Gly
            500                 505                 510
Phe Leu Glu Phe Lys Leu Leu Val Ile Ser Trp Val Ile Phe Ser Lys
        515                 520                 525
Leu Val Thr Cys Ile Leu Ser Leu Tyr Phe Met Gln Tyr Ser Phe Pro
    530                 535                 540
Leu Ala Tyr Val Ile Tyr Leu Ser Leu Ile Cys Asn Cys Leu Asn Ile
545                 550                 555                 560
Trp Asp Tyr Trp Leu Thr Asp Lys Lys Asn Leu Ile Leu Asp Thr Met
                565                 570                 575
Leu Tyr Ile Tyr Ile Tyr Ile Tyr Ile Tyr Ile Tyr Ile Tyr Ile Tyr
            580                 585                 590
```

-continued

```
Ile Tyr Ile Ile Ile Gly Arg Asn Leu Val Phe Thr Arg Met Phe Ala
            595                 600                 605

Leu Ser Glu Asn Glu Ser Phe Gln Cys Arg Leu Val Leu Leu His Leu
    610                 615                 620

Gln Met His Asp Gln Phe Ala Ser Ser Ile Glu His His Ser Val
625                 630                 635                 640

Ser Asp Val Phe Tyr Cys Arg Ser Ala Ile Asp Trp Cys Leu Leu Arg
                645                 650                 655

Asn Ala Arg Gln Gln Ser Ser Pro Ala Gln Arg Gly Gly Gln Ser Leu
            660                 665                 670

Gln Ile Gln Gln His Arg Glu Asp Glu Thr Leu Arg Ser Lys Pro Gly
            675                 680                 685

Arg Pro Ala Ser Pro Gln Glu Leu Gln His Pro Ser Pro Val Gly Cys
690                 695                 700

Pro Pro Ile Arg Arg Ala Val Thr Gly Leu Gln Ser Phe Gly Arg Arg
705                 710                 715                 720

Arg Leu Asp Pro Glu Glu Arg Arg Leu Leu Ala Gln Arg Leu Leu
                725                 730                 735

Ser Ile His Ser Cys Arg Lys Arg Ala Asp Pro Arg Ile Gly Ser Gly
            740                 745                 750

Ala Val His Pro Pro Arg His Ala Gln His Leu Gln Cys Phe Val Leu
            755                 760                 765

Gly Trp Pro Ala Lys Pro Asp Gln Gly Leu Asp Arg Gly Arg His Gly
            770                 775                 780

Arg Pro Arg His Val Leu Pro Ser Leu Arg Arg Arg Leu Leu Leu Arg
785                 790                 795                 800

Arg Pro Gly Val Pro Glu Pro His Arg Ala Val Leu Gly Glu Arg Ser
                805                 810                 815

Ala Ala Pro Gly Gln Cys Val Pro Leu Phe Leu His Arg Gln Pro Gly
            820                 825                 830

Thr Asp Leu Ala Ala Leu Arg Pro Val His Gly Leu Arg Arg Arg Arg
            835                 840                 845

Ala Gly Trp Ala Ile Gln Leu Ser Glu Pro Val Arg Arg His Arg Arg
850                 855                 860

Arg Gly Leu Arg Gly Ala Gly Glu Ser Gly Arg Gly Glu Arg Gly Gly
865                 870                 875                 880

Gly Gly Val Gly Glu Arg Val Ala Val Gly Arg Arg Ser Arg Ser
                885                 890                 895

Glu His Gln Gln Arg Ala Asp Val Gln Pro Glu Leu Asp Gln Ala Cys
            900                 905                 910

Trp Arg Arg Asn Ala Glu Glu Thr Arg Glu Gly Asp Arg Gly Ile His
            915                 920                 925

Ile Arg Asp Val Gln Arg Glu Pro Glu Gly Trp Arg Asp Arg Ala Glu
930                 935                 940

Leu Trp Pro Val Leu Ser Gln Gln Ala Ala Arg Ile Pro Asn Leu Leu
945                 950                 955                 960

Glu Thr Asn Leu Gly Ile Ile Ser Tyr Leu Pro Thr Tyr Leu Arg Ile
                965                 970                 975

Lys His Glu Ile Lys His Gln Asn Lys Gly Arg Ile Leu Ile Leu Glu
            980                 985                 990

Lys Val Glu Ser Tyr Ile Thr Asn Thr Pro Leu Tyr Ser Leu Ser Val
            995                 1000                1005
```

```
Cys Tyr Lys Phe Leu Glu Thr Thr Asp His Asn Leu Asp Leu Gln Val
            1010                1015                1020

Phe Trp Val Ile Ile Ile Ser Leu Asn Tyr Ile Phe Lys Lys Arg Cys
1025                1030                1035                1040

Val Trp Ser Ala Tyr Ser Met Thr Ser Val Cys Lys Ile Thr Ser Ser
                1045                1050                1055

Ala Ser Ala Ser Ala Cys Gln Lys Thr Ile Ile Cys Tyr Gly Ala Cys
            1060                1065                1070

Phe Thr Pro Cys Tyr Ile Ile Ile His Val Ser Phe Val Ser Cys
            1075                1080                1085

Ser Leu Tyr Arg Ser His Lys Ser Leu Asp Arg Phe Lys Phe Leu Gly
            1090                1095                1100

Tyr Ile Val Cys Ser Thr Leu Ser Leu Leu Asn Ile Val Thr Ala Phe
1105                1110                1115                1120

Asn Ile Gly Leu Gln Glu
            1125

<210> SEQ ID NO 21
<211> LENGTH: 1121
<212> TYPE: PRT
<213> ORGANISM: Musa acuminata

<400> SEQUENCE: 21

Asn Trp Thr His Ala Val Ala Ala Leu Glu Trp Ile Pro Arg Ala
 1               5                   10                  15

Ala Gly Ile Leu Lys Ser Ile Leu Phe Tyr Phe Ile Asn Ile Lys Ile
                20                  25                  30

Phe Tyr Cys Leu Val Phe Ser Leu Thr Phe Pro Asp Ser Ser Ile Phe
            35                  40                  45

Gly Asp Ile Gln Asn Ser Ser Pro Ile Ser Tyr Phe Asn Phe Glu Asp
 50                  55                  60

His Met Ala Asp Ile Ser Lys Tyr Val Lys Gly Ser Phe His Arg Pro
 65                  70                  75                  80

His Asp Arg Asn Asn Lys Val Gly Leu Asn Leu Phe Arg His His Lys
                85                  90                  95

Ala Gln His Gln Asn Ile His Leu Ile Lys Ser Ser Leu Ile Ile Ile
            100                 105                 110

Leu Gln Thr Ala Thr Leu Asn Asn Glu Val Leu Ser Pro Ser Asn Val
        115                 120                 125

Leu Phe Thr Gln Arg Phe Ala Thr Leu Ala Asp Phe Tyr Gln Trp
130                 135                 140

Ser Leu Asp Lys Ile Leu Val Ala Arg Asn Ser Asn Gln Ile Glu
145                 150                 155                 160

Leu Tyr Pro Leu Arg Leu Met Thr Glu Pro Ile Leu Arg Val Leu Ser
                165                 170                 175

Val Thr Trp Asp Asn Gly Arg Tyr Gln Leu Phe Met Ile Lys Ile Leu
            180                 185                 190

Ile Val Ile Ser Ser Ser Leu Ile Phe Asn Lys Phe Asp Ser Asp Trp
        195                 200                 205

Lys Lys Lys Lys Phe Ser Ser His Ser Leu Val Gly His Arg Asn Ile
210                 215                 220

Lys Leu Pro Gly Ile Phe Glu His Met Tyr Arg Lys Ile Asp Leu Leu
225                 230                 235                 240

Lys Ser Cys Leu Ile Asn Ala Ala Val Tyr Ser Leu Val Leu Pro Gln
                245                 250                 255
```

-continued

```
Leu Ala Tyr Pro Leu Gly Val Glu Asp Gln Thr Cys Glu Gln Tyr Ser
            260                 265                 270

Pro Phe Leu Met Ile Asn Tyr Asp Gly Cys Val Cys Lys His Ser Lys
            275                 280                 285

Phe Ser Ile Asn Val Glu Leu Glu Glu Phe Thr His Arg Thr Asn Ser
            290                 295                 300

Val Cys Ser Val Trp Leu Leu Ser Met Arg Lys Trp Leu Met Val
305                 310                 315                 320

Ala Ser Cys Lys Cys Thr Pro His Leu Lys Asp Cys Leu Asp Ala Cys
                325                 330                 335

Ile Asp Tyr Val Ser Ser Ile Phe Asn Ser Phe Asp Arg Cys Ile Val
            340                 345                 350

Leu Ile Arg Ser Arg Thr Cys Asp Asp Lys Asn Leu Phe His Tyr Leu
            355                 360                 365

Pro Ile Phe Gln Met Glu Gln Asp Phe Gln Val Leu Ile Gln Asn Phe
            370                 375                 380

Gly Arg Asp Lys Asp Gly Gly Glu Lys Glu Gln Ala Val Ala Phe Arg
385                 390                 395                 400

Phe Leu Leu Ser Gly Ser Gln Glu Phe Gln Glu Gly Arg Pro Glu
                405                 410                 415

Gly Met Met Pro Val Ser Lys Pro Leu Tyr Lys Glu Glu His Ser Met
                420                 425                 430

Leu Met Asn Thr Asn His Phe Ser Gly Glu Glu Glu Asn Pro Phe Asp
            435                 440                 445

Arg Val Val Met Ala Thr Lys Ala Ser Leu Ser Ile Lys Gly Phe
            450                 455                 460

Ala Leu Leu Val Ser Val Leu Val Ala Val Pro Thr Ser Ser Leu Ser
465                 470                 475                 480

Leu Ser Leu Ser Leu Ser Leu Ser Leu Ser Leu Ser Tyr Tyr
                485                 490                 495

Thr Phe Asp Cys Leu Leu Gln Ile Tyr Gly Phe Tyr Lys Ser Ser Ser
                500                 505                 510

Phe Trp Phe Asn His Gly Arg Leu Tyr Phe Gln Asn Leu Pro Ala Phe
            515                 520                 525

Cys Leu Phe Ile Ser Cys Asn Ile Leu Phe Leu Asp Trp Leu Thr Ser
            530                 535                 540

Phe Thr Val Ser Ser Tyr Val Thr Val Ile Phe Gly Ile Ile Gly Arg
545                 550                 555                 560

Ile Lys Lys Ile Asn Phe Ile Gln Cys Tyr Ile Tyr Ile Tyr Ile Tyr
            565                 570                 575

Ile Tyr Ile Tyr Ile Tyr Ile Tyr Ile Leu Val Glu Thr Trp
            580                 585                 590

Tyr Asn Ser His Val Cys Ser Leu Tyr Asn Lys Met Ser Ser Pro Phe
            595                 600                 605

Asn Ala Asp Ser Tyr Ser Thr Cys Arg Cys Thr Thr Asn Leu Leu Asp
            610                 615                 620

His Leu Pro Ser Thr Thr Ala Lys Ser Pro Met Cys Ser Thr Ala Gly
625                 630                 635                 640

Val Gln Ser Ile Gly Val Cys Tyr Gly Met Leu Gly Asn Asn Leu Pro
                645                 650                 655

Pro Pro Ser Glu Val Val Ser Leu Tyr Lys Ser Asn Asn Ile Ala Arg
            660                 665                 670
```

-continued

```
Met Arg Leu Tyr Asp Pro Asn Gln Ala Ala Leu Gln Ala Leu Arg Asn
            675                 680                 685

Ser Asn Ile Gln Val Leu Leu Asp Val Pro Arg Ser Asp Val Gln Ser
        690                 695                 700

Leu Ala Ser Asn Pro Ser Ala Ala Gly Asp Trp Ile Arg Arg Asn Val
705                 710                 715                 720

Val Ala Tyr Trp Pro Ser Val Ser Phe Arg Tyr Ile Ala Val Gly Asn
                725                 730                 735

Glu Leu Ile Pro Gly Ser Asp Leu Ala Gln Tyr Ile Leu Pro Ala Met
            740                 745                 750

Arg Asn Ile Tyr Asn Ala Leu Ser Ser Ala Gly Leu Gln Asn Gln Ile
            755                 760                 765

Lys Val Ser Thr Ala Val Asp Thr Gly Val Leu Gly Thr Ser Tyr Pro
            770                 775                 780

Pro Ser Ala Gly Ala Phe Ser Ala Ala Gln Ala Tyr Leu Ser Pro
785                 790                 795                 800

Ile Val Gln Phe Leu Ala Ser Asn Gly Ala Pro Leu Leu Val Asn Val
                805                 810                 815

Tyr Pro Tyr Phe Ser Tyr Thr Gly Asn Pro Gly Gln Ile Ser Leu Pro
            820                 825                 830

Tyr Ala Leu Phe Thr Ala Ser Gly Val Val Gln Asp Gly Arg Phe
            835                 840                 845

Ser Tyr Gln Asn Leu Phe Asp Ala Ile Val Asp Ala Val Phe Ala Ala
        850                 855                 860

Leu Glu Arg Val Gly Gly Ala Asn Val Ala Val Val Ser Glu Ser
865                 870                 875                 880

Gly Trp Pro Ser Ala Gly Gly Ala Glu Ala Ser Thr Ser Asn Ala
                885                 890                 895

Gln Thr Tyr Asn Gln Asn Leu Ile Arg His Val Gly Gly Thr Pro
            900                 905                 910

Arg Arg Pro Gly Lys Glu Ile Glu Ala Tyr Ile Phe Glu Met Phe Asn
            915                 920                 925

Glu Asn Cys Lys Ala Gly Gly Ile Glu Gln Asn Phe Gly Leu Phe Tyr
        930                 935                 940

Pro Asn Lys Gln Pro Val Tyr Gln Ile Ser Phe Lys Leu Thr Cys Lys
945                 950                 955                 960

Val Asp Glu Ser Ser Pro Thr Tyr Leu Pro Thr Tyr Glu Asn Met Lys
                965                 970                 975

Ser Thr Lys Ile Lys Gly Glu Phe Ser Trp Arg Lys Leu Asn His Asp
            980                 985                 990

Asp Ile Gln Thr Pro Leu Phe Thr His Tyr Gln Tyr Val Thr Ser Phe
        995                 1000                1005

Leu Lys Leu Glu Arg Ile Thr Ile Trp Thr Tyr Lys Tyr Phe Gly Ser
    1010                1015                1020

Leu Phe His Thr Ile Tyr Ser Lys Lys Asp Val Phe Gly Val Leu Asn
1025                1030                1035                1040

Thr Val Leu Gln Phe Ala Arg Leu Pro Leu Gln Arg Gln Leu Gln His
                1045                1050                1055

Ala Lys Lys Pro Ser Ser Ala Met Gly His Val Leu His Leu Asp Gly
            1060                1065                1070

Ala Thr Ser Ser Ser Phe Met Phe His Phe Arg Ser Arg Ala Leu Tyr
        1075                1080                1085

Ile Asp His Ile Lys Val Trp Ile Ala Ser Ser Phe Val Thr Leu Tyr
```

```
          1090              1095                1100
Ala Ala Leu Ala Tyr Thr Leu Leu Pro Phe Arg Thr Leu Asp Cys Arg
1105                 1110                1115                1120

Lys

<210> SEQ ID NO 22
<211> LENGTH: 7397
<212> TYPE: DNA
<213> ORGANISM: Musa acuminata
<220> FEATURE:
<221> NAME/KEY: misc_feature
<222> LOCATION: (82)..(1093)
<223> OTHER INFORMATION: Nucleotides 82, 601, 628, 641, 655, 692, 725,
      774, 793, 806, 813, 854, 867, 870, 876, 882, 890, 919,
      946, 959, 965, 995, 999, 1002, 1028, 1043, 1054,
      1075, 1093 are n wherein n = a or g or c or t/u.
<220> FEATURE:
<221> NAME/KEY: misc_feature
<222> LOCATION: (1515)..(4574)
<223> OTHER INFORMATION: Nucleotides 1515, 2166, 2216, 2265, 2345, 2533,
      2870, 2917, 3077, 3337, 3356, 3618, 3627, 3754,
      3810, 3819, 3884, 3893, 4494, 4503, 4524, 4533,
      4568, 4574 are n wherein n = a or g or c or t/u.
<220> FEATURE:
<221> NAME/KEY: misc_feature
<222> LOCATION: (4597)..(5708)
<223> OTHER INFORMATION: Nucleotides 4597, 4654, 4724, 4741, 4719, 4852,
      5027, 5233, 5546, 5565, 5567, 5575, 5578, 5618,
      5619, 5650, 5669, 5672, 5677, 5683, 5694, 5704,
      5708 are n wherein n = a or g or c or t/u.
<220> FEATURE:
<221> NAME/KEY: misc_feature
<222> LOCATION: (5732)..(5872)
<223> OTHER INFORMATION: Nucleotides 5732, 5741, 5754, 5758, 5772, 5778,
      5780, 5784, 5788, 5802, 5804, 5808, 5813, 5820,
      5824, 5832, 5834, 5836, 5854, 5858, 5863, 5872 are
      n wherein n = a or g or c or t/u.
<220> FEATURE:
<221> NAME/KEY: misc_feature
<222> LOCATION: (5875)..(6863)
<223> OTHER INFORMATION: Nucleotides 5875, 5889, 5915, 5922, 5940, 5990,
      6006, 6011, 6344, 6401, 6416, 6596, 6600, 6608,
      6612, 6712, 6748, 6753, 6756, 6762, 6830, 6844,
      6847, 6863 are n wherein n = a or g or c or t/u.
<220> FEATURE:
<221> NAME/KEY: misc_feature
<222> LOCATION: (6910)..(7395)
<223> OTHER INFORMATION: Nucleotides 6910, 6965, 6968, 7070, 7116, 7179,
      7291, 7322, 7325, 7345, 7351, 7359, 7387, 7395 are
      n wherein n = a or g or c or t/u.

<400> SEQUENCE: 22
agcgaggtcg actaatgagc tactaacatt aatgtcacag atagtaatag atgagaagcc      60
gtatccaaca cgcaatctgt anacttggtc acaggacttc ttatccaaag actcgcctct     120
gcgatttccc acattcacct catttggtcc ataggaagct tcacagcggg caggaatcca     180
tttctctata taagcaccac ctcccaccca caccaccacc actaccactg ctaaggagga     240
tgaaggcctt gttgttggtc atctttaccc tggcctcgtc gctcggcgcc ttcgccgagc     300
aatgcggaag gcaagccggg ggggctctct gccccggcgg gctgtgctgt agccagtacg     360
gctggtgcgg taacacggat ccatactgcg gccaaggatg ccagagccaa tgcggcggta     420
gcggcggtag cggcggtggc agcgtggcct cgatcatcag ctcctccctc ttcgagcaga     480
tgctgaagca tcgcaacgac gcagcctgcc ccggcaaggg tttctacacg tacaacgcct     540
tcatcgccgc cgccaactcc ttcagcgggt tcgggacgac cggcgacgac ccaagaagaa     600
naaggagatc gcggctttct tggcgcanac gtctcacgan acgacaggta attcncacat     660
ctcccgaagc tcgtaaactg tttatgggat anaaaactga atgtttgggg tttggcaggt     720
```

```
gggtnggcga cgcgcccgat ggtccgtacg ccttggggtta ctgcttcgtc caanaacaaa      780
accctcatcg gantactgcg tcccanctcc cantggccgt gcgctgcagc aaaaaatact      840
acggccgaag cccntccaaa tttcatngtn agccanattc tnacagttcn tcgccgcgat      900
cgagttcaca acgatgccnt ttctaacgca acaatccgat gtgttntgcg tgcagcaant      960
acaantacgg gccggccggg agagccatcg gttcngacnt gntcaacaac ccagacctgg     1020
tggccacnga cgcgaccatc tcnttcaaga cggntctgtg gttttggatg actcntcagt     1080
cgcccaagcc gtngtgccac gacgtgataa ccgggagctg gacgccatcc aacgccgacc     1140
aggcggccgg aaggcttccg ggctacggtg tcaccaccaa catcatcaat ggagggttgg     1200
agtgcgggaa agggtacgat gccagggtgg cggataggac cggcttctac aagaggtact     1260
gcgacttgct gggggtgagc tacggagaca acttggactg ctacaaccag agacccttg     1320 cttctacagc agctacagcc acattctagc ggtgagctat ggagacaact ggagtgcta     1380 caaccagaga ccctttactt agtccgatac tactgtgacg aatccatgta ataacgcaat     1440
aaacgctatt actgagatag cgactccgtg agttgactgt agaagttgcg gaggaagtct     1500
tcaataaaag cttanctaca tacatggccc acaactatcg ttgaccgtga tcatatgcat     1560
ccatcaaatg tcctcaaatg tcttggagta agtaaatgcg tattcgatcg gtaaaatgaa     1620
gatgttagaa taaataaaat taattatttt tttataatta taaatatttt aatatatttt     1680
ttaatcttaa agatcctaaa aatctaatta taaggatttt atatatggat tgggatacta     1740
agaatattta attataaaaa ttaatatact ttttaatctt aaagatctaa ttataagtat     1800
tttctatatg gattgggata ttaactcgat ttacttataa aaattttaat ataaaaattt     1860
taaatttaaa aattaaaata ctaaaaatat ctaaatataa cggtaatcat gagatcgaga     1920
acgtgatgat tgagatcatg agatcgaggt tgagagtaaa aaggaaatta cgttaatcat     1980
gggaaatttc gttttgtttg cacggtcgag atggtgaccg tggacaccta acatccacaa     2040
ccggcatgca ataaccatgt tgtcatatgt tagcttgtct catatcttat gaccatgaat     2100
cacatagtct tcacgaatat taattaagcc agcttagcat cacagttttg caccttttgta     2160 ccatanctga agtgttcgta tggcttgacc catcccgagt gtatggtctc ccggancctg     2220
gagcgtgtta acccgaggtc tagttgaggg gcatagacct tgttntctta ggcagaggtt     2280
gaagatcact cctttagcta tccgttgggt gcctatataa aggtcgaaat catgaggggg     2340
attcntaact cgacctattc aatatttgag ctagcaagag ttggagttac gtgtatgagg     2400
ttcgaccccc aatgctgttc ctgggggtcgc ttttataccct attcctgcat gtgatcatac     2460
atagtagctt taatcatctt cagtcatcat cgtacgttgg gtgcatgcat tgtctaattt     2520
actcgattca atntcgttcg acactgcttc ctacctacta tgtggcccaa tacatagttg     2580
tattgtctca tacggcctcg agcaaagcgt gtgcagagga actgtgtcaa gtggttggct     2640
ggcctcgggc tcatggcatt gagttggctc gatacaacac atcggcttag ggataccatg     2700
ccgagtctat tgtggtagtt gacatgtcat gtggggtgga tgccaaaata tgctatatca     2760
ttctctccct acaaaggagt tgtgccatag gagaatcgtg gacacggctt gggttctgtg     2820
gtcggtcctt gttcgcctca gttgggtgga ttacttcatc aagttggccn tctgttggct     2880
gggcaaagta cacttggtag ggatggtcga gacaagncca aggaaggttg gctaagactt     2940
ggttttcgac aatcaattgt ttatgaggcg aatggtatcc ctccgttggg gtgtctgctc     3000
gtttcgattt gttgcgatgg attgtttgtt gtaggaggct tggttcgatt gctcttaagt     3060
```

-continued

```
cgggagaagg tatttgntaa ggagttcaat ttgaccatgt tgaagtgaat aaaaggactt    3120
gccaagaagt ttggctcgac cgtgttaaag ccagagaatg tgtatgtcga ggtctattca    3180
accatgtgga agctagagaa tgcaccaatt gtgaggtttg gcttgctcac gtttaaagca    3240
gaaggatata cttgctacga ggtttgctca accatgtgga agcaatcaaa tgcacttgct    3300
atgaggtttg gcttgactta ctcgacaatg gacgctngta agtgagaagg gactanccaa    3360
gacttagttg gcaaggacta gtcgatactt gctcgacaat agatgcctat aggtaatgga    3420
ttgactgaga cttagtcgac aaagactagc tgagacttag tgggcaatgg atgcctataa    3480
gtaagaaagg atggctcgag attaataaag atcaaataat taatataaat ttatcaaaca    3540
cttaatggac gcataaagt gagaaaggac ggatcgagat taataaagat caaataatta    3600
atataagttt atcaaacnct tattaanaca ttggacaaaa gaggtactat gtaatattaa    3660
aattgggagg cacaaatatt atttccaaat acttttctcc ttaagcccct cgccaccatt    3720
gccatttaa tctatttttt ctatataatt atcncataac attcgtacat gagatatgac    3780
ataaaccttc gacctgcttt agtaaacatn ttgattatng tgacaccaga agccataata    3840
ttgcttacct taacatgatg gagatgaact ttagttggtc caantatcta atnaatggaa    3900
gtggacaagc acgatgacta ggatggctac atgttcatgt gttgacttc caagtaatca    3960
atcaagctgg aatcgaataa gacgattaaa gtagggcgat gaccattaag ttcaatgtca    4020
cgctcatcaa cataattcca acaccgtgca gaaagatctt atcttacatt gacttgccca    4080
tccggccgcc ggcatcgatt ggcggaaacg aagggtcagt ctcccaattc acattcaaag    4140
gacgaattca ttttcatcag atgagcactt cagtcctgct tgattatatt ttattattat    4200
tattattatt aattgaatgg taagtttaca gaatatatag atattttagt ttcaataaaa    4260
tattttaaaa aatgataaag ggagaaggtg gatttgatct taggattttt attgtgagca    4320
ataaaagtct ttagttagaa cttccaaaat gtgtcaaatg aaccctaata agtgggtttg    4380
gtctatggtt acgatgagat cagtatttgt atataaaaaa attatcaact tgatttttat    4440
tttttaaccc ttaataagtg gacatgatat atcataatca aatcatgtga tgntgatga    4500
gtnataacat attttttaat aatnaaaatt atnaatagag aaaaaataag attactatcc    4560
cttctatnga tgtnttataa tattttaatc cctttcnata tagattcacg tagaataaga    4620
aagattataa tcgcatcaaa tcaaatacag aatnaaatca tgcttttgac ttaattcgaa    4680
aaataatctt cctctcttga taatatcctt attgataagc attnttatat atatatatat    4740
ntatatcaac ttctaaaana tattttaaa ttaattaaat ttatcaaaat aaaaagataa    4800
actaaattag ttctgcatca taatgtagta agtgtaagaa cttgtgaaat anggatctag    4860
aacactgata gaaaattcca aaccattact agttctactt gatgaaaaca aaaccatata    4920
aaagaatcct cttatatata tatatatata tatactactt tacttattct ttggacgtac    4980
aacacaagtc aggaaaccga acaaaggtg gcggaaagtt ggcagangct gaagagactt    5040
ttcgtagaag tgaaggagac acacgtctat aagaattgtc atgactatac gctgaagaaa    5100
aagaggggag agagagagaa ggaagcgcca ctgttgaccg gtcttgtcca tgaggaattg    5160
tttgtcgact aatgagcagt acaaacattt gtgtcgacag atggcaacaa atgagaagcg    5220
gtatcccaac acgcaatctg tagcctttgg tcnccagact tatccaaaga cttgcctctg    5280
cgatttcctc atgcgcctca tctgttccaa aggaagcttc acagcgggca ggaatccatt    5340
tctctatata agcaccacct cccacccaca ccaccaccac caccaccact gctaaggagg    5400
atgaaggcct tgttgctggt cattttacc ctggcctcgt cgctcggcgc cttcgccgag    5460
```

```
caatgcggaa ggcaagccgg gggggctctc tgccccggcg ggctgtgctg tagccagtac    5520
ggctggtgcg gtaacacgga tccatnctgc ggtcaaggat gccanancca atgcncangc    5580
tccacgccct cccttccac tccgagcggc ggtggcanng ttggctcgat catcatctcc     5640
tccctcttcn agcagatgct gaagcatcnc ancgacncag ccngcccgg caanggcttc     5700 tacncgtnca ccgccttcat ctccgccgcc anctccttca ncgggttcgg gacnaccngc    5760
gaccactcca cnaataanan gganatcncg gctttcttgg tncngacntc tcncgagacn    5820
acangtaatc cntncntctc ccgaggctcg tctncagntt atngatagac anctnaatgc    5880
attgggttng gcacgtgggt ggtccaccgt gcccnatggc cnttcgcgtg gggttactgc    5940
ttcgtccagn aacagaaccc tcatcggact actgcgtcgc cagctcgcan tggccgtgcg    6000
ctgcangcaa naaatactac ggccgaagcc ccatccaaat ctcattcaac tacaactacg    6060
ggccggccgg gaaaaccatc ggctccgacc tgctcaacaa cccagacctg gtggccaccg    6120
acccgaccat ctccttcaag acggctctgt ggttctggat gactcctcag tcgcccaagc    6180
cgtcgtgcca cgacgtgata accgggagct ggacgccatc caacgccgac cgggcggccg    6240
gaaggcttcc gggctacggt gtcaccacca acatcatcaa tggagggttg gagtgcggga    6300
aagggtccga tgccagggtg gcggatagga tcggcttcta caanaggtac tgcgacttgc    6360
tgggggtgag ctacggagac aacttggact gctacaacca nagtcccttt acttantccg    6420
atactatgtg cgaatccatg taataacgca ataaacgcta ctgctgaaat agcgactccg    6480
tgagttgatt gtagaagttg cggaggaaat cttcaataaa agctaagctg aacaagttca    6540
tggccctcaa tcatcgttga tcgtcgtcag atgcatccat caaatgtctt ggagtnagtn    6600
aatgcgtntt cnatcggtaa attgaagatg ttagaataaa taaaattatt tatttttat     6660 aattataaat attttaatat atttttaat cttaaagatc ctaaaaaatc tnattataag    6720
gattttatat atggattggg atactaanaa aanttnatta tnaaaattaa tatacttta     6780 atcttaagga tcctaaaaaa acataattat aaggattttc tatatggatn gggatactaa    6840
caanatntaa ttgtaaaaat ttnaatataa aattgttaaa tctaaaaatt aaaatactaa    6900
aaatatatan taatcatgat atcgagaatg tggcgcttag atctcgagat cgaggttgag    6960
actanagngg aaattatgtt aatcatggga aattttcttt tgtttccaag acgatgaccg    7020 tggaaccta acatccgcaa tcggtcatgc aataaccatg ttatcatcan tgaacttgtc     7080
gtcgtcatct tacggccaca aatcacagtc ttctancaag gcacgaatat taatgagtcc    7140
aacgtagtat ctatattgtt ttacacttt ataccgtant cgaggtgttc gcacgatttg     7200
gcccatccca agtgcataag atcattgata tgacctctac gttggagcgt gttaacccga    7260
gatctagttg aggggggcata ggtctcattt ntctacgtgg aggttaaaga tcacctttat    7320
tncanccctt gtagattcta aactngaggt ngatctctnt aggagatcgg tctcccttgg    7380
aactctntag gggtncc                                                    7397
```

<210> SEQ ID NO 23
<211> LENGTH: 7397
<212> TYPE: DNA
<213> ORGANISM: Musa acuminata
<220> FEATURE:
<221> NAME/KEY: misc_feature
<222> LOCATION: (82)..(959)
<223> OTHER INFORMATION: Nucleotides 82, 601, 628, 640, 655, 692, 725, 774, 793, 806, 813, 854, 867, 870, 876, 882, 890, 919, 946, 959
<220> FEATURE:

```
<221> NAME/KEY: misc_feature
<222> LOCATION: (965)..(3356)
<223> OTHER INFORMATION: Nucleotides 965, 995, 999, 1002, 1028, 1033,
      1054, 1075, 1093, 1515, 2166, 2216, 2265, 2345, 2533,
      2870, 2917, 3077, 3337, 3356
<220> FEATURE:
<221> NAME/KEY: misc_feature
<222> LOCATION: (3618)..(5027)
<223> OTHER INFORMATION: Nucleotides 3618, 3627, 3754, 3810, 3819, 3884,
      3893, 4494, 4503, 4524, 4533, 4568, 4574, 4597,
      4654, 4724, 4741, 4759, 4852, 5027 are n wherein n
      = a or g or c or t/u.
<220> FEATURE:
<221> NAME/KEY: misc_feature
<222> LOCATION: (5253)..(5758)
<223> OTHER INFORMATION: Nucleotides 5253, 5546, 5565, 5567, 5575, 5578,
      5618, 5619, 5650, 5669, 5672, 5677, 5683, 5694,
      5704, 5708, 5732, 5741, 5754, 5758 are n wherein n
      = a or g or c or t/u.
<220> FEATURE:
<221> NAME/KEY: misc_feature
<222> LOCATION: (5772)..(5889)
<223> OTHER INFORMATION: Nucleotides 5772, 5778, 5780, 5784, 5788, 5802,
      5804, 5808, 5813, 5820, 5824, 5832, 5834, 5836,
      5854, 5858, 5863, 5872, 5875, 5889 are n wherein n
      = a or g or c or t/u.
<220> FEATURE:
<221> NAME/KEY: misc_feature
<222> LOCATION: (5915)..(6844)
<223> OTHER INFORMATION: Nucleotides 5915, 5922, 5950, 5990, 6006, 6011,
      6344, 6401, 6416, 6596, 6600, 6608, 6612, 6712,
      6748, 6753, 6756, 6762, 6830, 6844 are n wherein n
      = a or g or c or t/u.
<220> FEATURE:
<221> NAME/KEY: misc_feature
<222> LOCATION: (6847)..(7395)
<223> OTHER INFORMATION: Nucleotides 6847, 6863, 6910, 6965, 6968, 7070,
      7116, 7179, 7291, 7322, 7325, 7345, 7351, 7359,
      7387, 7395 are n wherein n = a or g or c or t/u.

<400> SEQUENCE: 23
tcgctccagc tgattactcg atgattgtaa ttacagtgtc tatcattatc tactcttcgg     60
cataggtggt gcgttagaca tntgaaccag tgtcctgaag aataggtttc tgagcggaga    120
cgctaaaggg tgtaagtgga gtaaaccagg tatccttcga agtgtcgccc gtccttaggt    180
aaagagatat attcgtggtg gagggtgggt gtggtggtgg tgattggtga cgattcctcc    240
tacttccgga acaacaacca gtagaatggg accggagcag cgagccgcgg aagcggctcg    300
ttacgccttc cgttcggccc ccccgagaga cggggccgcc cgacacgaca tcggtcatgc    360
cgaccacgcc attgtgccta ggtatgacgc cggttcctac ggtctcggtt acgccgccat    420
cgccgccatc gccgccaccg tcgcaccgga gctagtagtc gaggagggag aagctcgtct    480
acgacttcgt agcgttgctg cgtcggacgg ggccgttccc aaagatgtgc atgttgcgga    540
agtagcggcg gcggttgagg aagtcgccca agccctgctg gccgctgctg ggttcttctt    600
nttcctctag cgccgaaaga accgcctntg cagagtgctn tgctgtccat taagngtgta    660
gagggcttcg agcatttgac aaatacccta tnttttgact tacaaacccc aaaccgtcca    720
cccanccgct cgcgcgggcta ccaggcatgc ggaacccaat gacgaagcag gttnttgttt    780
tgggagtagc ctnatgacgc agggtngagg gtnaccggca cgcgacgtcg tttttttatga   840 tgccggcttc gggnaggttt aaagtancan tcggtntaag antgtcaagn agcggcgcta    900
gctcaagtgt tgctacggna aagattgcgt tgttaggcta cacaanacgc acgtcgttna    960
tgttnatgcc cggccggccc tctcggtagc caagnctgna cnagttgttg ggtctggacc   1020 accgtgnct cgcgctggtag agnaagttct gccnagacac caaaacctac tgagnagtca   1080
gcgggttcgg cancacggtg ctgcactatt ggccctcgac ctgcggtagg ttgcggctgg   1140
```

-continued

```
tccgccggcc ttccgaaggc ccgatgccac agtggtggtt gtattattta cctcccaacc    1200
tcacgccctt tcccatgcta cggtcccacc gcctatccta gccgaagatg ttctccatga    1260
cgctgaacga cccccactcg atgcctctgt tgaacctgac gatgttggtc tctgggaaac    1320
gaagatgtcg tcgatgtcgg tgtaagatcg ccactcgata cctctgttga acctcacgat    1380
gttggtctct gggaaatgaa tcaggctatg atgacactgc ttaggtacat tattgcgtta    1440
tttgcgataa tgactctatc gctgaggcac tcaactgaca tcttcaacgc ctccttcaga    1500
agttattttc gaatngatgt atgtaccggg tgttgatagc aactggcact agtatacgta    1560
ggtagtttac aggagtttac agaacctcat tcatttacgc ataagctagc cattttactt    1620
ctacaatctt atttatttta attaataaaa aaatattaat atttataaaa ttatataaaa    1680
aattagaatt tctaggattt ttagattaat attcctaaaa tatataccta accctatgat    1740
tcttataaat taatatttttt aattatatga aaaattagaa tttctagatt aatattcata    1800
aaagatatac ctaaccctat aattgagcta atgaatatt tttaaaatta tatttttaaa    1860
atttaaattt ttaattttat gatttttata gatttatatt gccattagta ctctagctct    1920
tgcactacta actctagtac tctagctcca actctcattt ttcctttaat gcaattagta    1980 cccttttaaag caaaacaaac gtgccagctc taccactggc acctgtggat tgtaggtgtt    2040
ggccgtacgt tattggtaca acagtataca atcgaacaga gtatagaata ctggtactta    2100
gtgtatcaga agtgcttata attaattcgg tcgaatcgta gtgtcaaaac gtggaaacat    2160
ggtatngact tcacaagcat accgaactgg gtagggctca cataccagag ggcctnggac    2220
ctcgcacaat tgggctccag atcaactccc cgtatctgga acaanagaat ccgtctccaa    2280
cttctattga ggaaatcgat aggcaaccca cggatatatt tccagcttta gtactccccc    2340
taagnattga gctggataag ttataaactc gatcgttctc aacctcaatg cacatactcc    2400
aagctggggg ttacgacaag gaccccagcg aaaatatgga taaggacgta cactagtatg    2460
tatcatcgaa attagtagaa gtcagtagta gcatgcaacc cacgtacgta acagattaaa    2520
tgagctaagt tanagcaagc tgtgacgaag gatggatgat acaccgggtt atgtatcaac    2580
ataacagagt atgccggagc tcgtttcgca cacgtctcct tgacacagtt caccaaccga    2640
ccggagcccg agtaccgtaa ctcaaccgag ctatgttgtg tagccgaatc cctatggtac    2700
ggctcagata acaccatcaa ctgtacagta caccccacct acggttttat acagatatag    2760
taagagaggg tgtttcctca acacggtatc ctcttagcac ctgtgccgaa cccaagacac    2820
cagccaggaa caagcggagt caacccacct aatgaagtag ttcaaccggn agacaaccga    2880
cccgtttcat gtgaaccatc cctaccagct ctgttcnggt tccttccaac cgattctgaa    2940
ccaaaagctg ttagttaaca aatactccgc ttaccatagg gaggcaaccc cacagacgag    3000
caaagctaaa caacgctacc taacaaacaa catcctccga accaagctaa cgagaattca    3060
gccctcttcc ataaacnatt cctcaagtta aactggtaca acttcactta ttttcctgaa    3120
cggttcttca aaccgagctg gcacaatttc ggtctcttac acatacagct ccagataagt    3180
tggtacacct tcgatctctt acgtggttaa cactccaaac cgaacgagtg caaatttcgt    3240
cttcctatat gaacgatgct ccaaacgagt tggtacacct tcgttagttt acgtgaacga    3300
tactccaaac cgaactgaat gagctgttac ctgcgancat tcactcttcc ctgatnggtt    3360
ctgaatcaac cgttcctgat cagctatgaa cgagctgtta tctacggata tccattacct    3420
aactgactct gaatcagctg tttctgatcg actctgaatc acccgttacc tacggatatt    3480
```

```
cattctttcc taccgagctc taattatttc tagtttatta attatatta aatagtttgt    3540
gaattacctg cgtatattca ctctttcctg cctagctcta attatttcta gttattaat     3600
tatattcaaa tagtttgnga ataattntgt aacctgtttt ctccatgata cattataatt    3660
ttaaccctcc gtgtttataa taaggttta tgaaagagg aattcgggaa gcggtggtaa      3720
cggtaaaatt agataaaaaa gatatattaa tagngtattg taagcatgta ctctatactg    3780
tatttggaag ctggacgaaa tcatttgtan aactaatanc actgtggtct tcggtattat   3840
aacgaatgga attgtactac ctctacttga aatcaaccag gttnatagat tanttacctt   3900
cacctgttcg tgctactgat cctaccgatg tacaagtaca caactgaaag gttcattagt   3960
tagttcgacc ttagcttatt ctgctaattt catcccgcta ctggtaattc aagttacagt   4020
gcgagtagtt gtattaaggt tgtggcacgt ctttctagaa tagaatgtaa ctgaacgggt   4080
aggccggcgg ccgtagctaa ccgcctttgc ttcccagtca gagggttaag tgtaagtttc   4140
ctgcttaagt aaaagtagtc tactcgtgaa gtcaggacga actaatataa aataataata   4200
ataataataa ttaacttacc attcaaatgt cttatatatc tataaaatca aagttatttt   4260
ataaaatttt ttactatttc cctcttccac ctaaactaga atcctaaaaa taacactcgt   4320
tattttcaga aatcaatctt gaaggtttta cacagtttac ttgggattat tcacccaaac   4380
cagataccaa tgctactcta gtcataaaca tatatttttt taatagttga actaaaaata   4440
aaaaattggg aattattcac ctgtactata tagtattagt ttagtacact acanactact   4500
cantattgta taaaaaatta ttantttaa tanttatctc ttttttattc taatgatagg    4560
gaagatanct acanaatatt ataaaattag ggaaagntat atctaagtgc atcttattct   4620
ttctaatatt agcgtagttt agtttatgtc ttantttagt acgaaaactg aattaagctt   4680
tttattagaa ggagagaact attataggaa taactattcg taanaatata tatatatata   4740
natatagttg aagattttnt ataaaaattt aattaattta aatagtttta tttttctatt   4800
tgatttaatc aagacgtagt attacatcat tcacattctt gaacacttta tnctagatc    4860
ttgtgactat cttttaaggt ttggtaatga tcaagatgaa ctactttgt tttggtatat    4920
tttcttagga gaatatatat atatatatat atatgatgaa atgaataaga aacctgcatg   4980
ttgtgttcag tcctttggct ttgtttccac cgcctttcaa ccgtctncga cttctctgaa   5040
aagcatcttc acttcctctg tgtgcagata ttcttaacag tactgatatg cgacttcttt   5100
ttctccctc tctctctctt ccttcgcggt gacaactggc cagaacaggt actccttaac    5160
aaacagctga ttactcgtca tgtttgtaaa cacagctgtc taccgttgtt tactcttcgc   5220
catagggttg tgcgttagac atcggaaacc agnggtctga ataggtttct gaacggagac   5280
gctaaaggag tacgcggagt agacaaggtt tccttcgaag tgtcgcccgt ccttaggtaa   5340
agagatatat tcgtggtgga gggtgggtgt ggtggtggtg gtggtggtga cgattcctcc   5400
tacttccgga acaacgacca gtaaaaatgg gaccggagca gcgagccgcg gaagcggctc   5460
gttacgccct ccgttcggcc cccccgagag acggggccgc ccgacacgac atcggtcatg   5520
ccgaccacgc cattgtgcct aggtangacg ccagttccta cggtntnggt tacgngtncg   5580
aggtgcggga gggaaggtg aggctcgccg ccaccgtnnc aaccgagcta gtagtagagg    5640
agggagaagn tcgtctacga cttcgtagng tngctgngtc ggncggggcc gttnccgaag   5700
atgngcangt ggcggaagta gaggcggcgg tngaggaagt ngcccaagcc ctgntggncg   5760
ctggtgaggt gnttattntn cctntagngc cgaaagaacc angctgnag agngctctgn    5820
tgtncattag gnangnagag ggctccgagc agangtcnaa tanctatctg tnganttacg   5880
```

```
taacccaanc cgtgcaccca ccaggtggca cgggntaccg gnaagcgcac cccaatgacg    5940
aagcaggtcn ttgtcttggg agtagcctga tgacgcagcg gtcgagcgtn accggcacgc    6000
gacgtncgtt ntttatgatg ccggcttcgg ggtaggttta gagtaagttg atgttgatgc    6060
ccggccggcc cttttggtag ccgaggctgg acgagttgtt gggtctggac caccggtggc    6120
tgggctggta gaggaagttc tgccgagaca ccaagaccta ctgaggagtc agcggggttcg   6180 gcagcacggt gctgcactat tggccctcga cctgcggtag gttgcggctg gcccgccggc    6240
cttccgaagg cccgatgcca cagtggtggt tgtagtagtt acctcccaac ctcacgcccc    6300
ttcccaggct acggtcccac cgcctatcct agccgaagat gttntccatg acgctgaacg    6360 accccccactc gatgcctctg ttgaacctga cgatgttggt ntcagggaaa tgaatnaggc   6420
tatgatacac gcttaggtac attattgcgt tatttgcgat gacgacttta tcgctgaggc    6480
actcaactaa catcttcaac gcctccttta gaagttattt tcgattcgac ttgttcaagt    6540
accgggagtt agtagcaact agcagcagtc tacgtaggta gtttacagaa cctcantcan    6600
ttacgcanaa gntagccatt taacttctac aatcttattt attttaataa ataaaaaata    6660
ttaatattta taaaattata taaaaaatta gaatttctag gattttttag antaatattc    6720
ctaaaatata tacctaaccc tatgattntt ttnaantaat antttaatt atatgaaaat     6780 tagaattcct aggatttttt tgtattaata ttcctaaaag atatacctan ccctatgatt    6840
gttntanatt aacatttta aanttatatt ttaacaattt agattttaa ttttatgatt     6900 tttatatatn attagtacta tagctcttac accgcgaatc tagagctcta gctccaactc    6960
tgatntcncc tttaatacaa ttagtaccct taaaagaaa acaaaggttc tgctactggc     7020
acctttggat tgtaggcgtt agccagtacg ttattggtac aatagtagtn acttgaacag    7080
cagcagtaga atgccggtgt ttagtgtcag aagatngttc cgtgcttata attactcagg    7140
ttgcatcata gatataacaa aatgtgaaaa tatggcatna gctccacaag cgtgctaaac    7200
cgggtagggt tcacgtattc tagtaactat actggagatg caacctcgca caattgggct    7260
ctagatcaac tcccccgtat ccagagtaaa nagatgcacc tccaatttct agtggaaata    7320
angtngggaa catctaagat ttganctcca nctagagana tcctctagcc agagggaacc    7380
ttgaganatc cccangg                                                   7397
```

<210> SEQ ID NO 24
<211> LENGTH: 2326
<212> TYPE: PRT
<213> ORGANISM: Musa acuminata

<400> SEQUENCE: 24

```
Ser Glu Val Asp Ala Thr Asn Ile Asn Val Thr Asp Ser Asn Arg Glu
 1               5                  10                  15

Ala Val Ser Asn Thr Gln Ser Val Xaa Leu Val Thr Gly Leu Leu Ile
             20                  25                  30

Gln Arg Leu Ala Ser Ala Ile Ser His Ile His Leu Ile Trp Ser Ile
         35                  40                  45

Gly Ser Phe Thr Ala Gly Arg Asn Pro Phe Leu Tyr Ile Ser Thr Thr
     50                  55                  60

Asn Ala Glu Gly Lys Pro Gly Gly Leu Ser Ala Pro Ala Gly Cys Ala
 65                  70                  75                  80

Val Ala Ser Thr Ala Gly Ala Val Thr Arg Ile His Thr Ala Ala Lys
                 85                  90                  95
```

```
Asp Ala Arg Ala Asn Ala Ala Val Ala Ala Val Ala Ala Val Ala Ala
                100                 105                 110

Trp Pro Arg Ser Ser Ala Pro Pro Ser Ser Arg Cys Ser Ile Ala
            115                 120                 125

Thr Thr Gln Pro Ala Pro Ala Arg Val Ser Thr Arg Thr Thr Pro Ser
        130                 135                 140

Ser Pro Pro Pro Thr Pro Ser Ala Gly Ser Gly Arg Pro Ala Thr Thr
145                 150                 155                 160

Gln Glu Glu Xaa Gly Asp Arg Gly Phe Leu Gly Ala Xaa Val Ser Arg
                165                 170                 175

Xaa Asp Arg Phe Xaa His Leu Pro Lys Leu Val Asn Cys Leu Trp Asp
            180                 185                 190

Xaa Lys Leu Asn Val Trp Gly Leu Ala Gly Gly Xaa Ala Thr Arg Pro
        195                 200                 205

Met Val Arg Thr Pro Trp Val Thr Ala Ser Ser Xaa Asn Lys Thr Leu
    210                 215                 220

Ile Gly Xaa Leu Arg Pro Xaa Ser Xaa Trp Pro Cys Ala Ala Ala Lys
225                 230                 235                 240

Asn Thr Thr Ala Glu Ala Xaa Pro Asn Phe Xaa Val Ser Xaa Ile Leu
                245                 250                 255

Thr Val Xaa Arg Arg Asp Arg Val His Asn Asp Ala Xaa Ser Asn Ala
            260                 265                 270

Thr Ile Arg Cys Val Xaa Arg Ala Ala Xaa Thr Xaa Thr Gly Arg Pro
        275                 280                 285

Gly Glu Pro Ser Val Xaa Thr Xaa Ser Thr Thr Gln Thr Trp Trp Pro
    290                 295                 300

Xaa Thr Arg Pro Ser Xaa Ser Arg Arg Xaa Cys Gly Phe Gly Leu Xaa
305                 310                 315                 320

Ser Arg Pro Ser Arg Xaa Ala Thr Thr Pro Gly Ala Gly Arg His Pro
                325                 330                 335

Thr Pro Thr Arg Arg Pro Glu Gly Phe Arg Ala Thr Val Ser Pro Pro
            340                 345                 350

Thr Ser Ser Met Glu Gly Trp Ser Ala Gly Lys Gly Thr Met Pro Gly
        355                 360                 365

Trp Arg Ile Gly Ser Ala Ser Thr Arg Gly Thr Ala Thr Cys Trp Gly
    370                 375                 380

Ala Thr Glu Thr Thr Trp Thr Ala Thr Arg Asp Pro Leu Leu Leu
385                 390                 395                 400

Gln Gln Leu Gln Pro His Ser Ser Gly Glu Leu Trp Arg Gln Leu Gly
                405                 410                 415

Val Leu Gln Pro Glu Thr Leu Tyr Leu Val Arg Tyr Cys Asp Glu
            420                 425                 430

Ser Met Arg Asn Lys Arg Tyr Tyr Asp Ser Asp Ser Val Ser Leu Lys
        435                 440                 445

Leu Arg Arg Lys Ser Ser Ile Lys Ala Xaa Leu His Thr Trp Pro Thr
    450                 455                 460

Thr Ile Val Asp Arg Asp His Met His Pro Ser Asn Val Leu Lys Cys
465                 470                 475                 480

Leu Gly Val Ser Lys Cys Val Phe Asp Arg Asn Glu Asp Val Arg Ile
                485                 490                 495

Asn Lys Ile Asn Tyr Phe Phe Ile Ile Ile Asn Ile Leu Ile Tyr Phe
            500                 505                 510

Leu Ile Leu Lys Ile Leu Lys Ile Leu Gly Phe Tyr Ile Trp Ile Gly
```

```
            515                 520                 525
Ile Leu Arg Ile Phe Asn Tyr Lys Asn Tyr Thr Phe Ser Arg Ser Asn
            530                 535                 540

Tyr Lys Tyr Phe Leu Tyr Gly Leu Gly Tyr Leu Asp Leu Leu Ile Lys
545                 550                 555                 560

Ile Leu Ile Lys Phe Ile Lys Leu Lys Tyr Lys Tyr Leu Asn Ile Thr
                565                 570                 575

Val Ile Met Arg Ser Arg Thr Leu Arg Ser Asp Arg Gly Glu Lys Gly
            580                 585                 590

Asn Tyr Val Asn His Gly Lys Phe Arg Phe Val Cys Thr Val Glu Met
            595                 600                 605

Val Thr Val Asp Thr His Pro Gln Pro Ala Cys Asn Asn His Val Val
            610                 615                 620

Ile Cys Leu Val Ser Tyr Leu Met Thr Met Asn His Ile Val Phe Thr
625                 630                 635                 640

Asn Ile Asn Ala Ser Leu Ala Ser Gln Phe Cys Thr Phe Val Pro Xaa
                645                 650                 655

Leu Lys Cys Ser Tyr Gly Leu Thr His Pro Glu Cys Met Val Ser Arg
                660                 665                 670

Xaa Leu Glu Arg Val Asn Pro Arg Ser Ser Gly Ala Thr Leu Xaa Ser
            675                 680                 685

Ala Glu Val Glu Asp His Ser Phe Ser Tyr Pro Leu Gly Ala Tyr Ile
            690                 695                 700

Lys Val Glu Ile Met Arg Gly Ile Xaa Asn Ser Thr Tyr Ser Ile Phe
705                 710                 715                 720

Glu Leu Ala Arg Val Gly Val Thr Cys Met Arg Phe Asp Pro Gln Cys
                725                 730                 735

Ser Ser Trp Gly Arg Phe Tyr Thr Tyr Ser Cys Met Ser Tyr Ile Val
                740                 745                 750

Ala Leu Ile Ile Phe Ser His His Arg Thr Leu Gly Ala Cys Ile Val
                755                 760                 765

Phe Thr Arg Phe Asn Xaa Val Arg His Cys Phe Leu Pro Thr Met Trp
            770                 775                 780

Pro Asn Thr Leu Tyr Cys Leu Ile Arg Pro Arg Ala Lys Arg Val Gln
785                 790                 795                 800

Arg Asn Cys Val Lys Trp Leu Ala Gly Leu Gly Leu Met Ala Leu Ser
                805                 810                 815

Trp Leu Asp Thr Thr His Arg Leu Arg Asp Thr Met Pro Ser Leu Leu
            820                 825                 830

Trp Leu Thr Cys His Val Gly Trp Met Pro Lys Tyr Ala Ile Ser Phe
            835                 840                 845

Ser Pro Tyr Lys Gly Val Val Pro Glu Asn Arg Gly His Gly Leu Gly
850                 855                 860

Ser Val Val Gly Pro Cys Ser Pro Gln Leu Gly Gly Leu Leu His Gln
865                 870                 875                 880

Val Gly Xaa Leu Leu Ala Gly Gln Ser Thr Leu Gly Arg Asp Gly Arg
                885                 890                 895

Asp Lys Xaa Lys Glu Gly Trp Leu Arg Leu Gly Phe Arg Gln Ser Ile
            900                 905                 910

Val Tyr Glu Ala Asn Gly Ile Pro Pro Leu Gly Cys Leu Leu Val Ser
            915                 920                 925

Ile Cys Cys Asp Gly Leu Phe Val Gly Gly Leu Val Arg Leu Leu
930                 935                 940
```

```
Leu Ser Arg Glu Lys Val Phe Xaa Lys Glu Phe Asn Leu Thr Met Leu
945                 950                 955                 960

Lys Ile Lys Gly Leu Ala Lys Lys Phe Gly Ser Thr Val Leu Lys Pro
            965                 970                 975

Glu Asn Val Tyr Val Glu Val Tyr Ser Thr Met Trp Lys Leu Glu Asn
            980                 985                 990

Ala Pro Ile Val Arg Phe Gly Leu Leu Thr Phe Lys Ala Glu Gly Tyr
            995                 1000                1005

Thr Cys Tyr Glu Val Cys Ser Thr Met Trp Lys Gln Ser Asn Ala Leu
    1010                1015                1020

Ala Met Arg Phe Gly Leu Thr Tyr Ser Thr Met Asp Ala Xaa Lys Glu
1025                1030                1035                1040

Gly Thr Xaa Gln Asp Leu Val Gly Lys Asp Ser Ile Leu Ala Arg Gln
            1045                1050                1055

Met Pro Ile Gly Asn Gly Leu Thr Glu Thr Ser Thr Lys Thr Ser Asp
                1060                1065                1070

Leu Val Gly Asn Gly Cys Leu Val Arg Lys Asp Gly Ser Arg Leu Ile
            1075                1080                1085

Lys Ile Lys Leu Ile Ile Tyr Gln Thr Leu Asn Gly Arg Ile Val Arg
        1090                1095                1100

Lys Asp Gly Ser Arg Leu Ile Lys Ile Lys Leu Ile Val Tyr Gln Thr
1105                1110                1115                1120

Leu Ile Thr Leu Asp Lys Arg Gly Thr Met Tyr Asn Trp Glu Ala Gln
                1125                1130                1135

Ile Leu Phe Pro Asn Thr Phe Leu Leu Lys Pro Phe Ala Thr Ile Ala
            1140                1145                1150

Ile Leu Ile Tyr Phe Phe Tyr Ile Ile Xaa His Ser Tyr Met Arg
            1155                1160                1165

Tyr Asp Ile Asn Leu Arg Pro Ala Leu Val Asn Xaa Leu Ile Xaa Val
    1170                1175                1180

Thr Pro Glu Ala Ile Ile Leu Thr Leu Thr Trp Arg Thr Leu Val Gly
1185                1190                1195                1200

Pro Xaa Ile Xaa Met Glu Val Asp Lys His Asp Asp Asp Gly Tyr Met
            1205                1210                1215

Phe Met Cys Leu Ser Lys Ser Ile Lys Leu Glu Ser Asn Lys Thr Ile
                1220                1225                1230

Lys Val Gly Arg Pro Leu Ser Ser Met Ser Arg Ser Ser Thr Phe Gln
            1235                1240                1245

His Arg Ala Glu Arg Ser Tyr Leu Thr Leu Thr Cys Pro Ser Gly Arg
    1250                1255                1260

Arg His Arg Leu Ala Glu Thr Lys Gly Gln Ser Pro Asn Ser His Ser
1265                1270                1275                1280

Lys Asp Glu Phe Ile Phe Ile Arg Ala Leu Gln Ser Cys Leu Ile Ile
            1285                1290                1295

Phe Tyr Tyr Tyr Tyr Tyr Tyr Leu Asn Gly Lys Phe Thr Glu Tyr Ile
            1300                1305                1310

Asp Ile Leu Val Ser Ile Lys Tyr Phe Lys Lys Arg Glu Lys Val Asp
        1315                1320                1325

Leu Ile Leu Gly Phe Leu Leu Ala Ile Lys Val Phe Ser Asn Phe Gln
1330                1335                1340

Asn Val Ser Asn Glu Pro Val Gly Leu Val Tyr Gly Tyr Asp Glu Ile
1345                1350                1355                1360
```

```
Ser Ile Cys Ile Lys Asn Tyr Gln Leu Asp Phe Tyr Phe Leu Thr Leu
            1365                1370                1375

Asn Lys Trp Thr Tyr Ile Ile Ile Lys Ser Cys Asp Val Val Ile Thr
            1380                1385                1390

Tyr Phe Leu Ile Xaa Lys Ile Xaa Asn Arg Glu Lys Ile Arg Leu Leu
            1395                1400                1405

Ser Leu Leu Xaa Met Xaa Tyr Asn Ile Leu Ile Pro Phe Xaa Ile Asp
    1410                1415                1420

Ser Arg Arg Ile Arg Lys Ile Ile Ala Ser Asn Gln Ile Gln Asn
1425                1430                1435                1440

Xaa Ile Met Leu Leu Thr Phe Glu Lys Ser Ser Ser Leu Asp Asn Ile
            1445                1450                1455

Leu Ile Asp Lys His Xaa Tyr Ile Tyr Ile Tyr Xaa Tyr Gln Leu Leu
            1460                1465                1470

Lys Xaa Ile Phe Lys Leu Ile Lys Phe Ile Lys Ile Lys Arg Thr Lys
            1475                1480                1485

Leu Val Leu His His Asn Val Val Ser Val Arg Thr Cys Glu Ile Xaa
    1490                1495                1500

Ile Asn Thr Asp Arg Lys Phe Gln Thr Ile Thr Ser Ser Thr Lys Gln
1505                1510                1515                1520

Asn His Ile Lys Glu Ser Ser Tyr Ile Tyr Ile Tyr Ile Tyr Thr Thr
            1525                1530                1535

Leu Leu Ile Leu Trp Thr Tyr Asn Thr Ser Gln Glu Thr Glu Thr Lys
            1540                1545                1550

Val Ala Glu Ser Trp Gln Xaa Leu Lys Arg Leu Phe Val Glu Val Lys
            1555                1560                1565

Glu Thr His Val Tyr Lys Asn Cys His Asp Tyr Thr Leu Lys Lys Lys
            1570                1575                1580

Arg Gly Glu Arg Glu Lys Glu Ala Pro Leu Leu Thr Gly Leu Val His
1585                1590                1595                1600

Glu Glu Leu Phe Val Asp Ala Val Gln Thr Phe Val Ser Thr Asp Gly
            1605                1610                1615

Asn Lys Glu Ala Val Ser Gln His Ala Ile Cys Ser Leu Trp Ser Pro
            1620                1625                1630

Asp Leu Ser Lys Asp Leu Pro Leu Arg Phe Pro His Ala Pro His Leu
            1635                1640                1645

Phe Gln Arg Lys Leu His Ser Gly Gln Glu Ser Ile Ser Leu Tyr Lys
    1650                1655                1660

His His Leu Pro Pro Thr Pro Pro Pro Pro Pro Leu Leu Arg Arg
1665                1670                1675                1680

Met Lys Ala Leu Leu Leu Val Ile Phe Thr Leu Ala Ser Ser Leu Gly
            1685                1690                1695

Ala Phe Ala Glu Gln Cys Gly Arg Gln Ala Gly Gly Ala Leu Cys Pro
            1700                1705                1710

Gly Gly Leu Cys Cys Ser Gln Tyr Gly Trp Cys Gly Asn Thr Asp Pro
            1715                1720                1725

Xaa Cys Gly Gln Gly Cys Xaa Xaa Gln Cys Xaa Xaa Ser Thr Pro Ser
    1730                1735                1740

Pro Ser Thr Pro Ser Gly Gly Gly Xaa Val Gly Ser Ile Ile Ile Ser
1745                1750                1755                1760

Ser Leu Phe Xaa Gln Met Leu Lys His Xaa Xaa Asp Xaa Ala Xaa Pro
            1765                1770                1775

Gly Xaa Gly Phe Tyr Xaa Xaa Thr Ala Phe Ile Ser Ala Ala Xaa Ser
```

-continued

```
                1780                1785                1790
Phe Xaa Gly Phe Gly Thr Thr Xaa Asp His Ser Thr Asn Xaa Xaa Xaa
    1795                1800                1805

Ile Xaa Ala Phe Leu Val Xaa Thr Ser Xaa Glu Thr Thr Xaa Asn Pro
    1810                1815                1820

Xaa Xaa Ser Arg Gly Ser Ser Xaa Xaa Tyr Xaa Thr Xaa Xaa Cys Ile
1825                1830                1835                1840

Gly Xaa Gly Thr Trp Val Val His Arg Ala Xaa Trp Pro Phe Ala Trp
            1845                1850                1855

Gly Tyr Cys Phe Val Gln Xaa Gln Asn Pro His Arg Thr Thr Ala Ser
        1860                1865                1870

Pro Ala Arg Xaa Gly Arg Ala Leu Xaa Ala Xaa Asn Thr Thr Ala Glu
    1875                1880                1885

Ala Pro Ser Lys Ser His Ser Thr Thr Thr Thr Gly Arg Pro Gly Lys
    1890                1895                1900

Pro Ser Ala Pro Thr Cys Ser Thr Thr Gln Thr Trp Trp Pro Pro Thr
1905                1910                1915                1920

Arg Pro Ser Pro Ser Arg Arg Leu Cys Gly Ser Gly Leu Leu Ser Arg
            1925                1930                1935

Pro Ser Arg Arg Ala Thr Thr Pro Gly Ala Gly Arg His Pro Thr Pro
        1940                1945                1950

Thr Gly Arg Pro Glu Gly Phe Arg Ala Thr Val Ser Pro Pro Thr Ser
    1955                1960                1965

Ser Met Glu Gly Trp Ser Ala Gly Lys Gly Pro Met Pro Gly Trp Arg
    1970                1975                1980

Ile Gly Ser Ala Ser Thr Xaa Gly Thr Ala Thr Cys Trp Gly Ala Thr
1985                1990                1995                2000

Glu Thr Thr Trp Thr Ala Thr Thr Xaa Val Pro Leu Leu Xaa Pro Ile
            2005                2010                2015

Leu Cys Ala Asn Pro Cys Asn Asn Ala Ile Asn Ala Thr Ala Glu Ile
        2020                2025                2030

Ala Thr Pro Val Asp Cys Arg Ser Cys Gly Gly Asn Leu Gln Lys Leu
    2035                2040                2045

Ser Thr Ser Ser Trp Pro Ser Ile Ile Val Asp Arg Arg Gln Met His
2050                2055                2060

Pro Ser Asn Val Leu Glu Xaa Val Asn Ala Xaa Ser Ile Gly Lys Leu
2065                2070                2075                2080

Lys Met Leu Glu Ile Lys Leu Phe Ile Phe Tyr Asn Tyr Lys Tyr Phe
            2085                2090                2095

Asn Ile Phe Phe Asn Leu Lys Asp Pro Lys Lys Ser Xaa Tyr Lys Asp
        2100                2105                2110

Phe Ile Tyr Gly Leu Gly Tyr Xaa Xaa Xaa Ile Xaa Lys Ile Asn Ile
    2115                2120                2125

Leu Leu Ile Leu Arg Ile Leu Lys Lys His Asn Tyr Lys Asp Phe Leu
    2130                2135                2140

Tyr Gly Xaa Gly Tyr Gln Xaa Xaa Ile Val Lys Ile Xaa Ile Asn Cys
2145                2150                2155                2160

Ile Lys Leu Lys Tyr Lys Tyr Ile Xaa Ile Met Ile Ser Arg Met Trp
            2165                2170                2175

Arg Leu Asp Leu Glu Ile Glu Val Glu Thr Xaa Xaa Glu Ile Met Leu
        2180                2185                2190

Ile Met Gly Asn Phe Leu Leu Phe Pro Arg Arg Pro Trp Lys Pro Asn
    2195                2200                2205
```

```
Ile Arg Asn Arg Ser Cys Asn Asn His Val Ile Ile Xaa Glu Leu Val
    2210                2215                2220

Val Val Ile Leu Arg Pro Gln Ile Thr Val Phe Xaa Gln Gly Thr Asn
2225            2230                2235                2240

Ile Asn Glu Ser Asn Val Val Ser Ile Leu Phe Tyr Thr Phe Ile Pro
            2245                2250                2255

Xaa Ser Arg Cys Ser His Asp Leu Ala His Pro Lys Cys Ile Arg Ser
        2260                2265                2270

Leu Ile Pro Leu Arg Trp Ser Val Leu Thr Arg Asp Leu Val Glu Gly
        2275                2280                2285

Ala Val Ser Phe Xaa Tyr Val Glu Val Lys Asp His Leu Tyr Xaa Xaa
    2290                2295                2300

Pro Cys Arg Phe Thr Xaa Gly Xaa Ser Leu Glu Ile Gly Leu Pro Trp
2305            2310                2315                2320

Asn Ser Xaa Gly Val Pro
            2325

<210> SEQ ID NO 25
<211> LENGTH: 2258
<212> TYPE: PRT
<213> ORGANISM: Musa acuminata

<400> SEQUENCE: 25

Ala Arg Ser Thr Asn Glu Leu Leu Thr Leu Met Ser Gln Ile Val Ile
1               5                   10                  15

Asp Glu Lys Pro Tyr Pro Thr Arg Asn Leu Xaa Thr Trp Ser Gln Asp
            20                  25                  30

Phe Leu Ser Lys Asp Ser Pro Leu Arg Phe Pro Thr Phe Thr Ser Phe
        35                  40                  45

Gly Pro Glu Ala Ser Gln Arg Ala Gly Ile His Phe Ser Ile Ala Pro
    50                  55                  60

Met Arg Lys Ala Ser Arg Gly Gly Ser Leu Pro Arg Arg Ala Val Leu
65                  70                  75                  80

Pro Val Arg Leu Val Arg His Gly Ser Ile Leu Arg Pro Arg Met Pro
                85                  90                  95

Glu Pro Met Arg Arg Arg Arg Arg Trp Gln Arg Gly Leu Asp His
            100                 105                 110

Gln Leu Leu Pro Leu Arg Ala Asp Ala Glu Ala Ser Gln Arg Arg Ser
        115                 120                 125

Leu Pro Arg Gln Gly Phe Leu His Val Gln Arg Leu His Arg Arg Arg
    130                 135                 140

Gln Leu Leu Gln Arg Val Arg Asp Asp Arg Arg Arg Pro Lys Lys Xaa
145                 150                 155                 160

Lys Glu Ile Ala Ala Phe Leu Ala Xaa Thr Ser His Xaa Thr Thr Gly
                165                 170                 175

Asn Ser His Ile Ser Arg Ser Thr Val Tyr Gly Ile Xaa Asn Met
            180                 185                 190

Phe Gly Val Trp Gln Val Gly Xaa Arg Arg Ala Arg Trp Ser Val Arg
        195                 200                 205

Leu Gly Leu Leu Leu Arg Pro Xaa Thr Lys Pro Ser Ser Xaa Tyr Cys
    210                 215                 220

Val Pro Xaa Pro Xaa Gly Arg Ala Leu Gln Gln Lys Ile Leu Arg Pro
225                 230                 235                 240

Lys Pro Xaa Gln Ile Ser Xaa Xaa Ala Xaa Phe Xaa Gln Phe Xaa Ala
```

```
                245                 250                 255
Ala Ile Glu Phe Thr Thr Met Pro Phe Leu Thr Gln Gln Ser Asp Val
            260                 265                 270

Xaa Cys Val Gln Gln Xaa Gln Xaa Arg Ala Gly Arg Glu Ser His Arg
            275                 280                 285

Phe Xaa Xaa Xaa Gln Gln Pro Arg Pro Gly Gly His Xaa Arg Asp His
            290                 295                 300

Leu Xaa Gln Asp Gly Ser Val Val Leu Asp Asp Ser Ser Val Ala Gln
305                 310                 315                 320

Ala Val Val Pro Arg Arg Asp Asn Arg Glu Leu Asp Ala Ile Gln Arg
            325                 330                 335

Arg Pro Gly Gly Arg Lys Ala Ser Gly Leu Arg Cys His His Gln His
            340                 345                 350

His Gln Trp Arg Val Gly Val Arg Glu Arg Val Arg Cys Gln Gly Gly
            355                 360                 365

Gly Asp Arg Leu Leu Gln Glu Val Leu Arg Leu Ala Gly Gly Glu Leu
            370                 375                 380

Arg Arg Gln Leu Gly Leu Leu Gln Pro Glu Thr Leu Cys Phe Tyr Ser
385                 390                 395                 400

Ser Tyr Ser His Ile Leu Ala Val Ser Tyr Gly Asp Asn Leu Glu Cys
            405                 410                 415

Tyr Asn Gln Arg Pro Phe Thr Ser Asp Thr Thr Val Thr Asn Pro Cys
            420                 425                 430

Asn Asn Ala Ile Asn Ala Ile Thr Glu Ile Ala Thr Pro Val Asp Cys
            435                 440                 445

Arg Ser Cys Gly Gly Ser Leu Gln Lys Leu Xaa Tyr Ile His Gly Pro
            450                 455                 460

Gln Leu Ser Leu Thr Val Ile Ile Cys Ile His Gln Met Ser Ser Asn
465                 470                 475                 480

Val Leu Glu Val Asn Ala Tyr Ser Ile Gly Lys Met Lys Met Leu Glu
            485                 490                 495

Ile Lys Leu Ile Ile Phe Leu Leu Ile Phe Tyr Ile Phe Ser Arg Ser
            500                 505                 510

Lys Ser Asn Tyr Lys Asp Phe Ile Tyr Gly Leu Gly Tyr Glu Tyr Leu
            515                 520                 525

Ile Ile Lys Ile Asn Ile Leu Phe Asn Leu Lys Asp Leu Ile Ile Ser
            530                 535                 540

Ile Phe Tyr Met Asp Trp Asp Ile Asn Ser Ile Tyr Leu Lys Phe Tyr
545                 550                 555                 560

Lys Asn Phe Lys Phe Lys Asn Asn Thr Lys Asn Ile Ile Arg Ser Asp
            565                 570                 575

Arg Glu Arg Asp Asp Asp His Glu Ile Glu Val Glu Ser Lys Lys Glu
            580                 585                 590

Ile Thr Leu Ile Met Gly Asn Phe Val Leu Phe Ala Arg Ser Arg Trp
            595                 600                 605

Pro Trp Thr Pro Asn Ile His Asn Arg His Ala Ile Thr Met Leu Ser
            610                 615                 620

Tyr Val Ser Leu Ser His Ile Leu Pro Ile Thr Ser Ser Arg Ile Leu
625                 630                 635                 640

Ile Lys Pro Ala His His Ser Phe Ala Pro Leu Tyr His Xaa Ser Val
            645                 650                 655

Arg Met Ala Pro Ile Pro Ser Val Trp Ser Pro Gly Xaa Trp Ser Val
            660                 665                 670
```

-continued

```
Leu Thr Arg Gly Leu Val Glu Gly His Arg Pro Cys Xaa Leu Arg Gln
            675                 680                 685
Arg Leu Lys Ile Thr Pro Leu Ala Ile Arg Trp Val Pro Ile Arg Ser
        690                 695                 700
Lys Ser Gly Gly Phe Xaa Thr Arg Pro Ile Gln Tyr Leu Ser Gln Glu
705                 710                 715                 720
Leu Glu Leu Arg Val Gly Ser Thr Pro Asn Ala Val Pro Gly Val Ala
                725                 730                 735
Phe Ile Pro Ile Pro Ala Cys Asp His Thr Leu Ser Ser Ser Val Ile
            740                 745                 750
Ile Val Arg Trp Val His Ala Leu Ser Asn Leu Leu Asp Ser Xaa Ser
        755                 760                 765
Phe Asp Thr Ala Ser Tyr Leu Leu Cys Gly Pro Ile His Ser Cys Ile
770                 775                 780
Val Ser Tyr Gly Leu Glu Gln Ser Val Cys Arg Gly Thr Val Ser Ser
785                 790                 795                 800
Gly Trp Leu Ala Ser Gly Ser Trp His Val Gly Ser Ile Gln His Ile
                805                 810                 815
Gly Leu Gly Ile Pro Cys Arg Val Tyr Cys Gly Ser His Val Met Trp
            820                 825                 830
Gly Gly Cys Gln Asn Met Leu Tyr His Ser Leu Pro Thr Lys Glu Leu
        835                 840                 845
Cys His Arg Arg Ile Val Asp Thr Ala Trp Val Leu Trp Ser Val Leu
850                 855                 860
Val Arg Leu Ser Trp Val Asp Tyr Phe Ile Lys Leu Ala Xaa Cys Trp
865                 870                 875                 880
Leu Gly Lys Val His Leu Val Gly Met Val Glu Thr Xaa Pro Arg Lys
                885                 890                 895
Val Gly Asp Leu Val Phe Asp Asn Gln Leu Phe Met Arg Arg Met Val
            900                 905                 910
Ser Leu Arg Trp Gly Val Cys Ser Phe Arg Phe Val Ala Met Asp Cys
        915                 920                 925
Leu Leu Glu Ala Trp Phe Asp Cys Ser Val Gly Arg Arg Tyr Leu Xaa
930                 935                 940
Arg Ser Ser Ile Pro Cys Ser Glu Lys Asp Leu Pro Arg Ser Leu Ala
945                 950                 955                 960
Arg Pro Cys Ser Gln Arg Met Cys Met Ser Arg Ser Ile Gln Pro Cys
                965                 970                 975
Gly Ser Arg Met His Gln Leu Gly Leu Ala Cys Ser Arg Leu Lys Gln
            980                 985                 990
Lys Asp Ile Leu Ala Thr Arg Phe Ala Gln Pro Cys Gly Ser Asn Gln
        995                 1000                1005
Met His Leu Leu Gly Leu Ala Leu Thr Arg Gln Trp Thr Leu Val Ser
    1010                1015                1020
Glu Lys Gly Leu Xaa Lys Thr Leu Ala Arg Thr Ser Arg Tyr Leu Leu
1025                1030                1035                1040
Asp Asn Arg Cys Leu Val Met Asp Leu Arg Leu Ser Arg Gln Arg Leu
                1045                1050                1055
Ala Glu Thr Trp Ala Met Asp Ala Tyr Lys Glu Arg Met Ala Arg Asp
            1060                1065                1070
Arg Ser Asn Asn Tyr Lys Phe Ile Lys His Leu Met Asp Ala Tyr Lys
        1075                1080                1085
```

-continued

```
Glu Arg Thr Asp Arg Asp Arg Ser Asn Asn Tyr Lys Phe Ile Lys Xaa
    1090                1095                1100

Leu Leu Xaa His Trp Thr Lys Glu Val Leu Cys Asn Ile Lys Ile Gly
1105            1110                1115                1120

Arg His Lys Tyr Tyr Phe Gln Ile Leu Phe Ser Leu Ser Pro Ser Pro
                1125                1130                1135

Pro Leu Pro Phe Ser Ile Phe Ser Ile Leu Ser His Asn Ile Arg Thr
        1140                1145                1150

Asp Met Thr Thr Phe Asp Leu Leu Thr Xaa Leu Xaa His Gln Lys Pro
    1155                1160                1165

Tyr Cys Leu Pro His Asp Gly Asp Glu Leu Leu Val Gln Xaa Ser Asn
    1170                1175                1180

Xaa Trp Lys Trp Thr Ser Thr Met Thr Arg Met Ala Thr Cys Ser Cys
1185            1190                1195                1200

Val Asp Phe Pro Ser Asn Gln Ser Ser Trp Asn Arg Ile Arg Arg Leu
                1205                1210                1215

Lys Gly Asp Asp His Val Gln Cys His Ala His Gln His Asn Ser Asn
        1220                1225                1230

Thr Val Gln Lys Asp Leu Ile Leu His Leu Ala His Pro Ala Ala Gly
    1235                1240                1245

Ile Asp Trp Arg Lys Arg Arg Val Ser Leu Pro Ile His Ile Gln Arg
    1250                1255                1260

Thr Asn Ser Phe Ser Ser Asp Glu His Phe Ser Pro Ala Leu Tyr Phe
1265            1270                1275                1280

Ile Ile Ile Ile Ile Ile Asn Met Val Ser Leu Gln Asn Ile Ile Phe
                1285                1290                1295

Phe Gln Asn Ile Leu Lys Asn Asp Lys Gly Arg Arg Trp Ile Ser Asp
        1300                1305                1310

Phe Tyr Cys Glu Gln Lys Ser Leu Val Arg Thr Ser Lys Met Cys Gln
    1315                1320                1325

Met Asn Pro Asn Lys Trp Val Trp Ser Met Val Thr Met Arg Ser Val
    1330                1335                1340

Phe Val Tyr Lys Lys Ile Ile Asn Leu Ile Phe Ile Phe Pro Leu Ile
1345            1350                1355                1360

Ser Gly His Asp Ile Ser Ser Asn His Val Met Xaa Asp Glu Xaa His
        1365                1370                1375

Ile Phe Xaa Lys Leu Xaa Ile Glu Lys Lys Asp Tyr Tyr Pro Phe Tyr
        1380                1385                1390

Xaa Cys Xaa Ile Ile Phe Ser Leu Ser Ile Ile His Val Glu Glu Arg
    1395                1400                1405

Leu Ser His Gln Ile Lys Tyr Arg Xaa Lys Ser Cys Phe Leu Asn Ser
    1410                1415                1420

Lys Asn Asn Leu Pro Leu Leu Ile Ile Ser Leu Leu Ile Ser Ile Xaa
1425            1430                1435                1440

Ile Tyr Ile Tyr Xaa Tyr Ile Asn Phe Xaa Ile Phe Leu Asn Leu Asn
                1445                1450                1455

Leu Ser Lys Lys Asp Lys Leu Asn Phe Cys Ile Ile Met Val Glu Leu
        1460                1465                1470

Val Lys Xaa Gly Ser Arg Thr Leu Ile Glu Asn Ser Lys Pro Leu Leu
    1475                1480                1485

Val Leu Leu Asp Glu Asn Lys Thr Ile Lys Asn Pro Leu Ile Tyr Ile
    1490                1495                1500

Tyr Ile Tyr Ile Leu Leu Tyr Leu Phe Phe Gly Arg Thr Thr Gln Val
```

-continued

```
          1505                1510                1515                1520
Arg Lys Pro Lys Gln Arg Trp Arg Lys Val Gly Arg Xaa Arg Asp Phe
                1525                1530                1535
Ser Lys Arg Arg His Thr Ser Ile Arg Ile Val Met Thr Ile Arg Arg
            1540                1545                1550
Lys Arg Gly Glu Arg Glu Arg Lys Arg His Cys Pro Val Leu Ser
        1555                1560                1565
Met Arg Asn Cys Leu Ser Thr Asn Glu Gln Tyr Lys His Leu Cys Arg
    1570                1575                1580
Gln Ile Cys Ser Lys Gly Ser Phe Thr Ala Gly Arg Asn Pro Phe Leu
1585                1590                1595                1600
Tyr Ile Ser Thr Thr Ser His Pro His His His His His His Cys
                1605                1610                1615
Gly Gly Arg Pro Cys Cys Trp Ser Phe Leu Pro Trp Pro Arg Arg Ser
            1620                1625                1630
Ala Pro Ser Pro Ser Asn Ala Glu Gly Lys Pro Gly Gly Leu Ser Ala
        1635                1640                1645
Pro Ala Gly Cys Ala Val Ala Ser Thr Ala Gly Ala Val Thr Arg Ile
    1650                1655                1660
His Xaa Ala Val Lys Asp Ala Xaa Xaa Asn Ala Xaa Ala Pro Arg Pro
1665                1670                1675                1680
Pro Leu Pro Leu Arg Ala Ala Val Ala Xaa Leu Ala Arg Ser Ser Ser
                1685                1690                1695
Pro Pro Ser Ser Ser Arg Cys Ser Ile Xaa Xaa Thr Gln Pro Ala Pro
            1700                1705                1710
Ala Xaa Ala Ser Thr Arg Xaa Pro Pro Ser Ser Pro Pro Pro Xaa Pro
        1715                1720                1725
Ser Xaa Gly Ser Gly Xaa Pro Ala Thr Thr Pro Xaa Ile Xaa Xaa Xaa
    1730                1735                1740
Ser Arg Leu Ser Trp Xaa Xaa Xaa Leu Xaa Arg Xaa Xaa Val Ile Xaa
1745                1750                1755                1760
Xaa Ser Pro Glu Ala Arg Leu Gln Xaa Xaa Asp Arg Xaa Leu Asn Ala
                1765                1770                1775
Leu Gly Xaa Ala Arg Gly Trp Ser Thr Val Pro Xaa Gly Xaa Ser Arg
            1780                1785                1790
Gly Val Thr Ala Ser Ser Xaa Asn Arg Thr Leu Ile Gly Leu Leu Arg
        1795                1800                1805
Arg Gln Leu Ala Xaa Ala Val Arg Cys Xaa Gln Xaa Ile Leu Arg Pro
    1810                1815                1820
Lys Pro His Pro Asn Leu Ile Gln Leu Gln Leu Arg Ala Gly Arg Glu
1825                1830                1835                1840
Asn His Arg Leu Arg Pro Ala Gln Gln Pro Arg Pro Gly Gly His Arg
                1845                1850                1855
Pro Asp His Leu Leu Gln Asp Gly Ser Val Val Leu Asp Asp Ser Ser
            1860                1865                1870
Val Ala Gln Ala Val Val Pro Arg Arg Asp Asn Arg Glu Leu Asp Ala
        1875                1880                1885
Ile Gln Arg Arg Pro Gly Gly Arg Lys Ala Ser Gly Leu Arg Cys His
    1890                1895                1900
His Gln His His Gln Trp Arg Val Gly Val Arg Glu Arg Val Arg Cys
1905                1910                1915                1920
Gln Gly Gly Gly Asp Arg Leu Leu Gln Xaa Val Leu Arg Leu Ala Gly
                1925                1930                1935
```

-continued

```
Gly Glu Leu Arg Arg Gln Leu Gly Leu Leu Gln Pro Xaa Ser Leu Tyr
            1940                1945                1950
Leu Xaa Arg Tyr Tyr Val Arg Ile His Val Ile Thr Gln Thr Leu Leu
        1955                1960                1965
Leu Lys Arg Leu Arg Glu Leu Ile Val Glu Val Ala Glu Glu Ile Phe
    1970                1975                1980
Asn Lys Ser Ala Glu Gln Val His Gly Pro Gln Ser Ser Leu Ile Val
1985                1990                1995                2000
Val Arg Cys Ile His Gln Met Ser Trp Ser Xaa Xaa Met Arg Xaa Xaa
            2005                2010                2015
Ser Val Asn Arg Cys Asn Lys Asn Tyr Leu Phe Phe Ile Ile Ile Asn
        2020                2025                2030
Ile Leu Ile Tyr Phe Leu Ile Leu Lys Ile Leu Lys Asn Leu Ile Ile
    2035                2040                2045
Arg Ile Leu Tyr Met Asp Trp Asp Thr Xaa Lys Xaa Xaa Leu Xaa Lys
2050                2055                2060
Leu Ile Tyr Phe Ser Gly Ser Lys Asn Ile Ile Ile Arg Ile Phe Tyr
2065                2070                2075                2080
Met Asp Xaa Asp Thr Asn Xaa Xaa Leu Lys Phe Xaa Tyr Lys Ile Val
            2085                2090                2095
Lys Ser Lys Asn Asn Thr Lys Asn Ile Xaa Ser Tyr Arg Glu Cys Gly
        2100                2105                2110
Ala Ile Ser Arg Ser Arg Leu Arg Leu Xaa Xaa Lys Leu Cys Ser Trp
            2115                2120                2125
Glu Ile Phe Phe Cys Phe Gln Asp Asp Asp Arg Gly Asn Leu Thr Ser
        2130                2135                2140
Ala Ile Gly His Ala Ile Thr Met Leu Ser Ser Xaa Asn Leu Ser Ser
2145                2150                2155                2160
Ser Ser Tyr Gly His Lys Ser Gln Ser Ser Xaa Lys Ala Arg Ile Leu
            2165                2170                2175
Met Ser Pro Thr Tyr Leu Tyr Cys Phe Thr Leu Leu Tyr Arg Xaa Arg
            2180                2185                2190
Gly Val Arg Thr Ile Trp Pro Ile Pro Ser Ala Asp His Tyr Asp Leu
            2195                2200                2205
Tyr Val Gly Ala Cys Pro Glu Ile Leu Arg Gly His Arg Ser His Xaa
    2210                2215                2220
Ser Thr Trp Arg Leu Lys Ile Thr Phe Ile Xaa Xaa Leu Val Asp Ser
2225                2230                2235                2240
Lys Leu Glu Val Asp Leu Xaa Arg Arg Ser Val Ser Leu Gly Thr Leu
            2245                2250                2255
Gly Xaa
```

<210> SEQ ID NO 26
<211> LENGTH: 2359
<212> TYPE: PRT
<213> ORGANISM: Musa acuminata

<400> SEQUENCE: 26

```
Gln Arg Gly Arg Leu Met Ser Tyr His Cys His Arg Met Arg Ser Arg
  1               5                  10                  15
Ile Gln His Ala Ile Cys Xaa Leu Gly His Arg Thr Ser Tyr Pro Lys
            20                  25                  30
Thr Arg Leu Cys Asp Phe Pro His Ser Pro His Leu Val His Arg Lys
        35                  40                  45
```

-continued

```
Leu His Ser Gly Gln Glu Ser Ile Ser Leu Tyr Lys His His Leu Pro
 50                      55                      60

Pro Thr Pro Pro Pro Leu Pro Leu Leu Arg Arg Met Lys Ala Leu Leu
 65                  70                  75                  80

Leu Val Ile Phe Thr Leu Ala Ser Ser Leu Gly Ala Phe Ala Glu Gln
                 85                  90                  95

Cys Gly Arg Gln Ala Gly Gly Ala Leu Cys Pro Gly Gly Leu Cys Cys
            100                 105                 110

Ser Gln Tyr Gly Trp Cys Gly Asn Thr Asp Pro Tyr Cys Gly Gln Gly
        115                 120                 125

Cys Gln Ser Gln Cys Gly Gly Ser Gly Gly Gly Ser Val
    130                 135                 140

Ala Ser Ile Ile Ser Ser Ser Leu Phe Glu Gln Met Leu Lys His Arg
145                 150                 155                 160

Asn Asp Ala Ala Cys Pro Gly Lys Gly Phe Tyr Thr Tyr Asn Ala Phe
                165                 170                 175

Ile Ala Ala Ala Asn Ser Phe Ser Gly Phe Gly Thr Thr Gly Asp Asp
                180                 185                 190

Pro Arg Arg Xaa Arg Arg Ser Arg Leu Ser Trp Arg Xaa Arg Leu Thr
            195                 200                 205

Xaa Arg Gln Val Ile Xaa Thr Ser Pro Glu Ala Arg Lys Leu Phe Met
210                 215                 220

Gly Xaa Lys Thr Glu Cys Leu Gly Phe Gly Arg Trp Val Gly Asp Ala
225                 230                 235                 240

Pro Asp Gly Pro Tyr Ala Leu Gly Tyr Cys Phe Val Gln Xaa Gln Asn
                245                 250                 255

Pro His Arg Xaa Thr Ala Ser Xaa Leu Pro Xaa Ala Val Arg Cys Ser
                260                 265                 270

Lys Lys Tyr Gly Arg Ser Pro Ser Lys Phe His Xaa Xaa Pro Xaa Ser
        275                 280                 285

Xaa Ser Ser Ser Pro Arg Ser Ser Gln Arg Cys Xaa Phe Arg Asn
290                 295                 300

Asn Pro Met Cys Xaa Ala Cys Ser Xaa Tyr Xaa Tyr Gly Pro Ala Gly
305                 310                 315                 320

Arg Ala Ile Gly Ser Asp Xaa Xaa Asn Asn Pro Asp Leu Val Ala Thr
                325                 330                 335

Asp Ala Thr Ile Ser Phe Lys Thr Xaa Leu Trp Phe Trp Met Thr Xaa
            340                 345                 350

Gln Ser Pro Lys Pro Xaa Cys His Asp Val Ile Thr Gly Ser Trp Thr
        355                 360                 365

Pro Ser Asn Ala Asp Gln Ala Ala Gly Arg Leu Pro Gly Tyr Gly Val
370                 375                 380

Thr Thr Asn Ile Ile Asn Gly Gly Leu Glu Cys Gly Lys Gly Tyr Asp
385                 390                 395                 400

Ala Arg Val Ala Asp Arg Ile Gly Phe Tyr Lys Arg Tyr Cys Asp Leu
                405                 410                 415

Leu Gly Val Ser Tyr Gly Asp Asn Leu Asp Cys Tyr Asn Gln Arg Pro
            420                 425                 430

Phe Ala Ser Thr Ala Ala Thr Ala Thr Phe Arg Ala Met Glu Thr Thr
        435                 440                 445

Trp Ser Ala Thr Thr Arg Asp Pro Leu Leu Ser Pro Ile Leu Leu Arg
450                 455                 460
```

-continued

```
Ile His Val Ile Thr Gln Thr Leu Leu Leu Arg Arg Leu Arg Glu Leu
465                 470                 475                 480

Thr Val Glu Val Ala Glu Val Phe Asn Lys Ser Leu Xaa Thr Tyr
            485                 490                 495

Met Ala His Asn Tyr Arg Pro Ser Tyr Ala Ser Ile Lys Cys Pro Gln
                500                 505                 510

Met Ser Trp Ser Lys Met Arg Ile Arg Ser Val Lys Arg Cys Asn Lys
            515                 520                 525

Asn Leu Phe Phe Tyr Asn Tyr Lys Tyr Phe Asn Ile Phe Phe Asn Leu
530                 535                 540

Lys Asp Pro Lys Asn Leu Ile Ile Arg Ile Leu Tyr Met Asp Trp Asp
545                 550                 555                 560

Thr Lys Asn Ile Leu Lys Leu Ile Tyr Phe Leu Ile Leu Lys Ile Leu
                565                 570                 575

Val Phe Ser Ile Trp Ile Gly Ile Leu Thr Arg Phe Thr Tyr Lys Asn
            580                 585                 590

Phe Asn Ile Lys Ile Leu Asn Leu Lys Ile Lys Ile Leu Lys Ile Ser
            595                 600                 605

Lys Tyr Asn Gly Asn His Glu Ile Glu Asn Val Met Ile Glu Ile Met
610                 615                 620

Arg Ser Arg Leu Arg Val Lys Arg Lys Leu Arg Ser Trp Glu Ile Ser
625                 630                 635                 640

Phe Cys Leu His Gly Arg Asp Gly Asp Arg Gly His Leu Thr Ser Thr
                645                 650                 655

Thr Gly Met Gln Pro Cys Cys His Met Leu Ala Cys Leu Ile Ser Tyr
                660                 665                 670

Asp His Glu Ser His Ser Leu His Glu Tyr Leu Ser Gln Leu Ser Ile
            675                 680                 685

Thr Val Leu His Leu Cys Thr Ile Xaa Glu Val Phe Val Trp Leu Asp
            690                 695                 700

Pro Ser Arg Val Tyr Gly Leu Pro Xaa Pro Gly Ala Cys Pro Glu Val
705                 710                 715                 720

Leu Arg Gly Ile Asp Leu Val Xaa Leu Gly Arg Gly Arg Ser Leu Leu
                725                 730                 735

Leu Ser Val Gly Cys Leu Tyr Lys Gly Arg Asn His Glu Gly Asp Ser
            740                 745                 750

Leu Asp Leu Phe Asn Ile Ala Ser Lys Ser Trp Ser Tyr Val Tyr Glu
            755                 760                 765

Val Arg Pro Pro Met Leu Phe Leu Gly Ser Leu Leu Tyr Leu Phe Leu
770                 775                 780

His Val Ile Ile His Ser Ser Phe Asn His Leu Gln Ser Ser Ser Tyr
785                 790                 795                 800

Val Gly Cys Met His Cys Leu Ile Tyr Ser Ile Gln Xaa Arg Ser Thr
                805                 810                 815

Leu Leu Pro Thr Tyr Tyr Val Ala Gln Tyr Ile Val Leu Ser His
                820                 825                 830

Thr Ala Ser Ser Lys Ala Cys Ala Glu Glu Leu Cys Gln Val Val Gly
            835                 840                 845

Trp Pro Arg Ala His Gly Ile Glu Leu Ala Arg Tyr Asn Thr Ser Ala
            850                 855                 860

Gly Tyr His Ala Glu Ser Ile Val Val Asp Met Ser Cys Gly Val
865                 870                 875                 880

Asp Ala Lys Ile Cys Tyr Ile Ile Leu Ser Leu Gln Arg Ser Cys Ala
```

-continued

```
                  885                 890                 895

Ile Gly Glu Ser Trp Thr Arg Leu Gly Phe Cys Gly Arg Ser Leu Phe
                900                 905                 910

Ala Ser Val Gly Trp Ile Thr Ser Ser Trp Pro Ser Val Gly Trp
                915                 920                 925

Ala Lys Tyr Thr Trp Gly Trp Ser Arg Gln Xaa Gln Gly Arg Leu Ala
            930                 935                 940

Lys Thr Trp Phe Ser Thr Ile Asn Cys Leu Gly Glu Trp Tyr Pro Ser
945                 950                 955                 960

Val Gly Val Ser Ala Arg Phe Gly Leu Leu Arg Trp Ile Val Cys Cys
                965                 970                 975

Arg Arg Leu Gly Ser Ile Ala Leu Lys Ser Gly Glu Gly Ile Xaa Gly
                980                 985                 990

Val Gln Phe Asp His Val Glu Val Asn Lys Arg Thr Cys Gln Glu Val
            995                 1000                 1005

Trp Leu Asp Arg Val Lys Ala Arg Glu Cys Val Cys Arg Gly Leu Phe
    1010                 1015                 1020

Asn His Val Glu Ala Arg Glu Cys Thr Asn Cys Glu Val Trp Leu Ala
1025                 1030                 1035                 1040

His Val Ser Arg Arg Ile Tyr Leu Leu Arg Gly Leu Leu Asn His Val
                1045                 1050                 1055

Glu Ala Ile Lys Cys Thr Cys Tyr Glu Val Trp Leu Asp Leu Asp
                1060                 1065                 1070

Asn Gly Arg Xaa Val Arg Arg Asp Xaa Pro Arg Leu Ser Trp Gln Gly
    1075                 1080                 1085

Leu Val Asp Thr Cys Ser Thr Ile Asp Ala Tyr Arg Trp Ile Asp Asp
    1090                 1095                 1100

Leu Val Asp Lys Asp Leu Arg Leu Ser Gly Gln Trp Met Pro Ile Ser
1105                 1110                 1115                 1120

Lys Lys Gly Trp Leu Glu Ile Asn Lys Asp Gln Ile Ile Asn Ile Asn
                1125                 1130                 1135

Leu Ser Asn Thr Trp Thr His Ile Ser Glu Lys Gly Arg Ile Glu Ile
            1140                 1145                 1150

Asn Lys Asp Gln Ile Ile Asn Ile Ser Leu Asn Ser Xaa Tyr Xaa Ile
            1155                 1160                 1165

Gly Gln Lys Arg Tyr Tyr Val Ile Leu Lys Leu Gly Gly Thr Asn Ile
    1170                 1175                 1180

Ile Ser Lys Tyr Phe Ser Pro Ala Leu Arg His His Cys His Phe Asn
1185                 1190                 1195                 1200

Leu Phe Phe Leu Tyr Asn Tyr Xaa Ile Thr Phe Val His Glu Ile His
            1205                 1210                 1215

Lys Pro Ser Thr Cys Phe Ser Lys His Xaa Asp Tyr Xaa Asp Thr Arg
            1220                 1225                 1230

Ser His Asn Ile Ala Tyr Leu Asn Met Met Glu Met Asn Phe Ser Trp
    1235                 1240                 1245

Ser Xaa Tyr Leu Xaa Asn Gly Ser Gly Gln Ala Arg Leu Gly Trp Leu
    1250                 1255                 1260

His Val His Val Leu Thr Phe Gln Val Ile Asn Gln Ala Gly Ile Glu
1265                 1270                 1275                 1280

Asp Asp Ser Arg Ala Met Thr Ile Lys Phe Asn Val Thr Leu Ile Asn
                1285                 1290                 1295

Ile Ile Pro Thr Pro Cys Arg Lys Ile Leu Ser Tyr Ile Asp Leu Pro
            1300                 1305                 1310
```

-continued

Ile Arg Pro Pro Ala Ser Ile Gly Gly Asn Glu Gly Ser Val Ser Gln
    1315                1320                1325

Phe Thr Phe Lys Gly Arg Ile His Phe His Gln Met Ser Thr Ser Val
    1330                1335                1340

Leu Leu Asp Tyr Ile Leu Leu Leu Leu Leu Leu Ile Glu Trp Val
1345                1350                1355                1360

Tyr Arg Ile Tyr Arg Tyr Phe Ser Phe Asn Lys Ile Phe Lys Met Ile
        1365                1370                1375

Lys Gly Glu Gly Gly Phe Asp Leu Arg Ile Phe Ile Val Ser Asn Lys
            1380                1385                1390

Ser Leu Leu Glu Leu Pro Lys Cys Val Lys Thr Leu Ile Ser Gly Phe
    1395                1400                1405

Gly Leu Trp Leu Arg Asp Gln Tyr Leu Tyr Ile Lys Lys Leu Ser Thr
    1410                1415                1420

Phe Leu Phe Phe Asn Pro Val Asp Met Ile Tyr His Asn Gln Ile Met
1425                1430                1435                1440

Cys Xaa Met Ser Xaa Asn Ile Phe Phe Asn Asn Xaa Asn Tyr Xaa Arg
            1445                1450                1455

Lys Asn Lys Ile Thr Ile Pro Ser Xaa Asp Val Leu Tyr Phe Asn Pro
        1460                1465                1470

Phe Xaa Tyr Arg Phe Thr Asn Lys Lys Asp Tyr Asn Arg Ile Lys Ser
    1475                1480                1485

Asn Thr Glu Xaa Asn His Ala Phe Asp Leu Ile Arg Lys Ile Ile Phe
    1490                1495                1500

Leu Ser Tyr Pro Tyr Ala Xaa Leu Tyr Ile Tyr Ile Xaa Ile Ser Thr
1505                1510                1515                1520

Ser Lys Xaa Tyr Phe Ile Asn Ile Tyr Gln Asn Lys Lys Ile Asn Ile
        1525                1530                1535

Ser Ser Ala Ser Cys Ser Lys Cys Lys Asn Leu Asn Xaa Asp Leu Glu
            1540                1545                1550

His Lys Ile Pro Asn His Tyr Phe Tyr Leu Met Lys Thr Lys Pro Tyr
        1555                1560                1565

Lys Arg Ile Leu Leu Tyr Ile Tyr Ile Tyr Ile Tyr Tyr Phe Thr Tyr
    1570                1575                1580

Ser Leu Asp Val Gln His Lys Ser Gly Asn Arg Asn Lys Gly Gly Gly
1585                1590                1595                1600

Lys Leu Ala Xaa Ala Glu Glu Thr Phe Arg Arg Ser Glu Gly Asp Thr
            1605                1610                1615

Arg Leu Glu Leu Ser Leu Tyr Ala Glu Glu Lys Glu Gly Arg Glu Arg
        1620                1625                1630

Glu Gly Ser Ala Thr Val Asp Arg Ser Cys Pro Gly Ile Val Cys Arg
    1635                1640                1645

Leu Met Ser Ser Thr Asn Ile Cys Val Asp Arg Trp Gln Gln Met Arg
    1650                1655                1660

Ser Gly Ile Pro Thr Arg Asn Leu Pro Leu Val Xaa Arg Leu Ile Gln
1665                1670                1675                1680

Arg Leu Ala Ser Ala Ile Ser Ser Cys Ala Ser Ser Val Pro Lys Glu
        1685                1690                1695

Ala Ser Gln Arg Ala Gly Ile His Phe Ser Ile Ala Pro Pro Pro Thr
            1700                1705                1710

His Thr Thr Thr Thr Thr Thr Ala Lys Glu Asp Glu Gly Leu Val
    1715                1720                1725

-continued

```
Ala Gly His Phe Tyr Pro Gly Leu Val Ala Arg Arg Leu Arg Arg Ala
   1730                1735                1740

Met Arg Lys Ala Ser Arg Gly Gly Ser Leu Pro Arg Arg Ala Val Leu
1745                1750                1755                1760

Pro Val Arg Leu Val Arg His Gly Ser Xaa Leu Arg Ser Arg Met Pro
               1765                1770                1775

Xaa Pro Met Xaa Xaa Leu His Ala Leu Pro Phe His Ser Glu Arg Arg
           1780                1785                1790

Trp Xaa Xaa Trp Leu Asp His His Leu Leu Pro Leu Xaa Ala Asp Ala
       1795                1800                1805

Glu Ala Ser Xaa Arg Xaa Ser Xaa Pro Arg Gln Xaa Leu Leu Xaa Val
   1810                1815                1820

His Arg Leu His Leu Arg Arg Xaa Leu Leu Xaa Arg Val Arg Asp Xaa
1825                1830                1835                1840

Xaa Arg Pro Leu His Xaa Xaa Gly Xaa Xaa Gly Phe Leu Gly Xaa Asp
               1845                1850                1855

Xaa Ser Arg Asp Xaa Xaa Ser Xaa Xaa Leu Pro Arg Leu Val Xaa Xaa
           1860                1865                1870

Leu Xaa Ile Asp Xaa Xaa Met His Trp Val Xaa His Val Gly Gly Pro
       1875                1880                1885

Pro Cys Pro Met Ala Xaa Arg Val Gly Leu Leu Leu Arg Pro Xaa Thr
   1890                1895                1900

Glu Pro Ser Ser Asp Tyr Cys Val Ala Ser Ser Xaa Trp Pro Cys Ala
1905                1910                1915                1920

Ala Xaa Xaa Lys Tyr Tyr Gly Arg Ser Pro Ile Gln Ile Ser Phe Asn
               1925                1930                1935

Tyr Asn Tyr Gly Pro Ala Gly Lys Thr Ile Gly Ser Asp Leu Leu Asn
           1940                1945                1950

Asn Pro Asp Leu Val Ala Thr Asp Pro Thr Ile Ser Phe Lys Thr Ala
       1955                1960                1965

Leu Trp Phe Trp Met Thr Pro Gln Ser Pro Lys Pro Ser Cys His Asp
   1970                1975                1980

Val Ile Thr Gly Ser Trp Thr Pro Ser Asn Ala Asp Arg Ala Ala Gly
1985                1990                1995                2000

Arg Leu Pro Gly Tyr Gly Val Thr Thr Asn Ile Ile Asn Gly Gly Leu
               2005                2010                2015

Glu Cys Gly Lys Gly Ser Asp Ala Arg Val Ala Asp Arg Ile Gly Phe
           2020                2025                2030

Tyr Xaa Arg Tyr Cys Asp Leu Leu Gly Val Ser Tyr Gly Asp Asn Leu
       2035                2040                2045

Asp Cys Tyr Asn Xaa Ser Pro Phe Thr Xaa Ser Asp Thr Met Cys Glu
   2050                2055                2060

Ser Met Arg Asn Lys Arg Tyr Cys Asn Ser Asp Ser Val Ser Leu Lys
2065                2070                2075                2080

Leu Arg Arg Lys Ser Ser Ile Lys Ala Lys Leu Asn Lys Phe Met Ala
               2085                2090                2095

Leu Asn His Arg Ser Ser Ser Asp Ala Ser Ile Lys Cys Leu Gly Val
           2100                2105                2110

Ser Xaa Cys Val Phe Xaa Arg Ile Glu Asp Val Arg Ile Asn Lys Ile
       2115                2120                2125

Ile Tyr Phe Leu Leu Ile Phe Tyr Ile Phe Ser Arg Ser Lys Ile Xaa
   2130                2135                2140

Leu Gly Phe Tyr Ile Trp Ile Gly Ile Leu Xaa Lys Xaa Xaa Tyr Xaa
```

-continued

```
                2145                2150                2155                2160

Asn Tyr Thr Phe Asn Leu Lys Asp Pro Lys Lys Thr Leu Gly Phe Ser
                2165                2170                2175

Ile Trp Xaa Gly Ile Leu Thr Xaa Xaa Asn Cys Lys Asn Xaa Asn Ile
        2180                2185                2190

Lys Leu Leu Asn Leu Lys Ile Lys Ile Leu Lys Ile Tyr Xaa Asn His
        2195                2200                2205

Asp Ile Glu Asn Val Ala Leu Arg Ser Arg Asp Arg Gly Asp Xaa Xaa
        2210                2215                2220

Gly Asn Tyr Val Asn His Gly Lys Phe Ser Phe Val Ser Lys Thr Met
2225                2230                2235                2240

Thr Val Glu Thr His Pro Gln Ser Val Met Gln Pro Cys Tyr His Xaa
                2245                2250                2255

Thr Cys Arg Arg His Leu Thr Ala Thr Asn His Ser Leu Leu Xaa Arg
            2260                2265                2270

His Glu Tyr Val Gln Arg Ser Ile Tyr Ile Val Leu His Phe Tyr Thr
        2275                2280                2285

Val Xaa Glu Val Phe Ala Arg Phe Gly Pro Ser Gln Val His Lys Ile
    2290                2295                2300

Ile Asp Met Thr Ser Thr Leu Glu Arg Val Asn Pro Arg Ser Ser Gly
2305                2310                2315                2320

Gly Ile Gly Leu Ile Xaa Leu Arg Gly Gly Arg Ser Pro Leu Xaa Xaa
                2325                2330                2335

Pro Leu Ile Leu Asn Xaa Arg Xaa Ile Ser Xaa Gly Asp Arg Ser Pro
            2340                2345                2350

Leu Glu Leu Xaa Arg Gly Xaa
        2355

<210> SEQ ID NO 27
<211> LENGTH: 4924
<212> TYPE: DNA
<213> ORGANISM: Musa acuminata
<220> FEATURE:
<221> NAME/KEY: misc_feature
<222> LOCATION: (879)..(4119)
<223> OTHER INFORMATION: Nucleotides 879, 3691 and 4119 are n wherein n
      = a or g or c or t/u.

<400> SEQUENCE: 27
ggatcccaac ttttaggaat ggatcttaaa attttagtta taagttcaaa gttagaaaaa      60
tctttaccaa gagctttgag tccattgatg acatccgtga aacggtgtac atgtctccga    120
tggactcact tggtttcatt cggaaaagtt cgaaagagtg cataagaata ttgattttgg    180
attctttcac tcggttggtg ccttcatgag tgacctcaag agtcctccaa atatcaaaag    240
ccgaatcaca aattgaaatg tgattgaatt cattttttgtc taatgcacaa aacagggcat    300
tcatagcctt tgtgtttaaa gcaaaaacat tcttctccga ttcatcccat tcgctcatcg    360
gaagagaaaa tttttgaaat ccattttcga caatagacca aagctcgaaa tccatggaaa    420
tgaggaagat cctcatatga gttttccaat acatgtaatt cgactcatta acataggtg     480 gatgtgtaat gaaatgaccc tcatgcscta tctctcttgg gtattaaacc aaatatgaga    540
gtgagccttg ctctgatacc aattgttagg atcagagtgg cactaagaga ggggggagt     600 gaattagtgc agtggattaa aacttataag tttaaaaatg aattcgtaaa tacgagaaga    660
tttcgtttta atagtaactt gagtagatga aaaccaaaag ttaacagtag tgtaaataac    720
aatttcggga agtaagaac tcacacattc aaggaacata ccaatttaaa gtggttcggt     780
```

```
caaaatgacc tacatccact tgtgaagcct tcttcgaaga ggctcccaac ttccactagc      840
aaatcacttt gaaggggaag gacaaatacc tctcttacna ccttttacaa tggttcatac      900
tcttacaaat tttcaacgag aaagaaggag gtgaacatgc aagcaattga aaacaagact      960
tgctaaagac tttgctaagg ctttttttct caatctattg cttctcaaaa gttgtattct     1020
ctgctgagaa ttgaggggta tttatagacc ccaagaggat ttaaatttgg gctccaaatt     1080
tcgaatgctc ttgggttccc gaggttgccg gtgccaccgc ctgtcagtgt ttgacactgg     1140
acagtgtact agcggtgcca ccgccggacc tctcgggtgt tgggcggtgc caccgcctag     1200 acttttttcag ctcactggtt ggattccaaa cttgacccaa accagtccga actcgggtcc     1260
aattgacccg taaccggatt ataggattaa cccttaatcc taaccctaat tatatgcaaa     1320
ctacgcaact gaaaatatag tcctaagcaa gttttaacc ggcaaacgtc gagtcttctt      1380
ccggcgatct ttcggcagac ttctgatata cctttggatt tcttctagcg gactcctagt     1440
agggtcccga tcttgtggcg agtttagcga gtagccgaac cttctcggtg atctccgcaa     1500
accgccgatg atctcttcgg cagactttcg aaaacttcga caagtccccg atttcttctc     1560
ggttggttcc gacagcatct ctaacgaaac ttcggactcc ttgaatgtcc atcgaacttg     1620
actccggtag gcttgcttta tattttcagg ctatcatagt taatcctaca tacttaactc     1680
aataatatgg attagattaa ttaacccatc aattgatttc atcatcaaaa ttcgacattc     1740
aacaaacatc cgtactcaat aacccatcag gctatagtta cgtgactatc tactgtgatc     1800
cgtacgtgaa gttagcgagt catgatccag gtcgtgtcac ttattggccg aacacgtatc     1860
ccttatccaa atccagtctt ctcaactctt ctagcctacc cgtctctttt tttattactt     1920
ttgaaagaat tcaaatcaaa acagatacaa aataacacgg tgagacactg tgacatgcta     1980
gtctctggaa agcattaatt cgcgcatcca cagacgtcgt cagcttcatc cccacttttt     2040
tcctacataa ccatgtcgca tggctttgtt gatgacagac caccacaagc ttgcctttgg     2100
ttgtgcctaa cagagagaga gagacagacc gatagcctcc tcattcacta tggcgatccg     2160
atcgccagct tcgctgctgt tatttgcgtt cctgatgctt gcgctcacgg gaagactgca     2220
ggcccggcgc agctcatgca ttggcgtcta ctggggacaa acaccgacg agggaagctt      2280 agcagatgct tgtgccacag gcaactacga atacgtgaac atcgccaccc ttttcaagtt     2340
tggcatgggc caaactccag agatcaacct cgccggccac tgtgaccctc ggaacaacgg     2400
ctgcgcgcgc ttgagcagcg aaatccagtc ctgccaggag cgtggcgtca aggtgatgct     2460
ctccatcgga ggtggcgggt cttatggcct gagttccacc gaagacgcca aggacgtagc     2520
gtcataccct tggcacagtt tcttgggtgg ttctgctgct cgctactcga gacccctcgg     2580
ggatgcggtt ctggatggca tagacttcaa catcgccgga gggagcacag aacactatga     2640
tgaacttgcc gctttcctca aggcctacaa cgagcaggag gccggaacga agaaagttca     2700
cttgagtgct cgtccgcagt gtccttccc ggattactgg cttggcaacg cactcagaac      2760
agatctcttc gacttcgtgt gggtgcagtt cttcaacaac ccttcgtgcc atttctccca     2820
gaacgctatc aatcttgcaa atgcgttcaa caattgggtc atgtccatcc ctgcgcaaaa     2880
gctgttcctt gggcttcctg ctgctcctga ggctgctcca actggtggct acattccacc     2940
ccatgatctc atatctaaag ttcttccgat cctaaaggat tccgacaagt acgcaggaat     3000
catgctgtgg actagatacc acgacagaaa ctccggctac agttctcaag tcaagtccca     3060
cgtgtgtcca gcgcgtcggt tctccaacat cttatctatg ccggtgaagt cttccaagta     3120
```

-continued

```
aacctgaacg gcgtagatga tcggtggtcg aaaactccga tcatcatggg tccccatccg      3180
tatccgtgcg ttgctacgtt atggtgtttc ccttgtatgt tggtcttttc aataatataa      3240 taagggggtta gttttacgtt tccatatttt ccatgttcga aaacagtata tttgctgccc     3300
cttccaaatt tgaaaaagat aaaataaata tataactaaa aatatcctct ttttttttc       3360 tttcgacaaa tatataactc ttaactttcc caattgttta agcaaaagat ataaatcctc      3420
ttccacacaa aagacgaatc catgattgct ggattgctgt ctactggtgc cgaaatggcg      3480
acgagagaag cttgtgctac ctgcaattac aagttcgtca acattgtctt ccttgccatg     3540
tttggtgacg ccatactccc gtgatcagga cacacctctg gaacagtttc ttgggaagtt     3600
aatcttcttc tcggctcctc ggcgaccaat cttgtgaggt tcttctcctg aatggtgtcc      3660
acttcgacat cgaaggtcta cctgagcgca natccacagt tccgactacg tgtgggtgca      3720
gttctactac acaggcaact cgcagatgcc cggtaacaat gggttctcca tcctgcatgg      3780
aaggtgttcc ctggacttcc tgctgctcct caggctgctg gaaggagctc cattccacta      3840
gtgatcttac acgtgtctta tcatcaagaa ttatagcaag taccgaggga ttattaaaat      3900
aaaaaaaaag ggaagaatgg gaattagaat taaaactgaa accggccatg aagaacgttt     3960
cgagtgaaga caaacgacag tatgagacgg tagtttgcta tggacatgga tcgttcccaa     4020
agcagtccaa gtctttatga accggtctat cggttcagcc ttcaagaacc gcgaggataa      4080
ccggcccaag agaaacaaca aattgtggtg agcttttant ataaaccgaa cggtgccgtc      4140
cgtcagatgt taaatggacg gcggatagat ctccagagta aatctgagga aaatcgttcc     4200 ggcccccctta ccacgaccca cgcgatccgt cctctccccc acccctaca ccttttttctt    4260 cttccgctcc tgcgatcggt tatttgattt tgtgtatgat atccaatttc ttttctggag     4320
tggtatccta ttctaatttc ttagattgtt gtattgaacc atcagttttg gtttaagcgc     4380
atgatggcgg agagtttcgg gagatgggag tcagatccct tgttttctgc tgccgaagtg     4440
gtgcaagatt cggccgatag gttttttctc tcattttaag ctcaattatg cggtcattct     4500
tgttaggctt tggagaattt gctctatttc gaaagaaatt gctgctttct agttttgatt     4560
agtccctata aaatttgctt tcggttctga atatccgaga atgtcgtatc gtcaatgacg     4620
attctttttt agaattctaa tactttgtcc tgttttctgt gatttaatgg agaaaatatt     4680 gttccttttta gtgatctatg ctctcccgac cattaggatg agggttgaag gtgaaaatac     4740
tttctggtaa ttttcctctc taaattcttc caaacacgac acaagtataa ttatagacca     4800
agattgattc ttcttatgca ccgattctca cttcccttcc ctctgtgtta tggttatcgt     4860
tgttactgat ggttgcttaa ctcatggggt agcgcctggg tgatccgttg acctgcaggt     4920
cgac                                                                  4924
```

<210> SEQ ID NO 28
<211> LENGTH: 4924
<212> TYPE: DNA
<213> ORGANISM: Musa acuminata
<220> FEATURE:
<221> NAME/KEY: misc_feature
<222> LOCATION: (879)..(4119)
<223> OTHER INFORMATION: Nucleotides 879, 3691 and 4119 are n wherein n
      = a or g or c or t/u.

<400> SEQUENCE: 28

```
cctagggttg aaaatcctta cctagaattt taaaatcaat attcaagttt caatcttttt       60
agaaatggtt ctcgaaactc aggtaactac tgtaggcact ttgccacatg tacagaggct      120
```

```
acctgagtga accaaagtaa gccttttcaa gctttctcac gtattcttat aactaaaacc    180
taagaaagtg agccaaccac ggaagtactc actggagttc tcaggaggtt tatagttttc    240
ggcttagtgt ttaactttac actaacttaa gtaaaaacag attacgtgtt ttgtcccgta    300
agtatcggaa acacaaattt cgttttgta agaagaggct aagtaggta agcgagtagc     360 cttctctttt aaaaacttta ggtaaaagct gttatctggt ttcgagcttt aggtaccttt    420
actccttcta ggagtatact caaaaggtta tgtacattaa gctgagtaat ttgtatccac    480
ctacacatta ctttactggg agtacgsgat agagagaacc cataatttgg tttatactct    540
cactcggaac gagactatgg ttaacaatcc tagtctcacc gtgattctct cccccctca    600 cttaatcacg tcacctaatt tgaatattc aaatttttac ttaagcattt atgctcttct    660
aaagcaaaat tatcattgaa ctcatctact tttggttttc aattgtcatc acatttattg    720
ttaaagccct ttcattcttg agtgtgtaag ttccttgtat ggttaaattt caccaagcca    780
gttttactgg atgtaggtga acacttcgga agaagcttct ccgagggttg aaggtgatcg    840
tttagtgaaa cttccccttc ctgtttatgg agagaatgnt ggaaaatgtt accaagtatg    900
agaatgttta aagttgctc tttcttcctc cacttgtacg ttcgttaact tttgttctga     960
acgatttctg aaacgattcc gaaaaaaga gttagataac gaaagttttt caacataaga    1020
gacgactctt aactccccat aaatatctgg ggttctccta aatttaaacc cgaggtttaa    1080
agcttacgag aacccaaggg ctccaacggc cacggtggcg gacagtcaca aactgtgacc    1140
tgtcacatga tcgccacggt ggcggcctgg agagcccaca acccgccacg gtggcggatc    1200
tgaaaaagtc gagtgaccaa cctaaggttt gaactgggtt tggtcaggct tgagcccagg    1260
ttaactgggc attggcctaa tatcctaatt gggaattagg attgggatta atatacgttt    1320
gatgcgttga ctttatatc aggattcgtt caaaaattgg ccgtttgcag ctcagaagaa     1380
ggccgctaga aagccgtctg aagactatat ggaaacctaa agaagatcgc ctgaggatca    1440
tcccagggct agaacaccgc tcaaatcgct catcggcttg aagagccac tagaggcgtt     1500 tggcggctac tagagaagcc gtctgaaagc ttttgaagct gttcagggc taaagaagag     1560 ccaaccaagg ctgtcgtaga gattgctttg aagcctgagg aacttacagg tagcttgaac    1620
tgaggccatc cgaacgaaat ataaagtcc gatagtatca attaggatgt atgaattgag     1680
ttattatacc taatctaatt aattgggtag ttaactaaag tagtagtttt aagctgtaag    1740
ttgtttgtag gcatgagtta ttgggtagtc cgatatcaat gcactgatag atgacactag    1800
gcatgcactt caatcgctca gtactaggtc cagcacagtg aataaccggc ttgtgcatag    1860
ggaataggtt taggtcagaa gagttgagaa gatcggatgg gcagagaaaa aaataatgaa    1920
aactttctta agtttagttt tgtctatgtt ttattgtgcc actctgtgac actgtacgat    1980 cagagaccett tcgtaattaa gcgcgtaggt gtctgcagca gtcgaagtag tgggtgaaaa    2040
aggatgtatt ggtacagcgt accgaaacaa ctactgtctg gtggtgttcg aacggaaacc    2100
aacacggatt gtctctctct ctctgtctgg ctatcggagg agtaagtgat accgctaggc    2160
tagcggtcga agcgacgaca ataaacgcaa ggactacgaa cgcgagtgcc cttctgacgt    2220
ccgggccgcg tcgagtacgt aaccgcagat gacccctgtt ttgtggctgc tcccttcgaa    2280
tcgtctacga acacggtgtc cgttgatgct tatgcacttg tagcggtggg aaaagttcaa    2340
accgtacccg gtttgaggtc tctagttgga gcggccggtg acactgggag ccttgttgcc    2400
gacgcgcgcg aactcgtcgc tttaggtcag gacggtcctc gcaccgcagt tccactacga    2460
gaggtagcct ccaccgccca gaataccgga ctcaaggtgg cttctgcggt tcctgcatcg    2520
```

```
cagtatggag accgtgtcaa agaacccacc aagacgacga gcgatgagct ctggggagcc  2580
cctacgccaa gacctaccgt atctgaagtt gtagcggcct ccctcgtgtc ttgtgatact  2640
acttgaacgg cgaaaggagt tccggatgtt gctcgtcctc cggccttgct tctttcaagt  2700
gaactcacga gcaggcgtca caggaaaggg cctaatgacc gaaccgttgc gtgagtcttg  2760
tctagagaag ctgaagcaca cccacgtcaa gaagttgttg ggaagcacgg taaagagggt  2820
cttgcgatag ttagaacgtt tacgcaagtt gttaacccag tacaggtagg gacgcgtttt  2880
cgacaaggaa cccgaaggac gacgaggact ccgacgaggt tgaccaccga tgtaaggtgg  2940
ggtactagag tatagatttc aagaaggcta ggatttccta aggctgttca tgcgtcctta  3000
gtacgacacc tgatctatgg tgctgtcttt gaggccgatg tcaagagttc agttcagggt  3060
gcacacaggt cgcgcagcca agaggttgta gaatagatac ggccacttca gaaggttcat  3120
ttggacttgc cgcatctact agccaccagc ttttgaggct agtagtaccc aggggtaggc  3180
ataggcacgc aacgatgcaa taccacaaag ggaacataca accagaaaag ttattatatt  3240
attccccaat caaaatgcaa aggtataaaa ggtacaagct tttgtcatat aaacgacggg  3300
gaaggtttaa acttttttcta ttttatttat atattgattt ttataggaga aaaaaaaaag  3360
aaagctgttt atatattgag aattgaaagg gttaacaaat tcgttttcta tatttaggag  3420
aaggtgtgtt ttctgcttag gtactaacga cctaacgaca gatgaccacg gctttaccgc  3480
tgctctcttc gaacacgatg gacgttaatg ttcaagcagt tgtaacgaaa ggaacggtac  3540
aaaccactgc ggtatgaggg cactagtcct gtgtggagac cttgtcaaag aacccttcaa  3600
ttagaagaag agccgaggag ccgctggtta gaacactcca agaagaggac ttaccacagg  3660
tgaagctgta gcttccagat ggactcgcgt ntaggtgtca aggctgatgc acacccacgt  3720
caagatgatg tgtccgttga gcgtctacgg gccattgtta cccaagaggt aggacgtacc  3780
ttccacaagg gacctgaagg acgacgagga gtccgacgac cttcctcgag gtaaggtgat  3840
cactagaatg tgcacagaat agtagttctt aatatcgttc atggctccct aataatttta  3900
tttttttttc ccttcttacc cttaatctta attttgactt tggccggtac ttcttgcaaa  3960
gctcacttct gtttgctgtc atactctgcc atcaaacgat acctgtacct agcaagggtt  4020
tcgtcaggtt cagaaatact tggccagata gccaagtcgg aagttcttgg cgctcctatt  4080
ggccgggttc tctttgttgt ttaacaccac tcgaaaatna tatttggctt gccacggcag  4140
gcagtctaca atttacctgc cgcctatcta gaggtctcat ttagactcct tttagcaagg  4200
ccggggggat ggtgctgggt gcgctaggca ggagaggggg tgggggatgt ggaaaaagaa  4260
gaaggcgagg acgctagcca ataaactaaa acacatacta taggttaaag aaaagacctc  4320
accataggat aagattaaag aatctaacaa cataacttgg tagtcaaaac caaattcgcg  4380
tactaccgcc tctcaaagcc ctctaccctc agtctaggga acaaaagacg acggcttcac  4440
cacgttctaa gccggctatc caaaaagag agtaaaattc gagttaatac gccagtaaga  4500
acaatccgaa acctcttaaa cgagataaag ctttctttaa cgacgaaaga tcaaaactaa  4560
tcagggatat tttaaacgaa agccaagact tataggctct tacagcatag cagttactgc  4620
taagaaaaaa tcttaagatt atgaaacagg acaaagacta ctaaattacc tcttttataa  4680
caaggaaaat cactagatac gagagggctg gtaatcctac tcccaacttc cacttttatg  4740
aaagaccatt aaaaggagag atttaagaag gtttgtgctg tgttcatatt aatatctggt  4800
tctaactaag aagaatacgt ggctaagagt gaagggaagg gagacacaat accaatagca  4860
```

```
acaatgacta ccaacgaatt gagtacccca tcgcggaccc actaggcaac tggacgtcca    4920
gctg                                                                  4924
```

<210> SEQ ID NO 29
<211> LENGTH: 1568
<212> TYPE: PRT
<213> ORGANISM: Musa acuminata

<400> SEQUENCE: 29

```
Gly Ser Gln Leu Leu Gly Met Asp Leu Lys Ile Leu Val Ile Ser Ser
 1               5                  10                  15

Lys Leu Glu Lys Ser Leu Pro Arg Ala Leu Ser Pro Leu Met Thr Ser
            20                  25                  30

Val Lys Arg Cys Thr Cys Leu Arg Trp Thr His Leu Val Ser Phe Gly
        35                  40                  45

Lys Val Arg Lys Ser Ala Glu Tyr Phe Trp Ile Leu Ser Leu Gly Trp
    50                  55                  60

Cys Leu His Glu Pro Gln Glu Ser Ser Lys Tyr Gln Lys Pro Asn His
65                  70                  75                  80

Lys Leu Lys Cys Asp Ile His Phe Cys Leu Met His Lys Thr Gly His
                85                  90                  95

Ser Pro Leu Cys Leu Lys Gln Lys His Ser Ser Pro Ile His Pro Ile
            100                 105                 110

Arg Ser Ser Glu Glu Lys Ile Phe Glu Ile His Phe Arg Gln Thr Lys
        115                 120                 125

Ala Arg Asn Pro Trp Lys Gly Arg Ser Ser Tyr Glu Phe Ser Asn Thr
    130                 135                 140

Cys Asn Ser Thr His Thr Val Asp Val Asn Asp Pro His Ala Leu Ser
145                 150                 155                 160

Leu Leu Gly Ile Lys Pro Asn Met Arg Val Ser Leu Ala Leu Ile Pro
                165                 170                 175

Ile Val Arg Ile Arg Val Ala Leu Arg Glu Gly Gly Ser Glu Leu Val
            180                 185                 190

Gln Trp Ile Lys Thr Tyr Lys Phe Lys Asn Glu Phe Val Asn Thr Arg
        195                 200                 205

Arg Phe Arg Phe Asn Ser Asn Leu Ser Arg Lys Pro Lys Val Asn Ser
    210                 215                 220

Ser Val Asn Asn Asn Phe Gly Lys Val Arg Thr His Thr Phe Lys Glu
225                 230                 235                 240

His Thr Asn Leu Lys Trp Phe Gly Gln Asn Asp Leu His Pro Leu Val
                245                 250                 255

Lys Pro Ser Ser Lys Arg Leu Pro Thr Ser Thr Lys Ser Leu Arg
            260                 265                 270

Gly Arg Thr Asn Thr Ser Leu Thr Thr Phe Tyr Asn Gly Ser Tyr Ser
        275                 280                 285

Tyr Lys Phe Ser Thr Arg Lys Lys Glu Val Asn Met Gln Ala Ile Glu
    290                 295                 300

Asn Lys Thr Cys Arg Leu Cys Gly Phe Phe Ser Gln Ser Ile Ala Ser
305                 310                 315                 320

Gln Lys Leu Tyr Ser Leu Leu Arg Ile Glu Gly Tyr Leu Thr Pro Arg
                325                 330                 335

Gly Phe Lys Phe Gly Leu Gln Ile Ser Asn Ala Leu Gly Phe Pro Arg
            340                 345                 350

Leu Pro Val Pro Pro Pro Val Ser Val His Trp Thr Val Tyr Arg Cys
```

```
              355                 360                 365
His Arg Arg Thr Ser Arg Val Leu Gly Gly Ala Thr Ala Thr Phe Ser
370                 375                 380

Ala His Trp Leu Asp Ser Lys Leu Asp Pro Asn Gln Ser Glu Leu Gly
385                 390                 395                 400

Ser Asn Pro Val Thr Gly Leu Asp Pro Leu Ile Leu Thr Leu Ile Ile
                405                 410                 415

Cys Lys Leu Arg Asn Lys Tyr Ser Pro Lys Gln Val Phe Asn Arg Gln
                420                 425                 430

Thr Ser Ser Leu Leu Pro Ala Ile Phe Arg Gln Thr Ser Asp Ile Pro
            435                 440                 445

Leu Asp Phe Phe Arg Thr Pro Ser Arg Val Pro Ile Leu Trp Arg Val
450                 455                 460

Arg Val Ala Glu Pro Ser Arg Ser Pro Gln Thr Ala Asp Asp Leu Phe
465                 470                 475                 480

Gly Arg Leu Ser Lys Thr Ser Thr Ser Pro Arg Phe Leu Leu Gly Trp
                485                 490                 495

Phe Arg Gln His Leu Arg Asn Phe Gly Leu Leu Glu Cys Pro Ser Asn
                500                 505                 510

Leu Thr Pro Val Gly Leu Leu Tyr Ile Phe Arg Leu Ser Leu Ile Leu
            515                 520                 525

His Thr Leu Asn Asn Met Asp Ile Asn Pro Ile Asn Phe His His Gln
            530                 535                 540

Asn Ser Thr Phe Asn Lys His Pro Tyr Ser Ile Thr His Gln Ala Ile
545                 550                 555                 560

Val Thr Leu Ser Thr Val Ile Thr Arg Ser Arg Val Met Ile Gln Val
                565                 570                 575

Val Ser Leu Ile Gly Arg Thr Arg Ile Pro Tyr Pro Asn Pro Val Phe
                580                 585                 590

Ser Thr Leu Leu Ala Tyr Pro Ser Leu Phe Leu Leu Leu Lys Glu
            595                 600                 605

Phe Lys Ser Lys Gln Ile Gln Asn Asn Thr Val Arg His Cys Asp Met
610                 615                 620

Leu Val Ser Gly Lys His Phe Ala His Pro Gln Thr Ser Ser Ala Ser
625                 630                 635                 640

Ser Pro Thr Phe Ser Tyr Ile Thr Met Ser His Gly Phe Val Asp Asp
                645                 650                 655

Arg Pro Pro Gln Ala Cys Leu Trp Leu Cys Leu Thr Glu Arg Glu Arg
                660                 665                 670

Gln Thr Asp Ser Leu Leu Ile His Tyr Gly Asp Pro Ile Ala Ser Phe
            675                 680                 685

Ala Ala Val Ile Cys Val Pro Asp Ala Cys Ala His Gly Lys Thr Ala
690                 695                 700

Gly Pro Ala Gln Leu Met His Trp Arg Leu Leu Gly Thr Lys His Arg
705                 710                 715                 720

Arg Gly Lys Leu Ser Arg Cys Leu Cys His Arg Gln Leu Arg Ile Arg
                725                 730                 735

Glu His Arg His Pro Phe Gln Val Trp His Gly Pro Asn Ser Arg Asp
                740                 745                 750

Gln Pro Arg Arg Pro Leu Pro Ser Glu Gln Arg Leu Arg Ala Leu Glu
            755                 760                 765

Gln Arg Asn Pro Val Leu Pro Gly Ala Trp Arg Gln Gly Asp Ala Leu
            770                 775                 780
```

-continued

```
His Arg Arg Trp Arg Val Leu Trp Pro Glu Phe His Arg Arg Gln
785                 790                 795                 800

Gly Arg Ser Val Ile Pro Leu Ala Gln Phe Leu Gly Trp Phe Cys Cys
            805                 810                 815

Ser Leu Leu Glu Thr Pro Arg Gly Cys Gly Ser Gly Trp His Arg Leu
            820                 825                 830

Gln His Arg Arg Arg Glu His Arg Thr Leu Thr Cys Arg Phe Pro Gln
            835                 840                 845

Gly Leu Gln Arg Ala Gly Gly Arg Asn Glu Glu Ser Ser Leu Glu Cys
850                 855                 860

Ser Ser Ala Val Ser Phe Pro Gly Leu Leu Ala Trp Gln Arg Thr Gln
865                 870                 875                 880

Asn Arg Ser Leu Arg Leu Arg Val Gly Ala Val Leu Gln Gln Pro Phe
            885                 890                 895

Val Pro Phe Leu Pro Glu Arg Tyr Gln Ser Cys Lys Cys Val Gln Gln
            900                 905                 910

Leu Gly His Val His Pro Cys Ala Lys Ala Val Pro Trp Ala Ser Cys
            915                 920                 925

Cys Ser Gly Cys Ser Asn Trp Trp Leu His Ser Thr Pro Ser His Ile
930                 935                 940

Ser Ser Ser Asp Pro Lys Gly Phe Arg Gln Val Arg Arg Asn His Ala
945                 950                 955                 960

Val Asp Ile Pro Arg Gln Lys Leu Arg Leu Gln Phe Ser Gln Val
            965                 970                 975

Pro Arg Val Ser Ser Ala Ser Val Leu Gln His Leu Ile Tyr Ala Gly
            980                 985                 990

Glu Val Phe Gln Val Asn Leu Asn Gly Val Asp Asp Arg Trp Ser Lys
            995                 1000                1005

Thr Pro Ile Ile Met Gly Pro His Pro Tyr Pro Cys Val Ala Thr Leu
    1010                1015                1020

Trp Cys Phe Pro Cys Met Leu Val Phe Ser Ile Ile Gly Val Ser Phe
1025                1030                1035                1040

Thr Phe Pro Tyr Phe Pro Cys Ser Lys Thr Val Tyr Leu Leu Pro Leu
        1045                1050                1055

Pro Asn Leu Lys Lys Ile Lys Ile Tyr Asn Lys Tyr Pro Leu Phe Phe
            1060                1065                1070

Phe Phe Arg Gln Ile Tyr Asn Ser Leu Ser Gln Leu Phe Lys Gln Lys
        1075                1080                1085

Ile Ile Leu Phe His Thr Lys Asp Glu Ser Met Ile Ala Gly Leu Leu
    1090                1095                1100

Ser Thr Gly Ala Glu Met Ala Thr Arg Glu Ala Cys Ala Thr Cys Asn
1105                1110                1115                1120

Tyr Lys Phe Val Asn Ile Val Phe Leu Ala Met Phe Gly Asp Ala Ile
            1125                1130                1135

Leu Pro Ser Gly His Thr Ser Gly Thr Val Ser Trp Glu Val Asn Leu
            1140                1145                1150

Leu Leu Gly Ser Ser Ala Thr Asn Leu Val Arg Phe Phe Ser Met Val
        1155                1160                1165

Ser Thr Ser Thr Ser Lys Val Tyr Leu Ser Ala Xaa Pro Gln Phe Arg
    1170                1175                1180

Leu Arg Val Gly Ala Val Leu Leu His Arg Gln Leu Ala Asp Ala Arg
1185                1190                1195                1200
```

-continued

```
Gln Trp Val Leu His Pro Ala Trp Lys Val Phe Pro Gly Leu Pro Ala
            1205                1210                1215

Ala Pro Gln Ala Ala Gly Arg Ser Ser Ile Pro Leu Val Ile Leu His
        1220                1225                1230

Val Ser Tyr His Gln Glu Leu Gln Val Pro Arg Asp Tyr Asn Lys Lys
    1235                1240                1245

Lys Gly Lys Asn Gly Asn Asn Asn Arg Pro Arg Thr Phe Arg Val
1250                1255                1260

Lys Thr Asn Asp Ser Met Arg Arg Phe Ala Met Asp Met Asp Arg Ser
1265                1270                1275                1280

Gln Ser Ser Pro Ser Leu Tyr Glu Pro Val Tyr Arg Phe Ser Leu Gln
            1285                1290                1295

Glu Pro Arg Gly Pro Ala Gln Glu Lys Gln Gln Ile Val Val Ser Phe
        1300                1305                1310

Xaa Tyr Lys Pro Asn Gly Ala Val Arg Gln Met Leu Asn Gly Arg Arg
    1315                1320                1325

Ile Asp Leu Gln Ser Lys Ser Glu Glu Asn Arg Ser Gly Pro Pro Thr
1330                1335                1340

Thr Thr His Ala Ile Arg Pro Leu Pro His Pro Leu His Leu Phe Leu
1345                1350                1355                1360

Leu Pro Leu Leu Arg Ser Val Ile Phe Cys Val Tyr Pro Ile Ser Phe
            1365                1370                1375

Leu Glu Trp Tyr Pro Ile Leu Ile Ser Ile Val Val Leu Asn His Gln
        1380                1385                1390

Phe Trp Phe Lys Arg Met Met Ala Glu Ser Phe Gly Arg Trp Glu Ser
    1395                1400                1405

Asp Pro Leu Phe Ser Ala Ala Glu Val Val Gln Asp Ser Ala Asp Arg
1410                1415                1420

Phe Phe Leu Ser Phe Ala Gln Leu Cys Gly His Ser Cys Ala Leu Glu
1425                1430                1435                1440

Asn Leu Leu Tyr Phe Glu Arg Asn Cys Cys Phe Leu Val Leu Ile Ser
            1445                1450                1455

Pro Tyr Lys Ile Cys Phe Arg Phe Ile Ser Glu Asn Val Val Ser Ser
        1460                1465                1470

Met Thr Ile Leu Phe Asn Ser Asn Thr Leu Ser Cys Phe Leu Phe Asn
    1475                1480                1485

Gly Glu Asn Ile Val Pro Phe Ser Asp Leu Cys Ser Pro Asp His Asp
    1490                1495                1500

Glu Gly Arg Lys Tyr Phe Leu Val Ile Phe Leu Ser Lys Phe Phe Gln
1505                1510                1515                1520

Thr Arg His Lys Tyr Asn Tyr Arg Pro Arg Leu Ile Leu Leu Met His
            1525                1530                1535

Arg Phe Ser Leu Pro Phe Pro Leu Cys Tyr Gly Tyr Arg Cys Tyr Trp
        1540                1545                1550

Leu Leu Asn Ser Trp Gly Ser Ala Trp Val Ile Arg Pro Ala Gly Arg
    1555                1560                1565
```

<210> SEQ ID NO 30
<211> LENGTH: 1574
<212> TYPE: PRT
<213> ORGANISM: Musa acuminata

<400> SEQUENCE: 30

```
Asp Pro Asn Phe Glu Trp Ile Leu Lys Phe Leu Val Gln Ser Lys Asn
 1               5                   10                  15
```

-continued

```
Leu Tyr Gln Glu Leu Val His His Pro Asn Gly Val His Val Ser Asp
         20                  25                  30
Gly Leu Thr Trp Phe His Ser Glu Lys Phe Glu Arg Val His Lys Asn
         35                  40                  45
Ile Asp Phe Gly Phe Phe His Ser Val Gly Ala Phe Met Ser Asp Leu
 50                  55                  60
Lys Ser Pro Pro Asn Ile Lys Ser Arg Ile Thr Asn Asn Val Ile Glu
 65                  70                  75                  80
Phe Ile Phe Val Cys Thr Lys Gln Gly Ile His Ser Leu Cys Val Ser
                 85                  90                  95
Lys Asn Ile Leu Leu Arg Phe Ile Pro Phe Ala His Arg Lys Arg Lys
                100                 105                 110
Phe Leu Lys Ser Ile Phe Asp Asn Arg Pro Lys Leu Glu Ile His Gly
            115                 120                 125
Asn Glu Glu Asp Pro His Met Ser Phe Pro Ile His Val Ile Arg Leu
130                 135                 140
Ile Lys His Arg Trp Met Cys Asn Glu Met Thr Leu Met Xaa Tyr Leu
145                 150                 155                 160
Ser Trp Val Leu Asn Gln Ile Glu Ala Leu Leu Tyr Gln Leu Leu Gly
                165                 170                 175
Ser Glu Trp His Glu Arg Gly Gly Val Asn Cys Ser Gly Leu Lys Leu
            180                 185                 190
Ile Ser Leu Lys Met Asn Ser Ile Arg Glu Asp Phe Val Leu Ile Val
            195                 200                 205
Thr Val Asp Glu Asn Gln Lys Leu Thr Val Val Ile Thr Ile Ser Gly
210                 215                 220
Lys Glu Leu Thr His Ser Arg Asn Ile Pro Ile Ser Gly Ser Val Lys
225                 230                 235                 240
Met Thr Tyr Ile His Leu Ser Leu Leu Arg Arg Gly Ser Gln Leu Pro
                245                 250                 255
Leu Ala Asn His Phe Glu Gly Glu Gly Gln Ile Pro Leu Leu Xaa Pro
            260                 265                 270
Phe Thr Met Val His Thr Leu Thr Asn Phe Gln Arg Glu Arg Arg Arg
            275                 280                 285
Thr Cys Lys Gln Leu Lys Thr Arg Leu Ala Lys Asp Phe Ala Lys Ala
290                 295                 300
Phe Phe Leu Asn Leu Leu Leu Lys Ser Cys Ile Leu Cys Glu Leu
305                 310                 315                 320
Arg Gly Ile Tyr Arg Pro Gln Glu Asp Leu Asn Leu Gly Ser Lys Phe
                325                 330                 335
Arg Met Leu Leu Gly Ser Arg Gly Cys Arg Cys His Arg Leu Ser Val
            340                 345                 350
Phe Asp Thr Gly Gln Cys Thr Ser Gly Ala Thr Ala Gly Pro Leu Gly
            355                 360                 365
Cys Trp Ala Val Pro Pro Arg Leu Phe Gln Leu Thr Gly Trp Ile
370                 375                 380
Pro Asn Leu Thr Gln Thr Ser Pro Asn Ser Gly Pro Ile Asp Pro Pro
385                 390                 395                 400
Asp Tyr Arg Ile Asn Pro Ser Pro Leu Tyr Ala Asn Tyr Ala Thr Glu
                405                 410                 415
Asn Ile Val Leu Ser Lys Phe Leu Thr Gly Lys Arg Arg Val Phe Phe
            420                 425                 430
```

```
Arg Arg Ser Phe Gly Arg Leu Leu Ile Tyr Leu Trp Ile Ser Ser Ser
        435                 440                 445

Gly Leu Leu Val Gly Ser Arg Ser Cys Gly Glu Phe Ser Glu Pro Asn
    450                 455                 460

Leu Leu Gly Asp Leu Arg Lys Pro Pro Met Ile Ser Ser Ala Asp Phe
465                 470                 475                 480

Arg Lys Leu Arg Gln Val Pro Asp Phe Phe Ser Val Gly Ser Asp Ser
                485                 490                 495

Ile Ser Asn Glu Thr Ser Asp Ser Leu Asn Val His Arg Thr Leu Arg
            500                 505                 510

Ala Cys Phe Ile Phe Ser Gly Tyr His Ser Ser Tyr Ile Leu Asn Ser
        515                 520                 525

Ile Ile Trp Ile Arg Leu Ile Asn Pro Ser Ile Asp Phe Ile Ile Lys
    530                 535                 540

Ile Arg His Ser Thr Asn Ile Arg Thr Gln Pro Ile Arg Leu Leu Arg
545                 550                 555                 560

Asp Tyr Leu Leu Ser Val Arg Glu Val Ser Glu Ser Ser Arg Ser Cys
                565                 570                 575

His Leu Leu Ala Glu His Val Ser Leu Ile Gln Ile Gln Ser Ser Gln
            580                 585                 590

Leu Phe Pro Thr Arg Leu Phe Phe Tyr Tyr Phe Lys Asn Ser Asn Gln
        595                 600                 605

Asn Arg Tyr Lys Ile Thr Arg Asp Thr Val Thr Cys Ser Leu Glu Ser
    610                 615                 620

Ile Asn Ser Arg Ile His Arg Arg Gln Leu His Pro Leu Phe
625                 630                 635                 640

Pro Thr Pro Cys Arg Met Ala Leu Leu Met Thr Asp His His Lys Leu
                645                 650                 655

Ala Phe Gly Cys Ala Gln Arg Glu Arg Asp Arg Pro Ile Ala Ser Ser
            660                 665                 670

Phe Thr Met Ala Ile Arg Ser Pro Ala Ser Leu Leu Leu Phe Ala Phe
        675                 680                 685

Leu Met Leu Ala Leu Thr Gly Arg Leu Gln Ala Arg Arg Ser Ser Cys
    690                 695                 700

Ile Gly Val Tyr Trp Gly Gln Asn Thr Asp Glu Gly Ser Leu Ala Asp
705                 710                 715                 720

Ala Cys Ala Thr Gly Asn Tyr Glu Tyr Val Asn Ile Ala Thr Leu Phe
                725                 730                 735

Lys Phe Gly Met Gly Gln Thr Pro Glu Ile Asn Leu Ala Gly His Cys
            740                 745                 750

Asp Pro Arg Asn Asn Gly Cys Ala Arg Leu Ser Ser Glu Ile Gln Ser
        755                 760                 765

Cys Gln Glu Arg Gly Val Lys Val Met Leu Ser Ile Gly Gly Gly Gly
    770                 775                 780

Ser Tyr Gly Leu Ser Ser Thr Glu Asp Ala Lys Asp Val Ala Ser Tyr
785                 790                 795                 800

Leu Trp His Ser Phe Leu Gly Gly Ser Ala Ala Arg Tyr Ser Arg Pro
                805                 810                 815

Leu Gly Asp Ala Val Leu Asp Gly Ile Asp Phe Asn Ile Ala Gly Gly
            820                 825                 830

Ser Thr Glu His Tyr Asp Glu Leu Ala Ala Phe Leu Lys Ala Tyr Asn
        835                 840                 845

Glu Gln Glu Ala Gly Thr Lys Lys Val His Leu Ser Ala Arg Pro Gln
```

```
            850             855             860
Cys Pro Phe Pro Asp Tyr Trp Leu Gly Asn Ala Leu Arg Thr Asp Leu
865                 870             875                 880

Phe Asp Phe Val Trp Val Gln Phe Phe Asn Asn Pro Ser Cys His Phe
                885             890                 895

Ser Gln Asn Ala Ile Asn Leu Ala Asn Ala Phe Asn Asn Trp Val Met
            900             905                 910

Ser Ile Pro Ala Gln Lys Leu Phe Leu Gly Leu Pro Ala Ala Pro Glu
        915             920             925

Ala Ala Pro Thr Gly Gly Tyr Ile Pro Pro His Asp Leu Ile Ser Lys
    930             935             940

Val Leu Pro Ile Leu Lys Asp Ser Asp Lys Tyr Ala Gly Ile Met Leu
945             950             955                 960

Trp Thr Arg Tyr His Asp Arg Asn Ser Gly Tyr Ser Ser Gln Val Lys
            965             970             975

Ser His Val Cys Pro Ala Arg Arg Phe Ser Asn Ile Leu Ser Met Pro
            980             985             990

Val Lys Ser Ser Lys Thr Thr Ala Met Ile Gly Gly Arg Lys Leu Arg
        995             1000            1005

Ser Ser Trp Val Pro Ile Arg Ile Arg Ala Leu Leu Arg Tyr Gly Val
    1010            1015            1020

Ser Leu Val Cys Trp Ser Phe Gln Tyr Asn Lys Gly Leu Val Leu Arg
1025            1030            1035            1040

Phe His Ile Phe His Val Arg Lys Gln Tyr Ile Cys Cys Pro Phe Gln
            1045            1050            1055

Ile Lys Arg Asn Lys Tyr Ile Thr Lys Asn Ile Leu Phe Phe Phe Ser
            1060            1065            1070

Phe Asp Lys Tyr Ile Thr Leu Asn Phe Pro Asn Cys Leu Ser Lys Arg
        1075            1080            1085

Tyr Lys Ser Ser Ser Thr Gln Lys Thr Asn Pro Leu Leu Asp Cys Cys
    1090            1095            1100

Leu Leu Val Pro Lys Trp Arg Arg Glu Lys Leu Val Leu Pro Ala Ile
1105            1110            1115            1120

Thr Ser Ser Ser Thr Leu Ser Ser Leu Pro Cys Leu Val Thr Pro Tyr
            1125            1130            1135

Ser Arg Asp Gln Asp Thr Pro Leu Glu Gln Phe Leu Gly Lys Leu Ile
        1140            1145            1150

Phe Phe Ser Ala Pro Arg Arg Pro Ile Leu Gly Ser Ser Pro Glu Trp
        1155            1160            1165

Cys Pro Leu Arg His Arg Arg Ser Thr Ala Xaa Ile His Ser Ser Asp
    1170            1175            1180

Tyr Val Trp Val Gln Phe Tyr Tyr Thr Gly Asn Ser Gln Met Pro Gly
1185            1190            1195            1200

Asn Asn Gly Phe Ser Ile Leu His Gly Arg Cys Ser Leu Asp Phe Leu
            1205            1210            1215

Leu Leu Leu Arg Leu Leu Glu Gly Ala Pro Phe His Ser Tyr Thr Cys
        1220            1225            1230

Leu Ile Ile Lys Asn Tyr Ser Lys Tyr Arg Gly Ile Ile Lys Ile Lys
        1235            1240            1245

Lys Lys Gly Arg Met Gly Ile Arg Ile Lys Thr Glu Thr Gly His Glu
    1250            1255            1260

Glu Arg Phe Glu Arg Gln Thr Thr Val Asp Gly Ser Leu Leu Trp Thr
1265            1270            1275            1280
```

-continued

Trp Ile Val Pro Lys Ala Val Gln Val Phe Met Asn Arg Ser Ile Gly
               1285                1290                1295

Ser Ala Phe Lys Asn Arg Glu Asp Asn Arg Pro Lys Arg Asn Asn Lys
           1300                1305                1310

Leu Trp Ala Phe Xaa Ile Asn Arg Thr Val Pro Ser Val Arg Cys Met
       1315                1320                1325

Asp Gly Gly Ile Ser Arg Val Asn Leu Arg Lys Ile Val Pro Ala Pro
   1330                1335                1340

Leu Pro Arg Pro Thr Arg Ser Val Leu Ser Pro Thr Pro Tyr Thr Phe
1345                1350                1355                1360

Phe Phe Phe Arg Ser Cys Asp Arg Leu Phe Asp Phe Val Tyr Asp Ile
               1365                1370                1375

Gln Phe Leu Phe Trp Ser Gly Ile Leu Phe Phe Leu Arg Leu Leu Tyr
           1380                1385                1390

Thr Ile Ser Phe Gly Leu Ser Ala Trp Arg Arg Val Ser Gly Asp Gly
       1395                1400                1405

Ser Gln Ile Pro Cys Phe Leu Leu Pro Lys Trp Cys Lys Ile Arg Pro
   1410                1415                1420

Ile Gly Phe Phe Ser His Phe Lys Leu Asn Tyr Ala Val Ile Leu Val
1425                1430                1435                1440

Arg Leu Trp Arg Ile Cys Ser Ile Ser Lys Glu Ile Ala Ala Phe Phe
               1445                1450                1455

Leu Val Pro Ile Lys Phe Ala Phe Gly Ser Glu Tyr Pro Arg Met Ser
           1460                1465                1470

Tyr Arg Gln Arg Phe Phe Phe Arg Ile Leu Ile Leu Cys Pro Val Phe
       1475                1480                1485

Cys Asp Leu Met Glu Lys Ile Leu Phe Leu Leu Val Ile Tyr Ala Leu
   1490                1495                1500

Pro Thr Ile Arg Met Arg Val Glu Gly Glu Asn Thr Phe Trp Phe Ser
1505                1510                1515                1520

Ser Leu Asn Ser Ser Lys His Asp Thr Ser Ile Ile Ile Asp Gln Asp
               1525                1530                1535

Phe Phe Leu Cys Thr Asp Ser His Phe Pro Ser Leu Cys Val Met Val
           1540                1545                1550

Ile Val Val Thr Asp Gly Cys Leu Thr His Gly Val Ala Pro Gly Ser
       1555                1560                1565

Val Asp Leu Gln Val Asp
   1570

<210> SEQ ID NO 31
<211> LENGTH: 1562
<212> TYPE: PRT
<213> ORGANISM: Musa acuminata

<400> SEQUENCE: 31

Arg Ile Pro Thr Phe Arg Asn Gly Ser Asn Phe Ser Tyr Lys Phe Lys
 1               5                  10                  15

Val Arg Lys Ile Phe Thr Lys Ser Phe Glu Ser Ile Asp Asp Ile Arg
            20                  25                  30

Glu Thr Val Tyr Met Ser Pro Met Asp Ser Leu Gly Phe Ile Arg Lys
        35                  40                  45

Ser Ser Lys Glu Cys Ile Arg Ile Leu Ile Leu Asp Ser Phe Thr Arg
    50                  55                  60

Leu Val Pro Ser Val Thr Ser Arg Val Leu Gln Ile Ser Lys Ala Glu

```
                65                  70                  75                  80
Ser Gln Ile Glu Met Leu Asn Ser Phe Leu Ser Asn Ala Gln Asn Arg
                    85                  90                  95

Ala Phe Ile Ala Phe Val Phe Lys Ala Lys Thr Phe Ser Asp Ser
            100                 105                 110

Ser His Ser Leu Ile Gly Arg Glu Asn Phe Asn Pro Phe Ser Thr Ile
            115                 120                 125

Asp Gln Ser Ser Lys Ser Met Glu Met Arg Lys Ile Leu Ile Val Phe
        130                 135                 140

Gln Tyr Met Phe Asp Ser Leu Asn Ile Gly Gly Cys Val Met Lys Pro
145                 150                 155                 160

Ser Cys Xaa Ile Ser Leu Gly Tyr Thr Lys Tyr Glu Ser Glu Pro Cys
            165                 170                 175

Ser Asp Thr Asn Cys Asp Gln Ser Gly Thr Lys Arg Gly Gly Glu Ile
            180                 185                 190

Ser Ala Val Asp Asn Leu Val Lys Ile Arg Lys Tyr Glu Lys Ile Ser
        195                 200                 205

Phe Leu Glu Met Lys Thr Lys Ser Gln Cys Lys Gln Phe Arg Glu Ser
        210                 215                 220

Lys Asn Ser His Ile Gln Gly Thr Tyr Gln Phe Lys Val Val Arg Ser
225                 230                 235                 240

Lys Pro Thr Ser Thr Cys Glu Ala Phe Phe Glu Glu Ala Pro Asn Phe
            245                 250                 255

His Gln Ile Thr Leu Lys Gly Lys Asp Lys Tyr Leu Ser Tyr Xaa Leu
            260                 265                 270

Leu Gln Trp Phe Ile Leu Leu Gln Ile Phe Asn Glu Lys Glu Gly Gly
        275                 280                 285

Glu His Ala Ser Asn Lys Gln Asp Leu Leu Lys Thr Leu Leu Arg Leu
        290                 295                 300

Phe Phe Ser Ile Tyr Cys Phe Ser Lys Val Val Phe Ser Ala Glu Asn
305                 310                 315                 320

Gly Val Phe Ile Asp Pro Lys Arg Ile Ile Trp Ala Pro Asn Phe Glu
            325                 330                 335

Cys Ser Trp Val Pro Glu Val Ala Gly Ala Thr Ala Cys Gln Cys Leu
            340                 345                 350

Thr Leu Asp Ser Val Leu Ala Val Pro Pro Asp Leu Ser Gly Val
        355                 360                 365

Gly Arg Cys His Arg Leu Asp Phe Phe Ser Ser Leu Val Gly Phe Gln
        370                 375                 380

Thr Pro Lys Pro Val Arg Thr Arg Val Gln Leu Thr Arg Asn Arg Ile
385                 390                 395                 400

Ile Gly Leu Thr Leu Asn Pro Asn Pro Asn Tyr Met Gln Thr Gln
            405                 410                 415

Leu Lys Ile Ser Ala Ser Phe Pro Ala Asn Val Glu Ser Ser Ser Gly
            420                 425                 430

Asp Leu Ser Ala Asp Phe Tyr Thr Phe Gly Phe Leu Leu Ala Asp Ser
        435                 440                 445

Gly Pro Asp Leu Val Ala Ser Leu Ala Ser Ser Arg Thr Phe Ser Val
    450                 455                 460

Ile Ser Ala Asn Arg Arg Ser Leu Arg Gln Thr Phe Glu Asn Phe Asp
465                 470                 475                 480

Lys Ser Pro Ile Ser Ser Arg Leu Val Pro Thr Ala Ser Leu Thr Lys
            485                 490                 495
```

-continued

```
Leu Arg Thr Pro Met Ser Ile Glu Leu Asp Ser Gly Arg Leu Ala Leu
            500                 505                 510

Tyr Phe Gln Ala Ile Ile Val Asn Pro Thr Tyr Leu Thr Gln Tyr Gly
        515                 520                 525

Leu Asp Leu Thr His Gln Leu Ile Ser Ser Lys Phe Asp Ile Gln
    530                 535                 540

Gln Thr Ser Val Leu Asn Asn Pro Ser Gly Tyr Ser Tyr Val Thr Ile
545                 550                 555                 560

Tyr Cys Asp Pro Tyr Val Lys Leu Ala Ser His Asp Pro Gly Arg Val
                565                 570                 575

Thr Tyr Trp Pro Asn Thr Tyr Pro Leu Ser Lys Ser Ser Leu Leu Asn
            580                 585                 590

Ser Ser Ser Leu Pro Val Ser Phe Phe Ile Thr Phe Glu Arg Ile Gln
        595                 600                 605

Ile Lys Thr Asp Thr Lys His Gly Glu Thr Leu His Ala Ser Leu Trp
    610                 615                 620

Lys Ala Leu Ile Arg Ala Ser Thr Asp Val Val Ser Phe Ile Thr His
625                 630                 635                 640

Phe Phe Leu His Asn His Val Ala Trp Leu Cys Gln Thr Thr Thr Ser
                645                 650                 655

Leu Pro Leu Val Val Pro Asn Arg Glu Arg Glu Thr Asp Arg Pro Pro
            660                 665                 670

His Ser Leu Trp Arg Ser Asp Arg Gln Leu Arg Cys Cys Tyr Leu Arg
        675                 680                 685

Ser Cys Leu Arg Ser Arg Glu Asp Cys Arg Pro Gly Ala Ala His Ala
    690                 695                 700

Leu Ala Ser Thr Gly Lys Thr Pro Thr Arg Glu Ala Gln Met Leu Val
705                 710                 715                 720

Pro Gln Ala Thr Thr Asn Thr Thr Ser Pro Pro Phe Ser Ser Leu Ala
                725                 730                 735

Trp Ala Lys Leu Gln Arg Ser Thr Ser Pro Ala Thr Val Thr Leu Gly
            740                 745                 750

Thr Thr Ala Ala Arg Ala Ala Ala Lys Ser Ser Pro Ala Arg Ser Val
        755                 760                 765

Ala Ser Arg Cys Ser Pro Ser Glu Val Ala Gly Leu Met Ala Val Pro
    770                 775                 780

Pro Lys Thr Pro Arg Thr Arg His Thr Ser Gly Thr Val Ser Trp Val
785                 790                 795                 800

Val Leu Leu Leu Ala Thr Arg Asp Pro Ser Gly Met Arg Phe Trp Met
                805                 810                 815

Ala Thr Ser Thr Ser Pro Glu Gly Ala Gln Asn Thr Met Met Asn Leu
            820                 825                 830

Pro Leu Ser Ser Arg Pro Thr Ser Arg Arg Pro Glu Arg Arg Lys
        835                 840                 845

Phe Thr Val Leu Val Arg Ser Val Leu Ser Arg Ile Thr Gly Leu Ala
    850                 855                 860

Thr His Ser Glu Gln Ile Ser Ser Thr Ser Cys Gly Cys Ser Ser Ser
865                 870                 875                 880

Thr Thr Leu Arg Ala Ile Ser Pro Arg Thr Leu Ser Ile Leu Gln Met
                885                 890                 895

Arg Ser Thr Ile Gly Ser Cys Pro Ser Leu Arg Lys Ser Cys Ser Leu
            900                 905                 910
```

-continued

```
Gly Phe Leu Leu Leu Leu Arg Leu Leu Gln Leu Val Ala Thr Phe His
            915                 920                 925
Pro Met Ile Ser Tyr Leu Lys Phe Phe Arg Ser Arg Ile Pro Thr Ser
            930                 935                 940
Thr Gln Glu Ser Cys Cys Gly Leu Asp Thr Thr Thr Glu Thr Pro Ala
945                 950                 955                 960
Thr Val Leu Lys Ser Ser Pro Thr Cys Val Gln Arg Val Gly Ser Pro
            965                 970                 975
Thr Ser Tyr Leu Cys Arg Ser Leu Pro Ser Lys Pro Glu Arg Arg Arg
            980                 985                 990
Ser Val Val Glu Asn Ser Asp His His Gly Ser Pro Ser Val Ser Val
            995                 1000                1005
Arg Cys Tyr Val Met Val Phe Pro Leu Tyr Val Gly Leu Phe Asn Asn
            1010                1015                1020
Ile Ile Arg Gly Phe Tyr Val Ser Ile Phe Ser Met Phe Glu Asn Ser
1025                1030                1035                1040
Ile Phe Ala Ala Pro Ser Lys Phe Glu Lys Asp Lys Ile Asn Ile Leu
            1045                1050                1055
Lys Ile Ser Ser Phe Phe Leu Ser Thr Asn Ile Leu Leu Thr Phe
            1060                1065                1070
Pro Ile Val Ala Lys Asp Ile Asn Pro Leu Pro His Lys Arg Arg Ile
            1075                1080                1085
His Asp Cys Trp Ile Ala Val Tyr Trp Cys Arg Asn Gly Asp Glu Arg
            1090                1095                1100
Ser Leu Cys Tyr Leu Gln Leu Gln Val Arg Gln His Cys Leu Pro Cys
1105                1110                1115                1120
His Val Trp Arg His Thr Pro Val Ile Arg Thr His Leu Trp Asn Ser
            1125                1130                1135
Phe Leu Gly Ser Ser Ser Ser Arg Leu Leu Gly Asp Gln Ser Cys Glu
            1140                1145                1150
Val Leu Leu Leu Asn Gly Val His Phe Asp Ile Glu Gly Leu Pro Glu
            1155                1160                1165
Arg Xaa Ser Thr Val Pro Thr Thr Cys Gly Cys Ser Ser Thr Thr Gln
            1170                1175                1180
Ala Thr Arg Arg Cys Pro Val Thr Met Gly Ser Pro Ser Cys Met Glu
1185                1190                1195                1200
Gly Val Pro Trp Thr Ser Cys Cys Ser Ser Gly Cys Trp Lys Glu Leu
            1205                1210                1215
His Ser Thr Ser Asp Leu Thr Arg Val Leu Ser Ser Arg Ile Ile Ala
            1220                1225                1230
Ser Thr Glu Gly Leu Leu Lys Lys Arg Glu Glu Trp Glu Leu Glu
            1235                1240                1245
Leu Lys Leu Lys Pro Ala Met Lys Asn Val Ser Ser Glu Asp Lys Arg
            1250                1255                1260
Gln Tyr Glu Thr Val Val Cys Tyr Gly His Gly Ser Phe Pro Lys Gln
1265                1270                1275                1280
Ser Lys Ser Leu Thr Gly Leu Ser Val Gln Pro Ser Arg Thr Ala Arg
            1285                1290                1295
Ile Thr Gly Pro Arg Glu Thr Thr Asn Cys Gly Glu Leu Leu Xaa Thr
            1300                1305                1310
Glu Arg Cys Arg Pro Ser Asp Val Lys Trp Thr Ala Asp Arg Ser Pro
            1315                1320                1325
Glu Ile Gly Lys Ser Phe Arg Pro Pro Tyr His Asp Pro Arg Asp Pro
```

```
                 1330              1335              1340
Ser Ser Pro Pro Pro Pro Thr Pro Phe Ser Ser Ala Pro Ala Ile
1345              1350              1355              1360

Gly Tyr Leu Ile Leu Cys Met Ile Ser Asn Phe Phe Ser Gly Val Val
             1365              1370              1375

Ser Tyr Ser Asn Phe Leu Asp Cys Cys Ile Glu Pro Ser Val Leu Val
        1380              1385              1390

Ala His Asp Gly Gly Glu Phe Arg Glu Met Gly Val Arg Ser Leu Val
   1395              1400              1405

Phe Cys Cys Arg Ser Gly Ala Arg Phe Gly Arg Val Phe Ser Leu Ile
1410              1415              1420

Leu Ser Ser Ile Met Arg Ser Phe Leu Leu Gly Phe Gly Glu Phe Ala
1425              1430              1435              1440

Leu Phe Arg Lys Lys Leu Leu Leu Ser Ser Phe Asp Ser Leu Asn Leu
             1445              1450              1455

Leu Ser Val Leu Asn Ile Arg Glu Cys Arg Ile Val Asn Asp Asp Ser
        1460              1465              1470

Phe Leu Glu Phe Tyr Phe Val Leu Phe Ser Val Ile Trp Arg Lys Tyr
   1475              1480              1485

Cys Ser Phe Ser Met Leu Ser Arg Pro Leu Gly Gly Leu Lys Val Lys
1490              1495              1500

Ile Leu Ser Gly Asn Phe Pro Leu Ile Leu Pro Asn Thr Thr Gln Val
1505              1510              1515              1520

Leu Thr Lys Ile Asp Ser Ser Tyr Ala Pro Ile Leu Thr Ser Leu Pro
             1525              1530              1535

Ser Val Leu Trp Leu Ser Leu Leu Leu Met Val Ala Leu Met Gly Arg
        1540              1545              1550

Leu Gly Asp Pro Leu Thr Cys Arg Ser Thr
   1555              1560
```

<210> SEQ ID NO 32
<211> LENGTH: 2392
<212> TYPE: DNA
<213> ORGANISM: Musa acuminata
<220> FEATURE:
<221> NAME/KEY: misc_feature
<222> LOCATION: (1720)..(1721)
<223> OTHER INFORMATION: Nucleotide 1721 is n wherein n = a or g or c or
      t/u.

<400> SEQUENCE: 32

```
tcactggtac ggggccccccc tcgaggtcga cggtatcgat aagctttgat ctcttctctc    60
aatctctctc tctctctctc tctctctctc tctctgtatg tctttaaata tggttgtaat   120
gctgaattgc tatgtttatc ttggccaaac tgtgtccatc tttgagcaga taaatctggc   180
gataatgttc ttttactga aagcactgca ggatgagggc ctgaaatcac atcggacgcc     240
cactgggtca tgatgatatg gactcctcca cagcgagcag ccatgggatg tgagatccac   300
atagcagcgt agataaggga agcccgcaac actaggctgt tgttgttcca gtaaagatcg   360
aaaggtcagg cgacagtgac gatcgacttt ttcgagcatg atgacaacga cgacctgctc   420
ctgcaatatc cgtccctac cgtagagtgg gaataaatgg gtttgtagtt gcactatttc    480
tcgcaggaat taattgaaag ccctgcaaat tgctgtttct ctttccttat attaaacctt   540
cctcctgtta cattaaaatt gcatgttaag acatttctgt atggatccga acatgagatc   600
tatcattgaa gtaatgggta ggatttacat tatcatcatc atcatcatct ccatgggttt   660
```

```
ggatctaatt agaccgaaaa cctcatttaa aatccaaccc caatattggc ttgacttgct    720
ccatctccaa gaaaaataca acaagaacaa caaaaattta ggatgcacat tgaattgatt    780
tggtcactat gagagaatca tggattaaaa atattaaaat aaaaaataaa tcataatcat    840
ctactcactc taacgattca cattctatcc accaaatttg acatcggctt ctaattaatt    900
tcatatatta ggttctaaaa aatctctccc tttgacagat gaataaatat ttcttttaat    960
tcgttaggga aggatctaat ataatatata tatatatata tatttattta ttagattcta   1020
accatttctc tcaccagaat atgaatcgac ggccatatct gcaaaaaccc accaattgtt   1080
cacagtaaac gctcattgaa ttaaggtcga aattacttt aaatttctag agatttccaa    1140
taaaatatac tcgtatcttt tacagtgatg atgctccgga tgataagatg aaggatgcg    1200 tgtgtcagcc gcctgcgatc tctgtggcgg ggacgagacg aagacaagga cgtgagcgga   1260
cgataccaag tcttctcctc ccccaccacg cacgtctcag attcccgata cggcctatcc   1320
cggtggcgtg tggactgcac agacgaacga gtaaatgccc atccccctc tttcattctt    1380 tctctttgcg tgtgtgagag gagcgcctat aaataagcac gaaacaagcc ctttttctct   1440
ccaagaacac accacaccat tcacacacta catcctctgc ttcttcgagc cttttcgcct   1500
tccttcctcg tctaaccatg tcgacctgcg gcaactgcga ctgcgttgac aagagccagt   1560
gcgtgtaagt catcctccat ccctccacct cttcttcttc ttcttcttct tcttcttcta   1620
acctcgcccc gtttgtgttt gatgagtcga ctcttcccac atcgctcgtc aaaactcaga   1680
gctttattag ggaacatcag caatactata tgtatatgta naaggtcaac gttggctgaa   1740
gaacttggtt ttgcctttgc aggaagaaag gaaacagcta cggtatcgat attgttgaga   1800
ccgagaagag gtactgatta gcttcttctc cctcctcctc gtcgaggatg atcaaactaa   1860
ttaggattac accttattac cttacctaat gcttttccg tattcgtttc gtctcttcag    1920
ctacgtcgac gaggtgatcg ttgccgcaga agctgccgag catgacggca agtgcaagtg   1980
cggcgccgcc tgcgcctgca ccgactgcaa gtgtggcaac tgagaagcac ttgtgtcact   2040
accactaaat aaaagtttgc aatgcataaa aaacaaaaga acaaaaaaaa aaaggaaga    2100 agaagaaggt gtggctatgt actctaataa ttcgggcagg ctgataggtt gtaagatggg    2160
ataacgcagt atcatctgtg ttatctctgt cctgtgttac aactctccta tctatcctag   2220
tcaatgaaat attattagta ttaatctggt tgtgtcattc atatatgctg ctgctgctgc   2280
tgcttcctct ttcaccaatc aacccaaagg atcgattgca ctgtaaggcc caacttcctc   2340
accgatatgc tcgctcagtt acgatgaatg aacagcaacc aaacgagtct gc           2392
```

<210> SEQ ID NO 33
<211> LENGTH: 2392
<212> TYPE: DNA
<213> ORGANISM: Musa acuminata
<220> FEATURE:
<221> NAME/KEY: misc_feature
<222> LOCATION: (1720)..(1721)
<223> OTHER INFORMATION: Nucleotide 1721 is n wherein n = a or g or c or t/u.

<400> SEQUENCE: 33

```
agtgaccatg ccccgggggg agctccagct gccatagcta ttcgaaacta gagaagagag     60
ttagagagag agagagagag agagagagag agagacatac agaaatttat accaacatta    120
cgacttaacg atacaaatag aaccggtttg acacaggtag aaactcgtct atttagaccg    180
ctattacaag aaaaatgact ttcgtgacgt cctactcccg gactttagtg tagcctgcgg    240
```

-continued

| | |
|---|---|
| gtgacccagt actactatac ctgaggaggt gtcgctcgtc ggtaccctac actctaggtg | 300 |
| tatcgtcgca tctattccct tcgggcgttg tgatccgaca acaacaaggt catttctagc | 360 |
| tttccagtcc gctgtcactg ctagctgaaa aagctcgtac tactgttgct gctggacgag | 420 |
| gacgttatag gcaggggatg gcatctcacc cttatttacc caaacatcaa cgtgataaag | 480 |
| agcgtcctta attaactttc gggacgttta acgacaaaga gaaaggaata taatttggaa | 540 |
| ggaggacaat gtaattttaa cgtacaattc tgtaaagaca tacctaggct tgtactctag | 600 |
| atagtaactt cattacccat cctaaatgta atagtagtag tagtagtaga ggtacccaaa | 660 |
| cctagattaa tctggctttt ggagtaaatt ttaggttggg gttataaccg aactgaacga | 720 |
| ggtagaggtt ctttttatgt tgttcttgtt gtttttaaat cctacgtgta acttaactaa | 780 |
| accagtgata ctctcttagt acctaatttt tataatttta tttttattt agtattagta | 840 |
| gatgagtgag attgctaagt gtaagatagg tggtttaaac tgtagccgaa gattaattaa | 900 |
| agtatataat ccaagatttt ttagagaggg aaactgtcta cttatttata aagaaaatta | 960 |
| agcaatccct tcctagatta tattatatat atatatatat ataaataaat aatctaagat | 1020 |
| tggtaaagag agtggtctta tacttagctg ccggtataga cgttttgggg tggttaacag | 1080 |
| gtgtcatttg cgagtaactt aattccagct ttaatgaaaa tttaaagatc tctaaaggtt | 1140 |
| attttatatg agcatagaaa atgtcactac tacgaggcct actattctac cttcctacgc | 1200 |
| acacagtcgg cggacgctag agacaccgcc cctgctctgc ttctgttcct gcactcgcct | 1260 |
| gctatggttc agaagaggag ggggtggtgc gtgcagagtc taagggctat gccggatagg | 1320 |
| gccaccgcac acctgacgtg tctgcttgct catttacggg taggggggag aaagtaagaa | 1380 |
| agagaaacgc acacactctc ctcgcggata tttattcgtg ctttgttcgg ggaaaagaga | 1440 |
| ggttcttgtg tggtgtggta agtgtgtgat gtaggagacg aagaagctcg gaaaagcgga | 1500 |
| aggaaggagc agattggtac agctggacgc cgttgacgct gacgcaactg ttctcggtca | 1560 |
| cgcacattca gtaggaggta gggaggtgga gaagaagaag aagaagaaga agaagaagat | 1620 |
| tggagcgggg caaacacaaa ctactcagct gagaagggtg tagcgagcag ttttgagtct | 1680 |
| cgaaataatc ccttgtagtc gttatgatat acatatacat nttccagttg caaccgactt | 1740 |
| cttgaaccaa aacggaaacg tccttctttc ctttgtcgat gccatagcta taacaactct | 1800 |
| ggctcttctc catgactaat cgaagaagag ggaggaggag cagctcctac tagtttgatt | 1860 |
| aatcctaatg tggaataatg gaatggatta cgaaaaaggc ataagcaaag cagagaagtc | 1920 |
| gatgcagctg ctccactagc aacggcgtct tcgacggctc gtactgccgt tcacgttcac | 1980 |
| gccgcggcgg acgcggacgt ggctgacgtt cacaccgttg actcttcgtg aacacagtga | 2040 |
| tggtgattta ttttcaaacg ttacgtattt tttgttttct tgttttttt ttttccttct | 2100 |
| tcttcttcca caccgataca tgagattatt aagcccgtcc gactatccaa cattctaccc | 2160 |
| tattgcgtca tagtagacac aatagagaca ggacacaatg ttgagaggat agataggatc | 2220 |
| agttacttta taataatcat aattagacca acacagtaag tatatacgac gacgacgacg | 2280 |
| acgaaggaga aagtggttag ttgggtttcc tagctaacgt gacattccgg gttgaaggag | 2340 |
| tggctatacg agcgagtcaa tgctacttac ttgtcgttgg tttgctcaga cg | 2392 |

<210> SEQ ID NO 34
<211> LENGTH: 758
<212> TYPE: PRT
<213> ORGANISM: Musa acuminata

<400> SEQUENCE: 34

```
Ser Leu Val Arg Gly Pro Pro Arg Gly Arg Arg Tyr Arg Ala Leu Ile
  1               5                  10                  15

Ser Ser Leu Asn Leu Ser Leu Ser Leu Ser Leu Ser Leu Tyr
         20                  25                  30

Val Phe Lys Tyr Gly Cys Asn Ala Glu Leu Leu Cys Leu Ser Trp Pro
         35                  40                  45

Asn Cys Val His Leu Ala Asp Lys Ser Gly Asp Asn Val Leu Phe Thr
 50                  55                  60

Glu Ser Thr Ala Gly Gly Pro Glu Ile Thr Ser Asp Ala His Trp Val
 65                  70                  75                  80

Met Met Ile Trp Thr Pro Pro Gln Arg Ala Ala Met Gly Cys Glu Ile
                 85                  90                  95

His Ile Ala Ala Ile Arg Glu Ala Arg Asn Thr Arg Leu Leu Leu Phe
                100                 105                 110

Gln Arg Ser Lys Gly Gln Ala Thr Val Thr Ile Asp Phe Phe Glu His
            115                 120                 125

Asp Asp Asn Asp Asp Leu Leu Leu Gln Tyr Pro Ser Pro Thr Val Glu
        130                 135                 140

Trp Glu Met Gly Leu Leu His Tyr Phe Ser Gln Glu Leu Ile Glu Ser
145                 150                 155                 160

Pro Ala Asn Cys Cys Phe Ser Phe Leu Ile Leu Asn Leu Pro Pro Val
                165                 170                 175

Thr Leu Lys Leu His Val Lys Thr Phe Leu Tyr Gly Ser Glu His Glu
            180                 185                 190

Ile Tyr His Ser Asn Gly Asp Leu His Tyr His His His His His Leu
        195                 200                 205

His Gly Phe Gly Ser Asn Thr Glu Asn Leu Ile Asn Pro Thr Pro Ile
210                 215                 220

Leu Ala Leu Ala Pro Ser Pro Arg Lys Ile Gln Gln Glu Gln Gln Lys
225                 230                 235                 240

Phe Arg Met His Ile Glu Leu Ile Trp Ser Leu Glu Asn His Gly Leu
                245                 250                 255

Lys Ile Leu Lys Ile Asn His Asn His Leu Leu Thr Leu Thr Ile His
            260                 265                 270

Ile Leu Ser Thr Lys Phe Asp Ile Gly Phe Leu Ile Ser Tyr Ile Arg
        275                 280                 285

Phe Lys Ile Ser Pro Phe Asp Arg Ile Asn Ile Ser Phe Asn Ser Leu
        290                 295                 300

Gly Lys Asp Leu Ile Tyr Ile Tyr Ile Tyr Ile Phe Ile Tyr Ile Leu
305                 310                 315                 320

Thr Ile Ser Leu Thr Arg Ile Ile Asp Gly His Ile Cys Lys Asn Pro
                325                 330                 335

Pro Ile Val His Ser Lys Arg Ser Leu Asn Gly Arg Asn Tyr Phe Ile
                340                 345                 350

Ser Arg Asp Phe Gln Asn Ile Leu Val Ser Phe Thr Val Met Met Leu
            355                 360                 365

Arg Met Ile Arg Trp Lys Asp Ala Cys Val Ser Arg Leu Arg Ser Leu
370                 375                 380

Trp Arg Gly Arg Asp Glu Asp Lys Asp Val Ser Gly Arg Tyr Gln Val
385                 390                 395                 400

Phe Ser Ser Pro Thr Thr His Val Ser Asp Ser Arg Tyr Gly Leu Ser
                405                 410                 415
```

```
Arg Trp Arg Val Asp Cys Thr Asp Glu Arg Val Asn Ala His Pro Pro
            420                 425                 430

Ser Phe Ile Leu Ser Leu Cys Val Cys Glu Arg Ser Ala Tyr Lys Ala
            435                 440                 445

Arg Asn Lys Pro Leu Phe Ser Pro Arg Thr His His Thr Ile His Thr
            450                 455                 460

Leu His Pro Leu Leu Arg Ala Phe Ser Pro Ser Phe Leu Val Pro
465                 470                 475                 480

Cys Arg Pro Ala Ala Thr Ala Thr Ala Leu Thr Arg Ala Ser Ala Cys
            485                 490                 495

Lys Ser Ser Ile Pro Pro Leu Leu Leu Leu Leu Leu Leu
            500                 505                 510

Leu Leu Thr Ser Pro Arg Leu Cys Leu Met Ser Arg Leu Phe Pro His
            515                 520                 525

Arg Ser Ser Lys Leu Arg Ala Leu Leu Gly Asn Ile Ser Asn Thr Ile
            530                 535                 540

Cys Ile Cys Xaa Arg Ser Thr Leu Ala Glu Glu Leu Gly Phe Ala Phe
545                 550                 555                 560

Ala Gly Arg Lys Glu Thr Ala Thr Val Ser Ile Leu Leu Arg Pro Arg
            565                 570                 575

Arg Gly Thr Asp Leu Leu Leu Pro Pro Arg Arg Gly Ser Asn Leu
            580                 585                 590

Gly Leu His Leu Ile Thr Leu Pro Asn Ala Phe Ser Val Phe Val Ser
            595                 600                 605

Ser Leu Gln Leu Arg Arg Arg Gly Asp Arg Cys Arg Arg Ser Cys Arg
            610                 615                 620

Ala Arg Gln Val Gln Val Arg Arg Arg Leu Arg Leu His Arg Leu Gln
625                 630                 635                 640

Val Trp Gln Leu Arg Ser Thr Cys Val Thr Thr Thr Lys Lys Phe Ala
            645                 650                 655

Met His Lys Lys Gln Lys Asn Lys Lys Lys Lys Gly Arg Arg Arg Arg
            660                 665                 670

Cys Tyr Val Leu Phe Gly Gln Ala Asp Arg Leu Asp Gly Ile Thr Gln
            675                 680                 685

Tyr His Leu Cys Tyr Leu Cys Pro Val Leu Gln Leu Ser Tyr Leu Ser
            690                 695                 700

Ser Met Lys Tyr Tyr Ser Gly Cys Val Ile His Ile Cys Cys
705                 710                 715                 720

Cys Cys Cys Phe Leu Phe His Gln Ser Thr Gln Arg Ile Asp Cys Thr
            725                 730                 735

Val Arg Pro Asn Phe Leu Thr Asp Met Leu Ala Gln Leu Arg Met Asn
            740                 745                 750

Ser Asn Gln Thr Ser Leu
            755

<210> SEQ ID NO 35
<211> LENGTH: 758
<212> TYPE: PRT
<213> ORGANISM: Musa acuminata

<400> SEQUENCE: 35

His Trp Tyr Gly Ala Pro Leu Glu Val Asp Gly Ile Asp Lys Leu Ser
 1               5                  10                  15

Leu Leu Ser Ile Ser Leu Ser Leu Ser Leu Ser Leu Cys Met
            20                  25                  30
```

-continued

```
Ser Leu Asn Met Val Val Met Leu Asn Cys Tyr Val Tyr Leu Gly Gln
         35                  40                  45

Thr Val Ser Ile Phe Glu Gln Ile Asn Leu Ala Ile Met Phe Phe Leu
         50                  55                  60

Leu Lys Ala Leu Gln Asp Glu Gly Leu Lys Ser His Arg Thr Pro Thr
 65                  70                  75                  80

Gly Ser Tyr Gly Leu Leu His Ser Glu Gln Pro Trp Asp Val Arg Ser
                 85                  90                  95

Thr Gln Arg Arg Gly Lys Pro Ala Thr Leu Gly Cys Cys Cys Ser Ser
             100                 105                 110

Lys Asp Arg Lys Val Arg Arg Gln Arg Ser Thr Phe Ser Ser Met Met
         115                 120                 125

Thr Thr Thr Thr Cys Ser Cys Asn Ile Arg Pro Leu Pro Ser Gly Asn
 130                 135                 140

Lys Trp Val Cys Ser Cys Thr Ile Ser Arg Arg Asn Leu Lys Ala Leu
 145                 150                 155                 160

Gln Ile Ala Val Ser Leu Ser Leu Tyr Thr Phe Leu Leu Leu His Asn
                 165                 170                 175

Cys Met Leu Arg His Phe Cys Met Asp Pro Asn Met Arg Ser Ile Ile
             180                 185                 190

Glu Val Met Gly Arg Ile Tyr Ile Ile Ile Ile Ile Ile Ile Ser Met
         195                 200                 205

Gly Leu Asp Leu Ile Arg Pro Lys Thr Ser Phe Lys Ile Gln Pro Gln
 210                 215                 220

Tyr Trp Leu Asp Leu Leu His Leu Gln Glu Lys Tyr Asn Lys Asn Asn
225                 230                 235                 240

Lys Asn Leu Gly Cys Thr Leu Asn Phe Gly His Tyr Glu Arg Ile Met
                 245                 250                 255

Asp Lys Tyr Asn Lys Lys Ile Ile Ile Tyr Ser Leu Arg Phe Thr
             260                 265                 270

Phe Tyr Pro Pro Asn Leu Thr Ser Ala Ser Asn Phe His Ile Leu Gly
         275                 280                 285

Ser Lys Lys Ser Leu Pro Leu Thr Asp Glu Ile Phe Leu Leu Ile Arg
 290                 295                 300

Gly Arg Ile Tyr Asn Ile Tyr Ile Tyr Ile Tyr Leu Phe Ile Arg Phe
305                 310                 315                 320

Pro Phe Leu Ser Pro Glu Tyr Glu Ser Thr Ala Ile Ser Ala Lys Thr
                 325                 330                 335

His Gln Leu Phe Thr Val Asn Ala His Ile Lys Val Glu Ile Thr Phe
             340                 345                 350

Lys Phe Leu Glu Ile Ser Asn Lys Ile Tyr Ser Tyr Leu Leu Gln Cys
         355                 360                 365

Ser Gly Asp Gly Arg Met Arg Val Ser Ala Ala Cys Asp Leu Cys Gly
 370                 375                 380

Gly Asp Glu Thr Lys Thr Arg Thr Ala Asp Thr Lys Ser Ser Pro
385                 390                 395                 400

Pro Pro Pro Arg Thr Ser Gln Ile Pro Asp Thr Ala Tyr Pro Gly Gly
                 405                 410                 415

Val Trp Thr Ala Gln Thr Asn Glu Met Pro Ile Pro Leu Ser Phe
             420                 425                 430

Phe Leu Phe Ala Cys Val Arg Gly Ala Pro Ile Asn Lys His Glu Thr
         435                 440                 445
```

```
Ser Pro Phe Ser Leu Gln Glu His Thr Thr Pro Phe Thr His Tyr Ile
    450                 455                 460

Leu Cys Phe Phe Glu Pro Phe Arg Leu Pro Ser Ser Ser Asn His Val
465                 470                 475                 480

Asp Leu Arg Gln Leu Arg Leu Arg Gln Glu Pro Val Arg Val Ser His
                485                 490                 495

Pro Pro Ser Leu His Leu Phe Phe Phe Phe Phe Phe Phe Phe Pro Arg
            500                 505                 510

Pro Val Cys Val Val Asp Ser Ser His Ile Ala Arg Gln Asn Ser Glu
        515                 520                 525

Leu Tyr Gly Thr Ser Ala Ile Leu Tyr Val Tyr Val Xaa Gly Gln Arg
    530                 535                 540

Trp Leu Lys Asn Leu Val Leu Pro Leu Gln Glu Arg Lys Gln Leu
545                 550                 555                 560

Arg Tyr Arg Tyr Cys Asp Arg Glu Glu Val Leu Ile Ser Phe Phe Ser
                565                 570                 575

Leu Leu Leu Val Glu Asp Asp Gln Thr Asn Asp Tyr Thr Leu Leu Pro
            580                 585                 590

Tyr Leu Met Leu Phe Pro Val Ser Phe Arg Leu Phe Ser Tyr Val Asp
        595                 600                 605

Glu Val Ile Val Ala Ala Glu Ala Ala Glu His Asp Gly Lys Cys Lys
    610                 615                 620

Cys Gly Ala Ala Cys Ala Cys Thr Asp Cys Lys Cys Gly Asn Glu Ala
625                 630                 635                 640

Leu Val Ser Leu Pro Leu Asn Asn Lys Ser Leu Gln Cys Ile Lys Asn
                645                 650                 655

Lys Arg Thr Lys Lys Lys Glu Glu Glu Gly Val Ala Met Tyr
            660                 665                 670

Ser Asn Asn Ser Gly Arg Leu Ile Gly Cys Lys Met Gly Arg Ser Ile
        675                 680                 685

Ile Cys Val Ile Ser Val Leu Cys Tyr Asn Ser Pro Ile Tyr Pro Ser
    690                 695                 700

Gln Asn Ile Ile Ser Ile Asn Leu Val Val Ser Phe Ile Tyr Ala Ala
705                 710                 715                 720

Ala Ala Ala Ala Ser Ser Phe Thr Asn Gln Pro Lys Gly Ser Ile Ala
                725                 730                 735

Leu Gly Pro Thr Ser Ser Pro Ile Cys Ser Leu Ser Tyr Asp Glu Thr
            740                 745                 750

Ala Thr Lys Arg Val Cys
        755

<210> SEQ ID NO 36
<211> LENGTH: 762
<212> TYPE: PRT
<213> ORGANISM: Musa acuminata

<400> SEQUENCE: 36

Leu Thr Gly Thr Gly Pro Pro Ser Arg Ser Thr Val Ser Ile Ser Phe
1               5                   10                  15

Asp Leu Phe Ser Gln Ser Leu Ser Leu Ser Leu Ser Leu Ser
                20                  25                  30

Val Cys Leu Ile Trp Leu Cys Ile Ala Met Phe Ile Leu Ala Lys Leu
            35                  40                  45

Cys Pro Ser Leu Ser Arg Ile Trp Arg Cys Ser Phe Tyr Lys His Cys
        50                  55                  60
```

```
Arg Met Arg Ala Asn His Ile Gly Arg Pro Leu Gly His Asp Asp Met
 65                  70                  75                  80

Asp Ser Ser Thr Ala Ser Ser His Gly Met Asp Pro His Ser Ser Val
                 85                  90                  95

Asp Lys Gly Ser Pro Gln His Ala Val Val Pro Val Lys Ile Glu
            100                 105                 110

Arg Ser Gly Asp Ser Asp Arg Leu Phe Arg Ala Gln Arg Arg Pro
            115                 120                 125

Ala Pro Ala Ile Ser Val Pro Tyr Arg Arg Val Gly Ile Asn Gly Phe
    130                 135                 140

Val Val Ala Leu Phe Leu Ala Gly Ile Asn Lys Pro Cys Lys Leu Leu
145                 150                 155                 160

Phe Leu Phe Pro Tyr Ile Lys Pro Ser Ser Cys Tyr Ile Lys Ile Ala
                165                 170                 175

Cys Asp Ile Ser Val Trp Ile Arg Thr Asp Leu Ser Leu Lys Trp Val
                180                 185                 190

Gly Phe Thr Leu Ser Ser Ser Ser Ser Pro Trp Val Trp Ile Leu
            195                 200                 205

Asp Arg Lys Pro His Leu Lys Ser Asn Pro Asn Ile Gly Leu Thr Cys
    210                 215                 220

Ser Ile Ser Lys Lys Asn Thr Thr Arg Thr Thr Lys Ile Asp Ala His
225                 230                 235                 240

Ile Asp Leu Val Thr Met Arg Glu Ser Trp Ile Lys Asn Ile Lys Ile
                245                 250                 255

Lys Asn Lys Ser Ser Ser Thr His Ser Asn Asp Ser His Ser Ile His
                260                 265                 270

Gln Ile His Arg Leu Leu Ile Asn Phe Ile Tyr Val Leu Lys Asn Leu
    275                 280                 285

Ser Leu Gln Met Asn Lys Tyr Phe Phe Val Arg Glu Gly Ser Asn
    290                 295                 300

Ile Ile Tyr Ile Tyr Ile Tyr Ile Tyr Leu Leu Asp Ser Asn His Phe
305                 310                 315                 320

Ser His Gln Asn Met Asn Arg Arg Pro Tyr Leu Gln Lys Pro Thr Asn
                325                 330                 335

Cys Ser Gln Thr Leu Ile Glu Leu Arg Ser Lys Leu Leu Asn Phe
            340                 345                 350

Arg Phe Pro Ile Lys Tyr Thr Arg Ile Phe Tyr Ser Asp Asp Ala Pro
            355                 360                 365

Asp Asp Lys Met Glu Gly Cys Val Cys Gln Pro Pro Ala Ile Ser Val
    370                 375                 380

Ala Gly Thr Arg Arg Gln Gly Arg Glu Arg Thr Ile Pro Ser Leu
385                 390                 395                 400

Leu Leu Pro His His Ala Arg Leu Arg Phe Pro Ile Arg Pro Ile Pro
                405                 410                 415

Val Ala Cys Gly Leu His Arg Arg Thr Ser Lys Cys Pro Ser Pro Leu
            420                 425                 430

Phe His Ser Phe Ser Leu Arg Val Glu Glu Arg Leu Ile Ser Thr Lys
            435                 440                 445

Gln Ala Pro Phe Leu Ser Lys Asn Thr Pro His His Ser His Thr Thr
    450                 455                 460

Ser Ser Ala Ser Ser Ser Leu Phe Ala Phe Leu Pro Arg Leu Thr Met
465                 470                 475                 480
```

```
Ser Thr Cys Gly Asn Cys Asp Cys Val Asp Lys Ser Gln Cys Val Val
                485                 490                 495

Ile Leu His Pro Ser Thr Ser Ser Ser Ser Ser Ser Ser Ser Ser Ser
                500                 505                 510

Asn Leu Ala Pro Phe Val Phe Asp Glu Ser Thr Leu Pro Thr Ser Leu
                515                 520                 525

Val Lys Thr Gln Ser Phe Ile Arg Glu His Gln Gln Tyr Tyr Met Tyr
    530                 535                 540

Met Xaa Lys Val Asn Val Gly Arg Thr Trp Phe Cys Leu Cys Arg Lys
545                 550                 555                 560

Lys Gly Asn Ser Tyr Gly Ile Asp Ile Val Glu Thr Glu Lys Arg Tyr
                565                 570                 575

Leu Ala Ser Ser Pro Ser Ser Ser Ser Arg Met Ile Lys Leu Ile Arg
                580                 585                 590

Ile Thr Pro Tyr Tyr Leu Thr Cys Phe Phe Arg Ile Arg Phe Val Ser
                595                 600                 605

Ser Ala Thr Ser Thr Arg Ser Leu Pro Gln Lys Leu Pro Ser Met Thr
                610                 615                 620

Ala Ser Ala Ser Ala Ala Pro Pro Ala Pro Ala Pro Thr Ala Ser Val
625                 630                 635                 640

Ala Thr Glu Lys His Leu Cys His Tyr His Ile Lys Val Cys Asn Ala
                645                 650                 655

Lys Thr Lys Glu Gln Lys Lys Arg Lys Lys Lys Val Trp Leu
                660                 665                 670

Cys Thr Leu Ile Ile Arg Ala Gly Val Val Arg Trp Asp Asn Ala Val
                675                 680                 685

Ser Ser Val Leu Ser Leu Ser Cys Val Thr Thr Leu Leu Ser Ile Leu
                690                 695                 700

Val Asn Glu Ile Leu Leu Val Leu Ile Trp Leu Cys His Ser Tyr Met
705                 710                 715                 720

Leu Leu Leu Leu Leu Leu Pro Leu Ser Pro Ile Asn Pro Lys Asp Arg
                725                 730                 735

Leu His Cys Lys Ala Gln Leu Pro His Arg Tyr Ala Arg Ser Val Thr
                740                 745                 750

Met Asn Glu Gln Gln Pro Asn Glu Ser Ala
                755                 760

<210> SEQ ID NO 37
<211> LENGTH: 1880
<212> TYPE: DNA
<213> ORGANISM: Musa acuminata
<220> FEATURE:
<221> NAME/KEY: misc_feature
<222> LOCATION: (1721)..(1799)
<223> OTHER INFORMATION: Nucleotides 1721, 1782, 1788 and 1799 are n
      wherein n = a or g or c or t/u.

<400> SEQUENCE: 37
tcactggtac ggggcccccc tcgaggtcga cggtatcgat aagctttgat ctcttctctc      60
aatctctctc tctctctctc tctctctctc tctctgtatg tctttaaata tggttgtaat     120
gctgaattgc tatgtttatc ttggccaaac tgtgtccatc tttgagcaga taatctggc      180 gataatgttc ttttactga aagcactgca ggatgagggc ctgaaatcac atcggacgcc     240
cactgggtca tgatgatatg gactcctcca cagcgagcag ccatgggatg tgagatccac     300
atagcagcgt agataaggga agcccgcaac actaggctgt tgttgttcca gtaaagatcg     360
```

-continued

```
aaaggtcagg cgacagtgac gatcgacttt ttcgagcatg atgacaacga cgacctgctc    420
ctgcaatatc cgtcccctac cgtagagtgg gaataaatgg gtttgtagtt gcactatttc    480
tcgcaggaat taattgaaag ccctgcaaat tgctgtttct ctttccttat attaaacctt    540
cctcctgtta cattaaaatt gcatgttaag acatttctgt atggatccga acatgagatc    600
tatcattgaa gtaatgggta ggatttacat tatcatcatc atcatcatct ccatgggttt    660
ggatctaatt agaccgaaaa cctcatttaa aatccaaccc caatattggc ttgacttgct    720
ccatctccaa gaaaaataca acaagaacaa caaaaattta ggatgcacat tgaattgatt    780
tggtcactat gagagaatca tggattaaaa atattaaaat aaaaaataaa tcataatcat    840
ctactcactc taacgattca cattctatcc accaaatttg acatcggctt ctaattaatt    900
tcatatatta ggttctaaaa aatctctccc tttgacagat gaataaatat ttcttttaat    960
tcgttaggga aggatctaat ataatatata tatatatata tatttattta ttagattcta   1020
accatttctc tcaccagaat atgaatcgac ggccatatct gcaaaaaccc accaattgtt   1080
cacagtaaac gctcattgaa ttaaggtcga aattactttt aaatttctag agatttccaa   1140
taaaatatac tcgtatcttt tacagtgatg atgctccgga tgataagatg aaggatgcg    1200 tgtgtcagcc gcctgcgatc tctgtggcgg ggacgagacg aagacaagga cgtgagcgga   1260
cgataccaag tcttctcctc ccccaccacg cacgtctcag attcccgata cggcctatcc   1320
cggtggcgtg tggactgcac agacgaacga gtaaatgccc atccccctc tttcattctt    1380 tctcttttgcg tgtgtgagag gagcgcctat aaataagcac gaaacaagcc ccttttctct   1440
ccaagaacac accacaccat tcacacacta catcctctgc ttcttcgagc cttttcgcct   1500
tccttcctcg tctaaccatg tcgacctgcg gcaactgcga ctgcgttgac aagagccagt   1560
gcgtgtaagt catcctccat ccctccacct cttcttcttc ttcttcttct tcttcttcta   1620
acctcgcccc gtttgtgttt gatgagtcga ctcttcccac atcgctcgtc aaaactcaga   1680
gctttattag ggaacatcag caatactata tgtatatgta naaggtcaac gttggctgaa   1740
gaacttggtt ttgcctttgc aggaagaaag gaaacagcta cngtatcnat attgttgana   1800
ccgagaagag gtactgatta gcttcttctc cctcctcctc gtcgaggatg atcaaactaa   1860
ttaggattac accttattac                                                1880
```

<210> SEQ ID NO 38
<211> LENGTH: 1878
<212> TYPE: DNA
<213> ORGANISM: Musa acuminata
<220> FEATURE:
<221> NAME/KEY: misc_feature
<222> LOCATION: (1720)..(1869)
<223> OTHER INFORMATION: Nucleotides 1720, 1768, 1781, 1787, 1798, 1807, 1820, 1845 and 1869 are n wherein n = a or g or c or t/u.

<400> SEQUENCE: 38

```
agtgaccatg ccccgggggg agctccagct gccatagcta ttcgaaacta gagaagagag     60
ttagagagag agagagagag agagagagag agagacatac tgaaatttat accaacatta    120
cgacttaacg atacaaatag aaccggtttg acacaggtag aaactcgtct atttagaccg    180
ctattacaag aaaaatgact ttcgtgacgt cctactcccg gactttagtg tagcctgcgg    240
gtgacccagt actactatac ctgaggaggt gtcgctcgtc ggtacccac actcctaggtg    300 tatcgtcgca tctattccct tcgggcgttg tgatccgaca caacaaggt catttctagc    360 tttccagtcc gctgtcactg ctagctgaaa aagctcgtac tactgttgct gctggacgag    420
```

```
gacgttatag gcaggggatg gcatctcacc cttatttacc caaacatcaa cgtgataaag    480
agcgtcctta attaactttc gggacgttta acgacaaaga gaaaggaata taatttggaa    540
ggaggacaat gtaattttaa cgtacaattc tgtaaagaca tacctaggct tgtactctag    600
atagtaactt cattacccat cctaaatgta atagtagtag tagtagtaga ggtacccaaa    660
cctagattaa tctggctttt ggagtaaatt ttaggttggg ttataaccga actgaacgag    720
gtagaggttc tttttatgtt gttcttgttg tttttaaatc ctacgtgtaa cttaactaaa    780
ccagtgatac tctcttagtg cctaattttt ataatttttat tttttattta gtattagtag   840
atgagtgaga ttgctaagtg taagataggt ggtttaaact gtagccgaag attaattaaa    900
gtatataatc caagattttt tagagaggga aactgtctac ttatttataa agaaaattaa    960
gcaatcccct tcctagattat attatatata tatatatata taaataaata atctaagatt  1020
ggtaaagaga gtggtcttat acttagctgc cggtatagac gttttgggt ggttaacaag   1080 tgtcatttgc gagtaactta tctccagctt taatgaaaat ttaaagatct ctaaaggtta   1140
ttttatatga gcatagaaaa tgtcactact acgaggccta ctattctacc ttcctacgca   1200
cacagtcggc ggacgctaga gacaccgccc ctgctctgct tctgttcctg cactcgcctg   1260
ctatggttca gaagaggagg gggtggtgcg tgcagagtct aagggctatg ccggataggg   1320
ccaccgcaca cctgacgtgt ctgcttgctc atttacgggt agggggagaa agtaagaaa    1380 gagaaacgca cacactctcc tcgcggatat ttattcgtgc tttgttcggg gaaaagagag   1440
gttcttgtgt ggtgtggtaa gtgtgtgatg taggagacga agaagctcgg aaaagcggaa   1500
ggaaggagca gattggtaca gctggacgcc gttgacgctg acgcaactgt tctcggtcac   1560
gcacattcag taggaggtag ggaggtggag aagaagaaga agaagaagaa gaagaagatt   1620
ggagcggggc aaacacaaac tactcagctg agaagggtgt agcgagcagt tttgagtctc   1680
gaaataatcc cttgtagtcg ttatgatata catatacatn ttccagttgc aaccgacttc   1740
ttgaaccaaa acgaaacgt ccttcttncc tttgtcgatg ncatagntat aacaactntg    1800
gcttttntcc atgactaatn gaagaagagg gaggaggagc agctntacta gtttgattaa   1860
tcctaatgng gaataatg                                                 1878
```

<210> SEQ ID NO 39
<211> LENGTH: 597
<212> TYPE: PRT
<213> ORGANISM: Musa acuminata

<400> SEQUENCE: 39

```
Ser Leu Val Arg Gly Pro Pro Arg Gly Arg Arg Tyr Arg Ala Leu Ile
  1               5                  10                  15

Ser Ser Leu Asn Leu Ser Leu Ser Leu Ser Leu Ser Leu Ser Leu Tyr
             20                  25                  30

Phe Lys Tyr Gly Cys Asn Ala Glu Leu Leu Cys Leu Ser Trp Pro Asn
         35                  40                  45

Cys Val His Leu Ala Asp Lys Ser Gly Asp Asn Val Leu Phe Thr Glu
     50                  55                  60

Ser Thr Ala Gly Gly Pro Glu Ile Thr Ser Asp Ala His Trp Val Met
 65                  70                  75                  80

Met Ile Trp Thr Pro Pro Gln Arg Ala Ala Met Gly Cys Glu Ile His
                 85                  90                  95

Ala Ala Ile Arg Glu Ala Arg Asn Thr Arg Leu Leu Leu Phe Gln Arg
            100                 105                 110
```

```
Ser Lys Gly Gln Ala Thr Val Thr Ile Asp Phe Phe Glu His Asp Asp
    115                 120                 125
Asn Asp Asp Leu Leu Leu Gln Tyr Pro Ser Pro Thr Val Glu Trp Glu
130                 135                 140
Met Gly Leu Leu His Tyr Phe Ser Gln Glu Leu Ile Glu Ser Pro Ala
145                 150                 155                 160
Asn Cys Cys Phe Ser Phe Leu Ile Leu Asn Leu Pro Pro Val Thr Leu
                165                 170                 175
Lys Leu His Val Lys Thr Phe Leu Tyr Gly Ser Glu His Glu Ile Tyr
            180                 185                 190
His Ser Asn Gly Asp Leu His Tyr His His His His Leu His Gly
        195                 200                 205
Phe Gly Ser Asn Thr Glu Asn Leu Ile Asn Pro Thr Ile Leu Ala Leu
    210                 215                 220
Ala Pro Ser Pro Arg Lys Ile Gln Gln Glu Gln Gln Lys Phe Arg Met
225                 230                 235                 240
His Ile Glu Leu Ile Trp Ser Leu Glu Asn His Gly Leu Lys Ile Leu
                245                 250                 255
Lys Lys Ile Asn His Asn His Leu Leu Thr Leu Thr Ile His Ile Leu
            260                 265                 270
Ser Thr Lys Phe Asp Ile Gly Phe Leu Ile Ser Tyr Ile Arg Phe Lys
        275                 280                 285
Ile Ser Pro Phe Asp Arg Ile Asn Ile Ser Phe Asn Ser Leu Gly Lys
    290                 295                 300
Asp Leu Ile Tyr Ile Tyr Ile Tyr Ile Phe Ile Tyr Ile Leu Thr Ile
305                 310                 315                 320
Ser Leu Thr Arg Ile Ile Asp Gly His Ile Cys Lys Asn Pro Pro Ile
                325                 330                 335
Val His Ser Lys Arg Ser Leu Asn Gly Arg Asn Tyr Phe Ile Ser Arg
            340                 345                 350
Asp Phe Gln Asn Ile Leu Val Ser Phe Thr Val Met Met Leu Arg Met
        355                 360                 365
Ile Arg Trp Lys Asp Ala Cys Val Ser Arg Leu Arg Ser Leu Trp Arg
    370                 375                 380
Gly Arg Asp Glu Asp Lys Asp Val Ser Gly Arg Tyr Gln Val Phe Ser
385                 390                 395                 400
Ser Pro Thr Thr His Val Ser Asp Ser Arg Tyr Gly Leu Ser Arg Trp
                405                 410                 415
Arg Val Asp Cys Thr Asp Glu Arg Val Asn Ala His Pro Pro Ser Phe
            420                 425                 430
Ile Leu Ser Leu Cys Val Cys Glu Arg Ser Ala Tyr Lys Ala Arg Asn
        435                 440                 445
Lys Pro Leu Phe Ser Pro Arg Thr His His Thr Ile His Thr Leu His
    450                 455                 460
Pro Leu Leu Leu Arg Ala Phe Ser Pro Ser Phe Leu Val Pro Cys Arg
465                 470                 475                 480
Pro Ala Ala Thr Ala Thr Ala Leu Thr Arg Ala Ser Ala Cys Lys Ser
                485                 490                 495
Ser Ser Ile Pro Pro Leu Leu Leu Leu Leu Leu Leu Leu Leu
            500                 505                 510
Thr Ser Pro Arg Leu Cys Leu Met Ser Arg Leu Phe Pro His Arg Ser
        515                 520                 525
```

```
Ser Lys Leu Arg Ala Leu Leu Gly Asn Ile Ser Asn Thr Ile Cys Ile
    530                 535                 540

Cys Xaa Arg Ser Thr Leu Ala Glu Glu Leu Gly Phe Ala Phe Ala Gly
545                 550                 555                 560

Arg Xaa Glu Thr Ala Thr Val Ser Ile Leu Leu Xaa Pro Lys Xaa Gly
                565                 570                 575

Thr Asp Xaa Leu Leu Pro Pro Arg Arg Xaa Ser Asn Leu Gly
            580                 585                 590

Leu Xaa Leu Ile Thr
        595

<210> SEQ ID NO 40
<211> LENGTH: 590
<212> TYPE: PRT
<213> ORGANISM: Musa acuminata

<400> SEQUENCE: 40

His Trp Tyr Gly Ala Pro Leu Glu Val Asp Gly Ile Asp Lys Leu Ser
  1               5                  10                  15

Leu Leu Ser Ile Ser Leu Ser Leu Ser Leu Ser Leu Ser Leu Cys Met
                 20                  25                  30

Ser Leu Asn Met Val Met Leu Asn Cys Tyr Val Tyr Leu Gly Gln
             35                  40                  45

Thr Val Ser Ile Phe Glu Gln Ile Asn Leu Ala Ile Met Phe Phe Leu
         50                  55                  60

Leu Lys Ala Leu Gln Asp Glu Gly Leu Lys Ser His Arg Thr Pro Thr
 65                  70                  75                  80

Gly Ser Tyr Gly Leu Leu His Ser Glu Gln Pro Trp Asp Val Arg Ser
                 85                  90                  95

Thr Gln Arg Arg Gly Lys Pro Ala Thr Leu Gly Cys Cys Cys Ser Ser
            100                 105                 110

Lys Asp Arg Lys Val Arg Arg Gln Arg Ser Thr Phe Ser Ser Met Met
        115                 120                 125

Thr Thr Thr Thr Cys Ser Cys Asn Ile Arg Pro Leu Pro Ser Gly Asn
    130                 135                 140

Lys Trp Val Cys Ser Cys Thr Ile Ser Arg Arg Asn Leu Lys Ala Leu
145                 150                 155                 160

Gln Ile Ala Val Ser Leu Ser Leu Tyr Thr Phe Leu Leu His Asn
                165                 170                 175

Cys Met Leu Arg His Phe Cys Met Asp Pro Asn Met Arg Ser Ile Ile
                180                 185                 190

Glu Val Met Gly Arg Ile Tyr Ile Ile Ile Ile Ile Ile Ser Met
            195                 200                 205

Gly Leu Asp Leu Ile Arg Pro Lys Thr Ser Phe Lys Ile Gln Pro Tyr
    210                 215                 220

Trp Leu Asp Leu Leu His Leu Gln Glu Lys Tyr Asn Lys Asn Lys
225                 230                 235                 240

Asn Leu Gly Cys Thr Leu Asn Phe Gly His Tyr Glu Arg Ile Asp Lys
                245                 250                 255

Tyr Asn Lys Lys Ile Ile Ile Tyr Ser Leu Arg Phe Thr Phe Tyr
            260                 265                 270

Pro Pro Asn Leu Thr Ser Ala Ser Asn Phe His Ile Leu Gly Ser Lys
        275                 280                 285

Lys Ser Leu Pro Leu Thr Asp Glu Ile Phe Leu Leu Ile Arg Gly Arg
    290                 295                 300
```

```
Ile Tyr Asn Ile Tyr Ile Tyr Ile Tyr Leu Phe Ile Arg Phe Pro Phe
305                 310                 315                 320

Leu Ser Pro Glu Tyr Glu Ser Thr Ala Ile Ser Ala Lys Thr His Gln
            325                 330                 335

Leu Phe Thr Val Asn Ala His Ile Lys Val Glu Ile Thr Phe Lys Phe
            340                 345                 350

Leu Glu Ile Ser Asn Lys Ile Tyr Ser Tyr Leu Leu Gln Cys Ser Gly
            355                 360                 365

Asp Gly Arg Met Arg Val Ser Ala Ala Cys Asp Leu Cys Gly Gly Asp
        370                 375                 380

Glu Thr Lys Thr Arg Thr Ala Asp Asp Thr Lys Ser Ser Pro Pro Pro
385                 390                 395                 400

Pro Arg Thr Ser Gln Ile Pro Asp Thr Ala Tyr Pro Gly Gly Val Trp
                405                 410                 415

Thr Ala Gln Thr Asn Glu Met Pro Ile Pro Pro Leu Ser Phe Phe Leu
            420                 425                 430

Phe Ala Cys Val Arg Gly Ala Pro Ile Asn Lys His Glu Thr Ser Pro
        435                 440                 445

Phe Ser Leu Gln Glu His Thr Thr Pro Phe Thr His Tyr Ile Leu Cys
450                 455                 460

Phe Phe Glu Pro Phe Arg Leu Pro Ser Ser Ser Asn His Val Asp Leu
465                 470                 475                 480

Arg Gln Leu Arg Leu Arg Gln Glu Pro Val Arg Val Ser His Pro Pro
                485                 490                 495

Ser Leu His Leu Phe Phe Phe Phe Phe Phe Phe Phe Pro Arg Pro
            500                 505                 510

Val Cys Val Val Asp Ser Ser His Ile Arg Ala Gln Asn Ser Glu Leu
            515                 520                 525

Tyr Gly Thr Ser Ala Ile Leu Tyr Val Tyr Val Xaa Gly Gln Arg Trp
            530                 535                 540

Leu Lys Asn Leu Val Leu Pro Leu Gln Glu Glu Xaa Lys Gln Leu Xaa
545                 550                 555                 560

Tyr Xaa Tyr Cys Xaa Arg Lys Xaa Val Leu Ile Xaa Phe Phe Ser Leu
                565                 570                 575

Leu Leu Val Xaa Asp Asp Gln Thr Asn Asp Tyr Xaa Leu Leu
            580                 585                 590

<210> SEQ ID NO 41
<211> LENGTH: 441
<212> TYPE: PRT
<213> ORGANISM: Musa acuminata

<400> SEQUENCE: 41

Thr Gly Thr Gly Pro Pro Ser Arg Ser Thr Val Ser Ile Ser Phe Asp
  1               5                  10                  15

Leu Phe Ser Gln Ser Leu Ser Leu Ser Leu Ser Leu Ser Leu Ser Val
                20                  25                  30

Cys Leu Ile Trp Leu Cys Ile Ala Met Phe Ile Leu Ala Lys Leu Cys
            35                  40                  45

Pro Ser Leu Ser Arg Ile Trp Arg Cys Ser Phe Tyr Lys His Cys Arg
        50                  55                  60

Met Arg Ala Asn His Ile Gly Arg Pro Leu Gly His Asp Asp Met Asp
65                  70                  75                  80

Ser Ser Thr Ala Ser Ser His Gly Met Asp Pro His Ser Ser Val Asp
```

-continued

```
                            85                      90                       95
Lys Gly Ser Pro Gln His Ala Val Val Pro Val Lys Ile Glu Arg
            100                 105             110
Ser Gly Asp Ser Asp Asp Arg Leu Phe Arg Ala Gln Arg Pro Ala
        115                 120             125
Pro Ala Ile Ser Val Pro Tyr Arg Arg Val Gly Ile Asn Gly Phe Val
    130                 135                 140
Val Ala Leu Phe Leu Ala Gly Ile Asn Lys Pro Cys Lys Leu Leu Phe
145                 150                 155                 160
Leu Phe Pro Tyr Ile Lys Pro Ser Ser Cys Tyr Ile Lys Ile Ala Cys
                165                 170             175
Asp Ile Ser Val Ser Trp Ile Arg Thr Asp Leu Ser Leu Lys Trp Val
            180                 185             190
Gly Phe Thr Leu Ser Ser Ser Ser Ser Pro Trp Val Trp Ile Leu
            195             200             205
Asp Arg Lys Pro His Leu Lys Ser Asn Pro Asn Ile Gly Leu Thr Cys
        210             215                 220
Ser Ile Ser Lys Lys Asn Thr Thr Arg Thr Thr Lys Ile Asp Ala His
225             230                 235                 240
Ile Asp Leu Val Thr Met Arg Glu Ser Trp Ile Lys Asn Ile Lys Ile
                245                 250                 255
Lys Asn Lys Ser Ser Ser Thr His Ser Asn Asp Ser His Ser Ile His
            260             265                 270
Gln Ile His Arg Leu Leu Ile Asn Phe Ile Tyr Val Leu Lys Asn Leu
        275             280                 285
Ser Leu Gln Met Asn Lys Tyr Phe Phe Phe Val Arg Glu Gly Ser Asn
    290             295                 300
Ile Ile Tyr Ile Tyr Ile Tyr Leu Arg Ser Lys Leu Leu Leu Asn Phe
305             310             315                 320
Arg Phe Pro Ile Lys Tyr Thr Arg Ile Phe Tyr Ser Asp Asp Ala Pro
                325                 330             335
Asp Asp Lys Met Glu Gly Cys Val Cys Gln Pro Pro Ala Ile Ser Val
            340                 345                 350
Ala Gly Thr Arg Arg Arg Gln Gly Arg Glu Arg Thr Ile Pro Ser Leu
        355                 360                 365
Leu Leu Pro His His Ala Arg Leu Arg Phe Pro Ile Arg Pro Ile Pro
    370                 375                 380
Val Ala Cys Gly Leu His Arg Arg Thr Ser Lys Cys Pro Ser Pro Leu
385                 390                 395                 400
Phe His Ser Phe Ser Leu Arg Val Glu Glu Arg Leu Ile Ser Thr Lys
                405                 410                 415
Gln Ala Pro Phe Leu Ser Lys Asn Thr Pro His His Ser His Thr Thr
            420                 425                 430
Ser Ser Ala Ser Ser Ser Leu Phe Ala
            435             440
```